US012435155B2

(12) United States Patent
Berezhnoy et al.

(10) Patent No.: US 12,435,155 B2
(45) Date of Patent: Oct. 7, 2025

(54) CD137 BINDING MOLECULES AND USES THEREOF

(71) Applicant: MACROGENICS, INC., Rockville, MD (US)

(72) Inventors: Alexey Yevgenyevich Berezhnoy, Rockville, MD (US); Gundo Diedrich, Rockville, MD (US); Paul A. Moore, Rockville, MD (US); Ezio Bonvini, Rockville, MD (US); Kalpana Shah, Rockville, MD (US)

(73) Assignee: MACROGENICS, INC., Rockville, MD (US)

( * ) Notice: Subject to any disclaimer, the term of this patent is extended or adjusted under 35 U.S.C. 154(b) by 635 days.

(21) Appl. No.: 17/798,285

(22) PCT Filed: Feb. 16, 2021

(86) PCT No.: PCT/US2021/018177

§ 371 (c)(1),
(2) Date: Aug. 8, 2022

(87) PCT Pub. No.: WO2021/167885

PCT Pub. Date: Aug. 26, 2021

(65) Prior Publication Data

US 2023/0094162 A1 Mar. 30, 2023

Related U.S. Application Data

(60) Provisional application No. 63/147,565, filed on Feb. 9, 2021, provisional application No. 63/104,685, filed on Oct. 23, 2020, provisional application No. 62/980,000, filed on Feb. 21, 2020.

(51) Int. Cl.

| | |
|---|---|
| ***C07K 16/28*** | (2006.01) |
| ***A61P 35/00*** | (2006.01) |
| *A61K 39/00* | (2006.01) |

(52) U.S. Cl.

CPC .......... *C07K 16/2896* (2013.01); *A61P 35/00* (2018.01); *C07K 16/2827* (2013.01); *A61K 2039/505* (2013.01); *C07K 2317/24* (2013.01); *C07K 2317/31* (2013.01); *C07K 2317/35* (2013.01); *C07K 2317/524* (2013.01); *C07K 2317/565* (2013.01); *C07K 2317/64* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 5,624,821 | A | 4/1997 | Winter et al. |
| 5,807,715 | A | 9/1998 | Morrison et al. |
| 5,821,337 | A | 10/1998 | Carter et al. |
| 5,866,692 | A | 2/1999 | Shitara et al. |
| 5,997,867 | A | 12/1999 | Waldmann et al. |
| 6,054,297 | A | 4/2000 | Carter et al. |
| 6,180,377 | B1 | 1/2001 | Morgan et al. |
| 6,277,375 | B1 | 8/2001 | Ward |
| 6,331,415 | B1 | 12/2001 | Cabilly et al. |
| 6,803,192 | B1 | 10/2004 | Chen |
| 7,083,784 | B2 | 8/2006 | Dall'Acqua et al. |
| 7,101,976 | B1 | 9/2006 | Kilpatrick et al. |
| 7,112,324 | B1 | 9/2006 | Dorken et al. |
| 7,192,698 | B1 | 3/2007 | Kinch et al. |

(Continued)

FOREIGN PATENT DOCUMENTS

| | | | |
|---|---|---|---|
| EP | 0519596 | A1 | 12/1992 |
| WO | 91/03493 | A1 | 3/1991 |

(Continued)

OTHER PUBLICATIONS

"WHO Drug Information", Recommended International Nonproprietary Names: List 62, 2009, 23(3):240-241.
"WHO Drug Information", Recommended International Nonproprietary Names: List 65, 2011, 25(1):89-90.
"WHO Drug Information", Recommended International Nonproprietary Names: List 66, 2011, 25(3):334.
"WHO Drug Information", Recommended International Nonproprietary Names: List 69, 2013, 27(1):68-69.

(Continued)

*Primary Examiner* — Tigabu Kassa
(74) *Attorney, Agent, or Firm* — MEDLER FERRO WOODHOUSE & MILLS PLLC

(57) ABSTRACT

The present invention is directed to binding molecules that possess one or more epitope-binding sites specific for an epitope of CD137, including antibodies, and molecules comprising epitope-binding fragments thereof. The invention is further directed to multispecific binding molecules comprising one or more epitope-binding sites specific for an epitope of CD137 and one or more epitope-binding sites specific for an epitope of a tumor antigen ("TA") (e.g., a "CD137×TA Binding Molecule"). In one embodiment, such CD137×TA Binding Molecules will be bispecific molecules, especially bispecific tetravalent diabodies possessing two epitope-binding sites each specific for an epitope of CD137 and two epitope-binding sites each specific for an epitope of a TA. Alternatively, such CD137×TA Binding Molecules will be bispecific molecules possessing two epitope-binding sites each specific for an epitope of CD137 and one epitope-binding sites each specific for an epitope of a TA. The invention also provides novel Binding Molecules, as well as derivatives thereof and uses thereof. The invention is directed to pharmaceutical compositions that contain such CD137 molecules. The invention is additionally directed to methods for the use of such molecules in the treatment of cancer and other diseases and conditions.

17 Claims, 29 Drawing Sheets

Specification includes a Sequence Listing.

(56) References Cited

U.S. PATENT DOCUMENTS

| | | | |
|---|---|---|---|
| 7,217,797 | B2 | 5/2007 | Hinton et al. |
| 7,527,969 | B2 | 5/2009 | Mather et al. |
| 7,666,424 | B2 | 2/2010 | Cheung et al. |
| 7,737,258 | B2 | 6/2010 | Cheung |
| 7,740,845 | B2 | 6/2010 | Cheung |
| 7,794,710 | B2 | 9/2010 | Chen et al. |
| 7,892,554 | B2 | 2/2011 | Marks et al. |
| 8,084,249 | B2 | 12/2011 | Kingsman et al. |
| 8,088,376 | B2 | 1/2012 | Chamberlain et al. |
| 8,137,667 | B2 | 3/2012 | Jure-Kunkel et al. |
| 8,148,154 | B2 | 4/2012 | Cheung et al. |
| 8,173,424 | B2 | 5/2012 | Marks et al. |
| 8,212,009 | B2 | 7/2012 | Kipps et al. |
| 8,287,865 | B2 | 10/2012 | Hansen et al. |
| 8,337,850 | B2 | 12/2012 | Ahrens et al. |
| 8,350,011 | B2 | 1/2013 | Cartlidge et al. |
| 8,409,577 | B2 | 4/2013 | Thompson et al. |
| 8,414,892 | B2 | 4/2013 | Cheung |
| 8,501,471 | B2 | 8/2013 | Cheung |
| 8,759,495 | B2 | 6/2014 | Boghaert et al. |
| 8,779,098 | B2 | 7/2014 | Mather et al. |
| 8,779,108 | B2 | 7/2014 | Queva et al. |
| 8,802,091 | B2 | 8/2014 | Johnson et al. |
| 8,802,093 | B2 | 8/2014 | Johnson et al. |
| 8,858,942 | B2 | 10/2014 | Cartlidge et al. |
| 8,974,792 | B2 | 3/2015 | Marks et al. |
| 9,062,110 | B2 | 6/2015 | Cheung |
| 9,228,023 | B2 | 1/2016 | Rohlff et al. |
| 9,758,586 | B2 | 9/2017 | Rader et al. |
| 9,873,740 | B2 | 1/2018 | Grogan et al. |
| 2002/0147311 | A1 | 10/2002 | Gillies et al. |
| 2004/0058400 | A1 | 3/2004 | Holliger et al. |
| 2004/0220388 | A1 | 11/2004 | Mertens et al. |
| 2007/0004909 | A1 | 1/2007 | Johnson et al. |
| 2007/0148164 | A1 | 6/2007 | Farrington et al. |
| 2009/0060910 | A1 | 3/2009 | Johnson et al. |
| 2010/0143245 | A1 | 6/2010 | Cheung |
| 2010/0174053 | A1 | 7/2010 | Johnson et al. |
| 2011/0081347 | A1 | 4/2011 | Gorlatov |
| 2011/0097323 | A1 | 4/2011 | Johnson et al. |
| 2013/0017114 | A1 | 1/2013 | Nakamura et al. |
| 2013/0045200 | A1 | 2/2013 | Irving et al. |
| 2013/0078234 | A1 | 3/2013 | Takahashi et al. |
| 2013/0295121 | A1 | 11/2013 | Johnson et al. |
| 2014/0099318 | A1 | 4/2014 | Huang et al. |
| 2014/0328836 | A1 | 11/2014 | Johnson et al. |
| 2015/0175697 | A1 | 6/2015 | Bonvini et al. |
| 2016/0017038 | A1 | 1/2016 | Koenig |
| 2016/0130360 | A1 | 5/2016 | Johnson et al. |
| 2016/0194396 | A1 | 7/2016 | Johnson et al. |
| 2016/0200827 | A1 | 7/2016 | Bonvini et al. |
| 2016/0257761 | A1 | 9/2016 | Koenig et al. |
| 2017/0081424 | A1 | 3/2017 | Bernett et al. |
| 2017/0204184 | A1 | 7/2017 | Zha et al. |
| 2017/0247452 | A1 | 8/2017 | Johnson et al. |
| 2017/0247455 | A1 | 8/2017 | Jure-Kunkel et al. |
| 2019/0161555 | A1 | 5/2019 | Ellmark et al. |
| 2020/0017595 | A1 | 1/2020 | Geuijen et al. |

FOREIGN PATENT DOCUMENTS

| | | | |
|---|---|---|---|
| WO | 92/22583 | A2 | 12/1992 |
| WO | 98/02463 | A1 | 1/1998 |
| WO | 99/55367 | A1 | 11/1999 |
| WO | 01/00245 | A2 | 1/2001 |
| WO | 03/012069 | A2 | 2/2003 |
| WO | 03/025018 | A2 | 3/2003 |
| WO | 03/094859 | A2 | 11/2003 |
| WO | 2004/001381 | A2 | 12/2003 |
| WO | 2005/070966 | A2 | 8/2005 |
| WO | 2006/084226 | A2 | 8/2006 |
| WO | 2006/107617 | A2 | 10/2006 |
| WO | 2006/107786 | A2 | 10/2006 |
| WO | 2007/024715 | A2 | 3/2007 |
| WO | 2007/046893 | A2 | 4/2007 |
| WO | 2007/075270 | A2 | 7/2007 |
| WO | 2007/106744 | A2 | 9/2007 |
| WO | 2008/019290 | A2 | 2/2008 |
| WO | 2008/024188 | A2 | 2/2008 |
| WO | 2008/027236 | A2 | 3/2008 |
| WO | 2008/116219 | A2 | 9/2008 |
| WO | 2008/146911 | A9 | 12/2008 |
| WO | 2010/028795 | A1 | 3/2010 |
| WO | 2010/028796 | A1 | 3/2010 |
| WO | 2010/028797 | A1 | 3/2010 |
| WO | 2010/108127 | A1 | 9/2010 |
| WO | 2010/136172 | A1 | 12/2010 |
| WO | 2011/086091 | A1 | 7/2011 |
| WO | 2011/133886 | A2 | 10/2011 |
| WO | 2011/147986 | A1 | 12/2011 |
| WO | 2012/147713 | A1 | 11/2012 |
| WO | 2012/156430 | A1 | 11/2012 |
| WO | 2012/162583 | A1 | 11/2012 |
| WO | 2013/003652 | A1 | 1/2013 |
| WO | 2013/006544 | A1 | 1/2013 |
| WO | 2013/026835 | A1 | 2/2013 |
| WO | 2013/041687 | A1 | 3/2013 |
| WO | 2013/158856 | A2 | 10/2013 |
| WO | 2013/174873 | A1 | 11/2013 |
| WO | 2014/022540 | A1 | 2/2014 |
| WO | 2014/047231 | A1 | 3/2014 |
| WO | 2014/072888 | A1 | 5/2014 |
| WO | 2014/110601 | A1 | 7/2014 |
| WO | 2014/131711 | A1 | 9/2014 |
| WO | 2014/137931 | A1 | 9/2014 |
| WO | 2015/026892 | A1 | 2/2015 |
| WO | 2015/026894 | A2 | 2/2015 |
| WO | 2015/184203 | A1 | 12/2015 |
| WO | 2015/184207 | A1 | 12/2015 |
| WO | 2016/022939 | A1 | 2/2016 |
| WO | 2016/036937 | A1 | 3/2016 |
| WO | 2016/048938 | A1 | 3/2016 |
| WO | 2016/182751 | A1 | 11/2016 |
| WO | 2017/019846 | A1 | 2/2017 |
| WO | 2017/091656 | A1 | 6/2017 |
| WO | 2017/118675 | A1 | 7/2017 |
| WO | 2017/142928 | A1 | 8/2017 |
| WO | 2017/220990 | A1 | 12/2017 |
| WO | 2018056821 | A1 | 3/2018 |
| WO | 2018119475 | A1 | 6/2018 |
| WO | 2018/156740 | A1 | 8/2018 |
| WO | 2019/025545 | A1 | 2/2019 |
| WO | 2019196309 | A1 | 10/2019 |
| WO | 2020/028444 | A1 | 2/2020 |
| WO | 2020/041404 | A1 | 2/2020 |
| WO | 2021133653 | A1 | 7/2021 |

OTHER PUBLICATIONS

"WHO Drug Information", Recommended International Nonproprietary Names: List 71, 2014, 28(1):93-94.

"WHO Drug Information", Recommended International Nonproprietary Names: List 72, 2014, 28(3):407.

"WHO Drug Information", Recommended International Nonproprietary Names: List 74, 2015, 29(3):387.

"WHO Drug Information", Recommended International Nonproprietary Names: List 74, 2015, 29(3):393-394.

"WHO Drug Information", Recommended International Nonproprietary Names: List 75, 2016, 30(1):100-101.

"WHO Drug Information", Recommended International Nonproprietary Names: List 77, 2017, 31(1):140-141.

"WHO Drug Information", Recommended International Nonproprietary Names: List 77, 2017, 31(1):149.

"WHO Drug Information", Proposed International Nonproprietary Names: List 116, 2016, 30(4):627-629.

"WHO Drug Information", Proposed International Nonproprietary Names: List 119, 2018.

Alt, et al., "Novel Tetravalent and Bispecific IgG-Like Antibody Molecules Combining Single-Chain Diabodies With the Immunoglobin Gamma 1 Fc or CH3 Region", FEBS Letters, 1999, 454(1-2):90-94.

Atwell, et al., "Stable Heterodimers from Remodeling the Domain Interface of a Homodimer Using a Phage Display Library", Journal of Molecular Biology, 1997, 270:26-35.

(56) References Cited

OTHER PUBLICATIONS

Avent et al., "The Rh blood group system: a review," Blood, 95(2):375-87 (2000).
Baeuerle, et al., "Bispecific T-Cell Engaging Antibodies for Cancer Therapy", Cancer Research, 2009, 69(12):4941-4944.
Bartkowiak, et al., "4-1 BB Agonists: Multi-Potent Potentiators of Tumor Immunity", Frontiers in Oncology, 2015, 5(117):1-16.
Chichili, et al., "A CD3xCD123 Bispecific DART for Redirecting Host T Cells to Myelogenous Leukemia: Preclinical Activity and Safety in Nonhuman Primates", Science Translational Medicine, 2015, 7(289):14 pages.
Chothia, et al., "Canonical Structures for The Hypervariable Regions of Immunoglobulins", Journal of Molecular Biology, 1987, 196:901-917.
Croft, "The Role of TNF Superfamily Members In T-Cell Function and Diseases", Nature Reviews Immunology, 2009, 9(4):271-285.
Dall'Acqua, et al., "Properties of Human Igg1s Engineered for Enhanced Binding to The Neonatal Fc Receptor (Fcrn)", The Journal of Biological Chemistry, 2006, 281(33):23514-23524.
Daugherty, et al., "Polymerase Chain Reaction Facilitates the Cloning, CDR-Grafting, and Rapid Expression of a Murine Monoclonal Antibody Directed Against the CD18 Component of Leukocyte Integrins", Nucleic Acids Research, 1991, 19(9):2471-2476.
Dohi et al., "Immunohistochemical Study of carbohydrate antigen expression in gastric carcinoma," Gastroenterologia Japonica, 24(3):239-45 (1989).
Flies, et al., "The New B7s: Playing a Pivotal Role in Tumor Immunity", Journal of Immunotherapy, 2007, 30(3):251-260.
Gooi et al., "Marker of peripheral blood granulocytes and monocytes of man recognized by two monoclonal antibodies VEP8 and VEP9 involves the trisaccharide 3-fucosyl-N-acetyllactosamine," European Journal of Immunology, 13(4):306-12 (1983).
Gooi, et al., "Monoclonal Antibody Reactive with the Human Epidermal-Growth-Factor Receptor Recognizes the Blood-Group-A Antigen", Bioscience Reports, Nov. 1983, 3(11):1045-1052.
Holliger, et al., "Diabodies': Small Bivalent and Bispecific Antibody Fragments", Proceedings of the National Academy of Sciences, 1993, 90:6444-6448.
Holmberg, et al., "Theratope Vaccine (STn-KLH)," Expert Opinion on Biological Therapy, Sep. 2001, 1(5):881-891.
Jones et al., "Replacing the complementarity-determining regions in a human antibody with those from a mouse," Nature, 321(6069):522-5 (1986).
Kohler, et al., "Continuous Cultures of Fused Cells Secreting Antibody Of Predefined Specificity", Nature, 1975, 256:495-497.
Krengel et al., "Molecular recognition of gangliosides and their potential for cancer immunotherapies," Frontiers in Immunology, 5:325 (2014).
Lefranc, et al., "Gm, Am and Km immunoglobulin allotypes of two populations in Tunisia", Human Genetics, 1979, 50:199-211.
Lefranc, et al., "Molecular Genetics of Immunoglobulin Allotype Expression", The Human IgG Subclasses: Molecular Analysis of Structure, Function and Regulation, Pergamon Press, 1990, 43-78.
Levine et al., "The D1.1 antigen: a cell surface marker for germinal cells of the central nervous system," Journal of Neuroscience, 4(3):820-31 (1984).
Li, et al., "Immunotherapy of Melanoma with the Immune Costimulatory Monoclonal Antibodies Targeting CD137", Clinical Pharmacology, Aug. 30, 2013, 5:47-53.
Lobuglio, et al., "Mouse-Human Chimeric Monoclonal Antibody in Man: Kinetics and Immune Response", Proceedings of the National Academy of Sciences, 1989, 86:4220-4224.
Lu, et al., "A Fully Human Recombinant IgG-Like Bispecific Antibody to Both the Epidermal Growth Factor Receptor And The Insulin-Like Growth Factor Receptor For Enhanced Antitumor Activity", Journal of Biological Chemistry, 2005, 280(20):19665-19672.
Martin A., "Protein Sequence and Structure Analysis of Antibody Variable Domains," Antibody Engineering, 33-51 (2010).
Moore, et al., "Application of Dual Affinity Retargeting Molecules to Achieve Optimal Redirected T-Cell Killing Of B-Cell Lymphoma", Blood, 2011, 117(17):4542-4551.
Nudelman et al., "Characterization of a human melanoma-associated ganglioside antigen defined by a monoclonal antibody, 4.2," Journal of Biological Chemistry, 257(21):12752-6 (1982).
Olafsen, et al., "Covalent Disulfide-Linked Anti-CEA Diabody Allows Site-Specific Conjugation and Radiolabeling for Tumor Targeting Applications", Protein Engineering, Design and Selection, 2004, 17(1):21-27.
Ridgway, et al., "'Knobs-Into-Holes' Engineering of Antibody CH3 Domains for Heavy Chain Heterodimerization", Protein Engineering, 1996, 9(7):617-621.
Riechmann, et al., "Reshaping Human Antibodies for Therapy", Nature, 1988, 332:323-327.
Stavenhagen, et al., "Fc Optimization of Therapeutic Antibodies Enhances Their Ability to Kill Tumor Cells In Vitro And Controls Tumor Expansion In Vivo Via Low-Affinity Activating Fcgamma Receptors", Cancer Research, 2007, 67(18):8882-8890.
Symington et al., "Monoclonal antibody specific for lactosylceramide," Journal of Biological Chemistry, 259(9):6008-12 (1984).
Veri, et al., "Therapeutic Control of B Cell Activation Via Recruitment of Fcgamma Receptor IIb (CD32B) Inhibitory Function with A Novel Bispecific Antibody Scaffold", Arthritis & Rheumatology, 2010, 62(7):1933-1943.
Vinay, et al., "Role of 4-1BB in Immune Responses", Seminars in Immunology, 1998, 10:481-489.
Xie, et al., "A New Format of Bispecific Antibody: Highly Efficient Heterodimerization, Expression and Tumor Cell Lysis", Journal of Immunological Methods, 2005, 296:95-101.
Yazawa et al., "Aberrant alpha 1→2fucosyltransferases found in human colorectal carcinoma involved in the accumulation of Leb and Y antigens in colorectal tumors," Jpn J Cancer Res., 84(9):989-95 (1993).

CD137 BINDING MOLECULES AND USES THEREOF

CROSS-REFERENCE TO RELATED APPLICATIONS

This patent application is a national stage of International Patent Application No. PCT/US2021/018177, filed on Feb. 16, 2021, which claims the benefit of U.S. Patent Application Nos. 62/980,000 (filed on Feb. 21, 2020), 63/104,685 (filed on Oct. 23, 2020), and 63/147,565 (filed on Feb. 9, 2021), each of which is incorporated herein by reference in its entirety for all purposes.

REFERENCE TO SEQUENCE LISTING

The instant application contains a Sequence Listing which has been submitted electronically in ASCII format and is hereby incorporated by reference in its entirety. Said ASCII copy, created on Feb. 12, 2021, is named MAC-0111-PC_SL.txt and is 224,061 bytes in size, which file is incorporated herein by reference in its entirety.

FIELD

The present technology is directed to CD137 Binding Molecules, such as monospecific antibodies, and molecules comprising epitope-binding fragments thereof, that are capable of binding to an epitope of CD137. The technology is further directed to multispecific CD137 Binding Molecules (e.g., bispecific antibodies, bispecific diabodies, BiTEs, trivalent binding molecules, etc.) that are capable of binding to both an epitope of CD137 and to an epitope of a second antigen, particularly a tumor antigen ("TA") (e.g., a "CD137×TA Binding Molecule"). The technology also provides novel PD-L1 Binding Molecules, such as monospecific antibodies, and molecules comprising epitope-binding fragments thereof, that are capable of binding to an epitope of PD-L1, as well as derivatives thereof and uses thereof. The present technology is also directed to pharmaceutical compositions that comprise such molecules. The technology also includes the use of such molecules in the treatment of disease, especially cancer or a disease or condition associated with or characterized by the presence of a suppressed immune system.

BACKGROUND

CD137 (also known as 4-1BB and "TNF receptor superfamily member 9" ("TNFRSF9")) is a costimulatory receptor member of the tumor necrosis factor receptor superfamily, mediating CD28-dependent and independent T-cell costimulation (Vinay, D. S. and Kwon, B. S. (1998) "*Role of 4-1BB in immune responses*," Semin Immunol. 10:481-489; Croft, M. (2009) "*The Role Of TNF Superfamily Members In T-Cell Function And Diseases*," Nat. Rev. Immunol. 9:271-285). CD137 is inducibly expressed by T cells, natural killer (NK) cells, dendritic cells (DC), B cells, and other cells of the immune system. Ligation of CD137 by its ligand CD137L (4-1BBL; TNFSF9), or agonist antibodies evokes various T cell responses such as cell expansion, increased cytokine secretion and the prevention of activation-induced cell death. Thus, antibodies stimulating CD137 can induce survival and proliferation of T cells, thereby enhancing the anti-tumor immune response. Such recognitions have led to the proposal that antibodies that are immunospecific for CD137 could be used to activate the immune system and thereby provide a therapy for cancer (Li, S. Y. et al. (2013) "*Immunotherapy Of Melanoma With The Immunecostimulatory Monoclonal Antibodies Targeting CD137*," Clin. Pharmacol. 5:47-53; Bartkowiak, T. et al. (2015) "*4-1BB Agonists: Multi-Potent Potentiators Of Tumor Immunity*," Frontiers Oncol. 5:117). The anti-CD137 antibodies utomilumab and urelumab have been described but their clinical development was hampered by low efficacy (utomilumab) or severe liver toxicity (urelumab).

SUMMARY

Provided are improved compositions capable of more vigorously stimulating and directing the body's immune system to attack cancer cells while avoiding toxicities associated with antibodies that exhibit high activity in the absence of cross-linking. For although the adaptive immune system can be a potent defense mechanism against cancer and disease, it is often hampered by immune suppressive/evasion mechanisms in the tumor microenvironment, mediated by the reduced/absent co-stimulatory activity of CD137. Furthermore, co-inhibitory molecules expressed by tumor cells, immune cells, and stromal cells in the tumor milieu can dominantly attenuate T-cell responses against cancer cells.

Provided are CD137 Binding Molecules, particularly CD137×TA Binding Molecules that are capable of binding to both an epitope of CD137 and to an epitope of a tumor antigen. Such bispecific molecules are capable of binding to tumor antigens that are expressed on the surfaces of tumor cells, and of co-localizing CD137-expressing immune cells to such tumor cells. Such co-localization upregulates the immune cells so as to promote the activation or continued activation of the immune system (e.g., stimulating a cytotoxic T cell response, against tumor cells). These attributes permit such bispecific molecules to have utility in stimulating the immune system and particularly in the treatment of cancer. The present technology is directed to these and other goals.

Thus, provided in certain aspects are CD137 Binding Molecules, such as monospecific antibodies, and molecules comprising epitope-binding fragments thereof, that are capable of binding to an epitope of CD137. The invention is further directed to multispecific CD137 Binding Molecules (e.g., bispecific antibodies, bispecific diabodies, BiTEs, trivalent binding molecules, etc.) that are capable of binding to both an epitope of CD137 and to an epitope of a second antigen, particularly a tumor antigen ("TA") (e.g., a "CD137×TA Binding Molecule"). The invention also provides novel PD-L1 Binding Molecules, such as monospecific antibodies, and molecules comprising epitope-binding fragments thereof, that are capable of binding to an epitope of PD-L1, as well as derivatives thereof and uses thereof. The present invention is also directed to pharmaceutical compositions that comprise such molecules. The invention also includes the use of such molecules in the treatment of disease, especially cancer or a disease or condition associated with or characterized by the presence of a suppressed immune system.

The present invention provides novel CD137 Binding Molecules that exhibit desirable characteristics particularly when incorporated into multispecific molecules. The present invention is also directed to multispecific CD137×TA Binding Molecules that are composed of polypeptide chains that associate with one another to form two binding sites each specific for an epitope of CD137 and two binding sites each specific for an epitope of a TA. Such CD137×TA Binding Molecules of the invention are termed "bispecific tetravalent." The present invention is also directed to CD137×TA Binding Molecules that are composed of polypeptide chains that associate with one another to form two binding sites each specific for an epitope of CD137 and one binding site specific for an epitope of a TA. Such CD137×TA Binding Molecules of the invention are termed "bispecific trivalent." The binding molecules of the invention (e.g., CD137 Binding Molecules) sometimes include a first binding site without including a second binding site that immunospecifically binds to an antigen different than the antigen to which the first binding site binds. The binding molecules of the invention therefore sometimes include only a first binding site, and a first Light Chain Variable Domain and a first Heavy Chain Variable Domain, and not a second binding site, second Light Chain Variable Domain or second Heavy Chain Variable Domain that bind to a different antigen than the first binding site, and non-limiting examples of such binding molecules include scFv, antibody and Fab binding molecules.

The present invention provides CD137×TA Binding Molecules that comprise four polypeptide chains (a "first," "second," "third," and "fourth" polypeptide chain), wherein the first and second polypeptide chains are covalently bonded to one another, the third and fourth polypeptide chains are covalent bonded to one another, and the first and third polypeptide chains are covalently bonded to one another. Also provided are CD137×TA Binding Molecules of the invention comprising five polypeptide chains (a "first," "second," "third," "fourth," and "fifth" polypeptide chain), wherein the first and second polypeptide chains are covalently bonded to one another, the third and fourth polypeptide chain are covalent bonded to one another, the third and fifth polypeptide chains are covalent bonded to one another, and the first and third polypeptide chains are covalently bonded to one another.

In detail, the invention provides a CD137 Binding Molecule comprising a first binding site that immunospecifically binds to an epitope of CD137, wherein the first binding site comprises a first Light Chain Variable Domain that comprises a $CDR_L1$, $CDR_L2$ and $CDR_L3$, and a first Heavy Chain Variable Domain that comprises a $CDR_H1$, $CDR_H2$ and $CDR_H3$; and wherein, (A) the first Light Chain Variable Domain $CDR_L1$, $CDR_L2$, and $CDR_L3$ are the Light Chain CDRs of CD137 MAB-6 VL1 (SEQ ID NO:50); and (B) the first Heavy Chain Variable Domain $CDR_H1$, $CDR_H2$, and $CDR_H3$ are the Heavy Chain CDRs of CD137 MAB-6 VH1 (SEQ ID NO:46).

The invention further concerns the embodiment of such a CD137 Binding Molecule, wherein the first Heavy Chain Variable Domain comprises the amino acid sequence of: hCD137 MAB-6 VH1 (SEQ ID NO:46).

The invention further concerns the embodiments of such a CD137 Binding Molecule, wherein the first Light Chain Variable Domain comprises the amino acid sequence of:

(A) hCD137 MAB-6 VLx (SEQ ID NO:54);
(B) hCD137 MAB-6 VL1 (SEQ ID NO:50);
(B) hCD137 MAB-6 VL2 (SEQ ID NO:55); or
(C) hCD137 MAB-6 VL3 (SEQ ID NO:56).

The invention further concerns the embodiment of such a CD137 Binding Molecule, wherein:

(A) the first Heavy Chain Variable Domain comprises the amino acid sequence of: hCD137 MAB-6 VH1 (SEQ ID NO:46); and (B) the first Light Chain Variable Domain comprises the amino acid sequence of: hCD137 MAB-6 VL3 (SEQ ID NO:56).

The invention further concerns all the above embodiments of such CD137 Binding Molecules, wherein the molecule is a bispecific molecule comprising a second binding site that immunospecifically binds a TA, and wherein the second binding site comprises a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$.

The invention further concerns the embodiment of such a CD137 Binding Molecule, wherein the TA is selected from the tumor antigens presented in Tables 1-2.

The invention further concerns the embodiment of such a CD137 Binding Molecule, wherein the TA is PD-L1 and wherein:

(A) the second Light Chain Variable Domain $CDR_L1$, $CDR_L2$, and $CDR_L3$ are the Light Chain CDRs of hPD-L1 MAB-2 VLx (SEQ ID NO:63); and (B) the second Heavy Chain Variable Domain $CDR_H1$, $CDR_H2$, and $CDR_H3$ are the Heavy Chain CDRs of hPD-L1 MAB-2 VHx (SEQ ID NO:59).

The invention further concerns the embodiment of such a CD137 Binding Molecule, wherein:

(A) (1) the second Light Chain Variable Domain $CDR_L1$, $CDR_L2$, and $CDR_L3$ are the Light Chain CDRs of hPD-L1 MAB-2 VL1 (SEQ ID NO:58); or
(2) the second Light Chain Variable Domain $CDR_L1$, $CDR_L2$, and $CDR_L3$ are the Light Chain CDRs of hPD-L1 MAB-2 VL2 (SEQ ID NO:72);
and
(B) (1) the second Heavy Chain Variable Domain $CDR_H1$, $CDR_H2$, and $CDR_H3$ are the Heavy Chain CDRs of hPD-L1 MAB-2 VH1 (SEQ ID NO:57);
(2) the second Heavy Chain Variable Domain $CDR_H1$, $CDR_H2$, and $CDR_H3$ are the Heavy Chain CDRs of hPD-L1 MAB-2 VH2 (SEQ ID NO:67);
(3) the second Heavy Chain Variable Domain $CDR_H1$, $CDR_H2$, and $CDR_H3$ are the Heavy Chain CDRs of hPD-L1 MAB-2 VH3 (SEQ ID NO:68);
(4) the second Heavy Chain Variable Domain $CDR_H1$, $CDR_H2$, and $CDR_H3$ are the Heavy Chain CDRs of hPD-L1 MAB-2 VH2 (SEQ ID NO:69);
(5) the second Heavy Chain Variable Domain $CDR_H1$, $CDR_H2$, and $CDR_H3$ are the Heavy Chain CDRs of hPD-L1 MAB-2 VH2 (SEQ ID NO:70); or
(6) the second Heavy Chain Variable Domain $CDR_H1$, $CDR_H2$, and $CDR_H3$ are the Heavy Chain CDRs of hPD-L1 MAB-2 VH2 (SEQ ID NO:71).

The invention further concerns the embodiment of such a CD137 Binding Molecule, wherein the second Heavy Chain Variable Domain comprises the amino acid sequence of:

(A) hPD-L1 MAB-2 VH1 (SEQ ID NO:57);
(B) hPD-L1 MAB-2 VH2 (SEQ ID NO:67);
(C) hPD-L1 MAB-2 VH3 (SEQ ID NO:68);
(D) hPD-L1 MAB-2 VH4 (SEQ ID NO:69);
(E) hPD-L1 MAB-2 VH5 (SEQ ID NO:70); or
(F) hPD-L1 MAB-2 VH6 (SEQ ID NO:71).

The invention further concerns the embodiments of such CD137 Binding Molecules, wherein the second Light Chain Variable Domain comprises the amino acid sequence of:

(A) hPD-L1 MAB-2 VL1 (SEQ ID NO:58); or
(B) hPD-L1 MAB-2 VL2 (SEQ ID NO:72).

The invention further concerns the embodiment of such a CD137 Binding Molecule, wherein the TA is 5T4 and wherein:

(A) (1) the second Light Chain Variable Domain $CDR_L1$, $CDR_L2$, and $CDR_L3$ are the Light Chain CDRs of 5T4 MAB-1 VL (SEQ ID NO:93); and (2) the second Heavy Chain Variable Domain $CDR_H1$, $CDR_H2$, and $CDR_H3$ are the Heavy Chain CDRs of 5T4 MAB-1 VH (SEQ ID NO:92); or (B) (1) the second Light Chain Variable Domain $CDR_L1$, $CDR_L2$, and $CDR_L3$ are the Light Chain CDRs of 5T4 MAB-2 VL (SEQ ID NO:95); and (2) the second Heavy Chain Variable Domain $CDR_H1$, $CDR_H2$, and $CDR_H3$ are the Heavy Chain CDRs of 5T4 MAB-2 VH (SEQ ID NO:96).

The invention further concerns the embodiment of such a CD137 Binding Molecule, wherein the second Heavy Chain Variable Domain comprises the amino acid sequence of: 5T4 MAB-1 VH (SEQ ID NO:92).

The invention further concerns the embodiments of such CD137 Binding Molecules, wherein the second Light Chain Variable Domain comprises the amino acid sequence of: 5T4 MAB-1 VL (SEQ ID NO:93).

The invention further concerns such a CD137 Binding Molecule, wherein the TA is HER2 and wherein:

(A) the second Light Chain Variable Domain $CDR_L1$, $CDR_L2$, and $CDR_L3$ are the Light Chain CDRs of hHER2-MAB-1 VLx (SEQ ID NO:79); and (B) the second Heavy Chain Variable Domain $CDR_H1$, $CDR_H2$, and $CDR_H3$ are the Heavy Chain CDRs of hHER2-MAB-1 VHx (SEQ ID NO:78);

The invention further concerns the embodiment of such a CD137 Binding Molecule, wherein:

(A) (1) the second Light Chain Variable Domain $CDR_L1$, $CDR_L2$, and $CDR_L3$ are the Light Chain CDRs of hHER2-MAB-1 VL1 (SEQ ID NO:83);

(2) the second Light Chain Variable Domain $CDR_L1$, $CDR_L2$, and $CDR_L3$ are the Light Chain CDRs of hHER2-MAB-1 VL2 (SEQ ID NO:84); or (3) the second Light Chain Variable Domain $CDR_L1$, $CDR_L2$, and $CDR_L3$ are the Light Chain CDRs of hHER2-MAB-1 VL3 (SEQ ID NO:85);

and (B) (1) the second Heavy Chain Variable Domain $CDR_H1$, $CDR_H2$, and $CDR_H3$ are the Heavy Chain CDRs of hHER2-MAB-1 VH1 (SEQ ID NO:80);

(2) the second Heavy Chain Variable Domain $CDR_H1$, $CDR_H2$, and $CDR_H3$ are the Heavy Chain CDRs of hHER2-MAB-1 VH2 (SEQ ID NO:81); or (3) the second Heavy Chain Variable Domain $CDR_H1$, $CDR_H2$, and $CDR_H3$ are the Heavy Chain CDRs of hHER2-MAB-1 VH3 (SEQ ID NO:82).

The invention further concerns the embodiment of such a CD137 Binding Molecule, wherein the second Heavy Chain Variable Domain comprises the amino acid sequence of:

(A) hHER2-MAB-1 VHx (SEQ ID NO:78);
(B) hHER2-MAB-1 VH1 (SEQ ID NO:80);
(C) hHER2-MAB-1 VH2 (SEQ ID NO:81); or
(D) hHER2-MAB-1 VH3 (SEQ ID NO:82).

The invention further concerns the embodiments of such CD137 Binding Molecules, wherein the second Light Chain Variable Domain comprises the amino acid sequence of (A) hHER2-MAB-1 VLx (SEQ ID NO:79);
(B) hHER2-MAB-1 VL1 (SEQ ID NO:83);
(C) hHER2-MAB-1 VL2 (SEQ ID NO:84); or
(D) hHER2-MAB-1 VL3 (SEQ ID NO:85).

The invention further concerns all the above embodiments of such CD137 Binding Molecules, wherein the molecule is an antibody, a bispecific tetravalent Fc-bearing diabody, or a bispecific trivalent molecule.

The invention further concerns the embodiment of such a CD137 Binding Molecule, wherein the molecule is bispecific and tetravalent, and comprises a first, a second, a third, a fourth, and optionally a fifth polypeptide chain, wherein the polypeptide chains form a covalently bonded complex.

The invention further concerns the embodiment of such a CD137 Binding Molecule, wherein the molecule is bispecific and trivalent, and comprises a first, a second, a third, and a fourth, polypeptide chain, wherein the polypeptide chains form a covalently bonded complex.

The invention additionally concerns the embodiment of all such CD137 Binding Molecules wherein the molecule comprises an Fc Region of the IgG1, IgG2, IgG3, or IgG4 isotype and optionally wherein the molecule further comprises a Hinge Domain.

The invention additionally concerns the embodiment of all such CD137 Binding Molecules wherein the Fc Region is a variant Fc Region that comprises one or more amino acid modifications that reduces the affinity of the variant Fc Region for an FcγR and/or enhances the serum half-life, and more particularly, wherein the modifications comprise at least one amino acid substitution selected from the group consisting of (A) L234A; L235A;
(B) L234A and L235A;
(C) M252Y; M252Y and S254T;
(D) M252Y and T256E;
(E) M252Y, S254T and T256E; or
(F) K288D and H435K;

wherein the numbering is that of the EU index as in Kabat.

The invention further concerns the embodiment of such a CD137 Binding Molecule, wherein the TA is PD-L1 and wherein:

(A) the first and third polypeptide chains comprise the amino acid sequence of SEQ ID NO:116, SEQ ID NO:118, SEQ ID NO:120; and (B) the second and fourth polypeptide chains comprise the amino acid sequence of SEQ ID NO:117, SEQ ID NO:119, SEQ ID NO:121, SEQ ID NO:122, SEQ ID NO:123, SEQ ID NO:124, SEQ ID NO:125, SEQ ID NO:126, or SEQ ID NO:139.

The invention further concerns the embodiment of such a CD137 Binding Molecule, wherein the molecule comprises:

(A) SEQ ID NO:116 and SEQ ID NO:117;
(B) SEQ ID NO:118 and SEQ ID NO:119;
(C) SEQ ID NO:120 and SEQ ID NO:119;
(D) SEQ ID NO:118 and SEQ ID NO:121;
(E) SEQ ID NO:120 and SEQ ID NO:121;
(F) SEQ ID NO:120 and SEQ ID NO:122;
(G) SEQ ID NO:120 and SEQ ID NO:123;
(H) SEQ ID NO:120 and SEQ ID NO:124;
(I) SEQ ID NO:120 and SEQ ID NO:125;
(J) SEQ ID NO:120 and SEQ ID NO:126; or
(K) SEQ ID NO:120 and SEQ ID NO:139.

The invention further concerns the embodiment of such a CD137 Binding Molecule, wherein the TA is PD-L1 and wherein:

(A) the first polypeptide chain comprises the amino acid sequence of SEQ ID NO:127, SEQ ID NO:133, or SEQ ID NO:135;

(B) the second polypeptide chain comprises the amino acid sequence of SEQ ID NO:128, SEQ ID NO:134, or SEQ ID NO:136;

(C) the third polypeptide chain comprises the amino acid sequence of SEQ ID NO:129, or SEQ ID NO:131; and (D) the fourth polypeptide chain comprises the amino acid sequence of SEQ ID NO:130, SEQ ID NO:132.

The invention further concerns the embodiment of such a CD137 Binding Molecule, wherein the molecule comprises:

(A) SEQ ID NO:127, SEQ ID NO:128, SEQ ID NO:129, and SEQ ID NO:130;

(B) SEQ ID NO:127, SEQ ID NO:128, SEQ ID NO:131, and SEQ ID NO:132;

(C) SEQ ID NO:133, SEQ ID NO:134, SEQ ID NO:131, and SEQ ID NO:132; or (D) SEQ ID NO:135, SEQ ID NO:136, SEQ ID NO:131, and SEQ ID NO:132.

The invention additionally concerns a pharmaceutical composition comprising any of the above-described CD137 Binding Molecules, and a physiologically acceptable carrier.

The invention additionally concerns the use of such CD137 Binding Molecules, or such a pharmaceutical composition, in the treatment of cancer characterized by the expression of the TA.

The invention additionally concerns a PD-L1 Binding Molecule that comprises a Light Chain Variable Domain that comprises a $CDR_L1$, $CDR_L2$ and $CDR_L3$, and a Heavy Chain Variable Domain that comprises a $CDR_H1$, $CDR_H2$ and $CDR_H3$; wherein:

(A) the Light Chain Variable Domain $CDR_L1$, $CDR_L2$, and $CDR_L3$ are the Light Chain CDRs of hPD-L1 MAB-2 VL2 (SEQ ID NO:72); and (B) (1) the Heavy Chain Variable Domain $CDR_H1$, $CDR_H2$, and $CDR_H3$ are the Heavy Chain CDRs of hPD-L1 MAB-2 VH2 (SEQ ID NO:67);

(2) the Heavy Chain Variable Domain $CDR_H1$, $CDR_H2$, and $CDR_H3$ are the Heavy Chain CDRs of hPD-L1 MAB-2 VH3 (SEQ ID NO:68)

(3) the second Heavy Chain Variable Domain $CDR_H1$, $CDR_H2$, and $CDR_H3$ are the Heavy Chain CDRs of hPD-L1 MAB-2 VH4 (SEQ ID NO:69)

(4) the second Heavy Chain Variable Domain $CDR_H1$, $CDR_H2$, and $CDR_H3$ are the Heavy Chain CDRs of hPD-L1 MAB-2 VH5 (SEQ ID NO:70); or (5) the second Heavy Chain Variable Domain $CDR_H1$, $CDR_H2$, and $CDR_H3$ are the Heavy Chain CDRs of hPD-L1 MAB-2 VH6 (SEQ ID NO:71).

The invention further concerns the embodiment of such a PD-L1 Binding Molecule, wherein the Heavy Chain Variable Domain comprises the amino acid sequence of:

(A) hPD-L1 MAB-2 VH2 (SEQ ID NO:67);

(B) hPD-L1 MAB-2 VH3 (SEQ ID NO:68);

(C) hPD-L1 MAB-2 VH4 (SEQ ID NO:69);

(D) hPD-L1 MAB-2 VH5 (SEQ ID NO:70); or (E) hPD-L1 MAB-2 VH6 (SEQ ID NO:71).

The invention further concerns the embodiment of such a PD-L1 Binding Molecule, wherein the Light Chain Variable Domain comprises the amino acid sequence of hPD-L1 MAB-2 VL2 (SEQ ID NO:72).

The invention further concerns the embodiment of such PD-L1 Binding Molecules, wherein the molecule is an antibody or an antigen binding fragment thereof.

The invention additionally concerns a pharmaceutical compositions comprising any of the above-described PD-L1 Binding Molecules, and a physiologically acceptable carrier.

The invention additionally concerns the use of such PD-L1 Binding Molecules, or such pharmaceutical compositions, in the treatment of a disease or condition associated with a suppressed immune system or characterized by the expression of PD-L1.

The invention further concerns such a use, wherein the condition associated with a suppressed immune system or characterized by the expression of PD-L1 is cancer.

The invention additionally concerns the embodiment of all such uses, wherein the cancer is selected from the group consisting: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer.

The invention further concerns a method of enhancing the activity of a tumor targeting agent comprising administering the tumor target agent in combination with any of the above-described CD137 Binding Molecules, any of the above-described PD-L1 Binding Molecules, or any of the above-described pharmaceutical compositions.

The invention additionally concerns a method of treating a disease or condition associated with a suppressed immune system or characterized by the expression of a TA comprising administering to a subject in need thereof and of the above-described CD137 Binding Molecules, any of the above-described PD-L1 Binding Molecules, or any of the above-described pharmaceutical compositions.

The invention further concerns such a method, further comprising administering a tumor targeting agent.

The invention further concerns such a method, wherein the condition associated with a suppressed immune system or characterized by the expression of the tumor TA is cancer.

The invention further concerns all the above embodiments of such a method, wherein the tumor target agent is an antibody, an epitope binding fragment of an antibody, or an agent that mediates T-cell redirected killing of a target cell.

The invention additionally concerns the embodiment such methods, wherein the cancer is selected from the group consisting: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer.

The invention additionally concerns a nucleic acid encoding the CD137 Binding Molecule of any of the above embodiments, or the PD-L1 Binding Molecule of any of the above embodiments.

The invention further concerns an expression vector comprising such nucleic acid.

The invention additionally concerns a cell comprising a nucleic acid according to any of the above embodiments or an expression vector of any of the above embodiments.

The invention further concerns a such cell, wherein said cell is a mammalian cell.

BRIEF DESCRIPTION OF THE DRAWINGS

FIGS. 1A-1D show tetravalent diabodies having four epitope-binding sites composed of two pairs of polypeptide chains, (i.e., four polypeptide chains in all). One polypeptide of each pair possesses a CH2 and CH3 Domain, such that the associated chains form all or part of an Fc Region. VL and VH Domains that recognize the same epitope are shown using the same shading or fill pattern. The two pairs of polypeptide chains may be same. In such embodiments wherein the VL and VH Domains recognize different epitopes (as shown in FIGS. 1A-1B), the resulting molecule possesses four epitope-binding sites and is bispecific and bivalent with respect to each bound epitope. In such embodiments wherein the VL and VH Domains recognize the same epitope (e.g., the same VL Domain CDRs and the same VH Domain CDRs are used on both chains), the resulting molecule possesses four epitope-binding sites and is monospecific and tetravalent with respect to a single epitope. Alternatively, the two pairs of polypeptides may be different. In such embodiments wherein the VL and VH Domains of each pair of polypeptides recognize different epitopes (as shown in FIG. 1C), the resulting molecule possesses four epitope-binding sites and is tetraspecific and monovalent with respect to each bound epitope. FIG. 1A shows an Fc diabody which contains a peptide Heterodimer-Promoting Domain comprising a cysteine residue. FIG. 1B shows an Fc diabody composed of two pairs of polypeptide chains each having an E-coil or K-coil Heterodimer-Promoting Domain (i.e., four polypeptide chains in all). The wavy line ((WWW) ) in this and all of the Figures providing schematic presentations of binding molecule domains represents one or more optional Heterodimer-Promoting Domains, that is/are present. As shown, a cysteine residue may be present in a linker (main diagram) and/or in the Heterodimer-Promoting Domain (boxed). One polypeptide chain of each pair possesses a linker comprising a cysteine (which linker may comprise all or a portion of a hinge region) and a CH2 and CH3 Domain, such that the associated chains form all or part of an Fc Region. FIG. 1C, shows an Fc-Region-Containing diabody, which contains antibody CH1 and CL domains. FIG. 1D, shows a representative covalently bonded diabody molecule having two epitope-binding sites composed of three polypeptide chains. Two of the polypeptide chains possess a CH2 and CH3 Domain, such that the associated chains form all or part of an Fc Region. The polypeptide chains comprising the VL and VH Domain further comprise a Heterodimer-Promoting Domain, shown here comprising a cysteine residue.

FIG. 3A illustrates schematically the domains of trivalent binding molecules comprising two diabody-type binding domains covalently bonded via linkers/Heterodimer-Promoting Domains (further described in FIG. 1B) and a Fab-type binding domain in which the binding domains are N-terminal to an Fc Region. The molecule in FIG. 3A comprises four chains. FIGS. 3B-3C, respectively, illustrate schematically the domains of trivalent binding molecules comprising two diabody-type binding domains, and a Fab-type binding domain in which the light chain and heavy chain are linked via a polypeptide spacer, or comprising an scFv-type binding domain. The trivalent binding molecules in FIGS. 3B-3C comprise three chains. VL and VH Domains that recognize the same epitope are shown using the same shading or fill pattern.

DETAILED DESCRIPTION

Figure 1A:
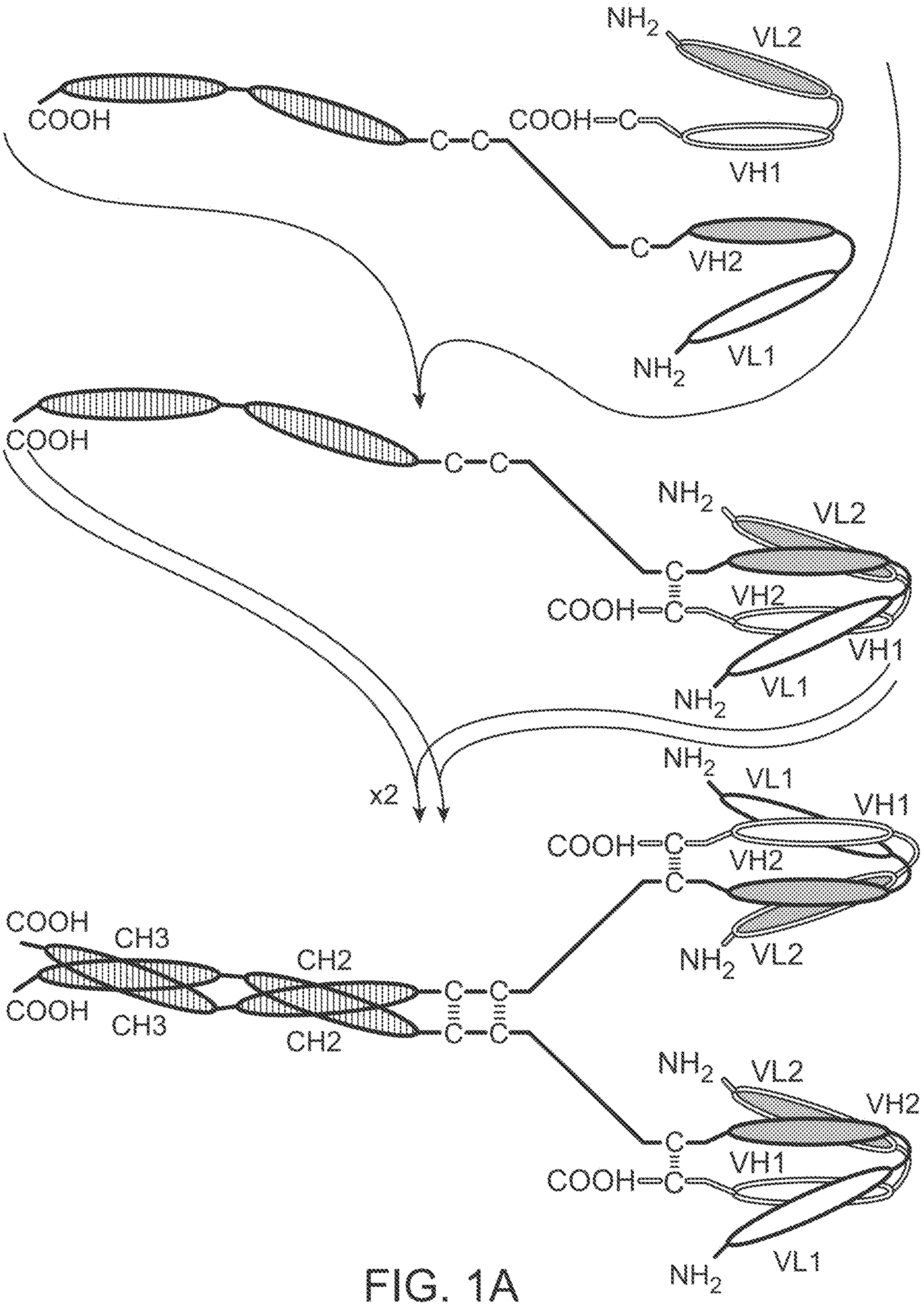
FIG. 1A-1D provides schematics showing representative covalently bonded diabodies comprising Fc Regions.

The present invention is directed to CD137 Binding Molecules, such as monospecific antibodies, and molecules comprising epitope-binding fragments thereof, that are capable of binding to an epitope of CD137. The invention is further directed to multispecific CD137 Binding Molecules (e.g., bispecific antibodies, bispecific diabodies, BiTEs, trivalent binding molecules, etc.) that are capable of binding to both an epitope of CD137 and to an epitope of a second antigen, particularly a tumor antigen ("TA") (e.g., a "CD137×TA Binding Molecule"). The invention also provides novel PD-L1 Binding Molecules, such as monospecific antibodies, and molecules comprising epitope-binding fragments thereof, that are capable of binding to an epitope of PD-L1, as well as derivatives thereof and uses thereof. The present invention is also directed to pharmaceutical compositions that comprise such molecules. The invention also includes the use of such molecules in the treatment of disease, especially cancer or a disease or condition associated with or characterized by the presence of a suppressed immune system.

I. ANTIBODIES AND OTHER BINDING MOLECULES

The CD137×TA Binding Molecules of the present invention may be antibodies, or be derivable from antibodies (e.g., by fragmentation, cleavage, etc. of antibody polypeptides, or from use of the amino acid sequences of antibody molecules or of polynucleotides (or their sequences) that encode such polynucleotides, etc.).

A. Antibodies

Antibodies are immunoglobulin molecules capable of specific binding to a target region ("epitope") of a molecule, such as a carbohydrate, polynucleotide, lipid, polypeptide, etc. ("antigen"), through at least one "epitope-binding site" located in the Variable Region of the immunoglobulin molecule. As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single-chain antibodies, Fab fragments, F(ab') fragments, disulfide-linked bispecific Fvs (sdFv), intrabodies, and epitope-binding fragments of any of the above. In particular, the term "antibody" includes immunoglobulin molecules and immunologically active fragments of immunoglobulin molecules, i.e., molecules that contain an epitope-binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. Antibodies are capable of "immunospecifically binding" to a polypeptide or protein or a non-protein molecule due to the presence on such molecule of a particular domain or moiety or conformation (an "epitope"). As used herein, an "epitope-binding fragment of an antibody" is intended to denote a portion of an antibody capable of immunospecifically binding to an epitope. As used herein, such term encompasses fragments (such as Fab, Fab', $F(ab')_2$ Fv), and single chain (scFv), as well as the epitope-binding domain of a diabody. As used herein, an antibody or an epitope-binding fragment thereof is said to "immunospecifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or an epitope-binding fragment thereof that immunospecifically binds to a first target may or may not specifically or preferentially bind to a second target. An epitope-containing molecule may have immunogenic activity, such that it elicits an antibody production response in an animal; such molecules are termed "antigens". Natural antibodies are capable of binding to only one epitope species (i.e., they are "monospecific"), although they can bind multiple copies of that species (i.e., exhibiting "bivalency" or "multivalency").

The term "monoclonal antibody" refers to a homogeneous antibody population wherein the monoclonal antibody is comprised of amino acids (naturally occurring or non-naturally occurring) that are involved in the selective binding of an antigen. Monoclonal antibodies are highly specific, being directed against a single epitope (or antigenic site). The term "monoclonal antibody" encompasses not only intact monoclonal antibodies and full-length monoclonal antibodies, but also fragments thereof (such as Fab, Fab', $F(ab')_2$ Fv), single-chain (scFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody." Methods of making monoclonal antibodies are known in the art. One method which may be employed is the method of Kohler, G. et al. (1975) "*Continuous Cultures Of Fused Cells Secreting Antibody Of Predefined Specificity*," Nature 256:495-497 or a modification thereof. Typically, monoclonal antibodies are developed in mice, rats or rabbits. The antibodies are produced by immunizing an animal with an immunogenic amount of cells, cell extracts, or protein preparations that contain the desired epitope. The immunogen can be, but is not limited to, primary cells, cultured cell lines, cancerous cells, proteins, peptides, nucleic acids, or tissue. Alternatively, existing monoclonal antibodies and any other equivalent antibodies that are immunospecific for a desired pathogenic epitope can be sequenced and produced recombinantly by any means known in the art. In one embodiment, such an antibody is sequenced, and the polynucleotide sequence is then cloned into a vector for expression or propagation. The sequence encoding the antibody of interest may be maintained in a vector in a host cell and the host cell can then be expanded and frozen for future use. The polynucleotide sequence of such antibodies may be used for genetic manipulation to generate the monospecific or multispecific (e.g., bispecific, trispecific and tetraspecific) molecules of the invention as well as an affinity optimized, a chimeric antibody, a humanized antibody, and/or a caninized antibody, to improve the affinity, or other characteristics of the antibody. The general principle in humanizing an antibody involves retaining the basic sequence of the epitope-binding portion of the antibody, while swapping the non-human remainder of the antibody with human antibody sequences.

The last few decades have seen a revival of interest in the therapeutic potential of antibodies, and antibodies have become one of the leading classes of biotechnology-derived drugs. Over 200 antibody-based drugs have been approved for use or are under development. 1. General Structural Attributes of Antibodies The basic structural unit of naturally occurring immunoglobulins (e.g., IgG) is a tetramer composed of two shorter "Light Chains" complexed with two longer "Heavy Chains" and is usually expressed as a glycoprotein of about 150,000 Da. Each chain is composed of an amino-terminal ("N-terminal") portion that comprises a "Variable Domain" and a carboxy-terminal ("C-terminal") portion that comprises at least one "Constant Domain." An IgG Light Chain is composed of a single "Light Chain Variable Domain" ("VL") and a single "Light Chain Constant Domain" ("CL"). Thus, the structure of the light chains of an IgG molecule is n-VL-CL-c (where n and c represent, respectively, the N-terminus and the C-terminus of the polypeptide). An IgG Heavy Chain is composed of a single "Heavy Chain Variable Domain" ("VH"), three "Heavy Chain Constant Domains" ("CH1," "CH2" and "CH3"), and a "Hinge" Region ("H"), located between the CH1 and CH2 Domains. Thus, the structure of an IgG heavy chain is n-VH-CH1-H-CH2-CH3-c (where n and c represent, respectively, the N-terminus and the C-terminus of the polypeptide). The ability of an intact, unmodified antibody (e.g., an IgG antibody) to bind an epitope of an antigen depends upon the presence and sequences of the Variable Domains.

a) Constant Domains (1) Light Chain Constant Domain

A representative CL Domain is a human IgG CL Kappa Domain. The amino acid sequence of an representative human CL Kappa Domain is (SEQ ID NO:1):

```
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC
```

Alternatively, an representative CL Domain is a human IgG CL Lambda Domain. The amino acid sequence of an representative human CL Lambda Domain is (SEQ ID NO:2):

```
QPKAAPSVTL FPPSSEELQA NKATLVCLIS DFYPGAVTVA
WKADSSPVKA GVETTPSKQS NNKYAASSYL SLTPEQWKSH
RSYSCQVTHE GSTVEKTVAP TECS
```

(2) Heavy Chain CH1 Domains

An representative CH1 Domain is a human IgG1 CH1 Domain. The amino acid sequence of an representative human IgG1 CH1 Domain is (SEQ ID NO:3):

```
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKRV
```

An representative CH1 Domain is a human IgG2 CH1 Domain. The amino acid sequence of an representative human IgG2 CH1 Domain is (SEQ ID NO:4):

```
ASTKGPSVFP LAPCSRSTSE STAALGCLVK DYFPEPVTVS
WNSGALTSGV HTFPAVLQSS GLYSLSSVVT VPSSNFGTQT
YTCNVDHKPS NTKVDKTV
```

An representative CH1 Domain is a human IgG3 CH1 Domain. The amino acid sequence of an representative human IgG3 CH1 Domain is (SEQ ID NO:5):

```
ASTKGPSVFP LAPCSRSTSG GTAALGCLVK DYFPEPVTVS
WNSGALTSGV HTFPAVLQSS GLYSLSSVVT VPSSSLGTQT
YTCNVNHKPS NTKVDKRV
```

An representative CH1 Domain is a human IgG4 CH1 Domain. The amino acid sequence of an representative human IgG4 CH1 Domain is (SEQ ID NO:6):

```
ASTKGPSVFP LAPCSRSTSE STAALGCLVK DYFPEPVTVS
WNSGALTSGV HTFPAVLQSS GLYSLSSVVT VPSSSLGTKT
YTCNVDHKPS NTKVDKRV
```

(3) Heavy Chain Hinge Regions

An representative Hinge Region is a human IgG1 Hinge Region. The amino acid sequence of an representative human IgG1 Hinge Region is (SEQ ID NO:7):

```
EPKSCDKTHT CPPCP
```

Another representative Hinge Region is a human IgG2 Hinge Region. The amino acid sequence of an representative human IgG2 Hinge Region is (SEQ ID NO:8):

```
ERKCCVECPP CP
```

Another representative Hinge Region is a human IgG3 Hinge Region. The amino acid sequence of an representative human IgG3 Hinge Region is (SEQ ID NO:9):

```
ELKTPLGDTT HTCPRCPEPK SCDTPPPCPR CPEPKSCDTP
PPCPRCPEPK SCDTPPPCPR CP
```

Another representative Hinge Region is a human IgG4 Hinge Region. The amino acid sequence of an representative human IgG4 Hinge Region is (SEQ ID NO:10):

```
ESKYGPPCPS CP
```

As described herein, an IgG4 Hinge Region may comprise a stabilizing mutation such as the S228P substitution (as numbered by the EU index as set forth in Kabat). The amino acid sequence of an representative stabilized IgG4 Hinge Region is (SEQ ID NO:11):

```
ESKYGPPCPP CP
```

(4) Heavy Chain CH2 and CH3 Domains

The CH2 and CH3 Domains of the two heavy chains interact to form the "Fc Region" of IgG antibodies that is recognized by cellular Fe Receptors, including but not limited to Fc gamma Receptors (FcγRs). As used herein, the term "Fc Region" is used to define a C-terminal region of an IgG heavy chain. A portion of an Fc Region (including a portion that encompasses an entire Fc Region) is referred to herein as an "Fc Domain." An Fc Region is said to be of a particular IgG isotype, class or subclass if its amino acid sequence is most homologous to that isotype relative to other IgG isotypes. In addition to their known uses in diagnostics, antibodies have been shown to be useful as therapeutic agents.

The amino acid sequence of the CH2-CH3 Domain of an representative human IgG1 is (SEQ ID NO:12):

```
231       240          250          260          270
APELLGGPSV FLFPPKPKDT LMISRTPEVT CVVVDVSHED

          280          290          300          310
PEVKFNWYVD GVEVHNAKTK PREEQYNSTY RVVSVLTVLH
```

-continued

```
        320        330        340        350
QDWLNGKEYK CKVSNKALPA PIEKTISKAK GQPREPQVYT

        360        370        380        390
LPPSREEMTK NQVSLTCLVK GFYPSDIAVE WESNGQPENN

        400        410        420        430
YKTTPPVLDS DGSFFLYSKL TVDKSRWQQG NVFSCSVMHE

        440    447
ALHNHYTQKS LSLSPGX
```

as numbered by the EU index as set forth in Kabat, wherein X is a lysine (K) or is absent.

The amino acid sequence of the CH2-CH3 Domain of an representative human IgG2 is (SEQ ID NO:13):

```
231     240        250        260        270
APPVA-GPSV FLFPPKPKDT LMISRTPEVT CVVVDVSHED

        280        290        300        310
PEVQFNWYVD GVEVHNAKTK PREEQFNSTF RVVSVLTVVH

        320        330        340        350
QDWLNGKEYK CKVSNKGLPA PIEKTISKTK GQPREPQVYT

        360        370        380        390
LPPSREEMTK NQVSLTCLVK GFYPSDISVE WESNGQPENN

        400        410        420        430
YKTTPPMLDS DGSFFLYSKL TVDKSRWQQG NVFSCSVMHE

        440    447
ALHNHYTQKS LSLSPGX
```

as numbered by the EU index as set forth in Kabat, wherein X is a lysine (K) or is absent.

The amino acid sequence of the CH2-CH3 Domain of an representative human IgG3 is (SEQ ID NO:14):

```
231     240        250        260        270
APELLGGPSV FLFPPKPKDT LMISRTPEVT CVVVDVSHED

        280        290        300        310
PEVQFKWYVD GVEVHNAKTK PREEQYNSTF RVVSVLTVLH

        320        330        340        350
QDWLNGKEYK CKVSNKALPA PIEKTISKTK GQPREPQVYT

        360        370        380        390
LPPSREEMTK NQVSLTCLVK GFYPSDIAVE WESSGQPENN

        400        410        420        430
YNTTPPMLDS DGSFFLYSKL TVDKSRWQQG NIFSCSVMHE

        440    447
ALHNRFTQKS LSLSPGX
```

as numbered by the EU index as set forth in Kabat, wherein X is a lysine K or is absent.

The amino acid sequence of the CH2-CH3 Domain of an representative human IgG4 is (SEQ ID NO:15):

```
231     240        250        260        270
APEFLGGPSV FLFPPKPKDT LMISRTPEVT CVVVDVSQED

        280        290        300        310
PEVQFNWYVD GVEVHNAKTK PREEQFNSTY RVVSVLTVLH

        320        330        340        350
QDWLNGKEYK CKVSNKGLPS SIEKTISKAK GQPREPQVYT
```

-continued

```
        360        370        380        390
LPPSQEEMTK NQVSLTCLVK GFYPSDIAVE WESNGQPENN

        400        410        420        430
YKTTPPVLDS DGSFFLYSRL TVDKSRWQEG NVFSCSVMHE

        440    447
ALHNHYTQKS LSLSLGX
```

as numbered by the EU index as set forth in Kabat, wherein X is a lysine (K) or is absent.

Throughout the present specification, the numbering of the residues in the constant region of an IgG heavy chain is that of the EU index as in Kabat et al., SEQUENCES OF PROTEINS OF IMMUNOLOGICAL INTEREST, $5^{th}$ Ed. Public Health Service, NH1, MD (1991) ("Kabat"), expressly incorporated herein by reference. The term "EU index as in Kabat" refers to the numbering of the constant domains of human IgG1 EU antibody.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., "*The Human IgG Subclasses: Molecular Analysis Of Structure, Function And Regulation.*" Pergamon, Oxford, pp. 43-78 (1990); Lefranc, G. et al., 1979, Hum. Genet.: 50, 199-211). It is specifically contemplated that the antibodies of the present invention may incorporate any allotype, isoallotype, or haplotype of any immunoglobulin gene, and are not limited to the allotype, isoallotype or haplotype of the sequences provided herein. Furthermore, in some expression systems the C-terminal amino acid residue (bolded above) of the CH3 Domain may be post-translationally removed. Accordingly, the C-terminal residue of the CH3 Domain is an optional amino acid residue in the molecules of the invention. Specifically encompassed by the instant invention are molecules of the invention lacking the C-terminal residue of the CH3 Domain. Also specifically encompassed by the instant invention are such molecules comprising the C-terminal lysine residue of the CH3 Domain.

b) Variable Domains

The Variable Domains of an IgG molecule consist of three "complementarity determining regions" ("CDRs"), which contain the amino acid residues of the antibody that will be in contact with the epitope, as well as intervening non-CDR segments, referred to as "framework regions" ("FR"), which, in general maintain the structure and determine the positioning of the CDR loops so as to permit such contacting (although certain framework residues may also contact the epitope). Thus, the VL and VH Domains have the structure n-FR1-CDR1-FR2-CDR2-FR3-CDR3-FR4-c. The amino acid sequences of the CDRs determine whether an antibody will be able to bind to a particular epitope. Interaction of an antibody light chain with an antibody heavy chain and, in particular, interaction of their VL and VH Domains, forms an epitope-binding site of the antibody.

Amino acids from the Variable Domains of the mature heavy and light chains of immunoglobulins are designated by the position of an amino acid in the chain. Kabat (Sequences of Proteins of Immunological Interest, $5^{th}$ Ed. Public Health Service, NH1, MD (1991)) described numerous amino acid sequences for antibodies, identified an amino acid consensus sequence for each subgroup, and assigned a residue number to each amino acid, and the CDRs and FRs are identified as defined by Kabat (it will be understood that $CDR_H1$ as defined by Chothia, C. & Lesk, A. M. ((1987) "*Canonical Structures For The Hypervariable Regions Of Immunoglobulins*," J. Mol. Biol. 196:901-917) begins five residues earlier). Kabat's numbering scheme is extendible to antibodies not included in his compendium by aligning the antibody in question with one of the consensus sequences in Kabat by reference to conserved amino acids. This method for assigning residue numbers has become standard in the field and readily identifies amino acids at equivalent positions in different antibodies, including chimeric or humanized variants. For example, an amino acid at position 50 of a human antibody light chain occupies the equivalent position to an amino acid at position 50 of a mouse antibody light chain. The positions within the VL and VH Domains at which the their CDRs commence and end are thus well defined and can be ascertained by inspection of the sequences of the VL and VH Domains (see, e.g., Martin, C. R. (2010) "*Protein Sequence and Structure Analysis of Antibody Variable Domains*," In: Antibody Engineering Vol. 2 (Kontermann, R. and Dubel, S. (eds.), Springer-Verlag Berlin Heidelberg, Chapter 3 (pages 33-51)).

Polypeptides that are (or may serve as) the first, second and third CDR of the Light Chain of an antibody are herein respectively designated as: $CDR_L1$ Domain, $CDR_L2$ Domain, and $CDR_L3$ Domain. Similarly, polypeptides that are (or may serve as) the first, second and third CDR of the Heavy Chain of an antibody are herein respectively designated as: $CDR_H1$ Domain, $CDR_H2$ Domain, and $CDR_H3$ Domain. Thus, the terms $CDR_L1$ Domain, $CDR_L2$ Domain, $CDR_L3$ Domain, $CDR_H1$ Domain, $CDR_H2$ Domain, and $CDR_H3$ Domain are directed to polypeptides that when incorporated into a protein cause that protein to be able to bind to a specific epitope regardless of whether such protein is an antibody having light and heavy chains or is a diabody or a single-chain binding molecule (e.g., an scFv, a BiTe, etc.), or is another type of protein. Accordingly, as used herein, the term "Epitope-Binding Fragment" denotes a fragment of a molecule capable of immunospecifically binding to an epitope. An epitope-binding fragment may contain any 1, 2, 3, 4, or 5 the CDR Domains of an antibody, or may contain all 6 of the CDR Domains of an antibody and, although capable of immunospecifically binding to such epitope, may exhibit an immunospecificity, affinity or selectivity toward such epitope that differs from that of such antibody. Typically, however, an epitope-binding fragment will contain all 6 of the CDR Domains of such antibody. An epitope-binding fragment of an antibody may be a single polypeptide chain (e.g., an scFv), or may comprise two or more polypeptide chains, each having an amino terminus and a carboxy terminus (e.g., a diabody, a Fab fragment, an $Fab_2$ fragment, etc.). Unless specifically noted, the order of domains of the protein molecules described herein is in the "N-Terminal to C-Terminal" direction.

The epitope-binding site may comprise either a complete Variable Domain fused onto Constant Domains or only the complementarity determining regions (CDRs) of such Variable Domain grafted to appropriate framework regions. Epitope-binding sites may be wild-type or modified by one or more amino acid substitutions.

c) Humanization of Antibodies

The invention particularly encompasses binding molecules (including antibodies and diabodies) that comprise a VL and/or VH Domain of a humanized antibody. The term "humanized" antibody refers to a chimeric molecule, generally prepared using recombinant techniques, having an epitope-binding site of an immunoglobulin from a non-human species and a remaining immunoglobulin structure of the molecule that is based upon the structure and/or sequence of a human immunoglobulin. The polynucleotide sequence of the variable domains of such antibodies may be used for genetic manipulation to generate such derivatives and to improve the affinity, or other characteristics of such antibodies. It is known that the variable domains of both heavy and light chains contain three CDRs which vary in response to the antigens in question and determine binding capability, flanked by four FRs which are relatively conserved in a given species and which putatively provide a scaffolding for the CDRs. When non-human antibodies are prepared with respect to a particular antigen, the variable domains can be "reshaped" or "humanized." The general principle in humanizing an antibody involves retaining the basic sequence of the epitope-binding portion of the antibody, while swapping the non-human remainder of the antibody with human antibody sequences. There are four general steps to humanize a monoclonal antibody. These are: (1) determining the nucleotide and predicted amino acid sequence of the starting antibody light and heavy variable domains (2) designing the humanized antibody or caninized antibody, i.e., deciding which antibody framework region to use during the humanizing or canonizing process (3) the actual humanizing or caninizing methodologies/techniques and (4) the transfection and expression of the humanized antibody. See, for example, U.S. Pat. Nos. 4,816,567; 5,807,715; 5,866,692; and 6,331,415.

A number of humanized antibody molecules comprising an epitope-binding site derived from a non-human immunoglobulin have been described, including chimeric antibodies having rodent or modified rodent Variable Domain and their associated CDRs fused to human constant domains (see, for example, Lobuglio et al. (1989) "*Mouse Human Chimeric Monoclonal Antibody In Man: Kinetics And Immune Response*," Proc. Natl. Acad. Sci. (U.S.A.) 86:4220-4224 (1989),). Other references describe rodent CDRs grafted into a human supporting framework region (FR) prior to fusion with an appropriate human antibody Constant Domain (see, for example, Riechmann, L. et al. (1988) "*Reshaping Human Antibodies for Therapy*," Nature 332:323-327; and Jones et al. (1986) "*Replacing The Complementarity-Determining Regions In A Human Antibody With Those From A Mouse*," Nature 321:522-525). Another reference describes rodent CDRs supported by recombinantly veneered rodent framework regions. See, for example, European Patent Publication No. 519,596. These "humanized" molecules are designed to minimize unwanted immunological response towards rodent anti-human antibody molecules, which limits the duration and effectiveness of therapeutic applications of those moieties in human recipients. Other methods of humanizing antibodies that may also be utilized are disclosed by Daugherty et al. (1991) "*Polymerase Chain Reaction Facilitates The Cloning, CDR-Grafting, And Rapid Expression Of A Murine Monoclonal Antibody Directed Against The CD18 Component Of Leukocyte Integrins*," Nucl. Acids Res. 19:2471-2476 and in U.S. Pat. Nos. 6,180,377; 6,054,297; and 5,997,867. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, or six) which differ in sequence relative to the original antibody.

2. CD137 Binding Domains

The present invention is directed to CD137 Binding Molecules, such as monospecific antibodies, and molecules comprising epitope-binding fragments thereof, that are capable of binding to an epitope of CD137. The CD137 binding domains of the novel human monoclonal antibody "CD137 MAB-6" are provided below. The present invention specifically includes and encompasses CD137 Binding Molecules and multispecific CD137 Binding Molecules (e.g., bispecific antibodies, bispecific diabodies, BiTEs, trivalent binding molecules, etc.) such as CD137×TA Binding Molecules that comprise the VL and/or VH Domain, and/or 1, 2 or all 3 of the CDR$_L$s of the VL Region and/or 1, 2 or all 3 of the CDR$_H$s of the VH Domain of CD137 MAB-6, or any of the variants thereof provided below.

a) Human CD137 MAB-6

CD137 MAB-6 is a novel human monoclonal antibody. The amino acid sequence of the VH Domain of CD137 MAB-6 (CD137 MAB-6 VH1) is (SEQ ID NO:46) (CDR$_H$ residues are shown underlined):

QVQLQESGPG LVKPSETLSL TCTVSGGSIS

SYYWSWIRQP PGKGLEWIGR IYTSGSTNYN

PSLKSRVTMS VDTSKNQFSL KLSSVTAADT

AVYYCARDGW YDEDYNYYGM DVWGQGTTVT

VSS

The amino acid sequences of the CDR$_H$s of CD137 MAB-6 VH1 are:

CDR$_H$1 (SEQ ID NO:47):
SYYWS

CDR$_H$2 (SEQ ID NO:48):
RIYTSGSTNYNPSLKS

CDR$_H$3 (SEQ ID NO:49):
DGWYDEDYNYYGMDV

The amino acid sequence of the VL Domain of CD137 MAB-6 (CD137 MAB-6 VL1) is (SEQ ID NO:50) (CDR$_L$ residues are shown underlined):

EIVMTQSPAT LSLTPGERAT LSCRASQSVS

SNYLSWFQQI PGQAPRLLIY GASTRATGIP

ARFSGSGSGT DFTLTISSLQ PEDFAVYYCQ

QDYDLPWTFG QGTKVEIK

The amino acid sequences of the CDR$_L$s of CD137 MAB-6 VL1 are:

CDR$_L$1 (SEQ ID NO:51):
RASQSVSSNYLS

CDR$_L$2 (SEQ ID NO:52):
GASTRAT

-continued

CDR$_L$3 (SEQ ID NO:53):
QQDYDLPWT b) Deimmunized CD137 MAB-6

As described in the examples below the VL Domain of CD137 MAB-6 was deimmunized to yield VL Domains designated "CD137 MAB-6 VLx" having the amino acid sequence of SEQ ID NO:54 (CDR$_L$ residues are shown underlined):

EIVMTQSPAT LSL$X_1$PGERAT LSCRASQSVS

SNYLSW$X_2$QQ$X_3$ PGQAPRLLIY GASTRATGIP

ARFSGSGSGT DFTLTISSLQ PEDFAVYYCQ

QDYDLPWTFG QGTKVEIK wherein: $X_1$, $X_2$, and $X_3$ are independently selected, and wherein: $X_1$ is S or T; $X_2$ is F or Y; and $X_3$ is I or K.

In particular embodiments a) $X_1$ is S; $X_2$ is Y; and $X_3$ is K; or b) $X_1$ is S; $X_2$ is F; and $X_3$ is K.

The amino acid sequences of variants of CD137 MAB-6 VL Domains designated CD137 MAB-6 VL2, and CD137 MAB-6 VL3 are presented below. Any of the variant VL Domains may be paired with the VH Domain. Molecules comprising particular combinations of CD137 MAB-6 VH/VL Domains are referred to by reference to the specific VH/VL Domains, for example, a molecule comprising the binding domains CD137 MAB-6 VH1 and CD137 MAB-6 VL3 is specifically referred to as "CD137 MAB-6(1.3)."

The amino acid sequence of the variant CD137 MAB-6 VL2 is (SEQ ID NO:55) (CDR$_L$ residues are shown underlined):

EIVMTQSPAT LSLSPGERAT LSCRASQSVS

SNYLSWYQQK PGQAPRLLIY GASTRATGIP

ARFSGSGSGT DFTLTISSLQ PEDFAVYYCQ

QDYDLPWTFG QGTKVEIK

The amino acid sequence of the variant CD137 MAB-6 VL3 is (SEQ ID NO:56) (CDR$_L$ residues are shown underlined):

EIVMTQSPAT LSLSPGERAT LSCRASQSVS

SNYLSWFQQK PGQAPRLLIY GASTRATGIP

ARFSGSGSGT DFTLTISSLQ PEDFAVYYCQ

QDYDLPWTFG QGTKVEIK

The CDRs, VL Domain, and/or VH Domain of any of such fully human, and/or variant VH and VL CD137 MAB-6 Domains, including any embraced within the generic sequence(s) of the CD137 MAB-6 VL Domains presented above may be used to form an antibody, diabody or binding molecule capable of binding CD137. In certain embodiments CD137 Binding Molecules of the invention, including CD137×TA Binding Molecules, comprise CD137 MAB-6 VH1 and CD137 MAB-6 VL3.

B. Bispecific Antibodies, Multi-Specific Diabodies and Trivalent Molecules

As indicated above, natural antibodies are capable of binding to only one epitope species, although they can bind multiple copies of that species. The ability of an antibody to bind an epitope of an antigen depends upon the presence and amino acid sequence of the antibody's VL and VH Domains. Interaction of an antibody's Light Chain and Heavy Chain and, in particular, interaction of its VL and VH Domains forms one of the two Epitope Binding Domains of a natural antibody, such as an IgG. Natural antibodies are capable of binding only one epitope species (i.e., they are mono-specific), although they can bind multiple copies of that species (i.e., exhibiting bi-valency or multi-valency).

The functionality of antibodies can be enhanced by generating multispecific antibody-based molecules that can simultaneously bind two separate and distinct antigens (or different epitopes of the same antigen) and/or by generating antibody-based molecule having higher valency (i.e., more than two Binding Domains) for the same epitope and/or antigen.

In order to provide molecules having greater capability than natural antibodies, a wide variety of recombinant bispecific antibody formats have been developed to produce such bispecific antibodies.

Most of such approaches use linker peptides to fuse a further binding domain (e.g. an scFv, VL, VH, etc.) to, or within the antibody core (IgA, IgD, IgE, IgG or IgM), or to fuse multiple antibody binding portions to one another (e.g. two Fab fragments or scFv). Alternative formats use linker peptides to fuse a binding protein (e.g., an scFv, VL, VH, etc.) to a dimerization domain such as the CH2-CH3 Domain or alternative polypeptides (WO 2005/070966, WO 2006/107786A WO 2006/107617A, WO 2007/046893). PCT Publication Nos. WO 2013/174873, WO 2011/133886 and WO 2010/136172 disclose multispecific antibodies in which the CL and CH1 Domains are switched from their respective natural positions WO 2008/027236; and WO 2010/108127 disclose antibodies in which the VL and VH Domains have been diversified to allow them to bind to more than one antigen. PCT Publication Nos. WO 2010/028797, WO2010028796 and WO 2010/028795 disclose recombinant antibodies whose Fc Regions have been replaced with additional VL and VH Domains, so as to form trivalent binding molecules. PCT Publication Nos. WO 2003/025018 and WO 2003/012069 disclose recombinant diabodies whose individual chains contain scFv domains. PCT Publication No. WO 2013/006544 discloses multi-valent Fab molecules that are synthesized as a single polypeptide chain and then subjected to proteolysis to yield heterodimeric structures. Thus, the molecules disclosed in these documents trade all or some of the capability of mediating effector function for the ability to bind additional antigen species. PCT Publication Nos. WO 2014/022540, WO 2013/003652, WO 2012/162583, WO 2012/156430, WO 2011/086091, WO 2008/024188, WO 2007/024715, WO 2007/075270, WO 1998/002463, WO 1992/022583 and WO 1991/003493 disclose adding additional Binding Domains or functional groups to an antibody or an antibody portion (e.g., adding a diabody to the antibody's light chain, or adding additional VL and VH Domains to the antibody's light and heavy chains, or adding a heterologous fusion protein or chaining multiple Fab Domains to one another).

The art has additionally noted the capability of producing diabodies that differ from natural antibodies in being capable of binding two or more different epitope species (i.e., exhibiting bispecificity or multispecificity in addition to bi-valency or multi-valency) (see, e.g., Holliger et al. (1993) "'*Diabodies': Small Bivalent And Bispecific Antibody Fragments*," Proc. Natl. Acad. Sci. (U.S.A.) 90:6444-6448; US 2004/0058400 (Hollinger et al.); US 2004/0220388 (Mertens et al.); Alt et al. (1999) FEBS Lett. 454(1-2):90-94; Lu, D. et al. (2005) "*A Fully Human Recombinant IgG-Like Bispecific Antibody To Both The Epidermal Growth Factor Receptor And The Insulin-Like Growth Factor Receptor For Enhanced Antitumor Activity*," J. Biol. Chem. 280(20): 19665-19672; Olafsen, T. et al. (2004) "*Covalent Disulfide-Linked Anti-CEA Diabody Allows Site-Specific Conjugation And Radiolabeling For Tumor Targeting Applications*," Protein Eng Des Sel. 17(1):21-27; Baeuerle, P. A. et al. (2009) "*Bispecific T cell Engaging Antibodies For Cancer Therapy*," Cancer Res. 69(12):4941-4944).

The provision of non-monospecific "diabodies" provides a significant advantage over antibodies: the capacity to co-ligate and co-localize cells that express different epitopes. Bispecific diabodies thus have wide-ranging applications including therapy and immunodiagnosis. Bispecificity allows for great flexibility in the design and engineering of the diabody in various applications, providing enhanced avidity to multimeric antigens, the cross-linking of differing antigens, and directed targeting to specific cell types relying on the presence of both target antigens.

The formation of such non-mono-specific diabodies requires the successful assembly of two or more distinct and different polypeptides (i.e., such formation requires that the diabodies be formed through the heterodimerization of different polypeptide chain species). In the face of this challenge, the art has succeeded in developing stable, covalently bonded heterodimeric non-mono-specific diabodies, (see, e.g., Chichili, G. R. et al. (2015) "*A CD3×CD123 Bispecific DART For Redirecting Host T Cells To Myelogenous Leukemia: Preclinical Activity And Safety In Nonhuman Primates*," Sci. Transl. Med. 7(289):289ra82; Veri, M. C. et al. (2010) "*Therapeutic Control Of B Cell Activation Via Recruitment Of Fcgamma Receptor IIB (CD32B) Inhibitory Function With A Novel Bispecific Antibody Scaffold*," Arthritis Rheum. 62(7):1933-1943; Moore, P. A. et al. (2011) "*Application Of Dual Affinity Retargeting Molecules To Achieve Optimal Redirected T cell Killing Of B-Cell Lymphoma*," Blood 117(17):4542-4551; US Patent Publication Nos. 2007/0004909; 2009/0060910; 2010/0174053; 20130295121; 2014/0099318; 2015/0175697; 2016/0017038; 2016/0194396; 2016/0200827; and 2017/0247452). Such diabodies comprise two or more covalently complexed polypeptides and involve engineering one or more cysteine residues into each of the employed polypeptide species. For example, the addition of a cysteine residue to the C-terminus of such constructs has been shown to allow disulfide bonding between the polypeptide chains, stabilizing the resulting heterodimer without interfering with the binding characteristics of the bivalent molecule.

C. Components of the Representative CD137×TA Binding Molecules of the Present Invention The CD137×TA Binding Molecules of the present invention are composed of polypeptides, and may be composed of two, three, four or more than four polypeptide chains. As used herein, the term "composed of" is intended to be open-ended, such that a CD137×TA Binding Molecules of the present invention that is composed of two polypeptide chains may possess additional polypeptide chains. Such chains may have the same sequence as another polypeptide chain of the binding molecule, or may be different in sequence from any other polypeptide chain of the Binding Molecule.

1. Representative "Linker" Peptides

The polypeptides of the CD137×TA Binding Molecules of the present invention comprise domains that are preceded by, followed by, and/or linked to one another by "linker" peptides, such as Linker 1, Linker 2, Linker 3, etc. Although the invention utilizes certain specific "linker" peptides, in light of the teachings provided herein, alternative linkers could readily be identified and employed to achieve CD137×TA Binding Molecules.

The length of Linker 1, which separates the VL and VH domains of a polypeptide chain is selected to substantially or completely prevent such VL and VH domains from binding to one another (e.g., 12 or less amino acid residues in length). Thus, the VL1 and VH2 domains of the first polypeptide chain are substantially or completely incapable of binding to one another, and do not form an epitope-binding site that is capable of substantially binding to either the first or second antigen. Likewise, the VL2 and VH1 domains of the second polypeptide chain are substantially or completely incapable of binding to one another, and do not form an epitope-binding site that is capable of substantially binding to either the first or second antigen. A representative intervening linker peptide (Linker 1) has the amino acid sequence (SEQ ID NO:16): GGGSGGGG, which is too short to allow the VL and VH Domains of the same polypeptide chain to complex together (in contrast to the longer intervening linker peptide that is employed to produce scFv molecules (e.g., GGGGSGGGGSGGGGS (SEQ ID NO:17)).

One purpose of Linker 2 is to separate the VH Domain of a polypeptide chain from the optionally present Heterodimer-Promoting Domain of that polypeptide chain. Any of a variety of linkers can be used for the purpose of Linker 2. A representative sequence for such Linker 2 comprises the amino acid sequence: GGCGGG (SEQ ID NO:18), which possesses a cysteine residue that may be used to covalently bond the first and second polypeptide chains to one another via a disulfide bond, or ASTKG (SEQ ID NO:19), which is derived from the IgG CH1 domain. Since the Linker 2, ASTKG (SEQ ID NO:19) does not possess such a cysteine, the use of such Linker 2 is typically associated with the use of a cysteine-containing Heterodimer-Promoting Domain, such as the E-coil of SEQ ID NO:39 or the K-coil of SEQ ID NO:40 (see below).

One purpose of Linker 3 is to separate the Heterodimer-Promoting Domain of a polypeptide chain from the Fc Domain of that polypeptide chain. A second purpose is to provide a cysteine-containing polypeptide domain. Any of a variety of linkers can be used for the purpose of Linker 3. A representative sequence for such Linker 3 comprises the amino acid sequence: DKTHTCPPCP (SEQ ID NO:20). Another representative sequence for Linker 3 comprises the amino acid sequence: GGGDKTHTCPPCP (SEQ ID NO:21). Still other representative sequences for Linker 3 comprise the amino acid sequence: LEPKSADKTHTCPPCP (SEQ ID NO:30), or LEPKSSDKTHTCPPCP (SEQ ID NO:31).

One purpose of Linker 4 is to separate the C-terminus of the CH2-CH3 domains of an Fc Region ("Fc Domain") from the N-terminus of a VL Domain. Any of a variety of linkers can be used for the purpose of Linker 4. A representative sequence for such Linker 4 comprises the amino acid sequence: APSSS (SEQ ID NO:22) or the amino acid sequence APSSSPME (SEQ ID NO:23), the amino acid sequence GGGSGGGSGGG (SEQ ID NO:24), or the amino acid sequence GGGGSGGGSGGG (SEQ ID NO:25).

The Fc Region-containing molecules of the present invention may include additional intervening linker peptides (Linkers), generally such Linkers will be incorporated between a Heterodimer-Promoting Domain (e.g., an E-coil or K-coil) and a CH2-CH3 Domain and/or between a CH2-CH3 Domain and a Variable Domain (i.e., VH or VL). Typically, the additional Linkers will comprise 3-20 amino acid residues and may optionally contain all or a portion of an IgG Hinge Region (preferably a cysteine-containing portion of an IgG Hinge Region). Linkers that may be employed in the bispecific Fc Region-containing diabody molecules of the present invention include: GGC, GGG, ASTKG (SEQ ID NO:19), DKTHTCPPCP (SEQ ID NO:20), APSSS (SEQ ID NO:22), APSSSPME (SEQ ID NO:23), GGGSGGGSGGG (SEQ ID NO:24), GGGGSGGGSGGG (SEQ ID NO:25), LGGGSG (SEQ ID NO:26), GGGS (SEQ ID NO:27), LEPKSS (SEQ ID NO:28), VEPKSADKTHTCPPCP (SEQ ID NO:29), LEPKSADKTHTCPPCP (SEQ ID NO:30), and LEPKSSDKTHTCPPCP (SEQ ID NO:31). LEPKSS (SEQ ID NO:28) may be used in lieu of GGG or GGC for ease of cloning. Additionally, the amino acids GGG, or LEPKSS (SEQ ID NO:28) may be immediately followed by DKTHTCPPCP (SEQ ID NO:20) to form the alternate linkers: GGGDKTHTCPPCP (SEQ ID NO:21); and LEPKSSDKTHTCPPCP (SEQ ID NO:31). Bispecific Fc Region-containing molecules of the present invention may incorporate an IgG Hinge Region, such as the IgG Hinge Region of a human IgG1, IgG2, IgG3 or IgG4 antibody, or a portion thereof.

2. Representative Heterodimer-Promoting Domains

As indicated above, the formation of the CD137×TA Binding Molecules of the present invention involves the assembly of two or more different polypeptide chains (i.e., heterodimerization). The formation of heterodimers of the first and second polypeptide chains can be driven by the inclusion of "Heterodimer-Promoting Domains." The Heterodimer-Promoting Domains may be a domain of a Hinge Region of an IgG (or a polypeptide derived from a Hinge Region, such as, for example, GVEPKSC (SEQ ID NO:32), VEPKSC (SEQ ID NO:33)) or AEPKSC (SEQ ID NO:34)) on one polypeptide chain, and a CL Domain (or a polypeptide derived from the CL Domain, such as, for example, GFNRGEC (SEQ ID NO:35) or FNRGEC (SEQ ID NO:36)) on the other polypeptide chain (US2007/0004909).

Alternatively, the Heterodimer-Promoting Domains of the present invention will comprise tandemly repeated coil domains of opposing charge, for example "E-coil" helical domains (SEQ ID NO:37: EVAALEK-EVAALEK-EVAALEK-EVAALEK), whose glutamate residues will form a negative charge at pH 7, while the other of the Heterodimer-Promoting Domains will comprise four tandem "K-coil" domains (SEQ ID NO:38: KVAALKE-KVAALKE-KVAALKE-KVAALKE), whose lysine residues will form a positive charge at pH 7. The presence of such charged domains promotes association between the first and second polypeptides, and thus fosters heterodimerization. In another embodiment, a Heterodimer-Promoting Domain in which one of the four tandem "E-coil" helical domains of SEQ ID NO:37 has been modified to contain a cysteine residue: EVAAQEK-EVAALEK-EVAALEK-EVAALEK (SEQ ID NO:39) is utilized. Likewise, in another embodiment, a Heterodimer-Promoting Domain in which one of the four tandem "K-coil" helical domains of SEQ ID NO:38 has been modified to contain a cysteine residue: KVAAQKE-KVAALKE-KVAALKE-KVAALKE (SEQ ID NO:40) is utilized.

3. Covalent Bonding of the Polypeptide Chains

The CD137×TA Binding Molecules of the present invention are engineered so that pairs of their polypeptide chains covalently bond to one another via one or more cysteine residues positioned along their length to produce a covalently associated molecular complex. Such cysteine residues may be introduced into the intervening linker that separates the VL and VH domains of the polypeptides. Optionally, or alternatively, Linker 2 or Linker 3, or an alternative linker may contain a cysteine residue. Optionally or alternatively, one or more coil domains of a coil-containing Heterodimer-Promoting Domain will comprise an amino acid substitution that incorporates a cysteine residue as in SEQ ID NO:39 or SEQ ID NO:40.

4. Representative Fc Domains

The Fc Domain of an Fc-bearing CD137×TA Binding Molecule of the present invention may comprise a complete Fc region (e.g., a complete IgG Fc region) or only a fragment of a complete Fc region. The Fc Domain of the Fc-bearing CD137×TA Binding Molecules of the present invention may thus include some or all of the CH2 Domain and/or some or all of the CH3 Domain of a complete Fc region, or may comprise a variant CH2 and/or a variant CH3 sequence (that may include, for example, one or more insertions and/or one or more deletions with respect to the CH2 or CH3 domains of a complete Fc region). The Fc Domain of the bispecific Fe diabodies of the present invention may comprise non-Fc polypeptide portions, or may comprise portions of non-naturally complete Fc regions, or may comprise non-naturally occurring orientations of CH2 and/or CH3 domains (such as, for example, two CH2 domains or two CH3 domains, or in the N-terminal to C-terminal direction, a CH3 Domain linked to a CH2 Domain, etc.).

Although the Fc Domain of an Fc-bearing CD137×TA Binding Molecule of the present invention may comprise the amino acid sequence of a naturally occurring Fc Domain, it may be desirable for the CH2-CH3 Domains that form such Fc Domain to comprise one or more substitutions such that the resultant Fc Domain exhibits decreased (e.g., less than 50%, less than 40%, less than 30%, less than 20%, or less than 10%, of the binding exhibited by such molecule if having an Fc Domain having the amino acid sequence of a naturally-occurring Fe Region), or substantially no detectable, binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region). Fc variants and mutant forms capable of mediating such altered binding are well known in the art and include amino acid substitutions at one or more positions elected from the group consisting of: 234, 235, 265, and 297, wherein said numbering is that of the EU index as in Kabat (see, for example, U.S. Pat. No. 5,624,821). In one embodiment, the CH2-CH3 Domain of the first and/or third polypeptide chains of the Fc-bearing molecules of the invention include any 1, 2, 3, or 4 of the substitutions: L234A, L235A, D265A, N297Q, and N297G. Alternatively, a CH2-CH3 Domain of a naturally occurring Fc region that inherently exhibits decreased (or substantially no) binding to FcγRIIIA (CD16a) and/or reduced effector function (relative to the binding and effector function exhibited by the wild-type IgG1 Fe Region (SEQ ID NO:12)) is utilized. In a specific embodiment, the Fc-bearing molecules of the present invention comprise an IgG2 Fe Region (SEQ ID NO:13) or an IgG4 Fe Region (SEQ ID NO:15). When an IgG4 Fe Region is utilized, the instant invention also encompasses the introduction of a stabilizing mutation, such as the Hinge Region S228P substitution described above (see, e.g., SEQ ID NO:11).

In a representative embodiment, the employed IgG1 CH2-CH3 Domain of Fc-bearing CD137×TA Binding Molecules of the present invention include a substitution at position 234 with alanine and 235 with alanine, wherein said numbering is that of the EU index as in Kabat (SEQ ID NO:41):

```
APEAAGGPSV FLFPPKPKDT LMISRTPEVT CVVVDVSHED
PEVKFNWYVD GVEVHNAKTK PREEQYNSTY RVVSVLTVLH
QDWLNGKEYK CKVSNKALPA PIEKTISKAK GQPREPQVYT
LPPSREEMTK NQVSLTCLVK GFYPSDIAVE WESNGQPENN
YKTTPPVLDS DGSFFLYSKL TVDKSRWQQG NVFSCSVMHE
ALHNHYTQKS LSLSPGX
```

wherein, X is a lysine K or is a sent.

The serum half-life of proteins comprising Fc Regions may be increased by increasing the binding affinity of the Fc Region for FcRn. The term "half-life" as used herein means a pharmacokinetic property of a molecule that is a measure of the mean survival time of the molecules following their administration. Half-life can be expressed as the time required to eliminate fifty percent (50%) of a known quantity of the molecule from a subject's body (e.g., a human patient or other mammal) or a specific compartment thereof, for example, as measured in serum, i.e., circulating half-life, or in other tissues. In general, an increase in half-life results in an increase in mean residence time (MRT) in circulation for the molecule administered.

In some embodiments, the Fc-bearing CD137×TA Binding Molecules of the present invention comprise a variant Fc Region, wherein said variant Fc Region comprises at least one amino acid modification relative to a wild-type Fc Region, such that said molecule has an increased half-life (relative to a molecule comprising a wild-type Fc Region). In some embodiments, the Fc-bearing CD137×TA Binding Molecules of the present invention comprise a variant IgG Fc Region, wherein said variant Fc Region comprises a half-live extending amino acid substitution. Numerous amino acid substitutions capable of increasing the half-life of an Fc-bearing molecule are known in the art see for example the amino acid substitutions described in U.S. Pat. Nos. 6,277,375, 7,083,784; 7,217,797, 8,088,376; U.S. Publication Nos. 2002/0147311; 2007/0148164; and 2011/0081347. A Fc-bearing CD137×TA Binding Molecule having enhanced half-life may comprise two or more substitutions selected from: T250Q, M252Y, S254T, T256E, K288D, T307Q, V308P, A378V, M428L, N434A, H435K, and Y436I, wherein said numbering is that of the EU index as in Kabat.

In particular, the employed CH2-CH3 Domain may comprise the substitutions:

(A) M252Y, S254T and T256E;
(B) M252Y and S254T;
(C) M252Y and T256E;
(D) T250Q and M428L;
(E) T307Q and N434A;
(F) A378V and N434A;
(G) N434A and Y436I;
(H) V308P and N434A;
(I) K288D and H435K; or
(J) M428L and N434S, wherein said numbering is that of the EU index as in Kabat.

A representative sequence for the CH2 and CH3 Domains comprises the triple amino acid substitution: M252Y/S254T/T256E (YTE), which significantly enhances serum-half life (Dall'Acqua, W. F. et al. (2006) "*Properties of Human IgGs Engineered for Enhanced Binding to the Neonatal Fc Receptor (FcRn)*," J. Biol. Chem. 281(33):23514-23524), as in SEQ ID NO:42 or SEQ ID NO:43, which are variants of the IgG1 CH2-CH3 domain, or as in SEQ ID NO:44, which is a variant of the IgG4 CH2-CH3 Domain:

```
SEQ ID NO: 42:
APELLGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
wherein, X is a lysine (K) or is absent.

SEQ ID NO: 43:
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLTCLVK GFYPSDIAVE WESNGQPENN

YKTTPPVLDS DGSFFLYSKL TVDKSRWQQG NVFSCSVMHE

ALHNHYTQKS LSLSPGX
wherein, X is a lysine (K) or is absent.

SEQ ID NO: 44:
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLTCLVK GFYPSDIAVE WESNGQPENN

YKTTPPVLDS DGSFFLYSRL TVDKSRWQEG NVFSCSVMHE

ALHNHYTQKS LSLSLGX
```

wherein, X is a lysine K or is absent.

The invention also encompasses Fc-bearing CD137×TA Binding Molecules comprising variant Fc Domains that exhibit altered effector function, altered serum half-life, altered stability, altered susceptibility to cellular enzymes or altered effector function as assayed in an NK dependent or macrophage dependent assay, etc. Fc Domain modifications identified as altering effector function are known in the art, including modifications that increase binding to activating receptors (e.g., FcγRIIA (CD16A) and reduce binding to inhibitory receptors (e.g., FcγRIIB (CD32B) (see, e.g., Stavenhagen, J. B. et al. (2007) "*Fc Optimization Of Therapeutic Antibodies Enhances Their Ability To Kill Tumor Cells In Vitro And Controls Tumor Expansion In Vivo Via Low-Affinity Activating Fcgamma Receptors*," Cancer Res. 57(18):8882-8890). Representative variants of human IgG1 Fc Domains with reduced binding to CD32B and/or increased binding to CD16A contain L235V, F243L, R292P, Y300L, V305I or P296L substitutions. These amino acid substitutions may be present in a human IgG1 Fc Domain in any combination. In one embodiment, the human IgG1 Fc Domain variant contains a F243L, R292P and Y300L substitution, wherein said numbering is that of the EU index as in Kabat. In another embodiment, the human IgG1 Fc Domain variant contains a F243L, R292P, Y300L, V305I and P296L substitution, wherein said numbering is that of the EU index as in Kabat. In another embodiment, the human IgG1 Fc Domain variant contains a L235V, F243L, R292P, Y300L and P396L substitution, wherein said numbering is that of the EU index as in Kabat.

The CH2 and/or CH3 Domains of the CD137×TA Binding Molecules of the present invention need not be identical in sequence, and advantageously are modified to promote heterodimerization between the two CH2-CH3-bearing polypeptide chains. For example, an amino acid substitution (preferably a substitution with an amino acid comprising a bulky side group forming a "knob," e.g., tryptophan) can be introduced into the CH2 or CH3 Domain such that steric interference will prevent interaction with a similarly mutated domain and will obligate the mutated domain to pair with a domain into which a complementary, or accommodating mutation has been engineered, i.e., a "hole" (e.g., a substitution with glycine). Such sets of mutations can be engineered into any pair of polypeptides comprising the bispecific Fc-bearing diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library,*" *J. Mol. Biol.* 270: 26-35, and Xie et al. (2005) "*A New Format Of Bispecific Antibody: Highly Efficient Heterodimerization, Expression And Tumor Cell Lysis*," J. Immunol. Methods 296:95-101; each of which documents is hereby incorporated herein by reference in its entirety). In one embodiment, the knob is engineered into the CH2-CH3 Domains of the first polypeptide chain and the hole is engineered into the CH2-CH3 Domains of the third polypeptide chain. Thus, the knob will help in preventing two molecules of the first polypeptide chain from homodimerizing via their CH2 and/or CH3 Domains. As the third polypeptide chain of this embodiment contains the hole substitution it will have the ability to heterodimerize with the first polypeptide chain as well as homodimerize with itself (however, such homodimerization does not form a molecule possessing epitope-binding sites). A representative knob is created by modifying a native IgG Fc Domain to contain the modification T366W, wherein said numbering is that of the EU index as in Kabat. A representative hole is created by modifying a native IgG Fc Domain to contain the modification T366S, L368A and Y407V, wherein said numbering is that of the EU index as in Kabat. To aid in purifying the third polypeptide chain homodimer from the final bispecific Fc-bearing diabody comprising heterodimers of the first and third polypeptide chains, the protein A binding site of the CH2 and CH3 Domains of the third polypeptide chain is preferably mutated by amino acid substitution at position 435 (H435R), wherein said numbering is that of the EU index as in Kabat. Thus, the third polypeptide chain homodimer will not bind to protein A, whereas the properly assembled bispecific Fc-bearing diabody will retain its ability to bind protein A via the protein A binding site on the first polypeptide chain.

SEQ ID NO:45, SEQ ID NO:146 and SEQ ID NO:147 provide representative sequences for "knob-bearing" CH2 and CH3 Domains that may be used in the CD137×TA Binding Molecules of the present invention:

```
SEQ ID NO: 45:
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
wherein X is a lysine (K) or is absent,

SEQ ID NO: 146:
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLWCLVK GFYPSDIAVE WESNGQPENN

YKTTPPVLDS DGSFFLYSKL TVDKSRWQQG NVFSCSVMHE

ALHNHYTQKS LSLSPGX
wherein X is a lysine (K) or is absent,

SEQ ID NO: 147:
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLWCLVK GFYPSDIAVE WESNGQPENN

YKTTPPVLDS DGSFFLYSRL TVDKSRWQEG NVFSCSVMHE

ALHNHYTQKS LSLSLGX
wherein X is a lysine (K) or is absent,
```

SEQ ID NO:148, SEQ ID NO:149 and SEQ ID NO:150 provide representative sequences for "hole-bearing" CH2 and CH3 Domains that may be used in the CD137×TA Binding Molecules of the present invention:

```
SEQ ID NO: 148:
APEAAGGPSV FLFPPKPKDT LMISRTPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE

ALHNRYTQKS LSLSPGX
wherein X is a lysine (K) or is absent.

SEQ ID NO: 149:
APEAAGGPSV FLFPPKPKDT LYITREPEVT CVVVDVSHED

PEVKFNWYVD GVEVHNAKTK PREEQYNSTY RVVSVLTVLH

QDWLNGKEYK CKVSNKALPA PIEKTISKAK GQPREPQVYT

LPPSREEMTK NQVSLSCAVK GFYPSDIAVE WESNGQPENN

YKTTPPVLDS DGSFFLVSKL TVDKSRWQQG NVFSCSVMHE
```

-continued

```
ALHNRYTQKS LSLSPGX
wherein X is a lysine (K) or is absent.

SEQ ID NO: 150:
APEFLGGPSV FLFPPKPKDT LYITREPEVT CVVVDVSQED

PEVQFNWYVD GVEVHNAKTK PREEQFNSTY RVVSVLTVLH

QDWLNGKEYK CKVSNKGLPS SIEKTISKAK GQPREPQVYT

LPPSQEEMTK NQVSLSCAVK GFYPSDIAVE WESNGQPENN

YKTTPPVLDS DGSFFLVSRL TVDKSRWQEG NVFSCSVMHE

ALHNRYTQKS LSLSLGX
wherein X is a lysine (K) or is absent.
```

As will be noted, the CH2-CH3 Domains of SEQ ID NOs:47 and 50 are IgG4 Domains, while the CH2-CH3 Domains of SEQ ID NOs:45, 146, 148 and 149 are IgG1 Domains. SEQ ID NOs:45, 146, 148 and 149 include a substitution at position 234 with alanine and 235 with alanine, and thus form an Fc Domain that exhibits decreased (or substantially no) binding to FcγRIA (CD64), FcγRIIA (CD32A), FcγRIIB (CD32B), FcγRIIIA (CD16a) or FcγRIIIB (CD16b) (relative to the binding exhibited by the wild-type Fc region (SEQ ID NO:12). The present invention specifically encompasses CD137×TA Binding Molecules comprising CH2-CH3 Domains from any class of human IgG comprising the substitutions described herein (e.g., M252Y/S254T/T256E; T366W; T366S/L368A/Y407V; and/or H435R). Furthermore, specifically encompassed by the instant invention are CD137×TA Binding Molecule constructs lacking the above-indicated C-terminal lysine residue.

In the embodiment described above, the first polypeptide chain will have a "knob-bearing" CH2-CH3 sequence, such as that of SEQ ID NOs:45, 146, and 147 and the third polypeptide chain will have a "hole-bearing" CH2-CH3 sequence, such as that of SEQ ID NO: 148, 149, and 150. However, as will be recognized, a "hole-bearing" CH2-CH3 Domain (e.g., SEQ ID NO:48) could be employed in the first polypeptide chain, in which case, a "knob-bearing" CH2-CH3 Domain (e.g., SEQ ID NO:45) would be employed in the third polypeptide chain.

5. Representative Tumor Antigens (TA) and Representative Variable Domains

The CD137×TA Binding Molecules of the present invention comprise at least one epitope-binding site specific for an epitope of a tumor antigen. Representative Tumor Antigens ("TAs"), which may be bound by the CD137×TA Binding Molecules of the present invention include, but are not limited to those presented in Table 1, and which may be referred to herein by a common name, short name, and/or a gene name.

TABLE 1

Representative Tumor Antigens

| Protein Tumor Antigen | Gene Name(s) | see e.g., UniProtKB ID No. |
|---|---|---|
| Alpha-N-acetylgalactosaminide alpha-2,6-sialyltransferase 6 | ST6GALNAC6; CA19-9 | Q969X2 |
| 5,6-dihydroxyindole-2-carboxylic acid oxidase | TYRP1; gp75 | P17643 |
| Activated leukocyte cell adhesion molecule | ALCAM; CD166 | Q13740 |

TABLE 1-continued

| Representative Tumor Antigens | | |
|---|---|---|
| Alpha-1,4-N-acetylglucosaminyltransferase | A4GNT | Q9UNA3 |
| B melanoma antigen 1 | BAGE; CT2.1 | Q13072 |
| Basigin | BSG; CD147 | P35613 |
| B-cell antigen receptor complex-associated protein alpha chain | CD79A | P11912 |
| B-cell antigen receptor complex-associated protein beta chain | CD79B | P40259 |
| B-cell receptor CD22 | BL-CAM; CD22 | P20273 |
| B-lymphocyte antigen CD19 | CD19 | P15391 |
| B-lymphocyte antigen CD20 | MS4A1; CD20 | P11836 |
| Bone marrow stromal antigen 2 | BST2; CD317 | Q10589 |
| Campath-1 antigen | CD52 | P31358 |
| Carbonic anhydrase 14 | CA14 | Q9ULX7 |
| Carboxypeptidase M | CPM | P14384 |
| Carcinoembryonic antigen-related cell adhesion molecule 5 | CEACAM5; CD66e | P06731 |
| Carcinoembryonic antigen-related cell adhesion molecule 6 | CEACAM6; CD66c | P40199 |
| Catenin beta-1 | CTNNB1; beta-catenin | P35222 |
| CD27 antigen | CD27 | P26842 |
| CD276 antigen | CD276; B7-H3 | Q5ZPR3 |
| CD40 ligand | CD40LG; CD154 | P29965 |
| Cell surface A33 antigen | GPA33 | Q99795 |
| Chondroitin sulfate proteoglycan 4 | CSPG4 | Q6UVK1 |
| C-type lectin domain family member 4 C | CLEC4C; BDCA2; CD303 | Q8WTT0 |
| Cyclin-dependent kinase 4 | CDK4 | P11802 |
| Cytotoxic T-lymphocyte protein 4 | CTLA4 | P16410 |
| Disintegrin and metalloproteinase domain-containing protein 9 | ADAM-9 | Q13443 |
| Ephrin type-A receptor 2 | EPHA2 | P29317 |
| Epidermal growth factor receptor | EGFR; ERBB1; HER1 | P00533 |
| Epithelial cell adhesion molecule | EPCAM; CD326 | P16422 |
| G antigen 1 | GAGEl; CT4.1 | Q13065 |
| G antigen 2A | GAGE2A | Q6NT46 |
| G antigen 2B/C | GAGE2B | Q13066 |
| G antigen 2D | GAGE2D | Q9UEU5 |
| G antigen 2E | GAGE2E | Q4V326 |
| G2/mitotic-specific cyclin-B1 | CCNB1 | P14635 |
| GDP-L-fucose synthase | TSTA3 | Q13630 |
| Glutamate carboxypeptidase 2 | FOLH1; PSMA | Q04609 |
| Hyaluronidase-2 | HYLA2; LUCA2 | Q12891 |
| Inactive tyrosine-protein kinase transmembrane receptor ROR1 | ROR1, NTRKR1 | Q01973 |
| Integrin alpha-E | ITGAE; CD103 | P38570 |
| Integrin beta-6 | ITGB6 | P18564 |
| Interleukin-13 receptor subunit alpha-2 (subunit of CD 123, interleukin-3 receptor) | IL13RA2; CD213a2 | Q14627 |
| Interleukin-2 receptor subunit alpha | IL2RA: CD25 | P01589 |
| Junctional adhesion molecule C | JAM3 | Q9BX67 |
| Keratin, type II cytoskeletal 8 | CK-8; KRT8 | P05787 |
| Lactadherin | MFGE8 | Q08431 |
| Low affinity immunoglobulin epsilon Fc receptor | FCER2; CD23 | P06734 |
| Melanocyte protein PMEL | PMEL; gp100 | P40967 |
| Melanoma antigen recognized by T-cells 1 | MLANA; MART1 | Q16655 |
| Melanoma-associated antigen 1 | MAGEA1; MAGE1 | P43355 |
| Melanoma-associated antigen 3 | MAGEA3; MAGE3 | P43357 |
| Melanotransferrin | MELTF; MAAp97; CD228 | P08582 |
| Membrane cofactor protein | CD46 | P15529 |
| Mesothelin | MSLN | Q13421 |
| Mucin-1 | MUC1; PEM | P15941 |
| Mucin-16 | MUC16; CA-125 | Q8WXI7 |
| Myeloid cell surface antigen CD33 | CD33 | P20138 |
| Neural cell adhesion molecule 1 | NCAM1; CD56 | P13591 |

TABLE 1-continued

| Representative Tumor Antigens | | |
|---|---|---|
| Oncostatin-M | OSM | P13725 |
| Oncostatin-M-specific receptor subunit beta | OSMR; IL31RB | Q99650 |
| Platelet glycoprotein 4 | CD36 | P16671 |
| Programmed cell death 1 ligand 1 | CD274 | Q9NZQ7 |
| Prosaposin receptor GPR37 | GPR37 | O15354 |
| Prostate-specific antigen | KLK3; PSA | P07288 |
| Prostatic acid phosphatase | ACPP | P15309 |
| Protein PML | PML; TRIM19; Myl | P29590 |
| PWWP domain-containing DNA repair factor 3A | PWWP3A; MUM1 | Q2TAK8 |
| Receptor tyrosine-protein kinase erbB-2 | ERBB2; HER2; CD340 | P04626 |
| Receptor tyrosine-protein kinase erbB-3 | ERBB3; HER3 | P21860 |
| Receptor tyrosine-protein kinase erbB-4 | ERBB4; HER4 | Q15303 |
| Receptor-type tyrosine-protein phosphatase C | PTPRC; CD45 | P08575 |
| T-cell surface glycoprotein CD5 | CD5 | P06127 |
| T-cell-specific surface glycoprotein CD28 | CD28 | Pl0747 |
| Transferrin receptor protein 1 | TFRC; CD71 | P02786 |
| Transmembrane 4 L6 family member 1 | TM4SF1; TAAL6 | P30408 |
| Trophoblast glycoprotein | TPBG; 5T4 | Q13641 |
| Tumor necrosis factor receptor superfamily member 10B | TNFRSF10B; DR5; CD262 | 014763 |
| Tumor necrosis factor receptor superfamily member 1A | TNFRSF1A; TNFR1; CD120a | P19438 |
| Tumor necrosis factor receptor superfamily member 1B | TNFRSF1B; TNFR2; CD120b | P20333 |
| Tumor necrosis factor receptor superfamily member 3 | LTBR; TNFR3 | P36941 |
| Tumor necrosis factor receptor superfamily member 5 | CD40 | P25942 |
| Tumor necrosis factor receptor superfamily member 6 | TNFR6; Apo-1; Fas; CD95 | P25445 |
| Ubiquitin-conjugating enzyme E2 K | UBE2K | P61086 |
| Ubiquitin-protein ligase E3A | UBE3A | Q05086 |
| Vascular endothelial growth factor A | VEGFA | P15692 |
| Vascular endothelial growth factor B | VEGFB | P49765 |
| Vascular endothelial growth factor receptor 1 | FLT1; VEGFR1 | P17948 |
| Vascular endothelial growth factor receptor 2 | KDR; VEGFR2; CD309 | P35968 |
| Vascular endothelial growth factor receptor 3 | FLT4; VEGFR3 | P35916 |
| Zinc finger protein 354C | ZNF354C; KID3 | Q86Y25 |

| Other Tumor Antigen(s) | see e.g., Citation(s) |
|---|---|
| 3-fucosyl-N-acetyllactosamine | Gooi, H. C. (1983), "Marker of peripheral blood granulocytes and monocytes of man recognized by two monoclonal antibodies VEP8 and VEP9 involves the trisaccharide 3-fucosyl-N-acetyllactosamine," Eur. J. Immuno. 13(4):306-12. |
| Blood group A antigen | Gooi, H. C., et al. (1983), "Monoclonal antibody reactive with the human epidermal-growth-factor receptor recognizes the blood-group-A antigen," Biosci. Rep. 3(11):1045-52. |
| Difucosyl type 1 chain (Aleb)<br>Difucosyl type 2 chain (ALey) | Dohi, T. et al. (1989), "Immunohistochemical Study of carbohydrate antigen expression in gastric carcinoma," Gastroenterol Jpn. 24(3): 239-45; Yazawa, S. et al. (1993), "Aberrant alpha1-->2Fucosyltransferases Found in Human Colorectal Carcinoma Involved in the Accumulation of Leb |

TABLE 1-continued

| Representative Tumor Antigens | |
|---|---|
| | and Y Antigens in Colorectal Tumors," Jpn. J. Cancer Res. 84:989-995 |
| Ganglioside antigen 4.2 | Nudelman, E. et al. (1982), "Characterization of a human melanoma-associated ganglioside antigen defined by monoclonal antibody, 4.2," J. Biol. Chern. 257(21): 12752-6 |
| Ganglioside antigen D1.1 | Levine, J. M., et al. (1984), "The D1.1 antigen: a cell surface marker for germinal cells of the central nervous system," J. Neurosci. 4(3): 820-31 |
| Gangliosides GD2/GD3/GM2/GM3 | Krengel, U. and Bousquet P. A. (2014), "Molecular Recognition of Gangliosides and Their Potential for Cancer Immunotherapies," Front. Immuno. 5(325): 1-11 |
| Lactosylceramide | Symington, F. W. (1984), "Monoclonal Antibody Specific for Lactosylceramide," J. Biol. Chem. 259(9):6008-6012 |
| Rh antigens (D, C, c, E or e) | Avent, N. D. and Reid, M. E. (2000), "The Rh blood group system: a review," Blood 95:375-387 |
| Sialyl-Tn | Holmberg, L. A. (2001) "Theratope Vaccine (STn-KLH)," Expert Opin. Biol. Ther. 1(5):881-91 |

Antibodies that recognize TAs are known in the art or can be generated using well-known methods, including those described herein. Representative antibodies that comprise VL and VH Domains capable of binding to a TA, and whose sequences or polypeptide chains may thus be employed in the construction of the CD137×TA Binding Molecules of the present invention, are listed in Table 2. Representative VH and VL Domains for antibodies binding to several Tumor Antigens are presented below.

TABLE 2

| Antibody Name | Tumor Antigen(s) | Therapeutic Target Application |
|---|---|---|
| Abagovomab | CA-125 | Ovarian Cancer |
| Adecatumumab | Epcam | Prostate And Breast Cancer |
| Afutuzumab | CD20 | Lymphoma |
| Alacizumab | VEGFR2 | Cancer |
| Altumomab | CEA | Colorectal Cancer |
| Amatuximab | Mesothelin | Cancer |
| Anatumomab Mafenatox | TAG-72 | Non-Small Cell Lung Carcinoma |
| Anifrolumab | Interferon A/B Receptor | Systemic Lupus Erythematosus |
| Anrukinzumab | IL-13 | Cancer |
| Apolizumab | HLA-DR | Hematological Cancers |
| Arcitumomab | CEA | Gastrointestinal Cancer |
| Atinumab | RTN4 | Cancer |
| Bectumomab | CD22 | Non-Hodgkin's Lymphoma (Detection) |
| Belimumab | BAFF | Non-Hodgkin Lymphoma |
| Bevacizumab | VEGF-A | Metastatic Cancer, Retinopathy Of Prematurity |
| Bivatuzumab | CD44 V6 | Squamous Cell Carcinoma |
| Blinatumomab | CD19 | Cancer |
| Brentuximab | CD30 (TNFRSF8) | Hematologic Cancers |
| Cantuzumab | MUC1 | Cancers |
| Cantuzumab Mertansine | Mucin Canag | Colorectal Cancer |
| Caplacizumab | VWF | Cancers |
| Capromab | Prostatic Carcinoma Cells | Prostate Cancer (Detection) |
| Carlumab | MCP-1 | Oncology/Immune Indications |
| Catumaxomab | Epcam, CD3 | Ovarian Cancer, Malignant Ascites, Gastric Cancer |

TABLE 2-continued

| Antibody Name | Tumor Antigen(s) | Therapeutic Target Application |
|---|---|---|
| Cetuximab | EGFR | Metastatic Colorectal Cancer And Head And Neck Cancer |
| Citatuzumab | Epcam | Ovarian Cancer And Other Solid Tumors |
| Cixutumumab | IGF-1 Receptor | Solid Tumors |
| Clivatuzumab | MUC1 | Pancreatic Cancer |
| Conatumumab | TRAIL-R2 | Cancer |
| Dacetuzumab | CD40 | Hematologic Cancers |
| Dalotuzumab | Insulin-Like Growth Factor 1 Receptor | Cancer |
| Daratumumab | CD38 | Cancer |
| Demcizumab | DLL4 | Cancer |
| Denintuzumab | CD19 | Acute Lymphoblastic Leukemia And B Cell Non-Hodgkin Lymphoma |
| Detumomab | B-Lymphoma Cell | Lymphoma |
| Drozitumab | DR5 | Cancer |
| Duligotumab | HER3 | Cancer |
| Dusigitumab | ILGF2 | Cancer |
| Ecromeximab | GD3 Ganglioside | Malignant Melanoma |
| Edrecolomab | Epcam | Colorectal Carcinoma |
| Elotuzumab | SLAMF7 | Multiple Myeloma |
| Elsilimomab | IL-6 | Cancer |
| Enavatuzumab | TWEAK Receptor | Cancer |
| Enlimomab | ICAM-1 (CD54) | Cancer |
| Enoblituzumab | B7-H3 | Cancer |
| Enoticumab | DLL4 | Cancer |
| Ensituximab | 5AC | Cancer |
| Epitumomab Cituxetan | Episialin | Cancer |
| Epratuzumab | CD22 | Cancer, SLE |
| Ertumaxomab | HER2, CD3 | Breast Cancer |
| Etaracizumab | Integrin $A_v\beta_3$ | Melanoma, Prostate Cancer, Ovarian Cancer |
| Faralimomab | Interferon Receptor | Cancer |
| Farletuzumab | Folate Receptor 1 | Ovarian Cancer |
| Fasinumab | HNGF | Cancer |
| FbtaO5 (Bi20) | CD20 | Chronic Lymphocytic Leukemia |
| Ficlatuzumab | HGF | Cancer |
| Figitumumab | IGF-1 Receptor | Adrenocortical Carcinoma, Non-Small Cell Lung Carcinoma |
| Flanvotumab | TYRP1 (Glycoprotein 75) | Melanoma |
| Flotetuzumab | CD123 | Acute Myeloid Leukemia |
| Fresolimumab | TGF-B | Cancer |
| Futuximab | EGFR | Cancer |
| Galiximab | CD80 | B Cell Lymphoma |
| Ganitumab | IGF-I | Cancer |
| Gemtuzumab Ozogamicin | CD33 | Acute Myelogenous Leukemia |
| Girentuximab | Carbonic Anhydrase 9 (CA-IX) | Clear Cell Renal Cell Carcinoma |
| Glembatumumab Vedotin | GPNMB | Melanoma, Breast Cancer |
| Ibritumomab Tiuxetan | CD20 | Non-Hodgkin's Lymphoma |
| Icrucumab | VEGFR-1 | Cancer |
| Imgatuzumab | EGFR | Cancer |
| Inclacumab | Selectin P | Cancer |
| Indatuximab Ravtansine | SDC1 | Cancer |
| Inotuzumab Ozogamicin | CD22 | Cancer |
| Intetumumab | CD51 | Solid Tumors (Prostate Cancer, Melanoma) |
| Ipilimumab | CD 152 | Melanoma |
| Iratumumab | CD30 (TNFRSF8) | Hodgkin's Lymphoma |
| Itolizumab | CD6 | Cancer |
| Labetuzumab | CEA | Colorectal Cancer |
| Lampalizumab | CFD | Cancer |
| Lebrikizumab | Il-13 | Hodgkin's Lymphoma |
| Lexatumumab | TRAIL-R2 | Cancer |
| Ligelizumab | IGHE | Cancer |
| Lintuzumab | CD33 | Cancer |
| Lirilumab | KIR2D | Cancer |

TABLE 2-continued

| Antibody Name | Tumor Antigen(s) | Therapeutic Target Application |
|---|---|---|
| Lorvotuzumab | CD56 | Cancer |
| Lucatumumab | CD40 | Multiple Myeloma, Non-Hodgkin's Lymphoma, Hodgkin's Lymphoma |
| Lumiliximab | CD23 | Chronic Lymphocytic Leukemia |
| Mapatumumab | TRAIL-R1 | Cancer |
| Margetuximab | HER2 | HER2 positive Cancer |
| Matuzumab | EGFR | Colorectal, Lung And Stomach Cancer |
| Milatuzumab | CD74 | Multiple Myeloma And Other Hematological Malignancies |
| Minretumomab | TAG-72 | Cancer |
| Mitumomab | GD3 Ganglioside | Small Cell Lung Carcinoma |
| Mogamulizumab | CCR4 | Cancer |
| Morolimumab | Rhesus Factor | Cancer |
| Moxetumomab Pasudotox | CD22 | Cancer |
| Nacolomab Tafenatox | C242 Antigen | Colorectal Cancer |
| Namilumab | CSF2 | Cancer |
| Naptumomab Estafenatox | 5T4 | Non-Small Cell Lung Carcinoma, Renal Cell Carcinoma |
| Narnatumab | RON | Cancer |
| Naxitamab | GD2 | Neuroblastoma, Osteosarcoma |
| Necitumumab | EGFR | Non-Small Cell Lung Carcinoma |
| Nerelimomab | TNF-A | Cancer |
| Nesvacumab | Angiopoietin 2 | Cancer |
| Nimotuzumab | EGFR | Squamous Cell Carcinoma, Head And Neck Cancer, Nasopharyngeal Cancer, Glioma |
| Nivolumab | PD-1 | Cancer |
| Nofetumomab Merpentan | Undetermined | Cancer |
| Ocaratuzumab | CD20 | Cancer |
| Ofatumumab | CD20 | Chronic Lymphocytic Leukemia |
| Olaratumab | PDGF-R A | Cancer |
| Olokizumab | IL6 | Cancer |
| Omburtamab | B7-H3 | Neuroblastoma, Sarcoma, Metastatic Brain Cancers |
| Onartuzumab | Human Scatter Factor Receptor Kinase | Cancer |
| Ontuxizumab | TEM1 | Cancer |
| Oportuzumab Monatox | Epcam | Cancer |
| Oregovomab | CA-125 | Ovarian Cancer |
| Orticumab | Oxldl | Cancer |
| Otlertuzumab | CD37 | Cancer |
| Panitumumab | EGFR | Colorectal Cancer |
| Pankomab | Tumor Specific Glycosylation Of MUC1 | Ovarian Cancer |
| Parsatuzumab | EGFL7 | Cancer |
| Patritumab | HER3 | Cancer |
| Pembrolizumab | PD-1 | Cancer |
| Pemtumomab | MUC1 | Cancer |
| Perakizumab | IL17A | Arthritis |
| Pertuzumab | HER2 | Cancer |
| Pidilizumab | PD-1 | Cancer |
| Pinatuzumab Vedotin | CD22 | Cancer |
| Pintumomab | Adenocarcinoma Antigen | Adenocarcinoma |
| Placulumab | Human TNF | Cancer |
| Polatuzumab Vedotin | CD79B | Cancer |
| Pritoxaximab | *E. Coli* Shiga Toxin Type-1 | Cancer |
| Pritumumab | Vimentin | Brain Cancer |
| Quilizumab | IGHE | Cancer |
| Racotumomab | N-Glycolylneuraminic Acid | Cancer |
| Radretumab | Fibronectin Extra Domain-B | Cancer |
| Ramucirumab | VEGFR2 | Solid Tumors |
| Rilotumumab | HGF | Solid Tumors |

TABLE 2-continued

| Antibody Name | Tumor Antigen(s) | Therapeutic Target Application |
|---|---|---|
| Rituximab | CD20 | Lymphomas, Leukemias, Some Autoimmune Disorders |
| Robatumumab | IGF-1 Receptor | Cancer |
| Roledumab | RHD | Cancer |
| Samalizumab | CD200 | Cancer |
| Satumomab Pendetide | TAG-72 | Cancer |
| Seribantumab | ERBB3 | Cancer |
| Sibrotuzumab | FAP | Cancer |
| Siltuximab | IL-6 | Cancer |
| Solitomab | Epcam | Cancer |
| Sontuzumab | Episialin | Cancer |
| Tabalumab | BAFF | B Cell Cancers |
| Tacatuzumab Tetraxetan | Alpha-F etoprotein | Cancer |
| Taplitumomab Paptox | CD19 | Cancer |
| Telimomab | Undetermined | Cancer |
| Tenatumomab | Tenascin C | Cancer |
| Teneliximab | CD40 | Cancer |
| Teprotumumab | CD221 | Hematologic Tumors |
| Ticilimumab | CTLA-4 | Cancer |
| Tigatuzumab | TRAIL-R2 | Cancer |
| Tositumomab | CD20 | Follicular Lymphoma |
| Tovetumab | CD140a | Cancer |
| Trastuzumab | HER2 | Breast Cancer |
| Trbs07 (Ektomab) | Gd2 | Melanoma |
| Tremelimumab | CTLA-4 | Cancer |
| Tucotuzumab Celmoleukin | Epcam | Cancer |
| Ublituximab | MS4A1 | Cancer |
| Urelumab | 4-1BB | Cancer |
| Vadastuximab | CD33 | Acute Myeloid Leukemia |
| Vantictumab | Frizzled Receptor | Cancer |
| Vapaliximab | AOC3 (VAP-1) | Cancer |
| Vatelizumab | ITGA2 | Cancer |
| Veltuzumab | CD20 | Non-Hodgkin's Lymphoma |
| Vesencumab | NRP1 | Cancer |
| Volociximab | Integrin A5β1 | Solid Tumors |
| Vorsetuzumab | CD70 | Cancer |
| Votumumab | Tumor Antigen CTAA16.88 | Colorectal Tumors |
| Zalutumumab | EGFR | Squamous Cell Carcinoma Of The Head And Neck |
| Zatuximab | HER1 | Cancer |
| Ziralimumab | CD147 | Cancer |
| Zolbetuximab | Cldn18.2 | Gastrointestinal Adenocarcinomas And Pancreatic Tumor |

a) PD-L1 Binding Domains

PD-L1 (also known as CD274 and B37-Hi), is a 40 kDa transmembrane protein commonly expressed on the surface of T lymphocytes, B lymphocytes, DCs, macrophages and in non-blood cells. In addition, PD-L1 also shows abnormally high expression in tumor cells, which is considered the main factor responsible for promoting the ability of tumor immune escape. Engagement of PD-L1 with its receptor, PD-1 on T cells activates the down-stream signaling of PD-1 receptor delivering a signal that inhibits the proliferation, cytokine generation and release, and cytotoxicity of T cells. Antibodies which block PD-L1/PD-1 disrupt PD-1 axis thereby reverses T cell suppression and enhances endogenous antitumor immunity. CD137×TA Binding Molecules that bind PD-L1 can co-ligate tumor cells expressing PD-L1, and immune cells expressing CD137. Without being limited to any particular method, such co-localization can stimulate the immune cells, while also attenuating or blocking the immune system inhibition that occurs upon PD-L1-PD-1 binding.

The epitope-binding site of any anti-PD-L1 antibody may be used in accordance with the present invention, and the principles of the present invention are illustrated with respect to the PD-L1 tumor antigen. Representative antibodies that bind human PD-L1 include atezolizumab, avelumab, and durvalumab, each recently approved for use in humans. Atezolizumab (marketed as TECENTRIQ®; CAS Reg No. 1380723-44-3; see, U.S. Pat. No. 9,873,740) is a humanized monoclonal antibody having modified IgG1 and kappa constant regions. Avelumab (marketed as BAVENCIO®; CAS Reg No. 1537032-82-8; see, U.S. Pat. No. 9,873,740) is a fully human monoclonal antibody having IgG1/lambda constant regions. Durvalumab (marked as IMFINZI®; CAS Reg. No. 1428935-60-7; see U.S. Pat. No. 8,779,108) is a fully human monoclonal antibody having modified IgG1 and kappa constant regions. The amino acid sequence of the complete heavy and Light Chains of atezolizumab (WHO Drug Information, 2015, Recommended INN: List 74, 29(3):387), durvalumab (WHO Drug Information, 2015, Recommended INN: List 74, 29(3):393-394) and avelumab (WHO Drug Information, 2016, Recommended INN: List 74, 30(i): 100-101) are known in the art. Additional anti-PD-L1 antibodies, including the humanized anti-PD-L1 antibody "hPD-L1 MAB-2" and optimized variants thereof, are also provided herein.

(1) hPD-L1 MAB-2

The amino acid sequence of the VH Domain of hPD-L1 MAB-2 (hPD-L1 MAB-2 VH1) is (SEQ ID NO:57) (CDR$_H$ residues are shown underlined):

EVQLVESGGG LVQPGGSLRL SCAASGFTFS SYTMSWVRQA

PGKGLEWVAY ISIGGGTTYY PDTVKGRFTI SRDNAKNTLY

LQMNSLKTED TAVYYCARQG LPYYFDYWGQ GTLVTVSS

The amino acid sequence of the VL Domain of hPD-L1 MAB-2 (hPD-L1 MAB-2 VL1) is (SEQ ID NO:58) (CDR$_L$ residues are shown underlined):

DIQMTQSPSS LSASVGDRVT ITCKASQDVN TAVAWYQQKP

GKAPKLLIYW ASTRHTGVPS RFSGSGSGTD FTLTISSLQP

EDFATYYCQQ HYNTPLTFGQ GTKVEIK (2) Deimmunized and Optimized hPD-L1 MAB-2

As described in the examples below hPD-L1 MAB-2 was deimmunized and optimized for binding and expression to yield variant VH Domains designated "hPD-L1 MAB-2 VHx" and VL Domains designated "hPD-L1 MAB-2 VLx." The amino acid sequences of particular deimmunized and optimized variant VH and VL Domains are presented below, additional variants are provided in the Examples.

The amino acid sequence of hPD-L1 MAB-2 VHx is (SEQ ID NO:59) (CDR$_H$ residues are shown underlined):

EVQLVESGGG LVQPGGSLRL SCAASGFTFS SYTMSWVRQA

PGKGLEWVAY ISIX$_4$GGTTYY PDTVKGRFTI SRDNAKNX$_5$LY

LQMNSLX$_6$X$_7$ED TAVYYCARX$_8$G LPYYX$_9$DYWGQ GTLVTVSS wherein: $X_4$, $X_5$, $X_6$, $X_7$, $X_8$, and $X_9$ are independently selected, and wherein: $X_4$ is G or K; $X_5$ is S or T; $X_6$ is K or R; $X_7$ is A or T; $X_8$ is A or Q; and $X_9$ is F or G.

In specific embodiments:

a) $X_4$ is G; $X_5$ is S; $X_6$ is R; $X_7$ is A; $X_8$ is Q; and $X_9$ is F;

b) $X_4$ is K; $X_5$ is S; $X_6$ is R; $X_7$ is A; $X_8$ is Q; and $X_9$ is G;

c) $X_4$ is G; $X_5$ is S; $X_6$ is R; $X_7$ is A; $X_8$ is A; and $X_9$ is F;

d) $X_4$ is K; $X_5$ is S; $X_6$ is R; $X_7$ is A; $X_8$ is A; and $X_9$ is F;

e) $X_4$ is G; $X_5$ is S; $X_6$ is R; $X_7$ is A; $X_8$ is A; and $X_9$ is G; or f) $X_4$ is K; $X_5$ is S; $X_6$ is R; $X_7$ is A; $X_8$ is Q; and $X_9$ is F.

The amino acid sequences of the CDR$_H$s of hPD-L1 MAB-2 VHx are:

CDR$_H$1 (SEQ ID NO: 60):
SYTMS

CDR$_H$2 (SEQ ID NO: 61):
YISIX$_4$GGTTYYPDTVKG

CDR$_H$3 (SEQ ID NO: 62):
X$_8$GLPYYX$_9$DY wherein: $X_4$ is G or K; $X_8$ is A or Q; and $X_9$ is F or G The amino acid sequence of hPD-L1 MAB-2 VLx is (SEQ ID NO:63) (CDR$_L$ residues are shown underlined):

DIQMTQSPSS LSASVGDRVT ITCKASQDVN X$_{10}$AVAWYQQKP

GKAPKLLIYW ASTRHTGVPS RFSGSGSGTD FTLTISSLQP

EDFATYYCQQ HYNTPLTFGQ GTKVEIK wherein: $X_{10}$ is E or T.

In a specific embodiment, $X_{10}$ is E.

The amino acid sequences of the CDR$_L$s of PD-L1 MAB-2 VLx are:

CDR$_L$1 (SEQ ID NO: 64):
KASQDVNX$_{10}$AVA

CDR$_L$2 (SEQ ID NO: 65):
WASTRHT

CDR$_L$3 (SEQ ID NO: 66):
QQHYNTPLT wherein: $X_{10}$ is E or T.

The amino acid sequences of five variant VH Domain designated herein as "hPD-L1 MAB-2 VH2," "hPD-L1 MAB-2 VH3," "hPD-L1 MAB-2 VH4," "hPD-L1 MAB-2 VH5," "hPD-L1 MAB-2 VH6," and one variant VL Domain designated herein as "hPD-L1 MAB-2 VL2" are presented below. Any of the variant hPD-L1 MAB-2 VH Domains disclosed herein may be paired with any of the hPD-L1 MAB-2 VL domains. Molecules comprising particular combinations of PD-L1 MAB-2 VH/VL Domains are referred to by reference to the specific VH/VL Domains, for example, a molecule comprising the binding domains PD-L1 MAB-2 VH3 and hPD-L1 MAB-2 VL2 is specifically referred to as "PD-L1 MAB-2(3.2)." The amino acid sequences of the variant VH and VL Domains are provided below, substitutions in the CDRs relative to VH1 or VL1 are double underlined.

The amino acid sequence of hPD-L1 MAB-2 VH2 is (SEQ ID NO:67) (CDR$_H$ residues are shown underlined):

EVQLVESGGG LVQPGGSLRL SCAASGFTFS SYTMSWVRQA

PGKGLEWVAY ISIGGGTTYY PDTVKGRFTI SRDNAKNSLY

LQMNSLRAED TAVYYCARQG LPYYFDYWGQ GTLVTVSS

The amino acid sequence of hPD-L1 MAB-2 VH3 is (SEQ ID NO:68) ($CDR_H$ residues are shown underlined; substitutions are doubled underlined):

EVQLVESGGG LVQPGGSLRL SCAASGFTFS SYTMSWVRQA

PGKGLEWVAY ISIKGGTTYY PDTVKGRFTI SRDNAKNSLY

LQMNSLRAED TAVYYCARQG LPYYGDYWGQ GTLVTVSS

The amino acid sequence of hPD-L1 MAB-2 VH4 is (SEQ ID NO:69) ($CDR_H$ residues are shown underlined; substitutions are doubled underlined):

EVQLVESGGG LVQPGGSLRL SCAASGFTFS SYTMSWVRQA

PGKGLEWVAY ISIGGGTTYY PDTVKGRFTI SRDNAKNSLY

LQMNSLRAED TAVYYCARAG LPYYFDYWGQ GTLVTVSS

The amino acid sequence of hPD-L1 MAB-2 VH5 is (SEQ ID NO:70) ($CDR_H$ residues are shown underlined):

EVQLVESGGG LVQPGGSLRL SCAASGFTFS SYTMSWVRQA

PGKGLEWVAY ISIKGGTTYY PDTVKGRFTI SRDNAKNSLY

LQMNSLRAED TAVYYCARAG LPYYFDYWGQ GTLVTVSS

The amino acid sequence of hPD-L1 MAB-2 VH6 is (SEQ ID NO:71) ($CDR_H$ residues are shown underlined):

EVQLVESGGG LVQPGGSLRL SCAASGFTFS SYTMSWVRQA

PGKGLEWVAY ISIGGGTTYY PDTVKGRFTI SRDNAKNSLY

LQMNSLRAED TAVYYCARAG LPYYGDYWGQ GTLVTVSS

The amino acid sequence of hPD-L1 MAB-2 VL2 is (SEQ ID NO:72) ($CDR_L$ residues are shown underlined):

DIQMTQSPSS LSASVGDRVT ITCKASQDVN EAVAWYQQKP

GKAPKLLIYW ASTRHTGVPS RFSGSGSGTD FTLTISSLQP

EDFATYYCQQ HYNTPLTFGQ GTKVEIK

It will be noted that the amino acid sequences of $CDR_H2$, $CDR_H3$, and $CDR_L1$ of the optimized hPD-L1 MAB-2 variants differ from those present in the parental molecule. The different CDRs are summarized below with differences from VH1 and VL1 double underlined:

| CDR | Amino Acid Sequence | hPD-L1 MAB-2 variant |
|---|---|---|
| $CDR_H2$ | YISI**K**GGTTYYPDTVKG (SEQ ID NO: 73) | VH3/VH4 |
| $CDR_H3$ | QGLPYY**G**DY (SEQ ID NO: 74) | VH3 |
| $CDR_H3$ | **A**GLPYYFDY (SEQ ID NO: 75) | VH4/VH5 |
| $CDR_H3$ | **A**GLPYY**G**DY (SEQ ID NO: 76) | VH6 |
| $CDR_L1$ | KASQDVN**E**AVA (SEQ ID NO: 77) | VL2 |

The present invention specifically includes and encompasses CD137×PD-L1 Binding Molecules that comprise the VL and/or VH Domain, and/or 1, 2 or all 3 of the $CDR_L$s of the VL Region and/or 1, 2 or all 3 of the $CDR_H$s of the VH Domain of any of atezolizumab, avelumab, durvalumab, hPD-L1 MAB-2 and the variants there of, or any of the other anti-PD-L1 antibodies provided herein; and more typically possess 1, 2 or all 3 of the $CDR_L$s of the VL Region and/or 1, 2 or all 3 of the $CDR_H$s of the VH Domain of such anti-PD-L1 monoclonal antibodies.

b) HER2 Binding Domains

HER2 is a 185 kDa receptor protein that was originally identified as the product of the transforming gene from neuroblastomas of chemically treated rats. HER2 has been extensively investigated because of its role in many human carcinomas include breast and gastric cancers.

The epitope-binding site of any anti-HER2 antibody may be used in accordance with the present invention, and the principles of the present invention are illustrated with respect to the HER2 tumor antigen. Representative antibodies that bind human HER2 include margetuximab, trastuzumab and pertuzumab. Margetuximab (also known as MGAH22; CAS Reg No. 1350624-75-7, see, for example, U.S. Pat. No. 8,802,093) is an Fc-optimized monoclonal antibody that binds to HER2 and mediates enhanced ADCC activity. Trastuzumab (also known as rhuMAB4D5, and marketed as HERCEPTIN®; CAS Reg No 180288-69-1; see, U.S. Pat. No. 5,821,337) is the humanized version of antibody 4D5, having IgG1/kappa constant regions. Pertuzumab (also known as rhuMAB2C4, and marketed as PERJET®; CAS Reg No 380610-27-5; see for example, WO2001/000245) is a humanized version of antibody 2C4 having IgG1/kappa constant regions. The amino acid sequence of the complete heavy and Light Chains of margetuximab (WHO Drug Information, 2014, Recommended INN: List 70, 28(1):93-94), and trastuzumab (see WHO Drug Information, 2011, Recommended INN: List 65, 25(1):89-90 for trastuzumab emtansine), and the Fab Domain of pertuzumab (Protein Data Bank Accession No. 1171) are known in the art. Additional anti-HER2 antibodies, including HER2 MAB-1 and humanized variants thereof, are also provided herein.

(1) hHER2 MAB-1

Antibody hHER2 MAB-1 is a humanized anti-HER2 monoclonal antibody that binds an epitope of HER2 that is distinct from the epitope recognized by Margetuximab, Trastuzumab and Pertuzumab (see, e.g., WO 2018/156740).

The amino acid sequence of the VH Domain of humanized antibody (hHER2 MAB-1 VHx) is (SEQ ID NO:78) ($CDR_H$ residues are shown underlined):

QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDX$_1$ X$_2$YGNRVSYWG QGTLVTVSS wherein: $X_1$ is D or E and $X_2$ is G or I The amino acid sequence of the VL Domain of such humanized antibody (hHER2 MAB-1 VLx) is (SEQ ID NO:79) ($CDR_L$ residues are shown underlined):

DIQMTQSPSS LSASVGDRVT ITCKASQDIX$_3$ X$_4$YLSWFQQKP

GKAPKTLIYR ANRLX$_5$X$_6$GVPS RFSGSGSGTD FTLTISSLQP

EDFATYYCLQ HDEFPWTFGQ GTKLEIK wherein: $X_3$ is N or S; $X_4$ is S, T or N; $X_5$ is V or Q and $X_6$ is D, E or S Three variant hHER2 MAB-1 VH Domains were isolated: hHER2 MAB-1 VH1, hHER2 MAB-1 VH2, and hHER2 MAB-1 VH3. The amino acid sequences of such variant hHER2 MAB-1 VH Domains are presented below.

The amino acid sequence of hHER2 MAB-1 VH1 is (SEQ ID NO:80) ($CDR_H$ residues are shown underlined; note that the second and third residues of $CDR_H3$ are D and G, respectively):

QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD GYGNRVSYWG QGTLVTVSS

The amino acid sequence of hHER2 MAB-1 VH2 is (SEQ ID NO:81) ($CDR_H$ residues are shown underlined; note that the second and third residues of $CDR_H3$ are E and G, respectively):

QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDE GYGNRVSYWG QGTLVTVSS

The amino acid sequence of hHER2 MAB-1 VH3 is (SEQ ID NO:82) ($CDR_H$ residues are shown underlined; note that the second and third residues of $CDR_H3$ are D and I, respectively):

QVQLVQSGAE VKKPGASVKV SCKASGYTFT NYGMNWVRQA

PGQGLEWMGW INTNIGEPTY TEEFKGRVTM TRDTSISTAY

MELSRLRSDD TAVYYCARDD IYGNRVSYWG QGTLVTVSS

Three variant hHER2 MAB-1 VL Domains were isolated: hHER2 MAB-1 VL1, hHER2 MAB-1 VL2, and hHER2 MAB-1 VL3. The amino acid sequences of such variant hHER2 MAB-1 VL Domains are presented below.

The amino acid sequence of hHER2 MAB-1 VL1 is (SEQ ID NO:83) ($CDR_L$ residues are shown underlined; note that the seventh and eighth residues of $CDR_L1$ are N and S, respectively, and that the sixth and seventh residues of $CDR_L2$ are V and D, respectively):

DIQMTQSPSS LSASVGDRVT ITCKASQDIN SYLSWFQQKP

GKAPKTLIYR ANRLVDGVPS RFSGSGSGTD FTLTISSLQP

EDFATYYCLQ HDEFPWTFGQ GTKLEIK

The amino acid sequence of hHER2 MAB-1 VL2 is (SEQ ID NO:84) ($CDR_L$ residues are shown underlined; note that the seventh and eighth residues of $CDR_L1$ are N and T, respectively, and that the sixth and seventh residues of $CDR_L2$ are V and E, respectively):

DIQMTQSPSS LSASVGDRVT ITCKASQDIN TYLSWFQQKP

GKAPKTLIYR ANRLVEGVPS RFSGSGSGTD FTLTISSLQP

EDFATYYCLQ HDEFPWTFGQ GTKLEIK

The amino acid sequence of hHER2 MAB-1 VL3 is (SEQ ID NO:85) ($CDR_L$ residues are shown underlined; note that the seventh and eighth residues of $CDR_L1$ are S and N, respectively, and that the sixth and seventh residues of $CDR_L2$ are Q and S, respectively):

DIQMTQSPSS LSASVGDRVT ITCKASQDIS NYLSWFQQKP

GKAPKTLIYR ANRLQSGVPS RFSGSGSGTD FTLTISSLQP

EDFATYYCLQ HDEFPWTFGQ GTKLEIK

Any of such humanized VH and VL hHER2 MAB-1 Domains, including any embraced within the generic sequence(s) of the hHER2 MAB-1 VH and/or VL Domains presented above may be used to form an antibody, diabody or binding molecule capable of binding Her2.

(2) Other HER2 Binding Domains

In addition to the above-identified HER2 binding domains, the invention contemplates the use of any of the epitope-binding site of any of the following anti-Her-2 binding domains: 1.44.1; 1.140; 1.43; 1.14.1; 1.100.1; 1.96; 1.18.1; 1.20; 1.39; 1.24; and 1.71.3 (U.S. Pat. Nos. 8,350,011; 8,858,942; and PCT Patent Publication WO 2008/019290); F5 and C1 (U.S. Pat. Nos. 7,892,554; 8,173,424; 8,974,792; and PCT Patent Publication WO 99/55367); and also the binding domains of the anti-HER2 antibodies of US Patent Publication 2011/0097323, 2013/017114, 2014/0328836, 2016/0130360 and 2016/0257761, and PCT Patent Publication WO2011/147986).

The present invention specifically includes and encompasses CD137×HER2 Binding Molecules that comprise the VL and/or VH Domain, and/or 1, 2 or all 3 of the $CDR_L$s of the VL Region and/or 1, 2 or all 3 of the $CDR_H$s of the VH Domain of any of Margetuximab, Trastuzumab, Pertuzumab, hHER2 MAB-1, or any of the other anti-HER2 antibodies provided herein; and more typically possess 1, 2 or all 3 of the CDRLs of the VL Region and/or 1, 2 or all 3 of the $CDR_H$s of the VH Domain of such anti-HER2 monoclonal antibodies.

c) EphA2 Binding Domains

The receptor tyrosine kinase, ephrin type-A receptor 2 (EphA2) is normally expressed at sites of cell-to-cell contact in adult epithelial tissues, however, recent studies have shown that it is also overexpressed in various types of epithelial carcinomas, with the greatest level of EphA2 expression observed in metastatic lesions. High expression levels of EphA2 have been found in a wide range of cancers and in numerous tumor cell lines, including prostate cancer, breast cancer, non-small cell lung cancer and melanoma. EphA2 does not appear to be merely a marker for cancer, but rather appears to be persistently overexpressed and functionally changed in numerous human cancers. The epitope-binding site of any anti-EphA2 antibody may be used in accordance with the present invention. Presented below are several representative anti-EphA2 antibodies that may be used to generate the molecules of the present invention.

(1) EphA2 MAB-1

Antibody EphA2 MAB-1 is a murine anti-EphA2 monoclonal antibody. The amino acid sequence of the VH Domain of EphA2 MAB-1 is (SEQ ID NO:86) (CDR residues are shown underlined):

QVQLKESGPG LVAPSQSLSI TCTVSGFSLS RYSVHWVRQP

PGKGLEWLGM IWGGGSTDYN SALKSRLSIS KDNSKSQVFL

KMNSLQTDDT AMYYCARKHG NYYTMDYWGQ GTSVTVSS

The amino acid sequence of the VL Domain of EphA2 MAB-1 is SEQ ID NO:87) (CDR residues are shown underlined):

DIQMTQTTSS LSASLGDRIT ISCRASQDIS NYLNWYQQKP

DGTVKLLIYY TSRLHSGVPS RFSGSGSGTD YSLTISNLEQ

EDIATYFCQQ GYTLYTFGGG TKLEIK (2) EphA2 MAB-2

Antibody EphA2 MAB-2 is a murine anti-EphA2 monoclonal antibody. The amino acid sequence of the VH Domain of EphA2 MAB-2 is (SEQ ID NO:88) (CDR residues are shown underlined):

QIQLVQSGPE LKKPGETVKI SCKASGFTFT NYGMNWVKQA

PGKGLKWMGW INTYIGEPTY ADDFKGRFVF SLETSASTAY

LQINNLKNED MATYFCAREL GPYYFDYWGQ GTTLTVSS

The amino acid sequence of the VL Domain of EphA2 MAB-2 is (SEQ ID NO:89) (CDR residues are shown underlined):

DVVMTQTPLS LPVSLGDQAS ISCRSSQSLV HSSGNTYLHW

YLQKPGQSPK LLIYKVSNRF SGVPDRFSGS GSGTDFTLKI

SRVEAEDLGV YFCSQSTHVP TFGSGTKLEI K (3) EphA2 MAB-3

Antibody EphA2 MAB-3 is a murine anti-EphA2 monoclonal antibody. The amino acid sequence of the VH Domain of EphA2 MAB-3 is (SEQ ID NO:90) (CDR residues are shown underlined):

EVQLVESGGG SVKPGGSLKL SCAASGFTFT DHYMYWVRQT

PEKRLEWVAT ISDGGSFTSY PDSVKGRFTI SRDIAKNNLY

LQMSSLKSED TAMYYCTRDE SDRPFPYWGQ GTLVTVSS

The amino acid sequence of the VL Domain of EphA2 MAB-3 is (SEQ ID NO:91) (CDR residues are shown underlined):

DIVLTQSHRS MSTSVGDRVN ITCKASQDVT TAVAWYQQKP

GQSPKLLIFW ASTRHAGVPD RFTGSGSGTD FTLTISSVQA

GDLALYYCQQ HYSTPYTFGG GTKLEIK (4) Other EphA2 Binding Domains

In addition to the above-identified EphA2 binding domains, the invention contemplates the use of any of the epitope-binding site of any of the following anti-EphA2 antibodies: SPL1, LUCA19, SG5, or LUCA40 (see, PCT Patent Publication WO 2006/084226); B13 (see, U.S. Pat. No. 7,101,976); D7 (see, U.S. Pat. No. 7,192,698); B-233, and EA2 (see, PCT Patent Publication WO 2003/094859).

The present invention specifically includes and encompasses CD137×EphA2 Binding Molecules that comprise the VL and/or VH Domain, and/or 1, 2 or all 3 of the $CDR_L$s of the VL Region and/or 1, 2 or all 3 of the $CDR_H$s of the VH Domain of the anti-EphA2 monoclonal antibodies EphA2 MAB-1, EphA2 MAB-2 or EphA2 MAB-3.

d) 5T4 Binding Domains

The oncofetal protein, 5T4, is a tumor-associated protein displayed on the cell membrane of many carcinomas, including kidney, colon, prostate, lung, carcinoma and in acute lymphoblastic leukemia. The epitope-binding site of any anti-5T4 antibody may be used in accordance with the present invention. Presented below are two representative anti-5T4 antibodies, the humanized "5T4 MAB-1," and the murine "5T4 MAB-2". Additional anti-5T4 antibodies are described in the art (see, e.g., U.S. Pat. Nos. 8,084,249; 8,409,577; 8,759,495; 8,409,577; PCT Publication Nos: WO 2013/041687; WO 2014/137931; WO 2016/022939)

(1) 5T4 MAB-1

The amino acid sequence of the VH Domain of 5T4 MAB-1 is (SEQ ID NO:92) (CDR residues are shown underlined):

QVQLVQSGAE VKKPGASVKV SCKASGYTFT SFWMHWVRQA

PGQGLEWMGR IDPNRGGTEY NEKAKSRVTM TADKSTSTAY

MELSSLRSED TAVYYCAGGN PYYPMDYWGQ GTTVTVSS

The amino acid sequence of the VL Domain of 5T4 MAB-1 is (SEQ ID NO:93) (CDR residues are shown underlined):

DIQMTQSPSS LSASVGDRVT ITCRASQGIS NYLAWFQQKP

GKAPKSLIYR ANRLQSGVPS RFSGSGSGTD FTLTISSLQP

EDVATYYCLQ YDDFPWTFGQ GTKLEIK (2) 5T4 MAB-2

The amino acid sequence of the VH Domain of 5T4 MAB-2 is (SEQ ID NO:94) (CDR residues are shown underlined):

QVQLQQPGAE LVKPGASVKM SCKASGYTFT SYWITWVKQR

PGQGLEWIGD IYPGSGRANY NEKFKSKATL TVDTSSSTAY

MQLSSLTSED SAVYNCARYG PLFTTVVDPN

SYAMDYWGQG TSVTVSS

The amino acid sequence of the VL Domain of 5T4 MAB-2 is (SEQ ID NO:95) (CDR residues are shown underlined):

DVLMTQTPLS LPVSLGDQAS ISCRSSQSIV YSNGNTYLEW

YLQKPGQSPK LLIYKVSNRF SGVPDRFSGS GSGTDFTLKI

SRVEAEDLGV YYCFQGSHVP FTFGSGTKLE IK

The present invention specifically includes and encompasses CD137×5T4 Binding Molecules that comprise the VL and/or VH Domain, and/or 1, 2 or all 3 of the $CDR_L$s of the VL Region and/or 1, 2 or all 3 of the $CDR_H$s of the VH Domain of the anti-5T4 monoclonal antibodies 5T4 MAB-1 or 5T4 MAB-2, or of any of the anti-5T4 antibodies provided in WO 2007/106744; WO 2013/041687 or WO 2015/184203.

e) B7-H3 Binding Domains

B7-H3 is a Tumor Antigen that is over-expressed on a wide variety of solid tumor types and is a member of the B7 family of molecules that are involved in immune regulation. In particular, several independent studies have shown that human malignant tumor cells (e.g., tumor cells of neuroblastomas and gastric, ovarian and non-small cell lung cancers) exhibit a marked increase in expression of B7-H3 protein and that this increased expression was associated with increased disease severity, suggesting that B7-H3 is exploited by tumors as an immune evasion pathway.

The epitope-binding site of any anti-B7-H3 antibody may be used in accordance with the present invention. One representative humanized antibody that bind human B7-H3 is "Enoblituzumab." Enoblituzumab (also known as MGA271; CAS Reg No. 1353485-38-7; see for example, U.S. Pat. No. 8,802,091) is an Fc-optimized monoclonal antibody that binds to B7-H3 and mediates enhanced ADCC activity. The amino acid sequence of the complete heavy and Light Chains of Enoblituzumab (WHO Drug Information, 2017, Recommended INN: List 77, 31(1):149) are known in the art. Additional representative anti-B7-H3 antibodies are presented.

(1) hBRCA69D

Representative VH and VL Domains of the humanized anti-B7-H3 antibody "hBRCA69D" are presented below. Two humanized VH Domains, hBRCA69D VH1 and hBRCA69D VH2; and two humanized VL Domains hBRCA69D VL1 and hBRCA69D VL2, which may be used in any combination of VH/VL to yield a functional humanized binding domain are provided below.

The amino acid sequence of the VH Domain of hBRCA69D VH1 is (SEQ ID NO:96) ($CDR_H$ residues are shown underlined):

QVQLVQSGAE VKKPGASVKV SCKASGYTFT SYWMQWVRQA
PGQGLEWMGT IYPGDGDTRY TQKFKGRVTI TADKSTSTAY
MELSSLRSED TAVYYCARRG IPRLWYFDVW GQGTTVTVSS

The amino acid sequence of the VH Domain of hBRCA69D VH2 is (SEQ ID NO:97) ($CDR_L$ residues are shown underlined):

QVQLVQSGAE VKKPGASVKV SCKASGYTFT SYWMQWVRQA
PGQGLEWMGT IYPGGGDTRY TQKFQGRVTI TADKSTSTAY
MELSSLRSED TAVYYCARRG IPRLWYFDVW GQGTTVTVSS

The amino acid sequence of the VL Domain of hBRCA69D VL1 is (SEQ ID NO:98) ($CDR_L$ residues are shown underlined).

DIQMTQSPSS LSASVGDRVT ITCRASQDIS NYLNWYQQKP
GKAPKLLIYY TSRLHSGVPS RFSGSGSGTD FTLTISSLQP
EDIATYYCQQ GNTLPPTFGG GTKLEIK

The amino acid sequence of the VL Domain of hBRCA69D VL2 is (SEQ ID NO:99) ($CDR_L$ residues are shown underlined).

DIQMTQSPSS LSASVGDRVT ITCRASQSIS SYLNWYQQKP
GKAPKLLIYY TSRLQSGVPS RFSGSGSGTD FTLTISSLQP
EDIATYYCQQ GNTLPPTFGG GTKLEIK (2) hPRCA157

Another representative humanized anti-B7-H3 antibody is "hPRCA157". The amino acid sequence of the VH Domain of hPRCA157 VH1 is (SEQ ID NO:100) ($CDR_H$ residues are shown underlined):

EVQLVESGGG LVKPGGSLRL SCAASGFTFS SYGMSWVRQA
PGKGLEWVAT INSGGSNTYY PDSLKGRFTI SRDNAKNSLY
LQMNSLRAED TAVYYCARHD GGAMDYWGQG TTVTVSS

The amino acid sequence of the VL Domain of hPRCA157 VL1 is (SEQ ID NO:101) ($CDR_L$ residues are shown underlined):

DIQMTQSPSS LSASVGDRVT ITCRASESIY SYLAWYQQKP
GKAPKLLVYN TKTLPEGVPS RFSGSGSGTD FTLTISSLQP
EDFATYYCQH HYGTPPWTFG QGTRLEIK (3) Other B7-H3 Binding Domains In addition to the above-identified B7-H3 binding domains, the invention contemplates the use of any of the epitope-binding site of any of the following anti-B7-H3 antibodies: LUCA1; BLA8; PA20; or SKN2 (see, U.S. Pat. Nos. 7,527,969; 8,779,098 and PCT Patent Publication WO 2004/001381); M30; cM30; M30-H1-L1; M30-H1-L2; M30-H1-L3; M30-H1-L4; M30-H1-L5; M30-H1-L6; M30-H1-L7; M30-H4-L1; M30-H4-L2; M30-H4-L3; and M30-H4-L4 (see, US Patent Publication 2013/0078234 and PCT Patent Publication WO 2012/147713; and 8H9 (see U.S. Pat. Nos. 7,666,424; 7,737,258; 7,740,845; 8,148,154; 8,414,892; 8,501,471; 9,062,110; US Patent Publication 2010/0143245 and PCT Patent Publication WO 2008/116219).

The present invention specifically includes and encompasses CD137×B7-H3 Binding Molecules that comprise the VL and/or VH Domain, and/or 1, 2 or all 3 of the $CDR_L$s of the VL Region and/or 1, 2 or all 3 of the $CDR_H$s of the VH Domain of any of, humanized BRCA69D, PRCA157, humanized PRCA157, or Enoblituzumab, or any of the other anti-B7-H3 antibodies provided herein; and more typically possess 1, 2 or all 3 of the $CDR_L$s of the VL Region and/or 1, 2 or all 3 of the $CDR_H$s of the VH Domain of such anti-B7-H3 monoclonal antibodies.

f) GpA33 Binding Domains

The 43 kD transmembrane glycoprotein A33 (gpA33) is expressed in >95% of all colorectal carcinomas. The epitope-binding site of any anti-gpA33 antibody may be used in accordance with the present invention. An representative humanized anti-gpA33 antibody ("gpA33 MAB-1") is presented below.

The amino acid sequence of the VH Domain of gpA33 MAB-1 is (SEQ ID NO:102) (CDR residues are shown underlined):

```
QVQLVQSGAE VKKPGASVKV SCKASGYTFT GSWMNWVRQA
PGQGLEWIGR IIYPGDGETNY NGKFKDRVTI TADKSTSTAY
MELSSLRSED TAVYYCARIY GNNVYFDVWG QGTTVTVSS
```

The amino acid sequence of the VL Domain of gpA33 MAB-1 is (SEQ ID NO:103) (CDR residues are shown underlined):

```
DIQLTQSPSF LSASVGDRVT ITCSARSSIS FMYWYQQKPG
KAPKLLIYDT SNLASGVPSR FSGSGSGTEF TLTISSLEAE
DAATYYCQQW SSYPLTFGQG TKLEIK
```

The present invention specifically includes and encompasses CD137×gpA33 Binding Molecules that comprise the VL and/or VH Domain, and/or 1, 2 or all 3 of the CDR$_L$s of the VL Region and/or 1, 2 or all 3 of the CDR$_H$s of the VH Domain of anti-gpA33 monoclonal antibodies gpA33 MAB-1, or of any of the anti-gpA33 monoclonal antibodies provided in WO 2015/026894.

g) CEACAM5 and CEACAM6 Binding Domains

Carcinoembryonic Antigen-Related Cell Adhesion Molecules 5 (CEACAM5) and 6 (CEACAM6) have been found to be associated with various types of cancers including medullary thyroid cancer, colorectal cancer, pancreatic cancer, hepatocellular carcinoma, gastric cancer, lung cancer, head and neck cancers, urinary bladder cancer, prostate cancer, uterine cancer, endometrial cancer, breast cancer, hematopoietic cancer, leukemia and ovarian cancer, and particularly colorectal, gastrointestinal, pancreatic, non-small cell lung cancer (NSCL), breast, thyroid, stomach, ovarian and uterine carcinomas. The epitope-binding site of any anti-CEACAM5/CEACAM6 antibody may be used in accordance with the present invention. Representative anti-CEACAM5/CEACAM6 antibodies are provided below.

(1) 16C3

The amino acid sequence of the VH Domain of the humanized anti-CEACAM5/CEACAM6 antibody 16C3 (EP 2585476) is (SEQ ID NO:104) (CDR residues are shown underlined):

```
QVQLQQSGPE VVRPGVSVKI SCKGSGYTFT DYAMHWVKQS
HAKSLEWIGL ISTYSGDTKY NQNFKGKATM TVDKSASTAY
MELSSLRSED TAVYYCARGD YSGSRYWFAY WGQGTLVTVS S
```

The amino acid sequence of the VL Domain of the humanized anti-CEACAM5/CEACAM6 antibody 16C3 (EP 2585476) is (SEQ ID NO:105) (CDR residues are shown underlined):

```
DIQMTQSPSS LSASVGDRVT ITCGASENIY GALNWYQRKP
GKSPKLLIWG ASNLADGMPS RFSGSGSGRQ YTLTISSLQP
EDVATYYCQN VLSSPYTFGG GTKLEIK
```

(2) hMN15

The amino acid sequence of the VH Domain of the humanized anti-CEACAM5/CEACAM6 antibody hMN15 (U.S. Pat. No. 8,287,865) is (SEQ ID NO:106) (CDR residues are shown underlined):

```
QVQLVESGGG VVQPGRSLRL SCSSSGFALT DYYMSWVRQA
PGKGLEWLGF IANKANGHTT DYSPSVKGRF TISRDNSKNT
LFLQMDSLRP EDTGVYFCAR DMGIRWNFDV WGQGTPVTVS
S
```

The amino acid sequence of the VL Domain of the humanized anti-CEACAM5/CEACAM6 antibody hMN15 (U.S. Pat. No. 8,287,865) is (SEQ ID NO:107) (CDR residues are shown underlined):

```
DIQLTQSPSS LSASVGDRVT MTCSASSRVS YIHWYQQKPG
KAPKRWIYGT STLASGVPAR FSGSGSGTDF TFTISSLQPE
DIATYYCQQW SYNPPTFGQG TKVEIKR
```

The present invention specifically includes and encompasses CD137×CEACAM5/CEACAM6 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CEACAM5/CEACAM6 monoclonal antibodies 16C3 or hMN15.

h) CD19 Binding Domains

CD19 (B lymphocyte surface antigen B4, Genbank accession number M28170) is a component of the B cell-receptor (BCR) complex, and is a positive regulator of B cell signaling that modulates the threshold for B cell activation and humoral immunity. CD19 is one of the most ubiquitously expressed antigens in the B cell lineage and is expressed on >95% of B cell malignancies, including acute lymphoblastic leukemia (ALL), chronic lymphocytic leukemia (CLL), and non-Hodgkin's Lymphoma (NHL). Notably, CD19 expression is maintained on B cell lymphomas that become resistant to anti-CD20 therapy. CD19 has also been suggested as a target to treat autoimmune diseases.

The epitope-binding site of any anti-CD19 antibody may be used in accordance with the present invention. An representative humanized antibody that binds to human CD19, and that may be employed in the present invention, is the humanized anti-CD19 antibody disclosed in WO 2016/048938 (referred to herein as "CD19 MAB-1").

The amino acid sequence of the VH Domain of CD19 MAB-1 is (SEQ ID NO:108) (CDR$_H$ residues are shown underlined):

```
QVTLRESGPA LVKPTQTLTL TCTFSGFSLS TSGMGVGWIR
QPPGKALEWL AHIWWDDDKR YNPALKSRLT ISKDTSKNQV
FLTMTNMDPV DTATYYCARM ELWSYYFDYW GQGTTVTVSS
```

The amino acid sequence of the VL Domain of CD19 MAB-1 is (SEQ ID NO:109) (CDR$_L$ residues are shown underlined):

```
ENVLTQSPAT LSVTPGEKAT ITCRASQSVS YMHWYQQKPG
QAPRLLIYDA SNRASGVPSR FSGSGSGTDH TLTISSLEAE
DAATYYCFQG SVYPFTFGQG TKLEIK
```

The present invention specifically includes and encompasses CD137×CD19 Binding Molecules that comprise the VL and/or VH Domain, and/or 1, 2 or all 3 of the CDR$_L$s of the VL Region and/or 1, 2 or all 3 of the CDR$_H$s of the VH Domain of the anti-CD19 monoclonal antibody CD19 MAB-1, or any of the anti-CD19 antibodies disclosed in U.S. Pat. No. 7,112,324, or present in blinatumomab (BLINCYTO®; amino acid sequence found in WHO Drug Information, 2009, Recommended INN: List 62, 23(3):240-241) and duvortuxizumab (aka MGD011; amino acid sequence found in WHO Drug Information, 2016, Proposed INN: List 116, 30(4):627-629).

i) CD123 Binding Domains

CD123 (interleukin 3 receptor) comprises a unique alpha chain, IL-3Ra that is a 40 kDa molecule. Interleukin 3 (IL-3) drives early differentiation of multipotent stem cells into cells of the erythroid, myeloid and lymphoid progenitors. CD123 has been reported to be overexpressed on malignant cells in a wide range of hematologic malignancies including acute myeloid leukemia (AML) and myelodysplastic syndrome (MDS). Overexpression of CD123 is associated with poorer prognosis in AML.

The epitope-binding site of any anti-CD123 antibody may be used in accordance with the present invention. An representative humanized antibody that binds to human CD123, and that may be employed in the present invention, is "CD123 MAB-1" (see, e.g., PCT Patent Publication WO 2015/026892).

The amino acid sequence of the VH Domain of CD123 MAB-1 is (SEQ ID NO:110) ($CDR_H$ residues are shown underlined):

```
EVQLVQSGAE LKKPGASVKV SCKASGYTFT DYYMKWVRQA

PGQGLEWIGD IIPSNGATFY NQKFKGRVTI TVDKSTSTAY

MELSSLRSED TAVYYCARSH LLRASWFAYW GQGTLVTVSS
```

The amino acid sequence of the VL Domain of D123 M B-1 is (SEQ ID NO:111) ($CDR_L$ residues are shown underlined):

```
DFVMTQSPDS LAVSLGERVT MSCKSSQSLL NSGNQKNYLT

WYQQKPGQPP KLLIYWASTR ESGVPDRFSG SGSGTDFTLT

ISSLQAEDVA VYYCQNDYSY PYTFGQGTKL EIK
```

The present invention specifically includes and encompasses CD137×CD123 Binding Molecules that comprise the VL and/or VH Domain, and/or 1, 2 or all 3 of the $CDR_L$s of the VL Region and/or 1, 2 or all 3 of the $CDR_H$s of the VH Domain of the anti-CD123 monoclonal antibody CD123 MAB-1, or any of the anti-CD123 antibodies disclosed in US 2017/081424 and WO 2016/036937, or present in JNJ-63709178 (Johnson & Johnson, also see, WO 2016/036937) and XmAb14045 (Xencor, also see, US 2017/081424).

j) IL13Rα2

Interleukin-13 Receptor α2 (IL13Rα2) is overexpressed in a variety of cancers, including glioblastoma, colorectal cancer, cervical cancer, pancreatic cancer, multiple melanoma, osteosarcoma, leukemia, lymphoma, prostate cancer and lung cancer Antibodies that immunospecifically bind to IL13Rα2 are commercially available and have been described in the art (see, e.g., WO 2008/146911). Representative humanized antibodies that bind to human IL13Rα2 include "hu08" (see, e.g., WO 2014/072888).

The amino acid sequence of the VH Domain of hu08 (SEQ ID NO:112) is shown below CDR residues are shown underlined):

```
EVQLVESGGG LVQPGGSLRL SCAASGFTFS RNGMSWVRQA

PGKGLEWVAT VSSGGSYIYY ADSVKGRFTI SRDNAKNSLY

LQMNSLRAED TAVYYCARQG TTALATRFFD VWGQGTLVTV

SS
```

The amino acid sequence of the VL Domain of hu08 (SEQ ID NO:113) is shown below CDR residues are shown underlined):

```
DIQMTQSPSS LSASVGDRVT ITCKASQDVG TAVAWYQQKP

GKAPKLLIYS ASYRSTGVPS RFSGSGSGTD FTLTISSLQP

EDFATYYCQH HYSAPWTFGG GTKVEIK
```

The present invention specifically includes and encompasses CD137×IL13Rα2 Binding Molecules that comprise the VL and/or VH Domain, and/or 1, 2 or all 3 of the $CDR_L$s of the VL Region and/or 1, 2 or all 3 of the $CDR_H$s of the VH Domain of the anti-IL13Rα2 monoclonal antibody hu08.

k) ROR1

Receptor Tyrosine Kinase-Like Orphan Receptor 1 ("ROR1") is a type I membrane protein belonging to the ROR subfamily of cell surface receptors. ROR1 is an onco-embryonic antigen that is expressed by many tissues during embryogenesis, is absent from most mature tissues and is expressed in numerous blood and solid malignancies including ovarian, colon, lung, lymphoma, skin, pancreatic, testicular, bladder, uterus, prostate, adrenal, breast, and B-cell malignancies, as well as in some cancer stem cells. ROR1 expression is associated with high-grade tumors exhibiting a less-differentiated morphology and is correlated with poor clinical outcomes. The epitope-binding site of any anti-ROR1 antibody may be used in accordance with the present invention. Presented below in an representative humanized/optimized anti-ROR1 antibody that may be used to generate the molecules of the present invention, variations of this antibody are described in WO 2017/142928.

(1) Anti-ROR1

The amino acid sequence of an representative VH of the anti-ROR1 antibody is (SEQ ID NO:114) (CDR residues are shown underlined):

```
QEQLVESGGG LVQPGGSLRL SCAASGFTFS DYYMSWXRQA

PGKGLEWVAT IIYPSSGKTYY ADSAKGRLTI SSDNAKDSLY

LQMNSLRAED TAVYYCTRDS YADDAALFDI WGQGTTVTVS

S
```

wherein X is I or V

The amino acid sequence of an representative VL of the anti-ROR1 antibody is (SEQ ID NO:115) (CDR residues are shown underlined):

```
QLVLTQSPSA SASLGSSVKL TCTLSSGHKT DTIDWYQQQP

GKAPRYLMKL EGSGSYNKGS GVPDRFSGSS SGADWYLTIS

SLQSEDEADY YCGTDYPGNY LFGGGTQLTV LG
```

(2) Other ROR1 Binding Domains

In addition to the above-identified ROR1 binding domains, the invention contemplates the use of any of the epitope-binding site of any of the following anti-ROR1 antibodies: 4A5 (see, U.S. Pat. No. 8,212,009); R11, R12, and Y31 (see, U.S. Pat. No. 9,758,586); and A1-A14 (see, e.g., U.S. Pat. No. 9,228,023).

The present invention specifically includes and encompasses CD137×ROR1 Binding Molecules that comprise the VL and/or VH Domain, and/or 1, 2 or all 3 of the CDRLs of the VL Region and/or 1, 2 or all 3 of the CDRHs of the VH Domain of any of the anti-ROR1 monoclonal antibodies provided herein.

D. CD137×TA Binding Molecules of the Present Invention

The present invention is particularly directed to Fc-bearing tetravalent and trivalent CD137×TA Binding Molecules capable of simultaneous binding to CD137 and a TA, and other Fc-bearing CD137×TA Binding Molecules capable of simultaneous binding to CD137 and a TA. The present invention is further directed to the use of such molecules in the treatment of cancer and other diseases and conditions.

1. Tetravalent CD137×TA Fc-Bearing Diabodies

The present invention particularly encompasses a wide variety of Fc-bearing diabodies capable of simultaneous binding to CD137 and a TA. Representative CD137×TA Fc-bearing Diabodies are described below.

Such tetravalent Fc-bearing diabodies will comprise two polypeptide chains. The first of such polypeptide chains may contain, in the N-terminal to C-terminal direction, an N-terminus, a Light Chain Variable Domain (VL) of an antibody capable of binding to an epitope of a "first" antigen (VL1) (either CD137 or TA), a Heavy Chain Variable Domain (VH) of an antibody capable of binding to an epitope of a "second" antigen (VH2) (TA, if VL1 was selected to bind to an epitope of CD137; CD137 if VL1 was selected to bind to an epitope of TA), a cysteine-containing domain, one or more additional domains as provided in more detail below, and a C-terminus. The second of such polypeptide chains may contain, in the N-terminal to C-terminal direction, an N-terminus, a Light Chain Variable Domain (VL) of an antibody capable of binding to an epitope of the "second" antigen (VL2) (TA, if the first antigen was CD137; CD137, if the first antigen was TA)), a Heavy Chain Variable Domain (VH) of an antibody capable of binding to an epitope of the "second" antigen (VH2) (TA, if VL2 was selected to bind to an epitope of CD137; CD137 if VL2 was selected to bind to an epitope of TA, a cysteine-containing domain, one or more additional domains as provided in more detail below, and a C-terminus. An intervening linker peptide (Linker 1) separates the Light Chain Variable Domain (VL1 or VL2) from the Heavy Chain Variable Domain (VH1 or VH2).

In certain embodiments, Fc-bearing diabodies of the present invention are covalently bonded tetravalent diabodies having four epitope-binding sites that comprise four polypeptide chains, and have the general structure depicted in FIG. 1A. The first and third polypeptide chains of such a diabody contain in the N-terminal to C-terminal direction: (i) a VL1-containing Domain, (ii) a VH2-containing Domain, (iii) Heterodimer-Promoting Domain and (iv) a Domain containing a CH2-CH3 sequence. The second and fourth polypeptide chains contain: (i) a VL2-containing Domain, (ii) a VH1-containing Domain and (iii) a Heterodimer-Promoting Domain, where the Heterodimer-Promoting Domains promote the dimerization and covalent bonding of the first/third polypeptide chains with the second/fourth polypeptide chains. The VH Domains are linked to the Heterodimer-Promoting Domains by intervening linker peptides (Linker 2), which may comprise a cysteine residue. Optionally, or additionally the Heterodimer Promoting Domains may comprise a cysteine residues. In a representative CD137×TA bispecific Fc-bearing diabody embodiment, the C-terminus of the Heterodimer-Promoting Domain of the first polypeptide chain is linked to CH2-CH3 domains by an intervening linker peptide (Linker 3). The VL and/or VH Domains of the third and fourth polypeptide chains, and VL and/or VH Domains of the first and second polypeptide chains may be the same or different so as to permit tetravalent binding that is either monospecific, bispecific or tetraspecific. In Table 3 below, notations "VL3" and "VH3" denote, respectively, the Light Chain Variable Domain and Variable Heavy Chain Domain that bind a "third" epitope of such diabody. Similarly, the notations "VL4" and "VH4" denote, respectively, the Light Chain Variable Domain and Variable Heavy Chain Domain that bind a "fourth" epitope of such diabody. The general structure of the polypeptide chains of a representative four-chain bispecific Fc Region-containing diabodies of invention is provided in Table 3:

TABLE 3

| | | |
|---|---|---|
| Bispecific | 2nd Chain | $NH_2$-VL2-VH1-(c)-HPD-COOH |
| | 1st Chain | $NH_2$-VL1-VH2-(c)-HPD-(c)-CH2—CH3—COOH |
| | 1st Chain | $NH_2$-VL1-VH2-(c)-HPD-(c)-CH2—CH3—COOH |
| | 2nd Chain | $NH_2$-VL2-VH1-(c)-HPD-COOH |
| Tetraspecific | 2nd Chain | $NH_2$-VL2-VH1-(c)-HPD-COOH |
| | 1st Chain | $NH_2$-VL1-VH2-(c)-HPD-(c)-CH2—CH3—COOH |
| | 3rd Chain | $NH_2$-VL3-VH4-(c)-HPD-(c)-CH2—CH3—COOH |
| | 4th Chain | $NH_2$-VL4-VH3-(c)-HPD-COOH |

(-(c)-denotes a cysteine-containing polypeptide domain that possesses one, two, or more than two cysteine residues. The representation is intended to be illustrative and non-limiting. Cysteine residues may be present in additional or alternative domains, such as within the Heterodimer-Promoting Domain (HPD))

Figure 1B:
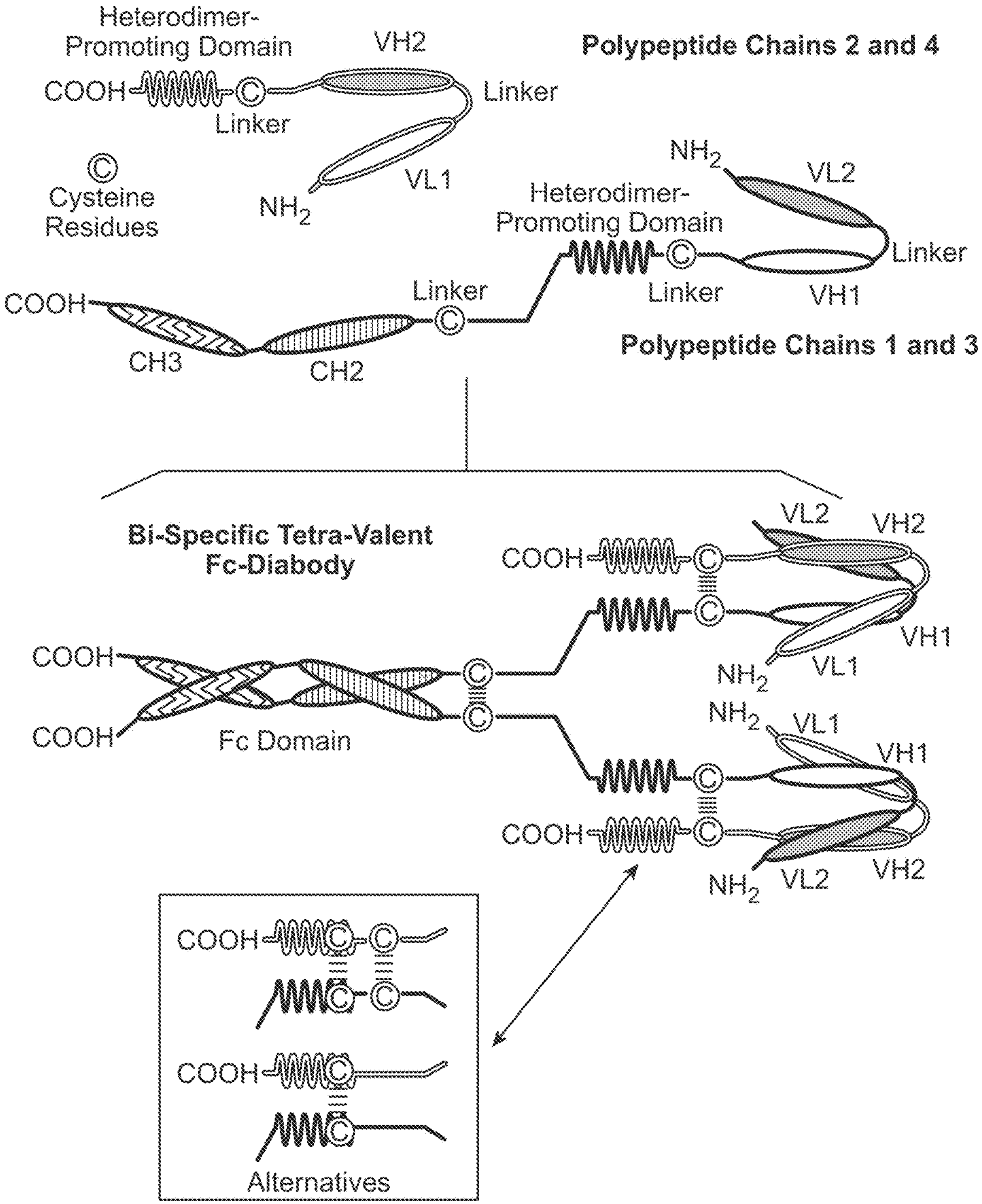
Figure 1C:
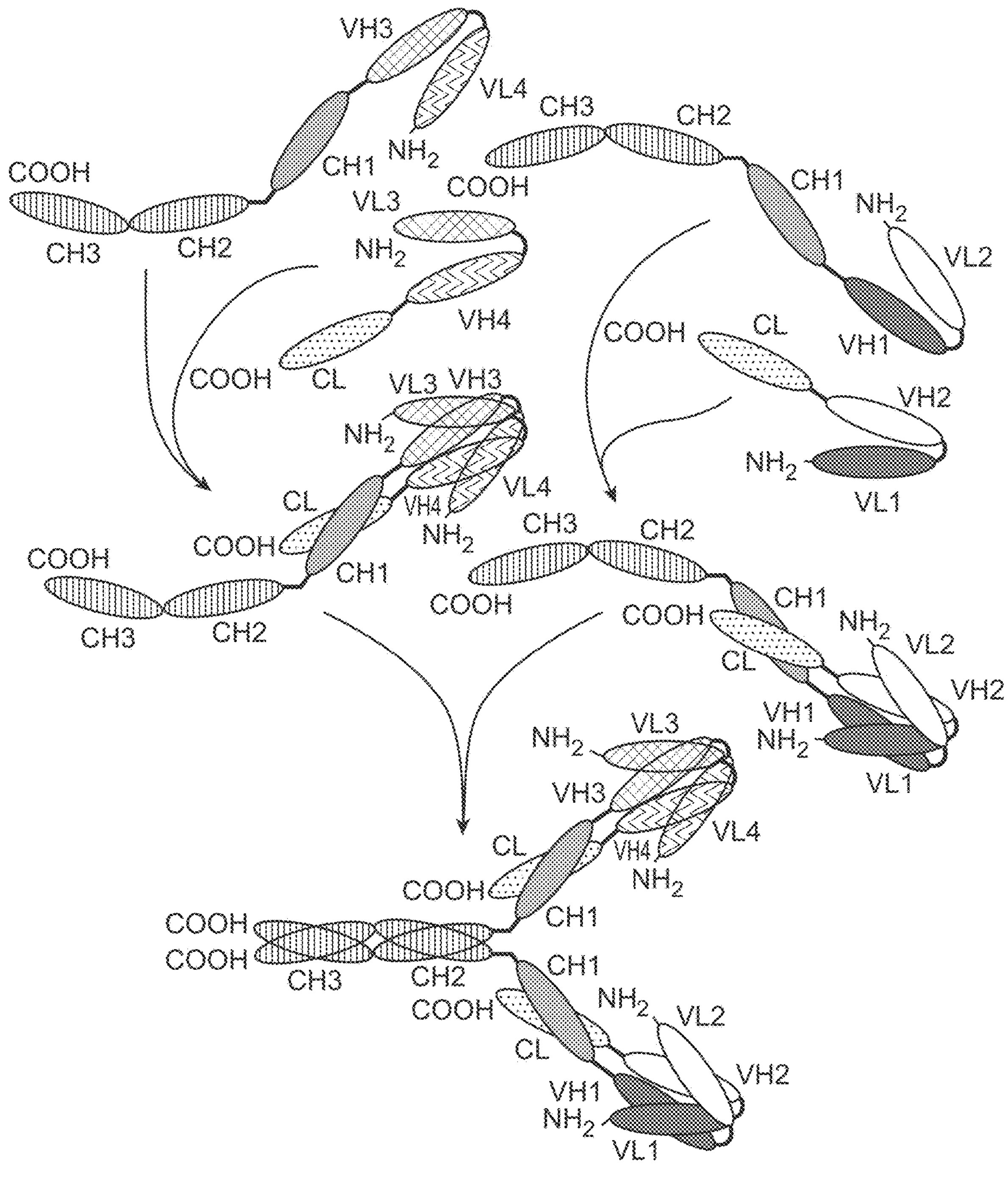

In certain embodiments, CD137×TA Binding Molecules of the present invention are bispecific, tetravalent (i.e., possess four epitope-binding sites), Fc-bearing diabodies that are composed of four total polypeptide chains (FIGS. 1A-1C). The CD137×TA Binding Molecules of the invention are bispecific, tetravalent, Fc-bearing diabodies that comprise two epitope-binding sites immunospecific for CD137 (which may be capable of binding to the same epitope of CD137 or to different epitopes of CD137), and two epitope-binding sites immunospecific for a tumor antigen (which may be capable of binding to the same epitope of a TA or to different epitopes of a TA or different epitopes of different TAs).

Figure 1D:
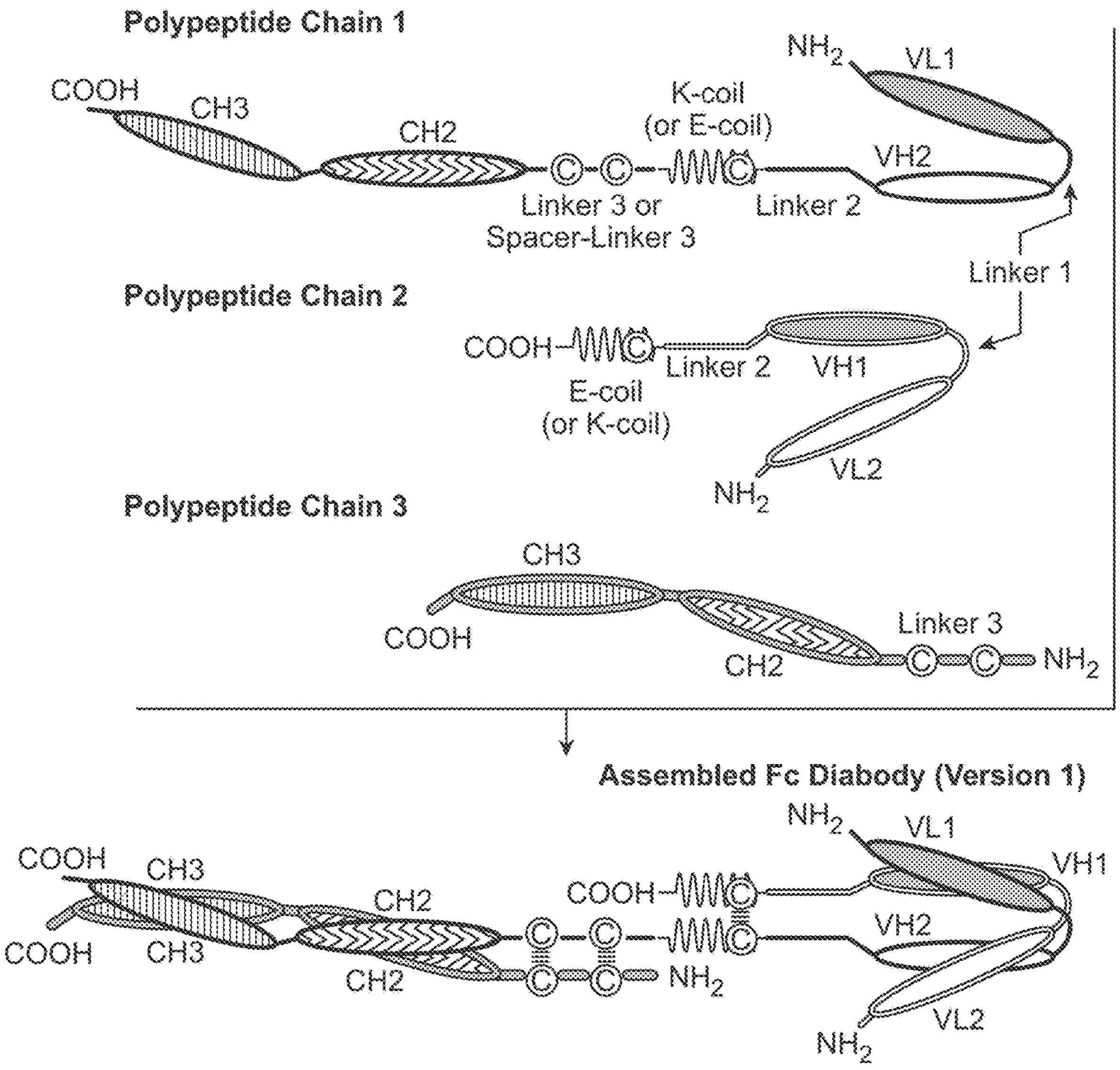

In a further embodiment, the Fc Domain-containing diabodies of the present invention may comprise three polypeptide chains. The first polypeptide of such a diabody often contains three domains: (i) a VL1-containing Domain, (ii) a VH2-containing Domain and (iii) a Domain containing a CH2-CH3 sequence. The second polypeptide of such a diabody often contains: (i) a VL2-containing Domain, (ii) a VH1-containing Domain and (iii) a Domain that promotes heterodimerization and covalent bonding with the diabody's first polypeptide chain. The third polypeptide of such a diabody often comprises a CH2-CH3 sequence. Thus, the first and second polypeptide chains of such a diabody often associate together to form a VL1/VH1 Epitope-Binding Domain that is capable of binding either the first or second epitope, as well as a VL2/VH2 Epitope-Binding Domain that is capable of binding the other of such epitopes. The first and second polypeptides often are bonded to one another through a disulfide bond involving cysteine residues in their respective Third Domains. Notably, the first and third polypeptide chains often complex with one another to form an Fc Domain that is stabilized via a disulfide bond. FIG. 1D illustrates a representative structure of such diabodies.

In each of the above embodiments, the Light Chain Variable Domain of the first polypeptide chain (VL1) is coordinately selected so as to permit it to interact with the Heavy Chain Variable Domain of the second polypeptide chain (VH1) to thereby form a functional epitope-binding site that is capable of immunospecifically binding an epitope of the first antigen (i.e., either TA or CD137). Likewise, the Light Chain Variable Domain of the second polypeptide chain (VL2) is coordinately selected so as to permit it to interact with the Heavy Chain Variable Domain of the first polypeptide chain (VH2) to thereby form a functional epitope-binding site that is capable of immunospecifically binding an epitope of the second antigen (i.e., either a TA or CD137). Thus, the selection of the Light Chain Variable Domains and the Heavy Chain Variable Domains are coordinated, such that the two polypeptide chains collectively comprise epitope-binding sites capable of binding to CD137 and a TA.

Figure 2:
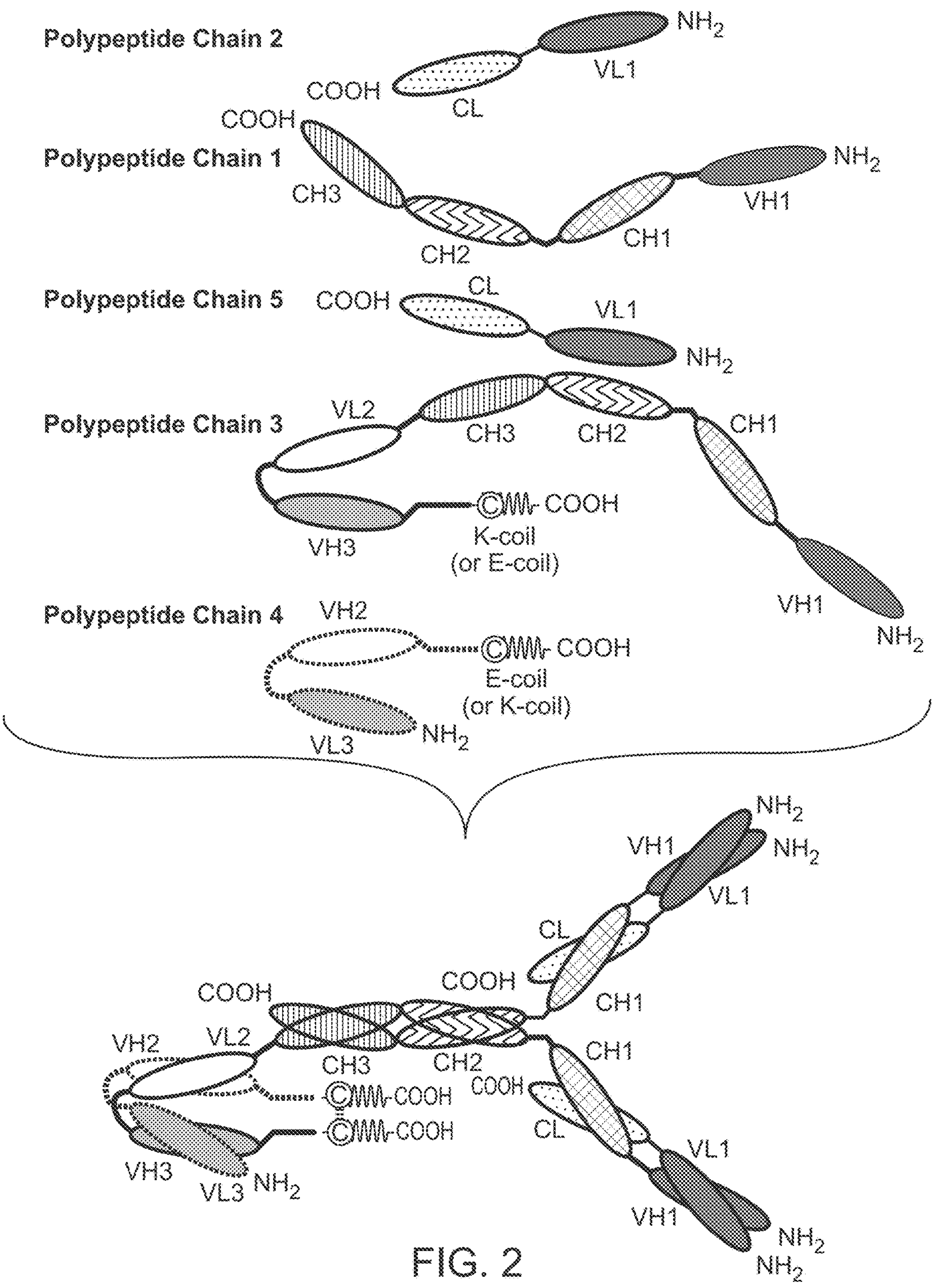
FIG. 2 provides schematics of a representative covalently bonded binding molecule having four epitope-binding sites composed of five polypeptide chains. Two of the polypeptide chains possess a linker comprising a cysteine (which linker may comprise all or a portion of a hinge region) and a CH2 and CH3 Domain, such that the associated chains form an Fc Region that comprises all or part of an Fc Region. The polypeptide chains comprising the linked VL and VH Domains further comprise a linker and a Heterodimer-Promoting Domain (further described in FIG. 1B). VL and VH Domains that recognize the same epitope are shown using the same shading or fill pattern. The variable domains may be been selected to yield a resultant CD137×TA Binding Molecule that possesses two non-diabody type binding domains specific for a TA, and two diabody-type binding domains specific for CD137. Alternatively, the variable domains may be selected to yield a resultant CD137×TA Binding Molecule that possesses two non-diabody type binding domains specific for CD137 and two diabody-type binding domains specific for a TA. Such molecules are bispecific and have two binding sites for CD137, which may bind the same or different CD137 epitopes, and two binding sites for a TA which may bind the same or different TA epitopes.

Additional Fc-bearing diabodies of the present invention comprise five polypeptide chains, and are depicted in FIG. 2. The first polypeptide chain of such a diabody contains: (i) a VH1-containing domain, (ii) a CH1-containing domain, and (iii) a Domain containing a CH2-CH3 sequence. The first polypeptide chain may be the heavy chain of an antibody that contains a VH1 and a heavy chain constant region. The second and fifth polypeptide chains of such a diabody contain: (i) a VL1-containing domain, and (ii) a CL-containing domain. The second and/or fifth polypeptide chains of such a diabody may be light chains of an antibody that contains a VL1 complementary to the VH1 of the first/third polypeptide chain. The first, second and/or fifth polypeptide chains may be isolated from a naturally occurring antibody. Alternatively, they may be constructed recombinantly. In one embodiment, the second and fifth polypeptide chains have the same amino acid sequence. The third polypeptide chain of such a diabody contains: (i) a VH1-containing domain, (ii) a CH1-containing domain, (iii) a Domain containing a CH2-CH3 sequence, (iv) a VL2-containing Domain, (v) a VH3-containing Domain and (vi) a Heterodimer-Promoting Domain, where the Heterodimer-Promoting Domains promote the dimerization of the third chain with the fourth chain. The fourth polypeptide of such diabodies contains: (i) a VL3-containing Domain, (ii) a VH2-containing Domain and (iii) a Domain that promotes heterodimerization and covalent bonding with the diabody's third polypeptide chain. The C-terminus of the VH3- and VH2-containing domains of the third and fourth polypeptide chains are linked to a Heterodimer-Promoting Domain by an intervening linker peptide (Linker 2), and the C-terminus of the CH2-CH3 domains of the third polypeptide chain is linked to the VL2-containing Domain by an intervening linker peptide (Linker 4).

Thus, the first and second, and the third and fifth, polypeptide chains of such diabodies associate together to form two VL1/VH1 binding sites capable of binding a first epitope. The third and fourth polypeptide chains of such diabodies associate together to form one diabody binding domain comprising a VL2/VH2 binding site that is capable of binding to a second epitope, as well as a VL3/VH3 binding site that is capable of binding to a third epitope. The first and third polypeptides are bonded to one another through a disulfide bond involving cysteine residues in their respective constant regions. Notably, the first and third polypeptide chains complex with one another to form an Fc Region. Such bispecific diabodies have enhanced potency. FIG. 2 illustrates the structure of such diabodies. It will be understood that the VL1/VH1, VL2/VH2, and VL3/VH3 Domains may be the same or different so as to permit binding that is monospecific, bispecific or trispecific. However, as provided herein, these domains are selected so as to bind CD137 and a TA.

The VL and VH Domains of the polypeptide chains are selected so as to form VL/VH binding sites specific for a desired epitope. The VL/VH binding sites formed by the association of the polypeptide chains may be the same or different so as to permit tetravalent binding that is monospecific, bispecific, trispecific or tetraspecific. In particular, the VL and VH Domains may be selected such that a bispecific diabody may comprise two binding sites for a first epitope and two binding sites for a second epitope, or three binding sites for a first epitope and one binding site for a second epitope, or two binding sites for a first epitope, one binding site for a second epitope and one binding site for a third epitope (as depicted in FIG. 2). The general structure of the polypeptide chains of representative five-chain Fc Region-containing diabodies of invention is provided in Table 4:

TABLE 4

| | | |
|---|---|---|
| Bispecific | $2^{nd}$ Chain | NH$_2$-VL1-CL-(c)-COOH |
| (2 × 2) | $1^{st}$ Chain | NH$_2$-VH1-CH1-(c)-(c)-CH2—CH3—COOH |
| | $3^{rd}$ Chain | NH$_2$-VH1-CH1-(c)-(c)-CH2—CH3-VL2-VH2-(c)-HPD-COOH |
| | $5^{nd}$ Chain | NH$_2$-VL1-CL-(c)-COOH |
| | $4^{th}$ Chain | NH$_2$-VL2-VH2-(c)-HPD-COOH |
| Bispecific | $2^{nd}$ Chain | NH$_2$-VL1-CL-(c)-COOH |
| (3 × 1) | $1^{st}$ Chain | NH$_2$-VH1-CH1-(c)-(c)-CH2—CH3—COOH |
| | $3^{rd}$ Chain | NH$_2$-VH1-CH1-(c)-(c)-CH2—CH3-VL1-VH2-(c)-HPD-COOH |
| | $5^{nd}$ Chain | NH$_2$-VL1-CL-(c)-COOH |
| | $4^{th}$ Chain | NH$_2$-VL2-VH1-(c)-HPD-COOH |
| Trispecific | $2^{nd}$ Chain | NH$_2$-VL1-CL-(c)-COOH |
| (2 × 1 × 1) | $1^{st}$ Chain | NH$_2$-VH1-CH1-(c)-(c)-CH2—CH3—COOH |
| | $3^{rd}$ Chain | NH$_2$-VH1-CH1-(c)-(c)-CH2—CH3-VL2-VH3-(c)-HPD-COOH |
| | $5^{nd}$ Chain | NH$_2$-VL1-CL-(c)-COOH |
| | $4^{th}$ Chain | NH$_2$-VL3-VH2-(c)-HPD-COOH |

(-(c)-denotes a cysteine-containing polypeptide domain that possesses one, two, or more than two cysteine residues. The representation is intended to be illustrative and non-limiting. Cysteine residues may be present in additional or alternative domains, such as within the Heterodimer-Promoting Domain (HPD))

In certain embodiments, CD137×TA Binding Molecules of the present invention are bispecific, tetravalent (i.e., possess four epitope-binding sites), Fc-bearing diabodies that are composed of five total polypeptide chains having two epitope-binding sites immunospecific for CD137 (which may be capable of binding to the same epitope of CD137 or to different epitopes of CD137), and two epitope-binding sites immunospecific for a TA (which may be capable of binding to the same epitope of a TA or to different epitopes of a TA or different epitopes of different TAs). In another embodiment, the CD137×TA Binding Molecules of the invention are bispecific, tetravalent, Fc-bearing diabodies that comprise three epitope-binding sites immunospecific for CD137 (which may be capable of binding to the same epitope of CD137 or to two or three different epitopes of CD137), and one epitope-binding site specific for a TA.

2. Trivalent CD137×TA Binding Molecules

In one embodiment, the CD137×TA Binding Molecules of the present invention are trivalent and will comprise a first epitope-binding site (e.g., a VL1 and VH1), a second epitope-binding site (e.g., a VL2 and VH2), and a third epitope-binding site (e.g., a VL3 and VH3), and will thus be able to bind to an epitope of TA, an epitope of CD137, and a third epitope, which third epitope may be:

(a) the same or a different epitope of the TA;

(b) the same or a different epitope of CD137; or (c) an epitope of a different TA.

In certain embodiments, such "Trivalent CD137×TA Binding Molecules" of the present invention will comprise two epitope-binding sites for an epitope of CD137 (which epitopes may be the same or different), and one epitope-binding site for an epitope of a TA.

In general, such Trivalent CD137×TA Binding Molecules of the present invention are composed of three, four, five or more than five polypeptide chains that, by virtue of one or more disulfide bonds between pairs of such polypeptides, form a covalently bonded molecular complex that comprises a "Diabody-Type Binding Domain" and a "Non-Diabody-Type Binding Domain."

A "Diabody-Type Binding Domain" is the Epitope-Binding Domain of a diabody, and especially, a DART® diabody. The terms "diabody" and "DART® diabody" have been discussed above. A "Non-Diabody-Type" Binding Domain is intended to denote a Binding Domain that does not have the structure of a Diabody-Type Binding Domain. Typically, a Non-Diabody-Type Binding Domain is a Fab-Type Binding Domain or an ScFv-Type Binding Domain. As used herein, the term "Fab-Type Binding Domain" refers to an Epitope-Binding Domain that is formed by the interaction of the VL Domain of an immunoglobulin Light Chain and a complementing VH Domain of an immunoglobulin heavy chain. Fab-Type Binding Domains differ from Diabody-Type Binding Domain in that the two polypeptide chains that form a Fab-Type Binding Domain comprise only a single Epitope-Binding Domain, whereas the two polypeptide chains that form a Diabody-Type Binding Domain comprise at least two Epitope-Binding Domains. ScFv-Type Binding Domains differ from Diabody-Type Binding Domain in that VL and VH Domains of the same polypeptide chain interact to form an Epitope-Binding Domain. Thus, as used herein, Fab-Type Binding Domains and ScFv-Type Binding Domains are distinct from Diabody-Type Binding Domain.

Thus, the Trivalent CD137×TA Binding Molecules of the present invention comprise:

(I) a "first" Epitope-Binding Domain that is capable of immunospecifically binding to a "first" epitope;

(II) a "second" Epitope-Binding Domain that is capable of immunospecifically binding to a "second" epitope;

(III) a "third" Epitope-Binding Domain that is capable of immunospecifically binding to a "third" epitope; and (IV) an Fc Domain that is formed by the association of two CH2-CH3 Domains to one another;

wherein:

(A) the "first" Epitope-Binding Domain and the "second" Epitope-Binding Domain are both "Diabody-Type Binding Domains;

(B) the "third" Epitope-Binding Domain is a Non-Diabody-Type Binding Domain; and (C) one of such "first," "second," or "third" Epitope-Binding Domains binds an epitope of TA, and another of such "first," "second," or "third" Epitope-Binding Domains binds an epitope of CD137;

The epitope that is bound by the remaining Epitope-Binding Domain may be any desired epitope, for example, an epitope of CD137. Such epitope which may be the same or different from the CD137 epitope that is bound by other Epitope-Binding Domains of the molecule.

Figure 3A:
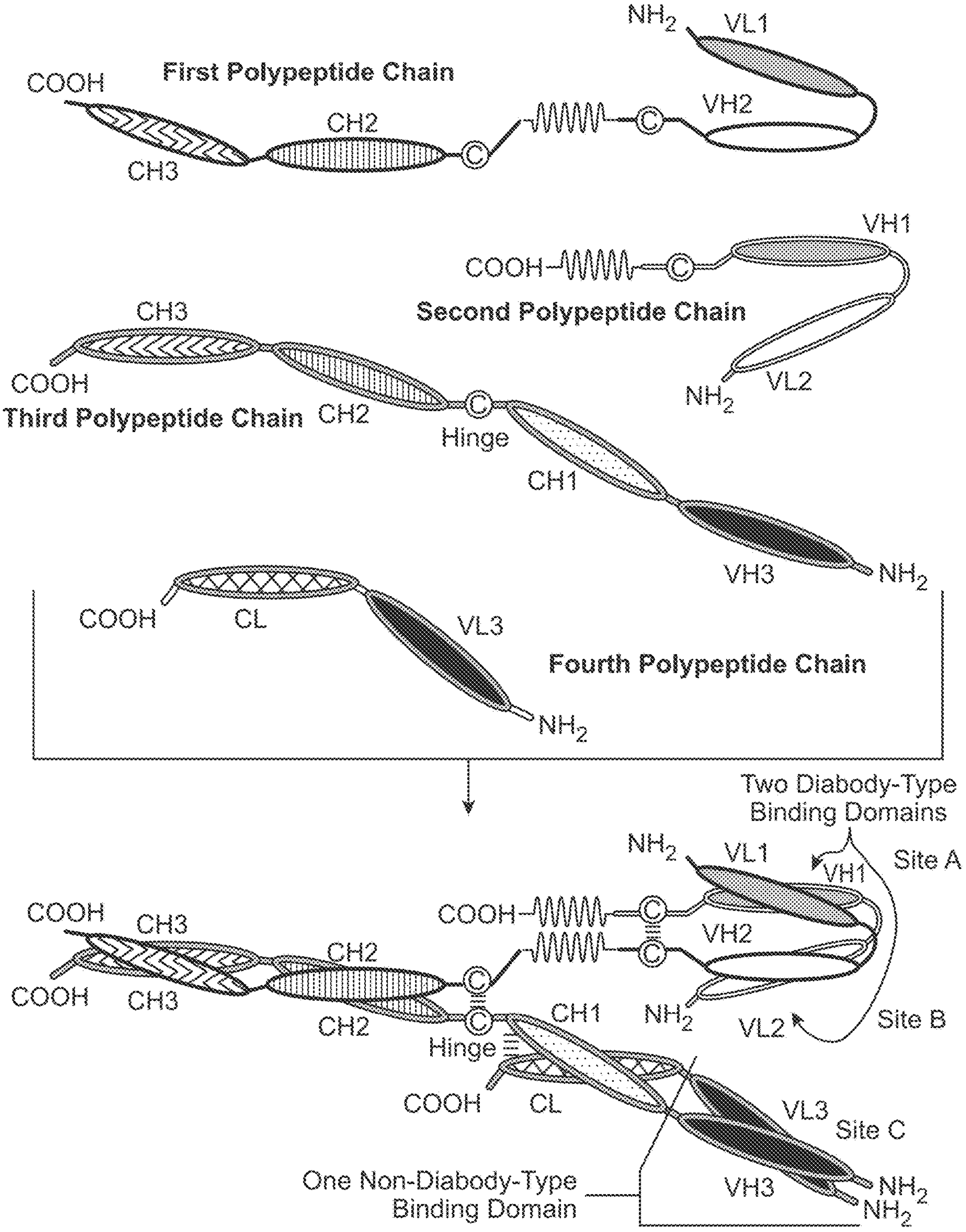
FIGS. 3A-3C provide schematics of representative Fc Region-containing trivalent binding molecules having three epitope-binding sites.
Figure 3B:
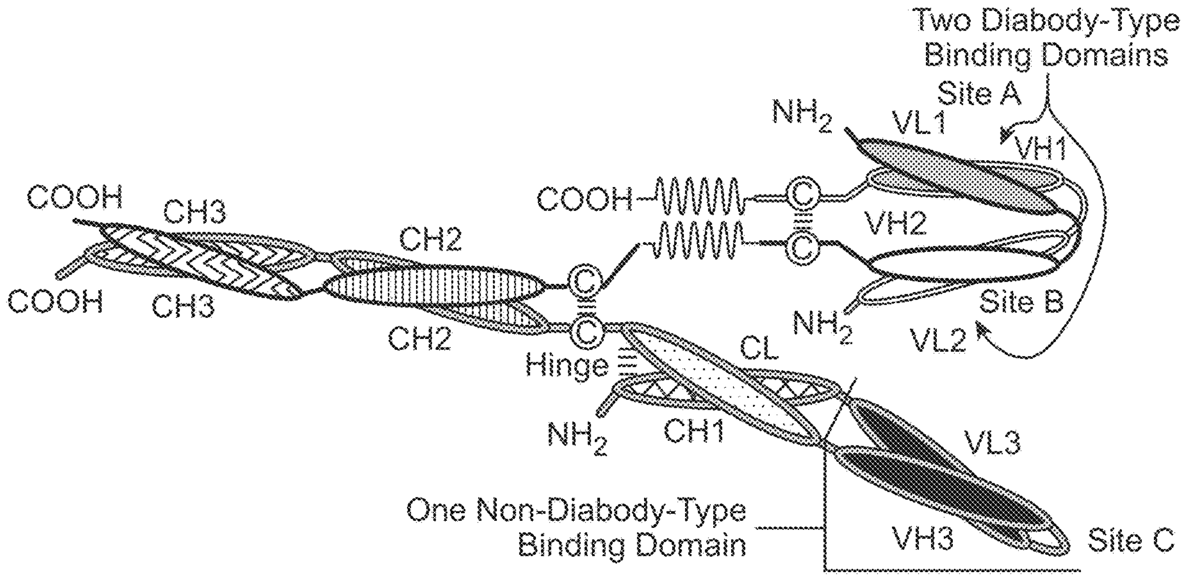
Figure 3C:
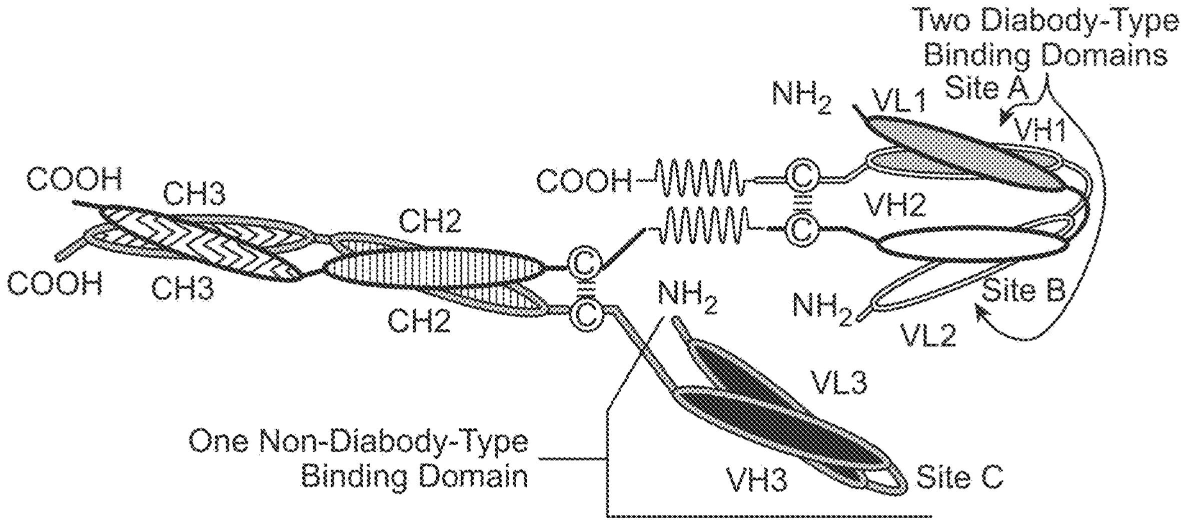

FIGS. 3A-3C provide a diagrammatic representation of the Domains of representative Trivalent CD137×TA Binding Molecules. FIG. 3A illustrates schematically the Domains of representative Trivalent CD137×TA Binding Molecules that are composed from the covalent complexing of four polypeptide chains and possess one Non-Diabody-Type Binding Site (VL3/VH3 and thus being monovalent for such epitope), and two Diabody-Type Binding Sites (VL1/VH1 and VL2/VH2, and thus being monovalent for each of such epitopes). FIGS. 3B-3C illustrate schematically the Domains of representative Trivalent CD137×TA Binding Molecules that are composed from the covalent complexing of three polypeptide chains and possess one Non-Diabody-Type Binding Site (VL3/VH3 and thus being monovalent for such epitope), and two Diabody-Type Binding Sites (VL1/VH1 and VL2/VH2, and thus being monovalent for each of such epitopes). The Non-Diabody-Type Binding Site is a Fab-Type Binding Domain in FIGS. 3A-3B and is an scFv-Type Binding Domain in FIG. 3C. As provided below, VL/VH binding sites formed by the association of the polypeptide chains may be the same or different so as to permit trivalent binding that is monospecific, bispecific, or trispecific.

II. REPRESENTATIVE CD137×TA BINDING MOLECULES

The invention provides CD137×TA Binding Molecules that are bispecific tetravalent Fc diabodies capable of simultaneously and specifically binding to CD137 and to a TA. As indicated above, the CD137×TA Binding Molecules of the present invention may comprise three, four or five polypeptide chains. The polypeptide chains of representative CD137×TA Binding Molecules capable of binding to CD137 and to the TA, PD-L1 or HER2 are provided below (designated "DART-A," "DART-A1," "DART-A2," "DART-A3," "DART-A4," "DART-A5," "DART-A6," "DART-A7," "DART-A8," "DART-A9," "DART-A10," "DART-B1," and "DART-B2"). The invention further provides CD137×TA Binding Molecule that are bispecific trivalent binding molecules capable of simultaneously and specifically binding to CD137 and to a TA. As indicated above, the trivalent CD137×TA Binding Molecules of the present invention may comprise four polypeptide chains. The polypeptide chains of representative trivalent CD137×TA Binding Molecules capable of binding to CD137 and to the TA, PD-L1, or HER2, (designated "TRIDENT-A," "TRIDENT-A4," "TRIDENT-A5," "TRIDENT-A6," "TRIDENT-B1," "TRIDENT-B1,").

A. Tetravalent CD137×TA Binding Molecules

1. DART-A

DART-A is a tetravalent CD137×CD137×TA×TA Binding Molecule having two CD137 binding sites and two binding site for the representative TA, PD-L1. DART-A is composed of four polypeptide chains, in which the first and third polypeptide chains are the same and the second and fourth polypeptide chains are the same (see FIG. 1B). DART-A comprises the binding domains of CD137 MAB-6(1.1) and hPD-L1 MAB-2(1.1).

The first and third polypeptide chains of DART-A comprise, in the N-terminal to C-terminal direction, an N-terminus, a VL domain of a monoclonal antibody capable of binding to PD-L1 ($VL_{PD-L1}$) (hPD-L1 MAB-2 VL1 (SEQ ID NO:58)), an intervening linker peptide (Linker 1; GGGSGGGG (SEQ ID NO:16)), a VH domain of a monoclonal antibody capable of binding to CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:39)), a linker (LEPKSADKTHTCPPCP (SEQ ID NO:30)), the CH2-CH3 Domain of a representative human IgG1 comprising the L234A/L235A/M252Y/S254T/T256E substitutions (SEQ ID NO:43, wherein X is absent), and a C-terminus.

Thus, the first and third polypeptide chain of DART-A are composed of: SEQ ID NO:58-SEQ ID NO:16-SEQ ID NO:46-SEQ ID NO:18-SEQ ID NO:39-SEQ ID NO:30-SEQ ID NO:43.

The amino acid sequence of the first and third polypeptide chains of DART-A is (SEQ ID NO:116):

```
DIQMTQSPSS LSASVGDRVT ITCKASQDVN TAVAWYQQKP
GKAPKLLIYW ASTRHTGVPS RFSGSGSGTD FTLTISSLQP
EDFATYYCQQ HYNTPLTFGQ GTKVEIKGGG SGGGGQVQLQ
ESGPGLVKPS ETLSLTCTVS GGSISSYYWS WIRQPPGKGL
EWIGRIYTSG STNYNPSLKS RVTMSVDTSK NQFSLKLSSV
TAADTAVYYC ARDGWYDEDY NYYGMDVWGQ GTTVTVSSGG
CGGGEVAACE KEVAALEKEV AALEKEVAAL EKLEPKSADK
THTCPPCPAP EAAGGPSVFL FPPKPKDTLY ITREPEVTCV
VVDVSHEDPE VKFNWYVDGV EVHNAKTKPR EEQYNSTYRV
VSVLTVLHQD WLNGKEYKCK VSNKALPAPI EKTISKAKGQ
PREPQVYTLP PSREEMTKNQ VSLTCLVKGF YPSDIAVEWE
SNGQPENNYK TTPPVLDSDG SFFLYSKLTV DKSRWQQGNV
FSCSVMHEAL HNHYTQKSLS LSPG
```

Alternative DART-A first and third polypeptide chains may be employed that comprise Heterodimer-Promoting (E-coil) Domain lacking a cysteine residue (EVAALEK-EVAALEK-EVAALEK-EVAALEK (SEQ ID NO:37)). Such alternative DART-A first and third polypeptide chains are composed of: SEQ ID NO:58-SEQ ID NO:16-SEQ ID NO:46-SEQ ID NO:18-SEQ ID NO:37-SEQ ID NO:30-SEQ ID NO:43. Additional alternative DART-A first and third polypeptide chains may be employed in which the amino acid residues SEQ ID NO:58 (hPD-L1 MAB-2 VL1) are replaced with the amino acid residues of SEQ ID NO:72 (hPD-L1 MAB-2 VL2). Alternative molecules comprising many of such polypeptide chains are described below.

The second and fourth polypeptide chain of DART-A comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to PD-L1 ($VH_{PD-L1}$ (hPD-L1 MAB-2 VH1, SEQ ID NO:57)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A are composed of: SEQ ID NO:50-SEQ ID NO:16-SEQ ID NO:57-SEQ ID NO:18-SEQ ID NO:40.

The amino acid sequence of the second and fourth polypeptide chain of DART-A is (SEQ ID NO:117):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIG GGTTYYPDTV KGRFTISRDN AKNTLYLQMN
SLKTEDTAVY YCARQGLPYY FDYWGQGTLV TVSSGGCGGG
KVAACKEKVA ALKEKVAALK EKVAALKE
```

Alternative DART-A second and fourth polypeptide chains may be employed that comprise a Heterodimer-Promoting (K-coil) Domain lacking a cysteine residue (e.g., KVAALKE-KVAALKE-KVAALKE-KVAALKE (SEQ ID NO:38)). Such alternative second and fourth polypeptide chains of DART-A sometimes are composed of: SEQ ID NO:50-SEQ ID NO:16-SEQ ID NO:57-SEQ ID NO:18-SEQ ID NO:38. Additional alternative DART-A first and third polypeptide chains may be employed in which the amino acid residues of SEQ ID NO:50 (CD137 MAB-6 VL1) are replaced with the amino acid residues of SEQ ID NO:55 (CD137 MAB-6 VL2), or SEQ ID NO:56 (CD137 MAB-6 VL3), and/or the amino acid residues of SEQ ID NO:57 (hPD-L1 MAB-2 VH1) are replaced with the amino acid residues of SEQ ID NO:67 (hPD-L1 MAB-2 VH2), SEQ ID NO:68 (hPD-L1 MAB-2 VH3), SEQ ID NO:69 (hPD-L1 MAB-2 VH4), SEQ ID NO:70 (hPD-L1 MAB-2 VH5), or SEQ ID NO:72 (hPD-L1 MAB-2 VH6). Alternatively, the PD-L1 VL/VH domains may be replaced with the VL/VH domains of a TA binding molecule that binds a different epitope of PD-L1 or that binds a different TA. Alternative molecules comprising many of such polypeptide chains are described below.

2. DART-A1

DART-A1 is a tetravalent CD137×CD137×TA×TA Binding Molecule having two CD137 binding sites and two binding sites for the representative TA, PD-L1. DART-A1 is composed of four polypeptide chains, in which the first and third polypeptide chains are the same and the second and fourth polypeptide chains are the same (see FIG. 3B). DART-A1 comprises the binding domains of CD137 MAB-6(1.1) and hPD-L1 MAB-2(2.1).

The first and third polypeptide chain of DART-A1 comprise, in the N-terminal to C-terminal direction, an N-terminus, a VL domain of a monoclonal antibody capable of binding to PD-L1 ($VL_{PD-L1}$) (hPD-L1 MAB-2 VL1 (SEQ ID NO:58)), an intervening linker peptide (Linker 1; GGGSGGGG (SEQ ID NO:16)), a VH domain of a monoclonal antibody capable of binding to CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:39)), a linker (LEPKSADKTHTCPPCP (SEQ ID NO:30)), the CH2-CH3 Domain of an representative human IgG1 comprising the L234A/L235A/M252Y/S254T/T256E substitutions (SEQ ID NO:43), and a C-terminus.

Thus, the first and third polypeptide chain of DART-A1 are composed of: SEQ ID NO:58-SEQ ID NO:16-SEQ ID NO:46-SEQ ID NO:18-SEQ ID NO:39-SEQ ID NO:30-SEQ ID NO:43.

The amino acid sequence of the first and third polypeptide chains of DART-A1 is (SEQ ID NO:118):

```
DIQMTQSPSS LSASVGDRVT ITCKASQDVN TAVAWYQQKP
GKAPKLLIYW ASTRHTGVPS RFSGSGSGTD FTLTISSLQP
EDFATYYCQQ HYNTPLTFGQ GTKVEIKGGG SGGGGQVQLQ
ESGPGLVKPS ETLSLTCTVS GGSISSYYWS WIRQPPGKGL
EWIGRIYTSG STNYNPSLKS RVTMSVDTSK NQFSLKLSSV
TAADTAVYYC ARDGWYDEDY NYYGMDVWGQ GTTVTVSSGG
CGGGEVAACE KEVAALEKEV AALEKEVAAL EKLEPKSADK
THTCPPCPAP EAAGGPSVFL FPPKPKDTLY ITREPEVTCV
VVDVSHEDPE VKFNWYVDGV EVHNAKTKPR EEQYNSTYRV
VSVLTVLHQD WLNGKEYKCK VSNKALPAPI EKTISKAKGQ
PREPQVYTLP PSREEMTKNQ VSLTCLVKGF YPSDIAVEWE
SNGQPENNYK TTPPVLDSDG SFFLYSKLTV DKSRWQQGNV
FSCSVMHEAL HNHYTQKSLS LSPGK
```

The second and fourth polypeptide chain of DART-A1 comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to PD-L1 ($VH_{PD-L1}$ (hPD-L1 MAB-2 VH2, SEQ ID NO:67)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A1 are composed of: SEQ ID NO:50-SEQ ID NO:16-SEQ ID NO:67-SEQ ID NO:18-SEQ ID NO:40.

The amino acid sequence of the second and fourth polypeptide chain of DART-A1 is (SEQ ID NO:119):

```
EIVMTQSPAT LSLTPGERAT LSCRASQSVS SNYLSWFQQI
PGQAPRLLIY GASTRATGIP ARFSGSGSGT DFTLTISSLQ
```

-continued

```
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIG GGTTYYPDTV KGRFTISRDN AKNSLYLQMN
SLRAEDTAVY YCARQGLPYY FDYWGQGTLV TVSSGGCGGG
KVAACKEKVA ALKEKVAALK EKVAALKE
```

It is specifically contemplated that alternative DART-A1 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A1 first/third polypeptide chains sometimes are composed of: SEQ ID NO:58-SEQ ID NO:16-SEQ ID NO:46-SEQ ID NO:18-SEQ ID NO:37-SEQ ID NO:30-SEQ ID NO:43, and such alternative DART-A1 second/fourth chains sometimes are composed of: SEQ ID NO:50-SEQ ID NO:16-SEQ ID NO:67-SEQ ID NO:18-SEQ ID NO:38.

3. DART-A2

DART-A2 is a tetravalent CD137×CD137×TA×TA Binding Molecule having two CD137 binding sites and two binding sites for the representative TA, PD-L1. DART-A2 is composed of four polypeptide chains, in which the first and third polypeptide chains are the same and the second and fourth polypeptide chains are the same (see FIG. 3B). DART-A2 comprises the binding domains of CD137 MAB-6(1.1) and hPD-L1 MAB-2(2.2).

The first and third polypeptide chain of DART-A2 comprise, in the N-terminal to C-terminal direction, an N-terminus, a VL domain of a monoclonal antibody capable of binding to PD-L1 ($VL_{PD-L1}$) (hPD-L1 MAB-2 VL2 (SEQ ID NO:72)), an intervening linker peptide (Linker 1; GGGSGGGG (SEQ ID NO:16)), a VH domain of a monoclonal antibody capable of binding to CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:39)), a linker (LEPKSADKTHTCPPCP (SEQ ID NO:30)), the CH2-CH3 Domain of an representative human IgG1 comprising the L234A/L235A/M252Y/S254T/T256E substitutions (SEQ ID NO:43), and a C-terminus.

Thus, the first and third polypeptide chain of DART-A2 are composed of: SEQ ID NO:72-SEQ ID NO:16-SEQ ID NO:46-SEQ ID NO:18-SEQ ID NO:39-SEQ ID NO:30-SEQ ID NO:43.

The amino acid sequence of the first and third polypeptide chains of DART-A2 is (SEQ ID NO:120):

```
DIQMTQSPSS LSASVGDRVT ITCKASQDVN EAVAWYQQKP
GKAPKLLIYW ASTRHTGVPS RFSGSGSGTD FTLTISSLQP
EDFATYYCQQ HYNTPLTFGQ GTKVEIKGGG SGGGGQVQLQ
ESGPGLVKPS ETLSLTCTVS GGSISSYYWS WIRQPPGKGL
EWIGRIYTSG STNYNPSLKS RVTMSVDTSK NQFSLKLSSV
TAADTAVYYC ARDGWYDEDY NYYGMDVWGQ GTTVTVSSGG
CGGGEVAACE KEVAALEKEV AALEKEVAAL EKLEPKSADK
THTCPPCPAP EAAGGPSVFL FPPKPKDTLY ITREPEVTCV
```

-continued

```
VVDVSHEDPE VKFNWYVDGV EVHNAKTKPR EEQYNSTYRV

VSVLTVLHQD WLNGKEYKCK VSNKALPAPI EKTISKAKGQ

PREPQVYTLP PSREEMTKNQ VSLTCLVKGF YPSDIAVEWE

SNGQPENNYK TTPPVLDSDG SFFLYSKLTV DKSRWQQGNV

FSCSVMHEAL HNHYTQKSLS LSPGK
```

The second and fourth polypeptide chain of DART-A2 are the same as the second and fourth polypeptide chain of DART-A1 (SEQ ID NO:119).

It is specifically contemplated that alternative DART-A2 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A2 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A2 second/fourth chains sometimes are composed of: SEQ ID NO:50-SEQ ID NO:16-SEQ ID NO:67-SEQ ID NO:18-SEQ ID NO:38.

4. DART-A3

DART-A3 is a tetravalent CD137×CD137×TA×TA Binding Molecule having two CD137 binding sites and two binding sites for the representative TA, PD-L1. DART-A3 is composed of four polypeptide chains, in which the first and third polypeptide chains are the same and the second and fourth polypeptide chains are the same (see FIG. 3B). DART-A3 comprises the binding domains of CD137 MAB-6(1.1) and hPD-L1 MAB-2(3.1).

The first and third polypeptide chain of DART-A3 are the same as the first and third polypeptide chain of DART-A1 (SEQ ID NO:118).

The second and fourth polypeptide chain of DART-A3 comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to PD-L1 ($VH_{PD\text{-}L1}$ (hPD-L1 MAB-2 VH3, SEQ ID NO:68)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A3 are composed of: SEQ ID NO:50-SEQ ID NO:16-SEQ ID NO:68-SEQ ID NO:18-SEQ ID NO:40.

The amino acid sequence of the second and fourth polypeptide chain of DART-A3 is (SEQ ID NO:121):

```
EIVMTQSPAT LSLTPGERAT LSCRASQSVS SNYLSWFQQI

PGQAPRLLIY GASTRATGIP ARFSGSGSGT DFTLTISSLQ

PEDFAVYYCQ QDYDLPWTFG QGTKVEIKGG GSGGGGEVQL

VESGGGLVQP GGSLRLSCAA SGFTFSSYTM SWVRQAPGKG

LEWVAYISIK GGTTYYPDTV KGRFTISRDN AKNSLYLQMN
```

-continued

```
SLRAEDTAVY YCARQGLPYY GDYWGQGTLV TVSSGGCGGG

KVAACKEKVA ALKEKVAALK EKVAALKE
```

It is specifically contemplated that alternative DART-A3 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A3 first/third polypeptide chains sometimes are composed of: SEQ ID NO:58-SEQ ID NO:16-SEQ ID NO:46-SEQ ID NO:18-SEQ ID NO:37-SEQ ID NO:30-SEQ ID NO:43, and such alternative DART-A3 second/fourth chains sometimes are composed of: SEQ ID NO:50-SEQ ID NO:16-SEQ ID NO:68-SEQ ID NO:18-SEQ ID NO:38.

5. DART-A4

DART-A4 is a tetravalent CD137×CD137×TA×TA Binding Molecule having two CD137 binding sites and two binding sites for the representative TA, PD-L1. DART-A4 is composed of four polypeptide chains, in which the first and third polypeptide chains are the same and the second and fourth polypeptide chains are the same (see FIG. 3B). DART-A4 comprises the binding domains of CD137 MAB-6(1.1) and hPD-L1 MAB-2(3.2).

The first and third polypeptide chain of DART-A4 are the same as the first and third polypeptide chain of DART-A2 (SEQ ID NO:120).

The second and fourth polypeptide chain of DART-A4 are the same as the second and fourth polypeptide chain of DART-A3 (SEQ ID NO:121).

It is specifically contemplated that alternative DART-A4 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A4 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A4 second/fourth chains sometimes are composed of: SEQ ID NO:50-SEQ ID NO:16-SEQ ID NO:68-SEQ ID NO:18-SEQ ID NO:38.

6. DART-A5

DART-A5 is a tetravalent CD137×CD137×TA×TA Binding Molecule having two CD137 binding sites and two binding sites for the representative TA, PD-L1. DART-A5 is composed of four polypeptide chains, in which the first and third polypeptide chains are the same and the second and fourth polypeptide chains are the same (see FIG. 3B). DART-A5 comprises the binding domains of CD137 MAB-6(1.2) and hPD-L1 MAB-2(3.2).

The first and third polypeptide chain of DART-A5 are the same as the first and third polypeptide chain of DART-A2 (SEQ ID NO:120).

The second and fourth polypeptide chain of DART-A5 comprise, in the N-terminal to C-terminal direction, an N-terminus, a VL domain of a monoclonal antibody capable of binding to CD137 ($VL_{CD137}$ (CD137 MAB-6 VL2 (SEQ ID NO:55)), an intervening linker peptide (Linker 1; GGGSGGGG (SEQ ID NO:16)), a VH domain of a monoclonal antibody capable of binding to PD-L1 ($VH_{PD\text{-}L1}$ (hPD-L1 MAB-2 VH2, SEQ ID NO:68)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A5 are composed of: SEQ ID NO:55-SEQ ID NO:16-SEQ ID NO:68-SEQ ID NO:18-SEQ ID NO:40.

The amino acid sequence of the second and fourth polypeptide chain of DART-A5 is (SEQ ID NO:122):

```
EIVMTQSPAT LSLSPGERAT LSCRASQSVS SNYLSWYQQK
PGQAPRLLIY GASTRATGIP ARFSGSGSGT DFTLTISSLQ
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIK GGTTYYPDTV KGRFTISRDN AKNSLYLQMN
SLRAEDTAVY YCARQGLPYY GDYWGQGTLV TVSSGGCGGG
KVAACKEKVA ALKEKVAALK EKVAALKE
```

It is specifically contemplated that alternative DART-A5 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A5 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A5 second/fourth chains sometimes are composed of: SEQ ID NO:55-SEQ ID NO:16-SEQ ID NO:68-SEQ ID NO:18-SEQ ID NO:38.

7. DART-A6

DART-A6 is a tetravalent CD137×CD137×TA×TA Binding Molecule having two CD137 binding sites and two binding sites for the representative TA, PD-L1. DART-A6 is composed of four polypeptide chains, in which the first and third polypeptide chains are the same and the second and fourth polypeptide chains are the same (see FIG. 3B). DART-A6 comprises the binding domains of CD137 MAB-6(1.3) and hPD-L1 MAB-2(3.2).

The first and third polypeptide chain of DART-A6 are the same as the first and third polypeptide chain of DART-A2 (SEQ ID NO:120).

The second and fourth polypeptide chain of DART-A6 comprise, in the N-terminal to C-terminal direction, an N-terminus, a VL domain of a monoclonal antibody capable of binding to CD137 ($VL_{CD137}$ (CD137 MAB-6 VL3 (SEQ ID NO:56)), an intervening linker peptide (Linker 1; GGGSGGGG (SEQ ID NO:16)), a VH domain of a monoclonal antibody capable of binding to PD-L1 ($VH_{PD\text{-}L1}$ (hPD-L1 MAB-2 VH3, SEQ ID NO:68)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A6 are composed of: SEQ ID NO:56-SEQ ID NO:16-SEQ ID NO:68-SEQ ID NO:18-SEQ ID NO:40.

The amino acid sequence of the second and fourth polypeptide chain of DART-A6 is (SEQ ID NO:123):

```
EIVMTQSPAT LSLSPGERAT LSCRASQSVS SNYLSWFQQK
PGQAPRLLIY GASTRATGIP ARFSGSGSGT DFTLTISSLQ
```

-continued

```
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIK GGTTYYPDTV KGRFTISRDN AKNSLYLQMN
SLRAEDTAVY YCARQGLPYY GDYWGQGTLV TVSSGGCGGG
KVAACKEKVA ALKEKVAALK EKVAALKE
```

It is specifically contemplated that alternative DART-A6 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A6 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A6 second/fourth chains sometimes are composed of: SEQ ID NO:56-SEQ ID NO:16-SEQ ID NO:68-SEQ ID NO:18-SEQ ID NO:38.

8. DART-A7

DART-A7 is a tetravalent CD137×CD137×TA×TA Binding Molecule having two CD137 binding sites and two binding sites for the representative TA, PD-L1. DART-A7 is composed of four polypeptide chains, in which the first and third polypeptide chains are the same and the second and fourth polypeptide chains are the same (see FIG. 3B). DART-A7 comprises the binding domains of CD137 MAB-6(1.1) and hPD-L1 MAB-2(4.2).

The first and third polypeptide chain of DART-A7 are the same as the first and third polypeptide chain of DART-A2 (SEQ ID NO:120).

The second and fourth polypeptide chain of DART-A7 comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to PD-L1 ($VH_{PD\text{-}L1}$ (hPD-L1 MAB-2 VH4, SEQ ID NO:69)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A7 are composed of: SEQ ID NO:50-SEQ ID NO:16-SEQ ID NO:69-SEQ ID NO:18-SEQ ID NO:40.

The amino acid sequence of the second and fourth polypeptide chain of DART-A7 is (SEQ ID NO:124):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIG GGTTYYPDTV KGRFTISRDN AKNSLYLQMN
SLRAEDTAVY YCARAGLPYY FDYWGQGTLV TVSSGGCGGG
KVAACKEKVA ALKEKVAALK EKVAALKE
```

It is specifically contemplated that alternative DART-A7 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A7 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A7 second/fourth chains sometimes are composed of: SEQ ID NO:50-SEQ ID NO:16-SEQ ID NO:69-SEQ ID NO:18-SEQ ID NO:38.

9. DART-A8

DART-A8 is a tetravalent CD137×CD137×TA×TA Binding Molecule having two CD137 binding sites and two binding sites for the representative TA, PD-L1. DART-A8 is composed of four polypeptide chains, in which the first and third polypeptide chains are the same and the second and fourth polypeptide chains are the same (see FIG. 3B). DART-A8 comprises the binding domains of CD137 MAB-6(1.1) and hPD-L1 MAB-2(5.2).

The first and third polypeptide chain of DART-A8 are the same as the first and third polypeptide chain of DART-A2 (SEQ ID NO:120).

The second and fourth polypeptide chain of DART-A8 comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to PD-L1 ($VH_{PD-L1}$ (hPD-L1 MAB-2 VH5, SEQ ID NO:70)), an intervening linker peptide (Linker 2; GGCGGG (SEQ ID NO:18)), a Heterodimer-Promoting (K-coil) Domain (KVAAQKE-KVAALKE-KVAALKE-KVAALKE (SEQ ID NO:40), and a C-terminus.

Thus, the second and fourth polypeptide chain of DART-A8 are composed of: SEQ ID NO:50-SEQ ID NO:16-SEQ ID NO:70-SEQ ID NO:18-SEQ ID NO:40.

The amino acid sequence of the second and fourth polypeptide chain of DART-A8 is (SEQ ID NO:125):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIK GGTTYYPDTV KGRFTISRDN AKNSLYLQMN
SLRAEDTAVY YCARAGLPYY FDYWGQGTLV TVSSGGCGGG
KVAACKEKVA ALKEKVAALK EKVAALKE
```

It is specifically contemplated that alternative DART-A8 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A8 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A8 second/fourth chains sometimes are composed of: SEQ ID NO:50-SEQ ID NO:16-SEQ ID NO:70-SEQ ID NO:18-SEQ ID NO:38.

10. DART-A9

DART-A9 is a tetravalent CD137×CD137×TA×TA Binding Molecule having two CD137 binding sites and two binding sites for the representative TA, PD-L1. DART-A9 is composed of four polypeptide chains, in which the first and third polypeptide chains are the same and the second and fourth polypeptide chains are the same (see FIG. 3B). DART-A9 comprises the binding domains of CD137 MAB-6(1.1) and hPD-L1 MAB-2(6.2).

The first and third polypeptide chain of DART-A9 are the same as the first and third polypeptide chain of DART-A2 (SEQ ID NO:120).

The second and fourth polypeptide chain of DART-A9 comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to PD-L1 ($VH_{PD-L1}$ (hPD-L1 MAB-2 VH6, SEQ ID NO:71)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A9 are composed of: SEQ ID NO:50-SEQ ID NO:16-SEQ ID NO:71-SEQ ID NO:18-SEQ ID NO:40.

The amino acid sequence of the second and fourth polypeptide chain of DART-A9 is (SEQ ID NO:126):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIG GGTTYYPDTV KGRFTISRDN AKNSLYLQMN
SLRAEDTAVY YCARAGLPYY GDYWGQGTLV TVSSGGCGGG
KVAACKEKVA ALKEKVAALK EKVAALKE
```

It is specifically contemplated that alternative DART-A9 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A9 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A9 second/fourth chains sometimes are composed of: SEQ ID NO:50-SEQ ID NO:16-SEQ ID NO:71-SEQ ID NO:18-SEQ ID NO:38.

11. DART-A10

DART-A10 is a tetravalent CD137×CD137×TA×TA Binding Molecule having two CD137 binding sites and two binding sites for the representative TA, PD-L1. DART-A10 is composed of four polypeptide chains, in which the first and third polypeptide chains are the same and the second and fourth polypeptide chains are the same (see FIG. 3B). DART-A10 comprises the binding domains of CD137 MAB-6(1.3) and hPD-L1 MAB-2(4.2).

The first and third polypeptide chain of DART-A10 are the same as the first and third polypeptide chain of DART-A2 (SEQ ID NO:120).

The second and fourth polypeptide chain of DART-A10 comprise, in the N-terminal to C-terminal direction, an N-terminus, a VL domain of a monoclonal antibody capable of binding to CD137 ($VL_{CD137}$ (CD137 MAB-6 VL3 (SEQ ID NO:56)), an intervening linker peptide (Linker 1; GGGSGGGG (SEQ ID NO:16)), a VH domain of a monoclonal antibody capable of binding to PD-L1 ($VH_{PD-L1}$ (hPD-L1 MAB-2 VH4, SEQ ID NO:69)), an intervening linker peptide (Linker 2; GGCGGG (SEQ ID NO:18)), a Heterodimer-Promoting (K-coil) Domain (KVAACKE-KVAALKE-KVAALKE-KVAALKE (SEQ ID NO:40), and a C-terminus.

Thus, the second and fourth polypeptide chain of DART-A10 are composed of: SEQ ID NO:56-SEQ ID NO:16-SEQ ID NO:69-SEQ ID NO:18-SEQ ID NO:40.

The amino acid sequence of the second and fourth polypeptide chain of DART-A10 is (SEQ ID NO:139):

```
EIVMTQSPAT LSLSPGERAT LSCRASQSVS SNYLSWFQQK
PGQAPRLLIY GASTRATGIP ARFSGSGSGT DFTLTISSLQ
PEDFAVYYCQ QDYDLPWTFG QGTKVEIKGG GSGGGGEVQL
VESGGGLVQP GGSLRLSCAA SGFTFSSYTM SWVRQAPGKG
LEWVAYISIG GGTTYYPDTV KGRFTISRDN AKNSLYLQMN
SLRAEDTAVY YCARAGLPYY FDYWGQGTLV TVSSGGCGGG
KVAACKEKVA ALKEKVAALK EKVAALKE
```

It is specifically contemplated that alternative DART-A10 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-A10 first/third polypeptide chains sometimes are composed of: SEQ ID NO:72-SEQ ID NO:16-SEQ ID NO:46-SEQ ID NO:18-SEQ ID NO:37-SEQ ID NO:30-SEQ ID NO:43, and such alternative DART-A10 second/fourth chains sometimes are composed of: SEQ ID NO:56-SEQ ID NO:16-SEQ ID NO:69-SEQ ID NO:18-SEQ ID NO:38.

12. DART-B1

DART-B1 is a bivalent CD137×TA Binding Molecule having one CD137 binding site and one binding site for the representative TA, HER2. DART-B1 is composed of three polypeptide chains, in which the first, second, and third polypeptide chains are different (see FIG. 1D). DART-B1 comprises the binding domains of CD137 MAB-6(1.1) and hHER2 MAB-1(1.3).

The first polypeptide chain of DART-B1 comprises, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to HER2 ($VH_{HER2}$ (hHER2 MAB-1 VH1, SEQ ID NO:80)), an intervening linker peptide (Linker 2; GGCGGG (SEQ ID NO:18)), a Heterodimer-Promoting (E-coil) Domain (EVAALEK-EVAALEK-EVAALEK-EVAALEK (SEQ ID NO:37)), an intervening linker peptide (GGGDKTHTCPPCP (SEQ ID NO:21)), a "knob-bearing" CH2 and CH3 Domain comprising the L234A/L235A/M252Y/S254T/T256E substitutions (SEQ ID NO:146), and a C-terminus.

Thus, the first polypeptide chain of DART-B1 is composed of: SEQ ID NO:50-SEQ ID NO:16-SEQ ID NO:80-SEQ ID NO:18-SEQ ID NO:37-SEQ ID NO:21-SEQ ID NO:146.

The amino acid sequence of the first polypeptide chain of DART-B1 is (SEQ ID NO:143):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGQVQL
VQSGAEVKKP GASVKVSCKA SGYTFTNYGM NWVRQAPGQG
LEWMGWINTN IGEPTYTEEF KGRVTMTRDT SISTAYMELS
RLRSDDTAVY YCARDDGYGN RVSYWGQGTL VTVSSGGCGG
GEVAALEKEV AALEKEVAAL EKEVAALEKG GGDKTHTCPP
CPAPEAAGGP SVFLFPPKPK DTLYITREPE VTCVVVDVSH
EDPEVKFNWY VDGVEVHNAK TKPREEQYNS TYRVVSVLTV
LHQDWLNGKE YKCKVSNKAL PAPIEKTISK AKGQPREPQV
YTLPPSREEM TKNQVSLWCL VKGFYPSDIA VEWESNGQPE
NNYKTTPPVL DSDGSFFLYS KLTVDKSRWQ QGNVFSCSVM
HEALHNHYTQ KSLSLSPGK
```

The second polypeptide chain of DART-B1 comprises, in the N-terminal to C-terminal direction, an N-terminus, a VL domain of a monoclonal antibody capable of binding to HER2 ($VL_{HER2}$ (hHER2 MAB-1 VL3, SEQ ID NO:85)), an intervening linker peptide (Linker 1; GGGSGGGG (SEQ ID NO:16)), a VH domain of a monoclonal antibody capable of binding to CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (K-coil) Domain (KVAALKE-KVAALKE-KVAALKE-KVAALKE (SEQ ID NO:38)), and a C-terminus.

Thus, the second polypeptide chain of DART-B1 is composed of: SEQ ID NO:85-SEQ ID NO:16-SEQ ID NO:46-SEQ ID NO:18-SEQ ID NO:38.

The amino acid sequence of the second polypeptide chain of DART-B1 is (SEQ ID NO:144):

```
DIQMTQSPSS LSASVGDRVT ITCKASQDIS NYLSWFQQKP
GKAPKTLIYR ANRLQSGVPS RFSGSGSGTD FTLTISSLQP
EDFATYYCLQ HDEFPWTFGQ GTKLEIKGGG SGGGGQVQLQ
ESGPGLVKPS ETLSLTCTVS GGSISSYYWS WIRQPPGKGL
EWIGRIYTSG STNYNPSLKS RVTMSVDTSK NQFSLKLSSV
TAADTAVYYC ARDGWYDEDY NYYGMDVWGQ GTTVTVSSGG
CGGGKVAALK EKVAALKEKV AALKEKVAAL KE
```

The third polypeptide chain of DART-B1 comprises, in the N-terminal to C-terminal direction, a Linker DKTHTCPPCP (SEQ ID NO:20) and a "hole-bearing" CH2 and CH3 Domain comprising the L234A/L235A/M252Y/S254T/T256E/H435R substitutions (SEQ ID NO:149).

Thus the third polypeptide chain of DART-B1 is composed of: SEQ ID NO:20-SEQ ID NO:149.

As will be recognized, the third polypeptide chain of DART-B does not contain any Epitope-Binding Domains and may thus be employed in various CD137×TA Binding Molecules having the diabody structure shown in FIG. 1D.

The third polypeptide chain of DART-B1 has the amino acid sequence of SEQ ID NO:145:

```
DKTHTCPPCP APEAAGGPSV FLFPPKPKDT LMISRTPEVT
CVVVDVSHED PEVKFNWYVD GVEVHNAKTK PREEQYNSTY
RVVSVLTVLH QDWLNGKEYK CKVSNKALPA PIEKTISKAK
GQPREPQVYT LPPSREEMTK NQVSLSCAVK GFYPSDIAVE
WESNGQPENN YKTTPPVLDS DGSFFLVSKL TVDKSRWQQG
NVFSCSVMHE ALHNRYTQKS LSLSPGK
```

13. DART-B2

DART-B2 is a tetravalent CD137×CD137×TA×TA Binding Molecule having two CD137 binding sites and two binding site for the representative TA, HER2. DART-B1 is composed of four polypeptide chains, in which the first and third polypeptide chains are the same and the second and fourth polypeptide chains are the same (see FIG. 1B). DART-B1 comprises the binding domains of CD137 MAB-6(1.1) and hHER2 MAB-1(1.3).

The first and third polypeptide chains of DART-B2 comprises, in the N-terminal to C-terminal direction, an N-terminus, a VL domain of a monoclonal antibody capable of binding to HER2 ($VL_{HER2}$ (hHER2 MAB-1 VL3, SEQ ID NO:85)), an intervening linker peptide (Linker 1; GGGSGGGG (SEQ ID NO:16)), a VH domain of a monoclonal antibody capable of binding to CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil) Domain (EVAACEK-EVAALEK-EVAALEK-EVAALEK (SEQ ID NO:39)), a linker (LEPKSADKTHTCPPCP (SEQ ID NO:30)), the CH2-CH3 Domain of a representative human IgG1 comprising the L234A/L235A/M252Y/S254T/T256E substitutions (SEQ ID NO:43, wherein X is absent), and a C-terminus.

Thus, the first and third polypeptide chain of DART-B2 are composed of: SEQ ID NO:85-SEQ ID NO:16-SEQ ID NO:46-SEQ ID NO:18-SEQ ID NO:39-SEQ ID NO:30-SEQ ID NO:43.

The amino acid sequence of the first and third polypeptide chains of DART-B2 is (SEQ ID NO:151):

```
DIQMTQSPSS LSASVGDRVT ITCKASQDIS NYLSWFQQKP
GKAPKTLIYR ANRLQSGVPS RFSGSGSGTD FTLTISSLQP
EDFATYYCLQ HDEFPWTFGQ GTKLEIKGGG SGGGGQVQLQ
ESGPGLVKPS ETLSLTCTVS GGSISSYYWS WIRQPPGKGL
EWIGRIYTSG STNYNPSLKS RVTMSVDTSK NQFSLKLSSV
TAADTAVYYC ARDGWYDEDY NYYGMDVWGQ GTTVTVSSGG
CGGGEVAACE KEVAALEKEV AALEKEVAAL EKLEPKSADK
THTCPPCPAP EAAGGPSVFL FPPKPKDTLY ITREPEVTCV
VVDVSHEDPE VKFNWYVDGV EVHNAKTKPR EEQYNSTYRV
VSVLTVLHQD WLNGKEYKCK VSNKALPAPI EKTISKAKGQ
PREPQVYTLP PSREEMTKNQ VSLTCLVKGF YPSDIAVEWE
```

-continued

```
SNGQPENNYK TTPPVLDSDG SFFLYSKLTV DKSRWQQGNV
FSCSVMHEAL HNHYTQKSLS LSPGK
```

The second and fourth polypeptide chain of DART-B2 comprise, in the N-terminal to C-terminal direction, an N-terminus, a VL domain of a monoclonal antibody capable of binding to CD137 ($VL_{CD137}$ (CD137 MAB-6 VL1 (SEQ ID NO:50)), an intervening linker peptide (Linker 1; GGGSGGGG (SEQ ID NO:16)), a VH domain of a monoclonal antibody capable of binding to HER2 ($VH_{HER2}$ (hHER2 MAB-1 VH1, SEQ ID NO:80)), an intervening linker peptide (Linker 2; GGCGGG (SEQ ID NO:18)), a Heterodimer-Promoting (K-coil) Domain (KVAAQKE-KVAALKE-KVAALKE-KVAALKE (SEQ ID NO:40), and a C-terminus.

Thus, the second and fourth polypeptide chain of DART-B2 are composed of: SEQ ID NO:50-SEQ ID NO:16-SEQ ID NO:80-SEQ ID NO:18-SEQ ID NO:40.

The amino acid sequence of the second and fourth polypeptide chains of DART-B2 is (SEQ ID NO:152):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGQVQL
VQSGAEVKKP GASVKVSCKA SGYTFTNYGM NWVRQAPGQG
LEWMGWINTN IGEPTYTEEF KGRVTMTRDT SISTAYMELS
RLRSDDTAVY YCARDDGYGN RVSYWGQGTL VTVSSGGCGG
GKVAACKEKV AALKEKVAAL KEKVAALKE
```

It is specifically contemplated that alternative DART-B2 first/third and second/forth polypeptide chains may be employed that comprise Heterodimer-Promoting (E-coil and K-coil) Domains lacking a cysteine residue (e.g., EVAALEK-EVAALEK-EVAALEK-EVAALEK (SEQ ID NO:37) and KVAALKE-KVAALKE-KVAALKE-KVAALKE (SEQ ID NO:38)). Such alternative DART-B2 first/third polypeptide chains sometimes are composed of: SEQ ID NO:85-SEQ ID NO:16-SEQ ID NO:46-SEQ ID NO:18-SEQ ID NO:37-SEQ ID NO:30-SEQ ID NO:43, and such alternative DART-B2 second/fourth chains sometimes are composed of: SEQ ID NO:50-SEQ ID NO:16-SEQ ID NO:80-SEQ ID NO:18-SEQ ID NO:38.

B. Trivalent CD137×TA Binding Molecules

1. TRIDENT-A

TRIDENT-A is a trivalent CD137×CD137×TA Binding Molecule having two CD137 binding sites and one binding site for the representative TA, PD-L1. TRIDENT-A is composed of four polypeptide chains (see, FIG. 3A, wherein VL1/VH1 (Site A) are the same as VL2/VH2 (Site B) and bind CD137, and VL3/VH3 (Site C) bind PD-L1). TRIDENT-A comprises the binding domains of CD137 MAB-6(1.1) and hPD-L1 MAB-2(1.1).

The first polypeptide chain of TRIDENT-A comprises, in the N-terminal to C-terminal direction, an N-terminus, a VL domain of a monoclonal antibody capable of binding CD137 ($VL_{CD137}$) (CD137 MAB-6 VL1 (SEQ ID NO:50)), an intervening linker peptide (Linker 1; GGGSGGGG (SEQ ID NO:16)), a VH domain of a monoclonal antibody capable of binding CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil)

Domain (EVAALEK-EVAALEK-EVAALEK-EVAALEK (SEQ ID NO:37)), an intervening linker peptide (GGGDKTHTCPPCP (SEQ ID NO:21)), a "knob-bearing" CH2 and CH3 Domain comprising the L234A/L235A/M252Y/S254T/T256E substitutions (SEQ ID NO:146), and a C-terminus.

Thus, the first polypeptide chain of TRIDENT-A is composed of: SEQ ID NO:50-SEQ ID NO:16-SEQ ID NO:46-SEQ ID NO:18-SEQ ID NO:37-SEQ ID NO:21-SEQ ID NO:146.

The amino acid sequence of the first polypeptide chain of TRIDENT-A is (SEQ ID NO:127):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGQVQL
QESGPGLVKP SETLSLTCTV SGGSISSYYW SWIRQPPGKG
LEWIGRIYTS GSTNYNPSLK SRVTMSVDTS KNQFSLKLSS
VTAADTAVYY CARDGWYDED YNYYGMDVWG QGTTVTVSSG
GCGGGEVAAL EKEVAALEKE VAALEKEVAA LEKGGGDKTH
TCPPCPAPEA AGGPSVFLFP PKPKDTLYIT REPEVTCVVV
DVSHEDPEVK FNWYVDGVEV HNAKTKPREE QYNSTYRVVS
VLTVLHQDWL NGKEYKCKVS NKALPAPIEK TISKAKGQPR
EPQVYTLPPS REEMTKNQVS LWCLVKGFYP SDIAVEWESN
GQPENNYKTT PPVLDSDGSF FLYSKLTVDK SRWQQGNVFS
CSVMHEALHN HYTQKSLSLS PGK
```

The second polypeptide chain of TRIDENT-A comprises, in the N-terminal to C-terminal direction, an N-terminus, a VL domain of a monoclonal antibody capable of binding CD137 ($VL_{CD137}$) (CD137 MAB-6 VL1 (SEQ ID NO:50)), an intervening linker peptide (Linker 1; GGGSGGGG (SEQ ID NO:16)), a VH domain of a monoclonal antibody capable of binding CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (K-coil) Domain (KVAALKE-KVAALKE-KVAALKE-KVAALKE (SEQ ID NO:38)), and a C-terminus.

Thus, the second polypeptide chain of TRIDENT-A is composed of: SEQ ID NO:50-SEQ ID NO:16-SEQ ID NO:46-SEQ ID NO:18-SEQ ID NO:38.

The amino acid sequence of the second polypeptide chain of TRIDENT-A is (SEQ ID NO:128):

```
EIVMTQSPAT LSLTPGERAT LSCRASQSVS SNYLSWFQQI
PGQAPRLLIY GASTRATGIP ARFSGSGSGT DFTLTISSLQ
PEDFAVYYCQ QDYDLPWTFG QGTKVEIKGG GSGGGGQVQL
QESGPGLVKP SETLSLTCTV SGGSISSYYW SWIRQPPGKG
LEWIGRIYTS GSTNYNPSLK SRVTMSVDTS KNQFSLKLSS
VTAADTAVYY CARDGWYDED YNYYGMDVWG QGTTVTVSSG
GCGGGKVAAL KEKVAALKEK VAALKEKVAA LKE
```

Alternative TRIDENT-A first and second polypeptide chains may be employed that comprise Heterodimer-Promoting (E-coil and K-coil) Domains comprising a cysteine residue (e.g., EVAACEK-EVAALEK-EVAALEK-EVAALEK (SEQ ID NO:39) and KVAACKE-KVAALKE-KVAALKE-KVAALKE (SEQ ID NO:40)). In such alternative TRIDENT-A molecules, the first polypeptide chain sometimes is composed of: SEQ ID NO:50-SEQ ID NO:16-SEQ ID NO:46-SEQ ID NO:18-SEQ ID NO:39-SEQ ID NO:21-SEQ ID NO:146 and the second polypeptide chain sometimes is composed of SEQ ID NO:50-SEQ ID NO:16-SEQ ID NO:46-SEQ ID NO:18-SEQ ID NO:40. Additional alternative TRIDENT-A first and second polypeptide chains may be employed in which the amino acid residues of SEQ ID NO:50 (CD137 MAB-6 VL1) are replaced with the amino acid residues of SEQ ID NO:55 (CD137 MAB-6 VL2), or SEQ ID NO:56 (CD137 MAB-6 VL3). It is also specifically contemplated that one CD137 VL/VH domain pair may be replaced with the VL/VH pair of a TA binding molecule. Alternative molecules comprising many of such polypeptide chains are described below.

The third polypeptide chain of TRIDENT-A comprises, in the N-terminal to C-terminal direction, an N-terminus, a VH domain of a monoclonal antibody capable of binding to PD-L1 ($VH_{PD-L1}$) (hPD-L1 MAB-2 VH1 (SEQ ID NO:57)), a human IgG1 CH1 Domain (SEQ ID NO:3), a human IgG1 Hinge Region (SEQ ID NO:7), and a "hole-bearing" CH2 and CH3 Domain comprising the L234A/L235A/M252Y/S254T/T256E/H435R substitutions (SEQ ID NO:149).

Thus, the third polypeptide chain of TRIDENT-A is composed of: SEQ ID NO:57-SEQ ID NO:3-SEQ ID NO:7-SEQ ID NO:149.

The amino acid sequence of the third polypeptide chain of TRIDENT-A is (SEQ ID NO:129):

```
EVQLVESGGG LVQPGGSLRL SCAASGFTFS SYTMSWVRQA
PGKGLEWVAY ISIGGGTTYY PDTVKGRFTI SRDNAKNTLY
LQMNSLKTED TAVYYCARQG LPYYFDYWGQ GTLVTVSSAS
TKGPSVFPLA PSSKSTSGGT AALGCLVKDY FPEPVTVSWN
SGALTSGVHT FPAVLQSSGL YSLSSVVTVP SSSLGTQTYI
CNVNHKPSNT KVDKRVEPKS CDKTHTCPPC PAPEAAGGPS
VFLFPPKPKD TLYITREPEV TCVVVDVSHE DPEVKFNWYV
DGVEVHNAKT KPREEQYNST YRVVSVLTVL HQDWLNGKEY
KCKVSNKALP APIEKTISKA KGQPREPQVY TLPPSREEMT
KNQVSLSCAV KGFYPSDIAV EWESNGQPEN NYKTTPPVLD
SDGSFFLVSK LTVDKSRWQQ GNVFSCSVMH EALHNRYTQK
SLSLSPGK
```

The fourth polypeptide chain of TRIDENT-A comprises, in the N-terminal to C-terminal direction, an N-terminus, a VL domain of a monoclonal antibody capable of binding to PD-L1 ($VL_{PD-L1}$) (hPD-L1 MAB-1 VL1 (SEQ ID NO:58)), a human IgG CL Kappa Domain (SEQ ID NO:1), and a C-terminus.

Thus, the fourth polypeptide chain of TRIDENT-A is composed of: SEQ ID NO:69-SEQ ID NO:1.

The amino acid sequence of the fourth polypeptide chain of TRIDENT-A is (SEQ ID NO:130):

```
DIQMTQSPSS LSASVGDRVT ITCKASQDVN TAVAWYQQKP
GKAPKLLIYW ASTRHTGVPS RFSGSGSGTD FTLTISSLQP
```

-continued

```
EDFATYYCQQ HYNTPLTFGQ GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

Alternative TRIDENT-A third and fourth polypeptide chains may be employed in which the amino acid residues of SEQ ID NO:57 (hPD-L1 MAB-2 VH1) are replaced with the amino acid residues of SEQ ID NO:67 (hPD-L1 MAB-2 VH2), SEQ ID NO:68 (hPD-L1 MAB-2 VH3), SEQ ID NO:69 (hPD-L1 MAB-2 VH4), SEQ ID NO:70 (hPD-L1 MAB-2 VH5), or SEQ ID NO:72 (hPD-L1 MAB-2 VH6), and/or the amino acid residues of SEQ ID NO:58 (hPD-L1 MAB-2 VL1) are replaced with the amino acid residues of SEQ ID NO:72 (hPD-L1 MAB-2 VL2). Alternatively, the PD-L1 VL/VH domains may be replaced with the VL/VH domains of a TA binding molecule that binds a different epitope of PD-L1 or that binds a different TA. It is also specifically contemplated that where a TA binding site is formed by the association of the first and second polypeptide chains, the VL/VH Domains of the third and fourth polypeptide chains may be replaced with any of the CD137 MAB-6 VL/VH domains provided herein. Alternative molecules comprising several of such polypeptide chains are described below.

2. TRIDENT-A4

TRIDENT-A4 is a trivalent CD137×CD137×TA Binding Molecule having two CD137 binding sites and one binding site for the representative TA, PD-L1. TRIDENT-A4 is composed of four polypeptide chains (see, FIG. 3A, wherein VL1/VH1 (Site A) are the same as VL2/VH2 (Site B) and bind CD137, and VL3/VH3 (Site C) bind PD-L1). TRIDENT-A4 comprises the binding domains of CD137 MAB-6(1.1) and hPD-L1 MAB-2(3.2).

The first polypeptide chain of TRIDENT-A4 is the same as the first polypeptide chain of TRIDENT-A (SEQ ID NO:127).

The second polypeptide chain of TRIDENT-A4 is the same as the second polypeptide chain of TRIDENT-A (SEQ ID NO:128).

It is specifically contemplated that alternative TRIDENT-A4 first and second polypeptide chains may be employed that comprise Heterodimer-Promoting (E-coil and K-coil) Domains comprising a cysteine residue (e.g., EVAACEK-EVAALEK-EVAALEK-EVAALEK (SEQ ID NO:39) and KVAACKE-KVAALKE-KVAALKE-KVAALKE (SEQ ID NO:40)). In such alternative TRIDENT-A4 molecules, the first polypeptide chain sometimes is composed of: SEQ ID NO:50-SEQ ID NO:16-SEQ ID NO:46-SEQ ID NO:18-SEQ ID NO:39-SEQ ID NO:21-SEQ ID NO:146 and the second polypeptide chain sometimes is composed of SEQ ID NO:50-SEQ ID NO:16-SEQ ID NO:46-SEQ ID NO:18-SEQ ID NO:40.

The third polypeptide chain of TRIDENT-A4 comprises, in the N-terminal to C-terminal direction, an N-terminus, a VH domain of a monoclonal antibody capable of binding to PD-L1 ($VH_{PD-L1}$) (hPD-L1 MAB-2 VH3 (SEQ ID NO:68)), a human IgG1 CH1 Domain (SEQ ID NO:3), a human IgG1 Hinge Region (SEQ ID NO:7), and a "hole-bearing" CH2 and CH3 Domain comprising the L234A/L235A/M252Y/S254T/T256E/H435R substitutions (SEQ ID NO:149).

Thus, the third polypeptide chain of TRIDENT-A4 is composed of: SEQ ID NO:68-SEQ ID NO:3-SEQ ID NO:7-SEQ ID NO:149.

The amino acid sequence of the third polypeptide chain of TRIDENT-A4 is (SEQ ID NO:131):

```
EVQLVESGGG LVQPGGSLRL SCAASGFTFS SYTMSWVRQA

PGKGLEWVAY ISIKGGTTYY PDTVKGRFTI SRDNAKNSLY

LQMNSLRAED TAVYYCARQG LPYYGDYWGQ GTLVTVSSAS

TKGPSVFPLA PSSKSTSGGT AALGCLVKDY FPEPVTVSWN

SGALTSGVHT FPAVLQSSGL YSLSSVVTVP SSSLGTQTYI

CNVNHKPSNT KVDKRVEPKS CDKTHTCPPC PAPEAAGGPS

VFLFPPKPKD TLYITREPEV TCVVVDVSHE DPEVKFNWYV

DGVEVHNAKT KPREEQYNST YRVVSVLTVL HQDWLNGKEY

KCKVSNKALP APIEKTISKA KGQPREPQVY TLPPSREEMT

KNQVSLSCAV KGFYPSDIAV EWESNGQPEN NYKTTPPVLD

SDGSFFLVSK LTVDKSRWQQ GNVFSCSVMH EALHNRYTQK

SLSLSPGK
```

The fourth polypeptide chain of TRIDENT-A4 comprises, in the N-terminal to C-terminal direction, an N-terminus, a VL domain of a monoclonal antibody capable of binding to PD-L1 ($VL_{PD-L1}$) (hPD-L1 MAB-1 VL2 (SEQ ID NO:72)), a human IgG CL Kappa Domain (SEQ ID NO:1), and a C-terminus.

Thus, the fourth polypeptide chain of TRIDENT-A4 is composed of: SEQ ID NO:72-SEQ ID NO:1.

The amino acid sequence of the fourth polypeptide chain of TRIDENT-A is (SEQ ID NO:132):

```
DIQMTQSPSS LSASVGDRVT ITCKASQDVN EAVAWYQQKP

GKAPKLLIYW ASTRHTGVPS RFSGSGSGTD FTLTISSLQP

EDFATYYCQQ HYNTPLTFGQ GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

3. TRIDENT-A5

TRIDENT-A5 is a trivalent CD137×CD137×TA Binding Molecule having two CD137 binding sites and one binding site for the representative TA, PD-L1. TRIDENT-A5 is composed of four polypeptide chains (see, FIG. 3A, wherein VL1/VH1 (Site A) are the same as VL2/VH2 (Site B) and bind CD137, and VL3/VH3 (Site C) bind PD-L1). TRIDENT-A5 comprises the binding domains of CD137 MAB-6(1.2) and hPD-L1 MAB-2(3.2).

The first polypeptide chain of TRIDENT-A5 comprises, in the N-terminal to C-terminal direction, an N-terminus, a VL domain of a monoclonal antibody capable of binding CD137 ($VL_{CD137}$) (CD137 MAB-6 VL2 (SEQ ID NO:55)), an intervening linker peptide (Linker 1; GGGSGGGG (SEQ ID NO:16)), a VH domain of a monoclonal antibody capable of binding CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil) Domain (EVAALEK-EVAALEK-EVAALEK-EVAALEK (SEQ ID NO:37)), an intervening linker peptide (GGGDKTHTCPPCP (SEQ ID NO:21)), a "knob-bearing"

CH2 and CH3 Domain comprising the L234A/L235A/M252Y/S254T/T256E substitutions (SEQ ID NO:146), and a C-terminus.

Thus, the first polypeptide chain of TRIDENT-A5 is composed of: SEQ ID NO:55-SEQ ID NO:16-SEQ ID NO:46-SEQ ID NO:18-SEQ ID NO:37-SEQ ID NO:21-SEQ ID NO:146.

The amino acid sequence of the first polypeptide chain of TRIDENT-A5 is (SEQ ID NO:133):

```
EIVMTQSPAT LSLSPGERAT LSCRASQSVS SNYLSWYQQK
PGQAPRLLIY GASTRATGIP ARFSGSGSGT DFTLTISSLQ
PEDFAVYYCQ QDYDLPWTFG QGTKVEIKGG GSGGGGQVQL
QESGPGLVKP SETLSLTCTV SGGSISSYYW SWIRQPPGKG
LEWIGRIYTS GSTNYNPSLK SRVTMSVDTS KNQFSLKLSS
VTAADTAVYY CARDGWYDED YNYYGMDVWG QGTTVTVSSG
GCGGGEVAAL EKEVAALEKE VAALEKEVAA LEKGGGDKTH
TCPPCPAPEA AGGPSVFLFP PKPKDTLYIT REPEVTCVVV
DVSHEDPEVK FNWYVDGVEV HNAKTKPREE QYNSTYRVVS
VLTVLHQDWL NGKEYKCKVS NKALPAPIEK TISKAKGQPR
EPQVYTLPPS REEMTKNQVS LWCLVKGFYP SDIAVEWESN
GQPENNYKTT PPVLDSDGSF FLYSKLTVDK SRWQQGNVFS
CSVMHEALHN HYTQKSLSLS PGK
```

The second polypeptide chain of TRIDENT-A5 comprises, in the N-terminal to C-terminal direction, an N-terminus, a VL domain of a monoclonal antibody capable of binding CD137 ($VL_{CD137}$) (CD137 MAB-6 VL2 (SEQ ID NO:55)), an intervening linker peptide (Linker 1; GGGSGGGG (SEQ ID NO:16)), a VH domain of a monoclonal antibody capable of binding CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (K-coil) Domain (KVAALKE-KVAALKE-KVAALKE-KVAALKE (SEQ ID NO:38)), and a C-terminus.

Thus, the second polypeptide chain of TRIDENT-A5 is composed of: SEQ ID NO:55-SEQ ID NO:16-SEQ ID NO:46-SEQ ID NO:18-SEQ ID NO:38.

The amino acid sequence of the second polypeptide chain of TRIDENT-A5 is (SEQ ID NO:134):

```
EIVMTQSPAT LSLSPGERAT LSCRASQSVS SNYLSWYQQK
PGQAPRLLIY GASTRATGIP ARFSGSGSGT DFTLTISSLQ
PEDFAVYYCQ QDYDLPWTFG QGTKVEIKGG GSGGGGQVQL
QESGPGLVKP SETLSLTCTV SGGSISSYYW SWIRQPPGKG
LEWIGRIYTS GSTNYNPSLK SRVTMSVDTS KNQFSLKLSS
VTAADTAVYY CARDGWYDED YNYYGMDVWG QGTTVTVSSG
GCGGGKVAAL KEKVAALKEK VAALKEKVAA LKE
```

It is specifically contemplated that alternative TRIDENT-A5 first and second polypeptide chains may be employed that comprise Heterodimer-Promoting (E-coil and K-coil) Domains comprising a cysteine residue (e.g., EVAACEK-EVAALEK-EVAALEK-EVAALEK (SEQ ID NO:39) and KVAAQKE-KVAALKE-KVAALKE-KVAALKE (SEQ ID NO:40)). In such alternative TRIDENT-A5 molecules, the first polypeptide chain sometimes is composed of: SEQ ID NO:55-SEQ ID NO:16-SEQ ID NO:46-SEQ ID NO:18-SEQ ID NO:39-SEQ ID NO:21-SEQ ID NO:146 and the second polypeptide chain sometimes is composed of SEQ ID NO:55-SEQ ID NO:16-SEQ ID NO:46-SEQ ID NO:18-SEQ ID NO:40.

The third polypeptide chain of TRIDENT-A5 is the same as the third polypeptide chain of TRIDENT-A4 (SEQ ID NO:131).

The fourth polypeptide chain of TRIDENT-A5 is the same as the fourth polypeptide chain of TRIDENT-A4 (SEQ ID NO:132).

4. TRIDENT-A6

TRIDENT-A6 is a trivalent CD137×CD137×TA Binding Molecule having two CD137 binding sites and one binding site for the representative TA, PD-L1. TRIDENT-A6 is composed of four polypeptide chains (see, FIG. 3A, wherein VL1/VH1 (Site A) are the same as VL2/VH2 (Site B) and bind CD137, and VL3/VH3 (Site C) bind PD-L1). TRIDENT-A6 comprises the binding domains of CD137 MAB-6(1.3) and hPD-L1 MAB-2(3.2).

The first polypeptide chain of TRIDENT-A6 comprises, in the N-terminal to C-terminal direction, an N-terminus, a VL domain of a monoclonal antibody capable of binding CD137 ($VL_{CD137}$) (CD137 MAB-6 VL3 (SEQ ID NO:56)), an intervening linker peptide (Linker 1; GGGSGGGG (SEQ ID NO:16)), a VH domain of a monoclonal antibody capable of binding CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (E-coil) Domain (EVAALEK-EVAALEK-EVAALEK-EVAALEK (SEQ ID NO:37)), an intervening linker peptide (GGGDKTHTCPPCP (SEQ ID NO:21)), a "knob-bearing" CH2 and CH3 Domain comprising the L234A/L235A/M252Y/S254T/T256E substitutions (SEQ ID NO:146), and a C-terminus.

Thus, the first polypeptide chain of TRIDENT-A6 is composed of: SEQ ID NO:56-SEQ ID NO:16-SEQ ID NO:46-SEQ ID NO:18-SEQ ID NO:37-SEQ ID NO:21-SEQ ID NO:146.

The amino acid sequence of the first polypeptide chain of TRIDENT-A6 is (SEQ ID NO:135):

```
EIVMTQSPAT LSLSPGERAT LSCRASQSVS SNYLSWFQQK
PGQAPRLLIY GASTRATGIP ARFSGSGSGT DFTLTISSLQ
PEDFAVYYCQ QDYDLPWTFG QGTKVEIKGG GSGGGGQVQL
QESGPGLVKP SETLSLTCTV SGGSISSYYW SWIRQPPGKG
LEWIGRIYTS GSTNYNPSLK SRVTMSVDTS KNQFSLKLSS
VTAADTAVYY CARDGWYDED YNYYGMDVWG QGTTVTVSSG
GCGGGEVAAL EKEVAALEKE VAALEKEVAA LEKGGGDKTH
TCPPCPAPEA AGGPSVFLFP PKPKDTLYIT REPEVTCVVV
DVSHEDPEVK FNWYVDGVEV HNAKTKPREE QYNSTYRVVS
VLTVLHQDWL NGKEYKCKVS NKALPAPIEK TISKAKGQPR
EPQVYTLPPS REEMTKNQVS LWCLVKGFYP SDIAVEWESN
GQPENNYKTT PPVLDSDGSF FLYSKLTVDK SRWQQGNVFS
CSVMHEALHN HYTQKSLSLS PGK
```

The second polypeptide chain of TRIDENT-A6 comprises, in the N-terminal to C-terminal direction, an N-terminus, a VL domain of a monoclonal antibody capable of binding CD137 ($VL_{CD137}$) (CD137 MAB-6 VL3 (SEQ ID NO:56)), an intervening linker peptide (Linker 1; GGGSGGGG (SEQ ID NO:16)), a VH domain of a monoclonal antibody capable of binding CD137 ($VH_{CD137}$) (CD137 MAB-6 VH1 (SEQ ID NO:46)), an intervening linker peptide (Linker 2; GGCGGG (SEQ ID NO:18)), a Heterodimer-Promoting (K-coil) Domain (KVAALKE-KVAALKE-KVAALKE-KVAALKE (SEQ ID NO:38)), and a C-terminus.

Thus, the second polypeptide chain of TRIDENT-A6 is composed of: SEQ ID NO:56-SEQ ID NO:16-SEQ ID NO:46-SEQ ID NO:18-SEQ ID NO:38.

The amino acid sequence of the second polypeptide chain of TRIDENT-A6 is (SEQ ID NO:136):

```
EIVMTQSPAT LSLSPGERAT LSCRASQSVS SNYLSWFQQK
PGQAPRLLIY GASTRATGIP ARFSGSGSGT DFTLTISSLQ
PEDFAVYYCQ QDYDLPWTFG QGTKVEIKGG GSGGGGQVQL
QESGPGLVKP SETLSLTCTV SGGSISSYYW SWIRQPPGKG
LEWIGRIYTS GSTNYNPSLK SRVTMSVDTS KNQFSLKLSS
VTAADTAVYY CARDGWYDED YNYYGMDVWG QGTTVTVSSG
GCGGGKVAAL KEKVAALKEK VAALKEKVAA LKE
```

It is specifically contemplated that alternative TRIDENT-A6 first and second polypeptide chains may be employed that comprise Heterodimer-Promoting (E-coil and K-coil) Domains comprising a cysteine residue (e.g., EVAACEK-EVAALEK-EVAALEK-EVAALEK (SEQ ID NO:39) and KVAAQKE-KVAALKE-KVAALKE-KVAALKE (SEQ ID NO:40)). In such alternative TRIDENT-A6 molecules, the first polypeptide chain sometimes is composed of: SEQ ID NO:56-SEQ ID NO:16-SEQ ID NO:46-SEQ ID NO:18-SEQ ID NO:39-SEQ ID NO:21-SEQ ID NO:146 and the second polypeptide chain sometimes is composed of SEQ ID NO:56-SEQ ID NO:16-SEQ ID NO:46-SEQ ID NO:18-SEQ ID NO:40.

The third polypeptide chain of TRIDENT-A6 is the same as the third polypeptide chain of TRIDENT-A4 (SEQ ID NO:131).

The fourth polypeptide chain of TRIDENT-A6 is the same as the fourth polypeptide chain of TRIDENT-A4 (SEQ ID NO:132).

5. TRIDENT-B1

TRIDENT-B1 is a trivalent CD137×CD137×TA Binding Molecule having two CD137 binding sites and one binding site for the representative TA, HER2. TRIDENT-B1 is composed of four polypeptide chains (see, FIG. 3A, wherein VL1/VH1 (Site A) are the same as VL2/VH2 (Site B) and bind CD137, and VL3/VH3 (Site C) bind HER2). TRIDENT-B1 comprises the binding domains of CD137 MAB-6(1.1) and hHER2 MAB-1(1.3).

The first polypeptide chain of TRIDENT-B1 is the same as the first polypeptide chain of TRIDENT-A (SEQ ID NO:127).

The second polypeptide chain of TRIDENT-B1 is the same as the second polypeptide chain of TRIDENT-A (SEQ ID NO:128).

It is specifically contemplated that alternative TRIDENT-B1 first and second polypeptide chains may be employed that comprise Heterodimer-Promoting (E-coil and K-coil) Domains comprising a cysteine residue (e.g., EVAACEK-EVAALEK-EVAALEK-EVAALEK (SEQ ID NO:39) and KVAACKE-KVAALKE-KVAALKE-KVAALKE (SEQ ID NO:40)). In such alternative TRIDENT-B1 molecules, the first polypeptide chain sometimes is composed of: SEQ ID NO:85-SEQ ID NO:16-SEQ ID NO:46-SEQ ID NO:18-SEQ ID NO:39-SEQ ID NO:21-SEQ ID NO:146 and the second polypeptide chain sometimes is composed of SEQ ID NO:85-SEQ ID NO:16-SEQ ID NO:46-SEQ ID NO:18-SEQ ID NO:40.

The third polypeptide chain of TRIDENT-B1 comprises, in the N-terminal to C-terminal direction, an N-terminus, a VH domain of a monoclonal antibody capable of binding to HER2 ($VH_{HER2}$ (hHER2 MAB-1 VH1, SEQ ID NO:80)), a human IgG1 CH1 Domain (SEQ ID NO:3), a human IgG1 Hinge Region (SEQ ID NO:7), and a "hole-bearing" CH2 and CH3 Domain comprising the L234A/L235A/M252Y/S254T/T256E/H435R substitutions (SEQ ID NO:149).

Thus, the third polypeptide chain of TRIDENT-B1 is composed of: SEQ ID NO:80-SEQ ID NO:3-SEQ ID NO:7-SEQ ID NO:149.

The amino acid sequence of the third polypeptide chain of TRIDENT-B1 is (SEQ ID NO:153):

```
QVQLVQSGAE VKKPGASVKV SCKASGYTFT NYGMNWVRQA
PGQGLEWMGW INTNIGEPTY TEEFKGRVTM TRDTSISTAY
MELSRLRSDD TAVYYCARDD GYGNRVSYWG QGTLVTVSSA
STKGPSVFPL APSSKSTSGG TAALGCLVKD YFPEPVTVSW
NSGALTSGVH TFPAVLQSSG LYSLSSVVTV PSSSLGTQTY
ICNVNHKPSN TKVDKRVEPK SCDKTHTCPP CPAPEAAGGP
SVFLFPPKPK DTLYITREPE VTCVVVDVSH EDPEVKFNWY
VDGVEVHNAK TKPREEQYNS TYRVVSVLTV LHQDWLNGKE
YKCKVSNKAL PAPIEKTISK AKGQPREPQV YTLPPSREEM
TKNQVSLSCA VKGFYPSDIA VEWESNGQPE NNYKTTPPVL
DSDGSFFLVS KLTVDKSRWQ QGNVFSCSVM HEALHNRYTQ
KSLSLSPGK
```

The fourth polypeptide chain of TRIDENT-B1 comprises, in the N-terminal to C-terminal direction, an N-terminus, a VL domain of a monoclonal antibody capable of binding to HER2 ($VL_{HER2}$ (hHER2 MAB-1 VL3, SEQ ID NO:85)), a human IgG CL Kappa Domain (SEQ ID NO:1), and a C-terminus.

Thus, the fourth polypeptide chain of TRIDENT-B1 is composed of: SEQ ID NO:85-SEQ ID NO:1.

The amino acid sequence of the fourth polypeptide chain of TRIDENT-B1 is (SEQ ID NO:154):

```
DIQMTQSPSS LSASVGDRVT ITCKASQDIS NYLSWFQQKP
GKAPKTLIYR ANRLQSGVPS RFSGSGSGTD FTLTISSLQP
EDFATYYCLQ HDEFPWTFGQ GTKLEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

6. TRIDENT-B2

TRIDENT-B2 is a trivalent CD137×CD137×TA Binding Molecule having two CD137 binding sites and one binding site for the representative TA, HER2. TRIDENT-B1 is composed of four polypeptide chains (see, FIG. 3A, wherein VL1/VH1 (Site A) are the same as VL3/VH3 (Site C) and bind CD137, and VL2/VH2 (Site B) bind HER2). TRIDENT-B1 comprises the binding domains of CD137 MAB-6(1.1) and hHER2 MAB-1(1.3).

The first polypeptide chain of TRIDENT-B2 is the same as the first polypeptide chain of DART-B1 (SEQ ID NO:143).

The second polypeptide chain of TRIDENT-B2 is the same as the second polypeptide chain of DART-B1 (SEQ ID NO:144).

It is specifically contemplated that alternative TRIDENT-B2 first and second polypeptide chains may be employed that comprise Heterodimer-Promoting (E-coil and K-coil) Domains comprising a cysteine residue (e.g., EVAACEK-EVAALEK-EVAALEK-EVAALEK (SEQ ID NO:39) and KVAAQKE-KVAALKE-KVAALKE-KVAALKE (SEQ ID NO:40)). In such alternative TRIDENT-B2 molecules, the first polypeptide chain sometimes is composed of: SEQ ID NO:50-SEQ ID NO:16-SEQ ID NO:46-SEQ ID NO:18-SEQ ID NO:39-SEQ ID NO:21-SEQ ID NO:146 and the second polypeptide chain sometimes is composed of SEQ ID NO:50-SEQ ID NO:16-SEQ ID NO:46-SEQ ID NO:18-SEQ ID NO:40.

The third polypeptide chain of TRIDENT-B2 comprises, in the N-terminal to C-terminal direction, an N-terminus, a VH domain of a monoclonal antibody capable of binding a VH domain of a monoclonal antibody capable of binding CD137 ($VH_{CD137}$) (CD137 MAB-6 VH1 (SEQ ID NO:46)), a human IgG1 CH1 Domain (SEQ ID NO:3), a human IgG1 Hinge Region (SEQ ID NO:7), and a "hole-bearing" CH2 and CH3 Domain comprising the L234A/L235A/M252Y/S254T/T256E/H435R substitutions (SEQ ID NO:149).

Thus, the third polypeptide chain of TRIDENT-B2 is composed of: SEQ ID NO:46-SEQ ID NO:3-SEQ ID NO:7-SEQ ID NO:149.

The amino acid sequence of the third polypeptide chain of TRIDENT-B2 is (SEQ ID NO:155):

```
QVQLQESGPG LVKPSETLSL TCTVSGGSIS SYYWSWIRQP
PGKGLEWIGR IYTSGSTNYN PSLKSRVTMS VDTSKNQFSL
KLSSVTAADT AVYYCARDGW YDEDYNYYGM DVWGQGTMVT
VSSASTKGPS VFPLAPSSKS TSGGTAALGC LVKDYFPEPV
TVSWNSGALT SGVHTFPAVL QSSGLYSLSS VVTVPSSSLG
TQTYICNVNH KPSNTKVDKR VEPKSCDKTH TCPPCPAPEA
AGGPSVFLFP PKPKDTLYIT REPEVTCVVV DVSHEDPEVK
FNWYVDGVEV HNAKTKPREE QYNSTYRVVS VLTVLHQDWL
NGKEYKCKVS NKALPAPIEK TISKAKGQPR EPQVYTLPPS
REEMTKNQVS LSCAVKGFYP SDIAVEWESN GQPENNYKTT
PPVLDSDGSF FLVSKLTVDK SRWQQGNVFS CSVMHEALHN
RYTQKSLSLS PGK
```

The fourth polypeptide chain of TRIDENT-B2 comprises, in the N-terminal to C-terminal direction, an N-terminus, a VL domain of a monoclonal antibody capable of binding CD137 ($VL_{CD137}$) (CD137 MAB-6 VL1 (SEQ ID NO:50)), a human IgG CL Kappa Domain (SEQ ID NO:1), and a C-terminus.

Thus, the fourth polypeptide chain of TRIDENT-B2 is composed of: SEQ ID NO:50-SEQ ID NO:1.

The amino acid sequence of the fourth polypeptide chain of TRIDENTB2 is (SEQ ID NO:156):

```
EDFAVYYCQQ DYDLPWTFGQ GTKVEIKRTV AAPSVFIFPP
SDEQLKSGTA SVVCLLNNFY PREAKVQWKV DNALQSGNSQ
ESVTEQDSKD STYSLSSTLT LSKADYEKHK VYACEVTHQG
LSSPVTKSFN RGEC
```

C. Alternative CD137×TA Binding Molecules

As will be recognized in view of the instant disclosure, additional CD137×TA Binding Molecules having the general structure of any of the above representative molecules and comprising a binding site for an alternative TA may be constructed by employing the VL and VH domains of alternative Tumor Antigen antibodies in lieu of the VL and VH domains of the anti-PD-L1 or anti-HER2. Similarly, as provided herein, alternative CD137×TA Binding Molecules may likewise be constructed incorporating alternative linkers and/or heterodimer promoting domains and/or antibody constant regions (e.g., CL, CH2-CH3 Domain).

D. Control Molecules

In order to more meaningfully demonstrate the properties of the CD137×TA Binding Molecules of the present invention, comparator and control antibodies, whose VL and VH domains may be used to produce control Fc-bearing diabodies and other comparator and control binding molecules, are described herein.

Palivizumab (see, e.g., Protein Data Bank (PDB) ID No. 2HWZ) is a humanized monoclonal antibody (IgG) directed against an epitope in the A antigenic site of the F protein of RSV, and is a suitable control antibody, whose VL and VH domains may be used to produce control diabodies and other control binding molecules. Alternative anti-RSV glycoprotein F antibodies include motavizumab (see, e.g., PDB ID No. 3IXT) and a variant of palivizumab engineered to remove a cysteine residues from CDR 1 of the light chain. The variant of palivizumab was used for generation of the negative control molecule described below.

The amino acid sequence of the VH Domain of the variant of palivizumab is (SEQ ID NO:137) ($CDR_H$ residues are shown underlined):

QVTLRESGPA LVKPTQTLTL TCTFSGFSLS TSGMSVGWIR
QPPGKALEWL ADIWWDDKKD YNPSLKSRLT ISKDTSKNQV
VLKVTNMDPA DTATYYCARS MITNWYFDVW GAGTTVTVSS

The amino acid sequence of the VL Domain of the variant of palivizumab is (SEQ ID NO:138) ($CDR_L$ residues are shown underlined):

DIQMTQSPST LSASVGDRVT ITCRASQSVG YMHWYQQKPG
KAPKLLIYDT SKLASGVPSR FSGSGSGTEF TLTISSLQPD
DFATYYCFQG SGYPFTFGGG TKLEIK

Several molecules comprising the epitope-binding site of previously described anti-CD137 antibodies including urelumab (also known as BMS-663513, see, U.S. Pat. No. 8,137,667) and utomilumab (also known as PF-05082566, see, U.S. Pat. No. 8,337,850) and murine and humanized hCD137 MAB-3 (see, WO 2018/156740) are used herein for comparison purposes. The amino acid sequence of the complete Heavy and Light Chains of urelumab (WHO Drug Information, 2011, Recommended INN: List 66, 25(3):334) and utomilumab (WHO Drug Information, 2017, Recommended INN: List 77, 31(1):140-141) are known in the art. The amino acid sequence of the VH and VL Domains of the humanized hCD137 MAB-3(1B.3) used as a comparator herein are provided in WO 2018/156740, see paragraphs [00254] and [00261].

E. Summary of CD137×TA Binding and Control Molecules

Table 5 summarizes the domain attributes of DART-A-DART-A9, TRIDENT-A, and TRIDENT-A4-A6:

TABLE 5

| Name (No. of Chains) | Parental mAbs | Fc Domain | Chain No. | SEQ ID NOs. | Other Components |
|---|---|---|---|---|---|
| DART-A | hPD-L1 | IgG1 | 1 | 116 | E/K Coils |
| (4 Chains) | MAB-2 (1.1) | (AA/YTE) | 2 | 117 | |
| | CD137 | | 3 | 116 | |
| | MAB-6 (1.1) | | 4 | 117 | |
| DART-A1 | hPD-L1 | IgG1 | 1 | 118 | E/K Coils |
| (4 Chains) | MAB-2 (2.1) | (AA/YTE) | 2 | 119 | |
| | CD137 | | 3 | 118 | |
| | MAB-6 (1.1) | | 4 | 119 | |
| DART-A2 | hPD-L1 | IgG1 | 1 | 120 | E/K Coils |
| (4 Chains) | MAB-2 (2.2) | (AA/YTE) | 2 | 119 | |
| | CD137 | | 3 | 120 | |
| | MAB-6 (1.1) | | 4 | 119 | |
| DART-A3 | hPD-L1 | IgG1 | 1 | 118 | E/K Coils |
| (4 Chains) | MAB-2 (3.1) | (AA/YTE) | 2 | 121 | |
| | CD137 | | 3 | 118 | |
| | MAB-6 (1.1) | | 4 | 121 | |
| DART-A4 | hPD-L1 | IgG1 | 1 | 120 | E/K Coils |
| (4 Chains) | MAB-2 (3.2) | (AA/YTE) | 2 | 121 | |
| | CD137 | | 3 | 120 | |
| | MAB-6 (1.1) | | 4 | 121 | |
| DART-A5 | hPD-L1 | IgG1 | 1 | 120 | E/K Coils |
| (4 Chains) | MAB-2 (3.2) | (AA/YTE) | 2 | 122 | |
| | CD137 | | 3 | 120 | |
| | MAB-6 (1.2) | | 4 | 122 | |
| DART-A6 | hPD-L1 | IgG1 | 1 | 120 | E/K Coils |
| (4 Chains) | MAB-2 (3.2) | (AA/YTE) | 2 | 123 | |
| | CD137 | | 3 | 120 | |
| | MAB-6 (1.3) | | 4 | 123 | |
| DART-A7 | hPD-L1 | IgG1 | 1 | 120 | E/K Coils |
| (4 Chains) | MAB-2 (4.2) | (AA/YTE) | 2 | 124 | |
| | CD137 | | 3 | 120 | |
| | MAB-6 (1.1) | | 4 | 124 | |
| DART-A8 | hPD-L1 | IgG1 | 1 | 120 | E/K Coils |
| (4 Chains) | MAB-2 (5.2) | (AA/YTE) | 2 | 125 | |
| | CD137 | | 3 | 120 | |
| | MAB-6 (1.1) | | 4 | 125 | |
| DART-A9 | hPD-L1 | IgG1 | 1 | 120 | E/K Coils |
| (4 Chains) | MAB-2 (6.2) | (AA/YTE) | 2 | 126 | |
| | CD137 | | 3 | 120 | |
| | MAB-6 (1.1) | | 4 | 126 | |
| DART-A10 | hPD-L1 | IgG1 | 1 | 120 | E/K Coils |
| (4 Chains) | MAB-2 (4.2) | (AA/YTE) | 2 | 139 | |
| | CD137 | | 3 | 120 | |
| | MAB-6 (1.3) | | 4 | 139 | |
| DART-B1 | hHER2 | IgG1 | 1 | 143 | E/K Coils |
| | MAB-1 (1.3) | (AA/TYE) | 2 | 144 | |
| | CD137 | (knob/hole) | 3 | 145 | |
| | MAB-6(1.1) | | | | |
| DART-B2 | hHER2 | IgG1 | 1 | 151 | E/K Coils |
| | MAB-1 (1.3) | (AA/YTE) | 2 | 152 | |
| | CD137 | | 3 | 151 | |
| | MAB-6(1.1) | | 4 | 152 | |
| TRIDENT-A | hPD-L1 | IgG1 | 1 | 127 | CL/CH1 and |
| | MAB-2 (1.1) | (knob/hole) | 2 | 128 | E/K Coils |
| (4 Chains) | CD137 | (AA/TYE) | 3 | 129 | |
| | MAB-6 (1.1) | | 4 | 130 | |
| TRIDENT-A4 | hPD-L1 | IgG1 (AA) | 1 | 127 | CL/CH1 and |
| | MAB-2 (3.2) | (knob/hole) | 2 | 128 | E/K Coils |
| (4 Chains) | CD137 | | 3 | 131 | |
| | MAB-6 (1.1) | | 4 | 132 | |
| TRIDENT A5 | hPD-L1 | IgG1 (AA) | 1 | 133 | CL/CH1 and |
| | MAB-2 (3.2) | (knob/hole) | 2 | 134 | E/K Coils |
| (4 chains) | CD137 | | 3 | 131 | |
| | MAB-6 (1.2) | | 4 | 132 | |
| TRIDENT-A6 | hPD-L1 | IgG1 (AA) | 1 | 135 | CL/CH1 and |
| | MAB-2 (3.2) | (knob/hole) | 2 | 136 | E/K Coils |
| | CD137 | | 3 | 131 | |
| | MAB-6 (1.3) | | 4 | 132 | |
| TRIDENT-B1 | hHER2 | IgG1 (AA) | 1 | 127 | CL/CH1 and |
| | MAB-1 (1.3) | (knob/hole) | 2 | 128 | E/K Coils |
| | CD137 | | 3 | 153 | |
| | MAB-6(1.1) | | 4 | 154 | |
| TRIDENT-B2 | hHER2 | IgG1 (AA) | 1 | 143 | CL/CH1 and |
| | MAB-1 (1.3) | (knob/hole) | 2 | 144 | E/K Coils |
| | CD137 | | 3 | 155 | |
| | MAB-6(1.1) | | 4 | 156 | |

Table 6 shows the attributes of additional DART and TRIDENT molecules that were prepared as comparators and negative controls:

TABLE 6

| Name (No. of Chains) | Parental mAbs | Fc Domain | Other Components |
|---|---|---|---|
| DART-1 (4 Chains) | hPD-L1 MAB-2 (1.1) variant palivizumab | IgG1 (AA/YTE) | Same as DART-A except comprising VH/VL of variant palivizumab in place of the VH/VL of CD137 MAB-6(1.1) |
| DART-2 (4 Chains) | hPD-L1 MAB-2 (1.1) CD137 MAB-2 | IgG1 (AA) | Same as DART-A except comprising VH/VL of CD137 MAB-2 in place of the VH/VL of hCD137 MAB-3(1B.3) |
| DART-3 (4 Chains) | hPD-L1 MAB-2 (1.1) VL/VL utomilumab | IgG1 (AA) | Same as DART-A except comprising VH/VL of utomilumab in place of the VH/VL of hCD137 MAB-6(1.1) |
| DART-4 (3 Chains) | variant palivizumab CD137 MAB-6(1.1) | IgG1 (AA) (knob/hole) | Same as DART-B1 except comprising the VH/VL of variant palivizumab in place of the VH/VL of hHER2 MAB-1 (1.3) |
| DART-5 (4 Chains) | variant palivizumab CD137 MAB-6(1.1) | IgG1 (AA) | Same as DART-B2 except comprising the VH/VL of variant palivizumab in place of the VH/VL of hHER2 MAB-1 (1.3) |
| TRIDENT-2 (4 Chains) | hPD-L1 MAB-2 (1.1) hCD137 MAB-3(1B.3) | IgG1 (AA) (knob/hole) | Same as TRIDENT-A except comprising the VH/VL of hCD137 MAB-3(1B.3) in place of the VH/VL of, andCD137 MAB6(1.1), SEQ ID NO: 19 for Linker 2 and cysteine-containing Heterodimer-Promoting Domains (see, paragraphs [00306]-[00311] of WO 2020/041404 for full sequences) |
| TRIDENT-3 | variant palivizumab CD137 MAB-6(1.1) | IgG1 (AA) (knob/hole) | Same as TRIDENT-B1 except comprising the VH/VL of VH/VL of variant palivizumab in place of the VH/VL of hHER2 MAB-1 (1.3) |
| TRIDENT-4 | variant palivizumab CD137 | IgG1 (AA) (knob/hole) | Same as TRIDENT-B2 except comprising the VH/VL of VH/VL of variant palivizumab |

TABLE 6-continued

| Name (No. of Chains) | Parental mAbs | Fc Domain | Other Components |
|---|---|---|---|
| | MAB-6(1.1) | | in place of the VH/VL of hHER2 MAB-1 (1.3) |

III. METHODS OF PRODUCTION

The binding molecules of the invention may be made recombinantly and expressed using any method known in the art. Such molecules may be made recombinantly by, obtaining the nucleic acids encoding the binding molecules, and using the nucleic acids to generate vectors useful for recombinant expression of the molecules in host cells (e.g., CHO cells). Another method that may be employed is to express the molecules in plants (e.g., tobacco) or transgenic milk.

Vectors containing polynucleotides of interest (e.g., polynucleotides encoding the polypeptide chains of the binding molecules of the present invention) can be introduced into the host cell by any of a number of appropriate means, including electroporation; microprojectile bombardment; lipofection; and infection (e.g., where the vector is an infectious agent such as vaccinia virus). Techniques for the introduction of nucleic acid or vectors into host cells are well established in the art and any suitable technique may be employed.

Any host cell capable of overexpressing heterologous DNAs can be used for the purpose of expressing a binding molecule (e.g., antibody, diabody, trivalent binding molecule) of interest. Non-limiting examples of suitable mammalian host cells include but are not limited to COS, NSO, HEK-293, HeLa, and CHO cells. Methods for culturing host cells are well-known in the art.

The binding molecules are typically isolated and/or purified from the host cell, culture media, etc. Techniques for the purification of recombinant binding molecules comprising antibody domains (e.g., Fc Domains) are well-known in the art and include, for example the use of HPLC, FPLC, or affinity chromatography, (e.g., using Protein A or Protein G). Following purification, the binding molecules of the invention may be formulated into a pharmaceutical composition, optionally with a pharmaceutically acceptable excipient or other substance as described below.

IV. PHARMACEUTICAL COMPOSITIONS

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a CD137×TA Binding Molecule of the present invention, or a combination of such agents and a pharmaceutically acceptable carrier. As provided herein, compositions of the invention comprise a prophylactically or therapeutically effective amount of the CD137×TA bispecific Fc-bearing diabody of the invention and a pharmaceutically acceptable carrier.

The invention also encompasses pharmaceutical compositions comprising a CD137×TA Binding Molecules of the invention and one or more additional molecules that are effective in stimulating an immune response (e.g., an immune checkpoint inhibitor) and/or in combination with one or more additional molecules that specifically bind a tumor antigen (e.g., a tumor-specific monoclonal antibody or diabody) that is specific for at least one particular TA, as described above, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids. Aqueous carriers, such as saline solutions, aqueous dextrose and glycerol solutions are preferred when the pharmaceutical composition is administered intravenously.

Generally, the ingredients of compositions of the invention are supplied either separately or mixed together in unit dosage form, for example, as a dry lyophilized powder or water free concentrate, or in liquid form in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers containing a CD137×TA Binding Molecule of the present invention alone or with other agents, for example, with a pharmaceutically acceptable carrier. Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

A kit can comprise a CD137×TA Binding Molecule of the invention. The kit can further comprise one or more other prophylactic and/or therapeutic agents useful for the treatment of cancer, in one or more containers; and/or the kit can further comprise one or more cytotoxic antibodies that bind one or more tumor antigens (TAs). In certain embodiments, the other prophylactic or therapeutic agent is a chemotherapeutic. In other embodiments, the prophylactic or therapeutic agent is a biological or hormonal therapeutic.

V. METHODS OF ADMINISTRATION

The compositions of the present invention may be provided for the treatment, prophylaxis, and amelioration of one or more symptoms associated with cancer or other disease, or disorder by administering to a subject an effective amount of a molecule of the invention, or a pharmaceutical composition comprising a molecule of the invention. In one aspect, such compositions are substantially purified (i.e., substantially free from substances that limit its effect or produce undesired side effects). In a specific embodiment, the subject is an animal. In another specific embodiment, the subject is a mammal such as non-primate (e.g., bovine, equine, feline, canine, rodent, etc.) or a primate (e.g., monkey such as, a cynomolgus monkey, human, etc.). In another embodiment, the subject is a human.

Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the CD137×TA Binding Molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

The invention also provides that the CD137×TA Binding Molecules of the invention are packaged in a hermetically sealed container such as an ampoule or sachette indicating the quantity of the molecule. In one embodiment, the CD137×TA Binding Molecules of the invention are supplied as a dry sterilized lyophilized powder or water free concentrate in a hermetically sealed container and can be reconstituted, e.g., with water or saline to the appropriate concentration for administration to a subject. The lyophilized CD137×TA Binding Molecules of the present invention should be stored at between 2 and 8° C. in their original container and the molecules should be administered within 12 hours, within 6 hours, within 5 hours, within 3 hours, or within 1 hour after being reconstituted.

In an alternative embodiment, CD137×TA Binding Molecules of the invention are supplied in liquid form in a hermetically sealed container indicating the quantity and concentration of the molecule, fusion protein, or conjugated molecule. In certain embodiments, the liquid form of the CD137×TA Binding Molecules of the invention are supplied in a hermetically sealed container and do not require reconstitution.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

As used herein, an "effective amount" of a pharmaceutical composition, in one embodiment, is an amount sufficient to effect beneficial or desired results including, without limitation, clinical results such as decreasing symptoms resulting from the disease attenuating a symptom of disease (e.g., the proliferation of cancer cells, tumor presence, tumor metastases, etc.), thereby increasing the quality of life of those suffering from the disease, decreasing the dose of other medications required to treat the disease, enhancing the effect of another medication such as via targeting and/or internalization, delaying the progression of the disease, and/or prolonging survival of individuals.

Such effective amount can be administered in one or more administrations. For purposes of this invention, an effective amount of drug, compound, or pharmaceutical composition is an amount sufficient to reduce the proliferation of (or the effect of) viral presence and to reduce and/or delay the development of the disease (e.g., cancer) either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more additional agents (e.g., chemotherapeutic agents, or other agents considered standard of care for the particular condition), and a single agent may be considered to be given in an effective amount if, in conjunction with one or more other agents, a desirable result may be or is achieved. While individual needs vary, determination of optimal ranges of effective amounts of each component is within the skill of the art.

For the CD137×TA Binding Molecules encompassed by the invention, the dosage administered to a patient may be determined based upon the body weight (kg) of the recipient subject, or alternatively may be based on a fixed dose.

The dosage and frequency of administration of the CD137×TA Binding Molecules of the present invention may be reduced or altered by enhancing uptake and tissue penetration of the CD137×TA Binding Molecules by modifications such as, for example, lipidation.

The dosage of the CD137×TA Binding Molecules of the invention administered to a patient may be calculated for use as a single agent therapy. Alternatively, the CD137×TA Binding Molecules of the invention are used in combination with other therapeutic compositions such that the dosage administered to a patient is lower than when said molecules are used as a single agent therapy.

Treatment of a subject with a therapeutically or prophylactically effective amount of a CD137×TA Binding Molecules of the invention can include a single treatment or, can include a series of treatments. In one example, a subject is treated with a molecule of the invention one time per week, one time bi-weekly (i.e., once every other week), or one time every three weeks, for between about 1 to 52 weeks. The pharmaceutical compositions of the invention can be administered once a day, twice a day, or three times a day. Alternatively, the pharmaceutical compositions can be administered once a week, twice a week, once every two weeks, once a month, once every six weeks, once every two months, twice a year or once per year. It will also be appreciated that the effective dosage of the molecules used for treatment may increase or decrease over the course of a particular treatment.

VI. USES OF THE COMPOSITIONS OF THE INVENTION

The CD137×TA Binding Molecules of the present invention have the ability to bind T cells (APCs) (for example, by binding to CD137 expressed on the surfaces of such T cells) and the ability to bind TA-expressing tumor cells (for example, by binding to a TA expressed on the surfaces of such tumor cells). Thus, the CD137×TA Binding Molecules of the present invention have the ability to co-localize T cells to TA-expressing tumor cells, and thus may be used to treat any disease or condition associated with or characterized by the expression of a TA. Thus, without limitation, pharmaceutical compositions comprising such molecules may be employed in the diagnosis or treatment of cancers that express a TA, including, but not limited to: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer. Particularly, such cancers which highly express TAs.

The CD137×TA Binding Molecules of the present invention may additionally be used in the manufacture of medicaments for the treatment of the above-described conditions.

In certain embodiments a CD137×TA Binding Molecule of the invention is used in combination with one or more other prophylactic and/or therapeutic agents useful for the treatment of cancer. In certain embodiments, the other prophylactic or therapeutic agent is a chemotherapeutic. In other embodiments, the prophylactic or therapeutic agent is a biological or hormonal therapeutic. In other embodiments, biological therapeutic is a cytotoxic antibody-based molecule, including but not limited to, an antibody, an antigen binding fragment of an antibody (e.g., an scFv, a Fab, a F(ab)2, etc.), a TandAb, etc.), a multispecific binding molecule (e.g., a diabody, a bispecific antibody, a trivalent binding molecule, etc.), that binds one or more tumor antigens (TAs).

The CD137×TA Binding Molecules of the present invention can enhance the activity of tumor targeting agents. According, the CD137×TA Binding Molecules of the present invention may additionally be used in combination with other a tumor targeting agents, including but not limited to an antibody, an antigen binding fragment of an antibody (e.g., an scFv, a Fab, a F(ab)2, etc.), a TandAb, etc.), a multispecific binding molecule (e.g., a diabody, a bispecific antibody, a trivalent binding molecule, etc.), capable of binding a desired TA. It is specifically contemplated that the tumor targeting agent may bind the same or a different TA as the CD137×TA Binding Molecule used in such combinations. In particular embodiments, the tumor targeting agent is a multispecific molecule that binds to a TA and to an epitope expressed on T-cells including, for example, CD3, and/or CD8, and mediate T cell redirected killing. Representative tumor targeting agents include, but are not limited to, molecules that bind to a TA and CD3 ("TA×CD3"). Representative TA×CD3 Binding Molecules (e.g., bispecific antibodies, DART® molecules, BiTe® molecules, TandAbs, etc. and trivalent molecules), and methods for making the same, which may be used in such combinations are well known in the art. (see for e.g., WO 2013/026835, WO 2013/158856, WO 2014/047231; WO 2014/110601; WO 2014/131711; WO 2015/026894; WO 2015/026892; WO 2015/184203; WO 2015/184207; WO 2016/036937; WO 2016/182751; WO 2017091656; WO 2017/142928; WO 2017/118675).

The use of CD137×TA Binding Molecules of the present invention in combination with a tumor targeting agent (e.g., a TA×CD3 Binding Molecule) can lead to up-regulation of the inhibitory immune modulator Programmed Death-1 ("PD-1," also known as "CD279"). PD-1 mediates its inhibition of the immune system by binding PD-L1 and PD-L2 (also known as B7-H1 and B7-DC) (Flies, D. B. et al. (2007) "*The New B7s: Playing a Pivotal Role in Tumor Immunity*," J. Immunother. 30(3):251-260; U.S. Pat. Nos. 6,803,192; 7,794,710). Thus, the further addition of an agent that inhibits the inhibitory activity of PD-1 ("PD-1/PD-L1 Checkpoint Inhibitor") down regulates the expression of PD-1 can further enhances the activity of the CD137×TA and tumor targeting agents such as TA×CD3 Binding Molecules. The invention particularly encompasses PD-1/PD-L1 Checkpoint Inhibitors comprising an epitope-binding site of an antibody that binds PD-1.

Accordingly, the CD137×TA Binding Molecules of the present invention may additionally be used in combination with other tumor targeting agents, in further combination with a PD-1/PD-L1 checkpoint inhibitor. PD-1/PD-L1 Checkpoint Inhibitors include, but not limited to, an antibody, an antigen binding fragment of an antibody (e.g., an scFv, a Fab, a F(ab)2, etc.), a TandAb, etc.), a multispecific binding molecule (e.g., a diabody, a bispecific antibody, a trivalent binding molecule, etc.), capable of binding to PD-1 and/or PD-L1. Representative PD-1/PD-L1 Checkpoint Inhibitors and methods for making the same, which may be used in such combinations are well known in the art. PD-1 Binding Molecules useful in the methods of the instant invention include: nivolumab (CAS Reg. No.: 946414-94-4, also known as 5C4, BMS-936558, ONO-4538, MDX-1106, and marketed as OPDIVO® by Bristol-Myers Squibb); pembrolizumab (formerly known as lambrolizumab), CAS Reg. No.: 1374853-91-4, also known as MK-3475, SCH-900475, and marketed as KEYTRUDA® by Merck); cemiplimab (CAS Reg. No.: 1801342-60-8, also known as REGN-2810, SAR-439684, and marketed as LIBTAYO®). The amino acid sequences of the complete Heavy and Light Chains of nivolumab (WHO Drug Information, 2013, Recommended INN: List 69, 27(1):68-69), pembrolizumab (WHO Drug Information, 2014, Recommended INN: List 75, 28(3):407), and cemiplimab (WHO Drug Information 2018, Proposed INN: List 119) are known in the art. Additional anti-PD-1 antibodies (e.g., hPD-1 mAb 7(1.2); possessing unique binding characteristics useful in the methods and compositions of the instant inventions have recently been identified (see, PCT Publication No. WO 2017/019846).

Where such combinations are employed, it is specifically contemplated that, one or more of the molecules may be administered to a subject "concurrently" (e.g., a CD137×TA Binding Molecule may be administered at the same time as a TA×CD3 Binding Molecule and/or a PD-1/PD-L1 Checkpoint Inhibitor is administered) and/or that one or more of the molecules may be administered "sequentially" (e.g., a CD137×TA Binding Molecule is administered and, at a later time, a TA×CD3 Binding Molecule and/or a PD-1/PD-L1 Checkpoint Inhibitor is administered, or vice versa).

VII. EMBODIMENTS OF THE INVENTION

Having now generally described the invention, the same will be more readily understood through reference to the following numbered Embodiments ("E"), which are provided by way of illustration and are not intended to be limiting of the present invention unless specified:

E1. A CD137 Binding Molecule comprising a first binding site that immunospecifically binds to an epitope of CD137, wherein said first binding site comprises a first Light Chain Variable Domain that comprises a $CDR_L1$, $CDR_L2$ and $CDR_L3$, and a first Heavy Chain Variable Domain that comprises a $CDR_H1$, $CDR_H2$ and $CDR_H3$; and wherein:

- (A) said first Light Chain Variable Domain $CDR_L1$, $CDR_L2$, and $CDR_L3$ are the Light Chain CDRs of CD137 MAB-6 VL1 (SEQ ID NO:50); and
- (B) said first Heavy Chain Variable Domain $CDR_H1$, $CDR_H2$, and $CDR_H3$ are the Heavy Chain CDRs of CD137 MAB-6 VH1 (SEQ ID NO:46).

E2. The CD137 Binding Molecule of E1, wherein said first Heavy Chain Variable Domain comprises the amino acid sequence of: hCD137 MAB-6 VH1 (SEQ ID NO:46).

E3. The CD137 Binding Molecule of any one of E1-E2, wherein said first Light Chain Variable Domain comprises the amino acid sequence of:
- (A) hCD137 MAB-6 VLx (SEQ ID NO:54);
- (B) hCD137 MAB-6 VL1 (SEQ ID NO:50);
- (C) hCD137 MAB-6 VL2 (SEQ ID NO:55); or
- (D) hCD137 MAB-6 VL3 (SEQ ID NO:56).

E4. The CD137 Binding Molecule of any one of E1-E3, wherein:
- (A) said first Heavy Chain Variable Domain comprises the amino acid sequence of: hCD137 MAB-6 VH1 (SEQ ID NO:46); and
- (B) said first Light Chain Variable Domain comprises the amino acid sequence of: hCD137 MAB-6 VL1 (SEQ ID NO:50).

E5. The CD137 Binding Molecule of any one of E1-E3, wherein:
- (A) said first Heavy Chain Variable Domain comprises the amino acid sequence of: hCD137 MAB-6 VH1 (SEQ ID NO:46); and
- (B) said first Light Chain Variable Domain comprises the amino acid sequence of: hCD137 MAB-6 VL3 (SEQ ID NO:56).

E6. The CD137 Binding Molecule of any one of E1-E5, wherein said molecule is a bispecific molecule comprising a second binding site that immunospecifically binds a tumor antigen (TA), and wherein said second binding site comprises a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$.

E7. The CD137 Binding Molecule of E6, wherein said TA is selected from the antigens presented in Tables 1-2.

E8. The CD137 Binding Molecule of E6, wherein said TA is PD-L1 and wherein:
- (A) said second Light Chain Variable Domain $CDR_L1$, $CDR_L2$, and $CDR_L3$ are the Light Chain CDRs of hPD-L1 MAB-2 VLx (SEQ ID NO:63); and
- (B) said second Heavy Chain Variable Domain $CDR_H1$, $CDR_H2$, and $CDR_H3$ are the Heavy Chain CDRs of hPD-L1 MAB-2 VHx (SEQ ID NO:59).

E9. The CD137 Binding Molecule of E8, wherein:
- (A) (1) said second Light Chain Variable Domain $CDR_L1$, $CDR_L2$, and $CDR_L3$ are the Light Chain CDRs of hPD-L1 MAB-2 VL1 (SEQ ID NO:63); or
  - (2) said second Light Chain Variable Domain $CDR_L1$, $CDR_L2$, and $CDR_L3$ are the Light Chain CDRs of hPD-L1 MAB-2 VLx (SEQ ID NO:58); or
  - (3) said second Light Chain Variable Domain $CDR_L1$, $CDR_L2$, and $CDR_L3$ are the Light Chain CDRs of hPD-L1 MAB-2 VL2 (SEQ ID NO:72);

and
- (B) (1) said second Heavy Chain Variable Domain $CDR_H1$, $CDR_H2$, and $CDR_H3$ are the Heavy Chain CDRs of hPD-L1 MAB-2 VH1 (SEQ ID NO:59);
  - (2) said second Heavy Chain Variable Domain $CDR_H1$, $CDR_H2$, and $CDR_H3$ are the Heavy Chain CDRs of hPD-L1 MAB-2 VHx (SEQ ID NO:57);
  - (3) said second Heavy Chain Variable Domain $CDR_H1$, $CDR_H2$, and $CDR_H3$ are the Heavy Chain CDRs of hPD-L1 MAB-2 VH2 (SEQ ID NO:67);
  - (4) said second Heavy Chain Variable Domain $CDR_H1$, $CDR_H2$, and $CDR_H3$ are the Heavy Chain CDRs of hPD-L1 MAB-2 VH3 (SEQ ID NO:68);
  - (5) said second Heavy Chain Variable Domain $CDR_H1$, $CDR_H2$, and $CDR_H3$ are the Heavy Chain CDRs of hPD-L1 MAB-2 VH2 (SEQ ID NO:69);
  - (6) said second Heavy Chain Variable Domain $CDR_H1$, $CDR_H2$, and $CDR_H3$ are the Heavy Chain CDRs of hPD-L1 MAB-2 VH2 (SEQ ID NO:70); or
  - (7) said second Heavy Chain Variable Domain $CDR_H1$, $CDR_H2$, and $CDR_H3$ are the Heavy Chain CDRs of hPD-L1 MAB-2 VH2 (SEQ ID NO:71).

E10. The CD137 Binding Molecule of E9, wherein said second Heavy Chain Variable Domain comprises the amino acid sequence of:
- (A) hPD-L1 MAB-2 VHx (SEQ ID NO:59);
- (B) hPD-L1 MAB-2 VH1 (SEQ ID NO:57);
- (C) hPD-L1 MAB-2 VH2 (SEQ ID NO:67);
- (D) hPD-L1 MAB-2 VH3 (SEQ ID NO:68);
- (E) hPD-L1 MAB-2 VH4 (SEQ ID NO:69);
- (F) hPD-L1 MAB-2 VH5 (SEQ ID NO:70); or
- (G) hPD-L1 MAB-2 VH6 (SEQ ID NO:71).

E11. The CD137 Binding Molecule of any one of E9 or E10, wherein said second Light Chain Variable Domain comprises the amino acid sequence of:
- (A) hPD-L1 MAB-2 VLx (SEQ ID NO:63);
- (B) hPD-L1 MAB-2 VL1 (SEQ ID NO:58); or
- (B) hPD-L1 MAB-2 VL2 (SEQ ID NO:72).

E12. The CD137 Binding Molecule of any one of E10-E11, wherein:
- (A) said second Heavy Chain Variable Domain comprises the amino acid sequence of: hPD-L1 MAB-2 VHx (SEQ ID NO:59); and
- (B) said second Light Chain Variable Domain comprises the amino acid sequence of: hPD-L1 MAB-2 VLx (SEQ ID NO:63).

E13. The CD137 Binding Molecule of any one of E10-E11, wherein:
- (A) said second Heavy Chain Variable Domain comprises the amino acid sequence of: hPD-L1 MAB-2 VH1 (SEQ ID NO:57); and
- (B) said second Light Chain Variable Domain comprises the amino acid sequence of: hPD-L1 MAB-2 VLx (SEQ ID NO:63).

E14. The CD137 Binding Molecule of any one of E10-E11, wherein:
- (A) said second Heavy Chain Variable Domain comprises the amino acid sequence of: hPD-L1 MAB-2 VH2 (SEQ ID NO:67); and
- (B) said second Light Chain Variable Domain comprises the amino acid sequence of: hPD-L1 MAB-2 VLx (SEQ ID NO:63).

E15. The CD137 Binding Molecule of any one of E10-E11, wherein:
- (A) said second Heavy Chain Variable Domain comprises the amino acid sequence of: hPD-L1 MAB-2 VH3 (SEQ ID NO:68); and
- (B) said second Light Chain Variable Domain comprises the amino acid sequence of: hPD-L1 MAB-2 VLx (SEQ ID NO:63).

E16. The CD137 Binding Molecule of any one of E10-E11, wherein:
- (A) said second Heavy Chain Variable Domain comprises the amino acid sequence of: hPD-L1 MAB-2 VH4 (SEQ ID NO:69); and
- (B) said second Light Chain Variable Domain comprises the amino acid sequence of: hPD-L1 MAB-2 VLx (SEQ ID NO:63).

E17. The CD137 Binding Molecule of any one of E10-E11, wherein:

(A) said second Heavy Chain Variable Domain comprises the amino acid sequence of: hPD-L1 MAB-2 VH5 (SEQ ID NO:70); and (B) said second Light Chain Variable Domain comprises the amino acid sequence of: hPD-L1 MAB-2 VLx (SEQ ID NO:63).

E18. The CD137 Binding Molecule of any one of E10-E11, wherein:

(A) said second Heavy Chain Variable Domain comprises the amino acid sequence of: hPD-L1 MAB-2 VH6 (SEQ ID NO:71); and (B) said second Light Chain Variable Domain comprises the amino acid sequence of: hPD-L1 MAB-2 VLx (SEQ ID NO:63).

E19. The CD137 Binding Molecule of any one of E10-E11, wherein:

(A) said second Heavy Chain Variable Domain comprises the amino acid sequence of: hPD-L1 MAB-2 VH1 (SEQ ID NO:57); and (B) said second Light Chain Variable Domain comprises the amino acid sequence of: hPD-L1 MAB-2 VL1 (SEQ ID NO:58).

E20. The CD137 Binding Molecule of any one of E10-E11, wherein:

(A) said second Heavy Chain Variable Domain comprises the amino acid sequence of: hPD-L1 MAB-2 VH3 (SEQ ID NO:68); and (B) said second Light Chain Variable Domain comprises the amino acid sequence of: hPD-L1 MAB-2 VL2 (SEQ ID NO:72).

E21. The CD137 Binding Molecule of E6, wherein the TA is 5T4 and wherein:

(A) (1) said second Light Chain Variable Domain $CDR_L1$, $CDR_L2$, and $CDR_L3$ are the Light Chain CDRs of 5T4 MAB-1 VL (SEQ ID NO:93); and (2) said second Heavy Chain Variable Domain $CDR_H1$, $CDR_H2$, and $CDR_H3$ are the Heavy Chain CDRs of 5T4 MAB-1 VH (SEQ ID NO:92); or (B) (1) said second Light Chain Variable Domain $CDR_L1$, $CDR_L2$, and $CDR_L3$ are the Light Chain CDRs of 5T4 MAB-2 VL (SEQ ID NO:95); and (2) said second Heavy Chain Variable Domain $CDR_H1$, $CDR_H2$, and $CDR_H3$ are the Heavy Chain CDRs of 5T4 MAB-2 VH (SEQ ID NO:96).

E22. The CD137×TA Binding Molecule of E21, wherein the second Heavy Chain Variable Domain comprises the amino acid sequence of: 5T4 MAB-1 VH (SEQ ID NO:92).

E23. The CD137×TA Binding Molecule of E21 or E22 wherein the second Light Chain Variable Domain comprises the amino acid sequence of: 5T4 MAB-1 VL (SEQ ID NO:93).

E24. The CD137 Binding Molecule of E6, wherein the TA is HER2 and wherein:

(A) said second Light Chain Variable Domain $CDR_L1$, $CDR_L2$, and $CDR_L3$ are the Light Chain CDRs of hHER2-MAB-1 VLx (SEQ ID NO:79); and (B) said second Heavy Chain Variable Domain $CDR_H1$, $CDR_H2$, and $CDR_H3$ are the Heavy Chain CDRs of hHER2-MAB-1 VHx (SEQ ID NO:78);

E25. The CD137 Binding Molecule of E24, wherein:

(A) (1) said second Light Chain Variable Domain $CDR_L1$, $CDR_L2$, and $CDR_L3$ are the Light Chain CDRs of hHER2-MAB-1 VL1 (SEQ ID NO:83);

(2) said second Light Chain Variable Domain $CDR_L1$, $CDR_L2$, and $CDR_L3$ are the Light Chain CDRs of hHER2-MAB-1 VL2 (SEQ ID NO:84); or (3) said second Light Chain Variable Domain $CDR_L1$, $CDR_L2$, and $CDR_L3$ are the Light Chain CDRs of hHER2-MAB-1 VL3 (SEQ ID NO:85);

and (B) (1) said second Heavy Chain Variable Domain $CDR_H1$, $CDR_H2$, and $CDR_H3$ are the Heavy Chain CDRs of hHER2-MAB-1 VH1 (SEQ ID NO:80);

(2) said second Heavy Chain Variable Domain $CDR_H1$, $CDR_H2$, and $CDR_H3$ are the Heavy Chain CDRs of hHER2-MAB-1 VH2 (SEQ ID NO:81); or (3) said second Heavy Chain Variable Domain $CDR_H1$, $CDR_H2$, and $CDR_H3$ are the Heavy Chain CDRs of hHER2-MAB-1 VH3 (SEQ ID NO:82).

E26. The CD137 Binding Molecule of E25, wherein said second Heavy Chain Variable Domain comprises the amino acid sequence of:

(A) hHER2-MAB-1 VHx (SEQ ID NO:78);

(B) hHER2-MAB-1 VH1 (SEQ ID NO:80);

(C) hHER2-MAB-1 VH2 (SEQ ID NO:81); or (D) hHER2-MAB-1 VH3 (SEQ ID NO:82).

E27. The CD137 Binding Molecule of any one of E25 or 26, wherein said second Light Chain Variable Domain comprises the amino acid sequence of:

(A) hHER2-MAB-1 VLx (SEQ ID NO:79);

(B) hHER2-MAB-1 VL1 (SEQ ID NO:83);

(C) hHER2-MAB-1 VL2 (SEQ ID NO:84); or (D) hHER2-MAB-1 VL3 (SEQ ID NO:85).

E28. The CD137 Binding Molecule of any one of E24-E26, wherein:

(A) (1) said second Heavy Chain Variable Domain comprises the amino acid sequence of: hHER2-MAB-1 VHx (SEQ ID NO:78); and (2) said second Light Chain Variable Domain comprises the amino acid sequence of: hHER2-MAB-1 VLx (SEQ ID NO:79);

or (B) (1) said second Heavy Chain Variable Domain comprises the amino acid sequence of: hHER2-MAB-1 VH1 (SEQ ID NO:80); and (2) said second Light Chain Variable Domain comprises the amino acid sequence of: hHER2-MAB-1 VL3 (SEQ ID NO:85).

E29. The CD137 Binding Molecule of any one of E1-E29, which is an antibody, a bispecific antibody, a bispecific bivalent Fc-bearing diabody, or a bispecific tetravalent Fc-bearing diabody, or a bispecific trivalent molecule.

E30 The CD137 Binding Molecule of any one of E1-E29, wherein said molecule is bispecific and bivalent, and comprises a first, a second, and a third polypeptide chain, wherein said polypeptide chains form a covalently bonded complex.

E31. The CD137 Binding Molecule of any one of E1-E29, wherein said molecule is bispecific and tetravalent, and comprises a first, a second, a third, and a fourth polypeptide chain, wherein said polypeptide chains form a covalently bonded complex.

E32. The CD137 Binding Molecule of any one of E1-E29, wherein said molecule is bispecific and trivalent, and comprises a first, a second, a third, and a fourth, polypeptide chain, wherein said polypeptide chains form a covalently bonded complex.

E33. The CD137 Binding Molecule of E31, wherein said TA is PD-L1 and wherein:

(A) said first and third polypeptide chains comprise in the N-terminal to C-terminal direction:

(i) SEQ ID NO:63-SEQ ID NO:16-SEQ ID NO:46-SEQ ID NO:18-SEQ ID NO:39-SEQ ID NO:30-SEQ ID NO:43;
(ii) SEQ ID NO:63-SEQ ID NO:16-SEQ ID NO:46-SEQ ID NO:18-SEQ ID NO:37-SEQ ID NO:30-SEQ ID NO:43;
(iii) SEQ ID NO:58-SEQ ID NO:16-SEQ ID NO:46-SEQ ID NO:18-SEQ ID NO:39-SEQ ID NO:30-SEQ ID NO:43;
(iv) SEQ ID NO:58-SEQ ID NO:16-SEQ ID NO:46-SEQ ID NO:18-SEQ ID NO:37-SEQ ID NO:30-SEQ ID NO:43;
(v) SEQ ID NO:72-SEQ ID NO:16-SEQ ID NO:46-SEQ ID NO:18-SEQ ID NO:39-SEQ ID NO:30-SEQ ID NO:43; or
(vi) SEQ ID NO:72-SEQ ID NO:16-SEQ ID NO:46-SEQ ID NO:18-SEQ ID NO:37-SEQ ID NO:30-SEQ ID NO:43;

and (B) said second and fourth polypeptide chains comprise in the N-terminal to C-terminal direction:
(i) SEQ ID NO:54-SEQ ID NO:16-SEQ ID NO:59-SEQ ID NO:18-SEQ ID NO:40;
(ii) SEQ ID NO:54-SEQ ID NO:16-SEQ ID NO:59-SEQ ID NO:18-SEQ ID NO:38;
(iii) SEQ ID NO:50-SEQ ID NO:16-SEQ ID NO:57-SEQ ID NO:18-SEQ ID NO:40;
(iv) SEQ ID NO:50-SEQ ID NO:16-SEQ ID NO:57-SEQ ID NO:18-SEQ ID NO:38;
(v) SEQ ID NO:50-SEQ ID NO:16-SEQ ID NO:67-SEQ ID NO:18-SEQ ID NO:40;
(vi) SEQ ID NO:50-SEQ ID NO:16-SEQ ID NO:67-SEQ ID NO:18-SEQ ID NO:38;
(vii) SEQ ID NO:50-SEQ ID NO:16-SEQ ID NO:68-SEQ ID NO:18-SEQ ID NO:40;
(viii) SEQ ID NO:50-SEQ ID NO:16-SEQ ID NO:68-SEQ ID NO:18-SEQ ID NO:38;
(ix) SEQ ID NO:55-SEQ ID NO:16-SEQ ID NO:68-SEQ ID NO:18-SEQ ID NO:40;
(x) SEQ ID NO:55-SEQ ID NO:16-SEQ ID NO:68-SEQ ID NO:18-SEQ ID NO:38;
(xi) SEQ ID NO:56-SEQ ID NO:16-SEQ ID NO:68-SEQ ID NO:18-SEQ ID NO:40;
(xii) SEQ ID NO:56-SEQ ID NO:16-SEQ ID NO:68-SEQ ID NO:18-SEQ ID NO:38;
(xiii) SEQ ID NO:50-SEQ ID NO:16-SEQ ID NO:69-SEQ ID NO:18-SEQ ID NO:40;
(xiv) SEQ ID NO:50-SEQ ID NO:16-SEQ ID NO:69-SEQ ID NO:18-SEQ ID NO:38;
(xv) SEQ ID NO:50-SEQ ID NO:16-SEQ ID NO:70-SEQ ID NO:18-SEQ ID NO:40;
(xvi) SEQ ID NO:50-SEQ ID NO:16-SEQ ID NO:70-SEQ ID NO:18-SEQ ID NO:38;
(xvii) SEQ ID NO:50-SEQ ID NO:16-SEQ ID NO:71-SEQ ID NO:18-SEQ ID NO:40;
(xviii) SEQ ID NO:50-SEQ ID NO:16-SEQ ID NO:71-SEQ ID NO:18-SEQ ID NO:38;
(xix) SEQ ID NO:56-SEQ ID NO:16-SEQ ID NO:69-SEQ ID NO:18-SEQ ID NO:40; or
(xx) SEQ ID NO:56-SEQ ID NO:16-SEQ ID NO:69-SEQ ID NO:18-SEQ ID NO:38.

E34. The CD137 Binding Molecule of E31 or E33, wherein said TA is PD-L1 and wherein:

(A) said first and third polypeptide chains comprise the amino acid sequence of SEQ ID NO:116, SEQ ID NO:118, or SEQ ID NO:120; and (B) said second and fourth polypeptide chains comprise the amino acid sequence of SEQ ID NO:117, SEQ ID NO:119, SEQ ID NO:121, SEQ ID NO:122, SEQ ID NO:123, SEQ ID NO:124, SEQ ID NO:125, SEQ ID NO:126, or SEQ ID NO:139.

E35. The CD137 Binding Molecule of E34, wherein said molecule comprises:

(A) SEQ ID NO:116 and SEQ ID NO:117;
(B) SEQ ID NO:118 and SEQ ID NO:119;
(C) SEQ ID NO:120 and SEQ ID NO:119;
(D) SEQ ID NO:118 and SEQ ID NO:121;
(E) SEQ ID NO:120 and SEQ ID NO:121;
(F) SEQ ID NO:120 and SEQ ID NO:122;
(G) SEQ ID NO:120 and SEQ ID NO:123;
(H) SEQ ID NO:120 and SEQ ID NO:124;
(I) SEQ ID NO:120 and SEQ ID NO:125;
(J) SEQ ID NO:120 and SEQ ID NO:126; or
(K) SEQ ID NO:120 and SEQ ID NO:139.

E36. The CD137 Binding Molecule of E32, wherein said TA is PD-L1 and wherein:

(A) said first polypeptide chain comprises in the N-terminal to C-terminal direction:
(i) SEQ ID NO:54-SEQ ID NO:16-SEQ ID NO:46-SEQ ID NO:18-SEQ ID NO:37-SEQ ID NO:21-SEQ ID NO:146;
(ii) SEQ ID NO:54-SEQ ID NO:16-SEQ ID NO:46-SEQ ID NO:18-SEQ ID NO:39-SEQ ID NO:21-SEQ ID NO:146;
(iii) SEQ ID NO:50-SEQ ID NO:16-SEQ ID NO:46-SEQ ID NO:18-SEQ ID NO:37-SEQ ID NO:21-SEQ ID NO:146;
(iv) SEQ ID NO:50-SEQ ID NO:16-SEQ ID NO:46-SEQ ID NO:18-SEQ ID NO:39-SEQ ID NO:21-SEQ ID NO:146;
(v) SEQ ID NO:55-SEQ ID NO:16-SEQ ID NO:46-SEQ ID NO:18-SEQ ID NO:37-SEQ ID NO:21-SEQ ID NO:146;
(vi) SEQ ID NO:55-SEQ ID NO:16-SEQ ID NO:46-SEQ ID NO:18-SEQ ID NO:39-SEQ ID NO:21-SEQ ID NO:146;
(vi) SEQ ID NO:56-SEQ ID NO:16-SEQ ID NO:46-SEQ ID NO:18-SEQ ID NO:37-SEQ ID NO:21-SEQ ID NO:146; or
(vii) SEQ ID NO:56-SEQ ID NO:16-SEQ ID NO:46-SEQ ID NO:18-SEQ ID NO:39-SEQ ID NO:21-SEQ ID NO:146;

(B) said second polypeptide chain comprises in the N-terminal to C-terminal direction:
(i) SEQ ID NO:54-SEQ ID NO:16-SEQ ID NO:46-SEQ ID NO:18-SEQ ID NO:38;
(ii) SEQ ID NO:54-SEQ ID NO:16-SEQ ID NO:46-SEQ ID NO:18-SEQ ID NO:40;
(iii) SEQ ID NO:50-SEQ ID NO:16-SEQ ID NO:46-SEQ ID NO:18-SEQ ID NO:38;
(iv) SEQ ID NO:50-SEQ ID NO:16-SEQ ID NO:46-SEQ ID NO:18-SEQ ID NO:40;
(v) SEQ ID NO:55-SEQ ID NO:16-SEQ ID NO:46-SEQ ID NO:18-SEQ ID NO:38;
(vi) SEQ ID NO:55-SEQ ID NO:16-SEQ ID NO:46-SEQ ID NO:18-SEQ ID NO:40;
(vi) SEQ ID NO:56-SEQ ID NO:16-SEQ ID NO:46-SEQ ID NO:18-SEQ ID NO:38; or
(vii) SEQ ID NO:56-SEQ ID NO:16-SEQ ID NO:46-SEQ ID NO:18-SEQ ID NO:40;

(C) said third polypeptide chain comprises in the N-terminal to C-terminal direction:

(i) SEQ ID NO:59-SEQ ID NO:3-SEQ ID NO:7-SEQ ID NO:149;
(ii) SEQ ID NO:57-SEQ ID NO:3-SEQ ID NO:7-SEQ ID NO:149;
(iii) SEQ ID NO:67-SEQ ID NO:3-SEQ ID NO:7-SEQ ID NO:149;
(iv) SEQ ID NO:68-SEQ ID NO:3-SEQ ID NO:7-SEQ ID NO:149;
(v) SEQ ID NO:69-SEQ ID NO:3-SEQ ID NO:7-SEQ ID NO:149;
(vi) SEQ ID NO:70-SEQ ID NO:3-SEQ ID NO:7-SEQ ID NO:149; or
(vii) SEQ ID NO:71-SEQ ID NO:3-SEQ ID NO:7-SEQ ID NO:149;

and (D) said fourth polypeptide chain comprises in the N-terminal to C-terminal direction:
(i) SEQ ID NO:63-SEQ ID NO:1; or
(ii) SEQ ID NO:72-SEQ ID NO:1.

E37. The CD137 Binding Molecule of E32, wherein said TA is PD-L1 and wherein:

(A) said first polypeptide chain comprises in the N-terminal to C-terminal direction:
(i) SEQ ID NO:54-SEQ ID NO:16-SEQ ID NO:59-SEQ ID NO:18-SEQ ID NO:37-SEQ ID NO:21-SEQ ID NO:146; or
(ii) SEQ ID NO:54-SEQ ID NO:16-SEQ ID NO:59-SEQ ID NO:18-SEQ ID NO:39-SEQ ID NO:21-SEQ ID NO:146;
(B) said second polypeptide chain comprises in the N-terminal to C-terminal direction:
(i) SEQ ID NO:63-SEQ ID NO:16-SEQ ID NO:46-SEQ ID NO:18-SEQ ID NO:38; or
(ii) SEQ ID NO:63-SEQ ID NO:16-SEQ ID NO:46-SEQ ID NO:18-SEQ ID NO:40;
(C) said third polypeptide chain comprises in the N-terminal to C-terminal direction:
(i) SEQ ID NO:46-SEQ ID NO:3-SEQ ID NO:7-SEQ ID NO:149;

and (D) said fourth polypeptide chain comprises in the N-terminal to C-terminal direction:
(i) SEQ ID NO:54-SEQ ID NO:1; or
(ii) SEQ ID NO:50-SEQ ID NO:1.

E38. The CD137 Binding Molecule of E32 or E36, wherein said TA is PD-L1 and wherein:

(A) said first polypeptide chain comprises the amino acid sequence of SEQ ID NO:127, SEQ ID NO:133, or SEQ ID NO:135;
(B) said second polypeptide chain comprises the amino acid sequence of SEQ ID NO:128, SEQ ID NO:134, or SEQ ID NO:136;
(C) said third polypeptide chain comprises the amino acid sequence of SEQ ID NO:129, or SEQ ID NO:131; and
(D) said fourth polypeptide chain comprises the amino acid sequence of SEQ ID NO:130, SEQ ID NO:132.

E39. The CD137 Binding Molecule of E38, wherein said molecule comprises:

(A) SEQ ID NO:127, SEQ ID NO:128, SEQ ID NO:129, and SEQ ID NO:130;
(B) SEQ ID NO:127, SEQ ID NO:128, SEQ ID NO:131, and SEQ ID NO:132;
(C) SEQ ID NO:133, SEQ ID NO:134, SEQ ID NO:131, and SEQ ID NO:132; or
(D) SEQ ID NO:135, SEQ ID NO:136, SEQ ID NO:131, and SEQ ID NO:132.

E40. The CD137 Binding Molecule of E31, wherein said TA is HER2 and wherein:

(A) said first and third polypeptide chains comprise in the N-terminal to C-terminal direction:
(i) SEQ ID NO:79-SEQ ID NO:16-SEQ ID NO:46-SEQ ID NO:18-SEQ ID NO:39-SEQ ID NO:30-SEQ ID NO:43; or
(ii) SEQ ID NO:79-SEQ ID NO:16-SEQ ID NO:46-SEQ ID NO:18-SEQ ID NO:37-SEQ ID NO:30-SEQ ID NO:43;
(iii) SEQ ID NO:85-SEQ ID NO:16-SEQ ID NO:46-SEQ ID NO:18-SEQ ID NO:39-SEQ ID NO:30-SEQ ID NO:43; or
(iv) SEQ ID NO:85-SEQ ID NO:16-SEQ ID NO:46-SEQ ID NO:18-SEQ ID NO:37-SEQ ID NO:30-SEQ ID NO:43;

and (B) said second and fourth polypeptide chains comprise in the N-terminal to C-terminal direction:
(i) SEQ ID NO:54-SEQ ID NO:16-SEQ ID NO:78-SEQ ID NO:18-SEQ ID NO:40;
(ii) SEQ ID NO:54-SEQ ID NO:16-SEQ ID NO:78-SEQ ID NO:18-SEQ ID NO:38.
(iii) SEQ ID NO:50-SEQ ID NO:16-SEQ ID NO:80-SEQ ID NO:18-SEQ ID NO:40; or
(iv) SEQ ID NO:50-SEQ ID NO:16-SEQ ID NO:80-SEQ ID NO:18-SEQ ID NO:38.

E41. The CD137 Binding Molecule of E32, wherein said TA is HER2 and wherein:

(A) said first polypeptide chain comprises in the N-terminal to C-terminal direction:
(i) SEQ ID NO:54-SEQ ID NO:16-SEQ ID NO:46-SEQ ID NO:18-SEQ ID NO:37-SEQ ID NO:21-SEQ ID NO:146;
(ii) SEQ ID NO:54-SEQ ID NO:16-SEQ ID NO:46-SEQ ID NO:18-SEQ ID NO:39-SEQ ID NO:21-SEQ ID NO:146;
(iii) SEQ ID NO:50-SEQ ID NO:16-SEQ ID NO:46-SEQ ID NO:18-SEQ ID NO:37-SEQ ID NO:21-SEQ ID NO:146; or
(iv) SEQ ID NO:50-SEQ ID NO:16-SEQ ID NO:46-SEQ ID NO:18-SEQ ID NO:39-SEQ ID NO:21-SEQ ID NO:146;
(B) said second polypeptide chain comprises in the N-terminal to C-terminal direction:
(i) SEQ ID NO:54-SEQ ID NO:16-SEQ ID NO:46-SEQ ID NO:18-SEQ ID NO:38;
(ii) SEQ ID NO:54-SEQ ID NO:16-SEQ ID NO:46-SEQ ID NO:18-SEQ ID NO:40;
(iii) SEQ ID NO:50-SEQ ID NO:16-SEQ ID NO:46-SEQ ID NO:18-SEQ ID NO:38; or
(iv) SEQ ID NO:50-SEQ ID NO:16-SEQ ID NO:46-SEQ ID NO:18-SEQ ID NO:40;
(C) said third polypeptide chain comprises in the N-terminal to C-terminal direction:
(i) SEQ ID NO:78-SEQ ID NO:3-SEQ ID NO:7-SEQ ID NO:149; or
(ii) SEQ ID NO:80-SEQ ID NO:3-SEQ ID NO:7-SEQ ID NO:149;

and (D) said fourth polypeptide chain comprises in the N-terminal to C-terminal direction:
(i) SEQ ID NO:79-SEQ ID NO:1; or
(ii) SEQ ID NO:85-SEQ ID NO:1.

E42. The CD137 Binding Molecule of E32, wherein said TA is HER2 and wherein:

(A) said first polypeptide chain comprises in the N-terminal to C-terminal direction:

(i) SEQ ID NO:54-SEQ ID NO:16-SEQ ID NO:78-SEQ ID NO:18-SEQ ID NO:37-SEQ ID NO:21-SEQ ID NO:146;

(ii) SEQ ID NO:54-SEQ ID NO:16-SEQ ID NO:78-SEQ ID NO:18-SEQ ID NO:39-SEQ ID NO:21-SEQ ID NO:146;

(iii) SEQ ID NO:50-SEQ ID NO:16-SEQ ID NO:80-SEQ ID NO:18-SEQ ID NO:37-SEQ ID NO:21-SEQ ID NO:146; or (iv) SEQ ID NO:50-SEQ ID NO:16-SEQ ID NO:46-SEQ ID NO:18-SEQ ID NO:39-SEQ ID NO:21-SEQ ID NO:146;

(B) said second polypeptide chain comprises in the N-terminal to C-terminal direction:

(i) SEQ ID NO:79-SEQ ID NO:16-SEQ ID NO:46-SEQ ID NO:18-SEQ ID NO:38;

(ii) SEQ ID NO:79-SEQ ID NO:16-SEQ ID NO:46-SEQ ID NO:18-SEQ ID NO:40;

(iii) SEQ ID NO:85-SEQ ID NO:16-SEQ ID NO:46-SEQ ID NO:18-SEQ ID NO:38; or (iv) SEQ ID NO:85-SEQ ID NO:16-SEQ ID NO:46-SEQ ID NO:18-SEQ ID NO:40;

(C) said third polypeptide chain comprises in the N-terminal to C-terminal direction:

(i) SEQ ID NO:46-SEQ ID NO:3-SEQ ID NO:7-SEQ ID NO:149;

and (D) said fourth polypeptide chain comprises in the N-terminal to C-terminal direction:

(i) SEQ ID NO:54-SEQ ID NO:1; or (ii) SEQ ID NO:50-SEQ ID NO:1.

E43. The CD137 Binding Molecule of any one of E40-E42, wherein said molecule comprises:

(A) SEQ ID NO:151, and SEQ ID NO:152;

(B) SEQ ID NO:127, SEQ ID NO:128, SEQ ID NO:153, and SEQ ID NO:154; or (C) SEQ ID NO:143, SEQ ID NO:144, SEQ ID NO:155, and SEQ ID NO:165.

E44. A pharmaceutical composition comprising the CD137 Binding Molecule of any one E1-43, and a physiologically acceptable carrier.

E45. Use of the CD137 Binding Molecule of any one of E6-E43, or the pharmaceutical composition of E44, in the treatment of a disease or condition associated with or characterized by the expression of said TA.

E46. A PD-L1 Binding Molecule comprising a Light Chain Variable Domain that comprises a $CDR_L1$, $CDR_L2$ and $CDR_L3$, and a Heavy Chain Variable Domain that comprises a $CDR_H1$, $CDR_H2$ and $CDR_H3$; wherein:

(A) said Light Chain Variable Domain $CDR_L1$, $CDR_L2$, and $CDR_L3$ are the Light Chain CDRs of hPD-L1 MAB-2 VL2 (SEQ ID NO:72);

and (B) (1) said Heavy Chain Variable Domain $CDR_H1$, $CDR_H2$, and $CDR_H3$ are the Heavy Chain CDRs of hPD-L1 MAB-2 VH2 (SEQ ID NO:67);

(2) said Heavy Chain Variable Domain $CDR_H1$, $CDR_H2$, and $CDR_H3$ are the Heavy Chain CDRs of hPD-L1 MAB-2 VH3 (SEQ ID NO:68)

(3) said second Heavy Chain Variable Domain $CDR_H1$, $CDR_H2$, and $CDR_H3$ are the Heavy Chain CDRs of hPD-L1 MAB-2 VH4 (SEQ ID NO:69)

(4) said second Heavy Chain Variable Domain $CDR_H1$, $CDR_H2$, and $CDR_H3$ are the Heavy Chain CDRs of hPD-L1 MAB-2 VH5 (SEQ ID NO:70); or (5) said second Heavy Chain Variable Domain $CDR_H1$, $CDR_H2$, and $CDR_H3$ are the Heavy Chain CDRs of hPD-L1 MAB-2 VH6 (SEQ ID NO:71).

E47. The PD-L1 Binding Molecule of E46, wherein said Heavy Chain Variable Domain comprises the amino acid sequence of:

(A) hPD-L1 MAB-2 VH2 (SEQ ID NO:67);

(B) hPD-L1 MAB-2 VH3 (SEQ ID NO:68);

(C) hPD-L1 MAB-2 VH4 (SEQ ID NO:69);

(D) hPD-L1 MAB-2 VH5 (SEQ ID NO:70); or (E) hPD-L1 MAB-2 VH6 (SEQ ID NO:71).

E48. The PD-L1 Binding Molecule of any one of E46-E47, wherein said Light Chain Variable Domain comprises the amino acid sequence of hPD-L1 MAB-2 VL2 (SEQ ID NO:72).

E49. The PD-L1 Binding Molecule of any one E46-E48, wherein said molecule is an antibody or an antigen binding fragment thereof.

E50. The PD-L1 Binding Molecule of any one E46-E48, wherein said molecule is a multispecific binding molecule.

E51. The PD-L1 Binding Molecule of any one E50, wherein said molecule is a bispecific diabody, a bispecific antibody, or a trivalent binding molecule.

E52. A pharmaceutical composition comprising the PD-L1 Binding Molecule of any one E46-E51, and a physiologically acceptable carrier.

E53. Use of the PD-L1 Binding Molecule of any one of E46-E51, or the pharmaceutical composition of E52, in the treatment of a disease or condition associated with a suppressed immune system or characterized by the expression of PD-L1.

E54. The use of E53, wherein said disease or condition associated with a suppressed immune system or characterized by the expression of PD-L1 is cancer.

E55. The use of any one of E45, or E54, wherein said cancer is selected from the group consisting: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer.

E56. A method of enhancing the activity of a tumor targeting agent comprising administering said tumor target agent in combination with the CD137 Binding Molecule of any one of E1-E43, the PD-L1 Binding Molecule of any one of E46-E51, or the pharmaceutical composition of any one of E44 or E52.

E57. A method of treating a disease or condition associated with a suppressed immune system or characterized by the expression of a TA comprising administering to a subject in need thereof of the CD137 Binding Molecule of any one of E1-E43, the PD-L1 Binding Molecule of any one of E46-E53, or the pharmaceutical composition of E44 or E53.

E58. The method of E57, wherein the condition associated with a suppressed immune system or characterized by the expression of the TA is cancer.

E59. The method of E57 or E58, further comprising administering a tumor targeting agent.

E60. The method of E56 or E59, wherein said tumor target agent is an antibody, an epitope binding fragment of an antibody, or an agent that mediates T-cell redirected killing of a target cell.

E61. The method of any one of E57-E60, wherein the cancer is selected from the group consisting: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer.

E62. A nucleic acid encoding the CD137 Binding Molecule of any one of E1-E43, or the PD-L1 Binding Molecule of any one of E46-E51.

E63. An expression vector comprising a nucleic acid according to E62.

E64. A cell comprising a nucleic acid according to E62 or an expression vector according to E63.

E65. The cell according to E64, wherein said cell is a mammalian cell.

EXAMPLES

Having now generally described the invention, the same will be more readily understood through reference to the following Examples. The following examples illustrate various methods for compositions in the diagnostic or treatment methods of the invention. The examples are intended to illustrate, but in no way limit, the scope of the invention.

Example 1

Methods

The ability of a test article (e.g., antibody, diabody, or trivalent molecule) to mediate target-dependent signal transduction of NF/kB pathway was evaluated using a CD137 expressing reporter cell line (Jurkat-NF-κB-Luc) in a CD137 reporter assay performed essentially as follows: for bispecific molecules target cells (type and number indicated in figures and below) in 100 μL of assay media (RPMI-1640, 10% FBS)) were plated into sterile assay microplates and incubated at 37° C. overnight. On day 2, Jurkat-NF-κB-Luc reporter cells overexpressing CD137 ($4\times10^4$ to $7.5\times10^4$ cells in 50 μL of assay media) and 50 uL of serially diluted test articles were added to each well containing target cells and to control wells without target cells in quick succession. The plates were incubated for 4-5 hours at 37° C. BioGlo Substrate (Promega) was then added to each well (50 μL) and the plates incubated for an additional 5-10 minutes at room temperature ("RT"), the signal transduction was measured by detecting luminescence for example using Perkin Elmer Envision device) with luminescence relative light unit (RLU) as the read-out. For mono-specific anti-CD137 antibodies, no target cells were used, instead a four-fold excess of goat anti-mouse or goat anti-human antibody was added to cross link the antibodies.

ELISA assays to evaluate the test articles for CD137 binding were performed essentially as follows: flat bottom maxisorb 96-well plates were coated with soluble human or cynomolgus monkey CD137 (the extracellular domain of human or cynomolgus monkey CD137 fused to a His tag (shCD137 His or scyCD137 His) or to a human Fc Region (shCD137 hFc or scyCD137 hFc)), each at 0.5 or 1 μg/mL. The plates were washed, blocked with PBS buffer containing 0.5% bovine serum albumin and 0.1% Tween20, and incubated with a test article (e.g., cell supernatants or purified mAb). For the hybridoma supernatants anti-CD137 antibody was utilized at 1.0 μg/mL and six three-fold serial dilutions. The amount of test article binding to the immobilized CD137 (human or cynomolgus monkey) was assessed using a goat anti-mouse IgG-HRP secondary antibody. All samples were analyzed on a plate reader (Victor 2 Wallac, Perkin Elmer) and EC50 values were calculated from dose-response curves by nonlinear regression analysis.

The T cell cytokine release assays (using suboptimal stimulated primary T cells in the absence of target cells) were performed essentially as follows: 50 μL of serially diluted test article (antibodies (+/− cross-linking with anti-human Fc (Fab)'$_2$)), 50 μL of prewashed Dynabeads αCD3 (REF 11151D; Invitrogen by Thermo Fisher Scientific, or similar) at $2\times10^6$ beads/mL, and 100 μL/well of human pan T cells (purified from donor PBMC using Dynabeads Untouched Human T Cells Kit (Invitrogen Cat #11344D) or similar, per manufacture's protocol) at $10^6$ cells/mL were added to each well of the assay plate. The final volume of each well on the plate was 200 μL. For those control wells that did not contain test article or αCD3 beads, assay media was added to bring up the total volume to 200 μL and the plates were incubated for 72 hours in a tissue culture incubator. The supernatants were then collected from each well and the released cytokines of IL-2, IL-10, TNF-α, and IFN-γ, were measured using a Cytokine ELISA Kit (e.g., R&D System Human IL-2 DuoSet ELISA (Cat: DY202), Human IFN-gamma DuoSet ELISA (Cat: DY285) and Human TNF-alpha DuoSet ELISA (Cat: DY210) or similar commercial reagents) according to the manufacturer's instructions. Microsoft Excel and SoftMax Pro were used for data analysis to extrapolate cytokine levels, which were plotted with Prism.

FACS analysis to evaluate the test articles for binding to cell surface CD137 was performed essentially as follows: 100 μL of CHO cells expressing CD137 (CHO/CD137) ($1.0\times10^5$ to $1\times10^6$ cells/well) and 100 μL of serially diluted test article or control was added to each well of microtiter assay plate(s), mixed and incubated at RT for about 30 min. The cells were washed with FACS Buffer and secondary antibody (goat anti-human-APC, PE, or FITC) was then added to each well (1:1000), after which, the components were mixed and the wells were incubated at RT for about 30 min. Cells were washed and resuspended in 250 μL FACS Buffer and analyzed by flow cytometry (BD LSR Fortessa or FACSCanto II) for cell events collection. Data analysis were performed via FloJo v10.

Competition between anti-CD137 antibodies and CD137 ligand for binding to CD137 was determined using a real-time, label-free biolayer interferometry assay on an Octet biosensor (Pall ForteBio) essentially as follows: Anti-CD137 antibodies were immobilized on an anti-human Fc biosensor and then associated with the extracellular domain of human CD137 fused to a murine Fc domain (shCD137 mFc; 10 ug/mL) for 30 seconds. The sensors were then dipped into recombinant human CD137 ligand (R&D Systems; 5 ug/mL) for 30 seconds to monitor if the ligand could bind to the preformed CD137/antibody complex or if its binding was blocked.

The binding kinetics of the anti-CD137 antibodies (having human Fc regions) were investigated using BIACORE™ SPR analysis. The anti-CD137 antibodies were captured on a Fab'2 goat-anti-human Fc surface. The association and dissociation of shCD137 His or scyCD137 His (12.5 nM, 50 nM, 200 nM) were monitored and sensograms were fitted using a 1:1 binding model to calculate association and dissociation rate constants and the KD determined.

FACS analysis to evaluate the test articles for binding to cell surface PD-L1 was performed essentially as follows: 100 μL of CHO cells expressing PD-L1 (CHO/PD-L1) ($1.0\times10^5$ to $1.0\times10^6$ cells/well) and 100 μL of serially diluted test article was added to each well of microtiter assay plate(s), mixed and incubated at RT for about 30 min. The cells were washed with FACS Buffer and secondary antibody (goat anti-human-FITC, PE, or APC) was then added to each well, after which, the components were mixed and the wells were incubated at RT for about 30 min. Cells were washed and resuspended in 250 μL FACS Buffer and analyzed by flow cytometry (BD LSR Fortessa or FACSCanto II) for cell events collection. Data analysis were performed via FloJo v10.

The ability of a test article to antagonize the PD-1/PD-L1 axis (i.e., block the PD-1/PD-L1 interaction and prevent down-regulation of T-cell responses) was evaluated in a Jurkat-luc-NFAT/CHO/PD-L1 luciferase PD-L1 reporter assay, performed essentially as follows: CHO/PD-L1 cells were plated at 40,000/well in 100 μL of culture medium (DMEM/F12+10% FBS+200 μg/mL Hygromycin B+250 μg/mL G418) and incubated overnight. The next day the media was removed and NFAT-luc2/PD-1 Jurkat cells (Promega) at 125,000 cells/well in 50 μL assay buffer (RPMI+2% FBS), and 50 μL of serial diluted test articles were added to each well and incubated for 6 hours at 37° C. 80 μL of BioGlo Substrate (Promega) was then added to each well and the plate was incubated for an additional 5-10 minutes at RT, PD-1/PD-L1 blockade was measured by detecting luminescence (for example using Perkin Elmer Envision device) with luminescence relative light unit (RLU) as the read-out.

The T cell cytokine release assay (using suboptimal stimulated primary T cells in the presence of target cells) were performed essentially as follows: human pan T cells (purified from donor PBMC, see above) were resuspended in assay media and placed in a tissue culture incubator overnight. TA positive target cells (e.g., CHO/PD-L1 cells, JIMT-1 cells, N87 cells), and control TA negative cells (e.g., CHO cells) were obtained from culture. After washing, target cells (number indicated in figures and below) were pre-seeded in flat-bottom bright 96-well plates and placed in a tissue culture incubator overnight. The next day, rested human pan T cells were measured for density and viability by trypan blue exclusion using a Beckman Coulter Vi-Cell counter and adjusted to a density of $2\times10^6$ cells/mL. The next day the supernatants were discarded and 50 μL of serially diluted test article (antibodies, diabodies, trivalent molecules, etc.), 50 μL of prewashed Dynabeads αCD3 (REF 11151D; Invitrogen by Thermo Fisher Scientific) at $2.0\times10^6$ beads/mL, 50 μL/well of human pan T cells at $2.0\times10^6$ cells/mL, and 50 μL of assay media were added to each well of the assay plate. The final volume of each well on the plate was 200 μL. For control wells that did not contain test article or αCD3 beads, assay media was added to bring up the total volume to 200 μL and the plates were incubated for 72 hours in a tissue culture incubator. The supernatants were then collected from each well and the released cytokines of IFN-γ and IL-2 were measured using a Cytokine ELISA Kit (e.g., R&D System (Human IL-2 DuoSet ELISA (Cat: DY202), Human IFN-gamma DuoSet ELISA (Cat: DY285) or similar commercial regents) according to the manufacturer's instructions. Microsoft Excel and SoftMax Pro were used for data analysis to extrapolate cytokine levels, which were plotted with Prism.

Quantification of CD137×TA Binding Molecules in cynomolgus monkey serum was performed essentially as follows: Assay Plates were coated with 2.0 μg/mL of a His-tagged soluble human CD137 fusion protein (huCD137) (containing an extracellular portion of human CD137 fused to a histidine-containing peptide) overnight. After blocking the non-specific sites with 0.5% bovine serum albumin (BSA) in phosphate buffered saline (PBS) with 0.1% Tween-20 (PBST), the plate was incubated with CD137×TA Binding Molecule standard calibrators, quality controls and test samples. The immobilized huCD137-His captures the CD137×TA Binding Molecules present in the standard calibrators, quality controls and test samples. The captured CD137×TA Binding Molecule was detected by the addition of 0.05 μg/mL goat anti-human IgG(Fc)-HRP. The bound HRP activity was quantified by the luminescence light generation using Thermo Scientific SuperSignal ELISA Pico Chemiluminescent Substrate. The luminescence light intensity, expressed as relative light unit (RLU), was measured by the Victor $X_4$ plate reader. The standard curve was generated by fitting RLU signal from AEX3370 standards with a five-parameter logistic model. The concentration of the CD137×TA Binding Molecule in the serum samples was then interpolated from the samples' RLU signal and the equation describing the standard curve. Lower limit of quantification (LLOQ) for the assay was 6.1 ng/mL.

T cell and NK cell proliferation assays were performed essentially as follows: A panel T cell and NK cell marker antibodies including CD3, CD4, CD8, CD56 and CD159a was added into sample plate wells containing well-mixed anticoagulated whole blood samples obtained from the cynomolgus monkey studies, mixed thoroughly using a pipette, and incubated in the dark for 25-35 minutes at ambient temperature. 1× BD FACS lysing solution was then added to each well and mixed using a pipette; each plate was then incubated in the dark for an additional 10-20 minutes at ambient temperature. Each plate was centrifuged at 400×g for 5 minutes and the supernatant was discarded. FACS buffer was added in each well and mixed as a washing step. Each plate was then centrifuged at 400×g for 5 minutes and the supernatant was discarded. The cell pellet was resuspended with BD Cytofix/Cytoperm solution and incubated for 20-40 minutes at 2-8° C. At the end of incubation, each plate was washed as in previous wash steps and the cell pellet was resuspended with Ki67 antibody or isotype control and incubated for 30-60 minutes at 2-8° C. Each plate was again washed as in previous wash steps and the cell pellet was finally resuspended in FACS buffer and the samples were analyzed with a BD FACSCanto II cell analyzer. The proliferation of T-cells and NK cells were quantified by monitoring $CD3^+CD8^+Ki67^+$ and $CD56^+CD159a^+Ki67^+$ populations, respectively.

Example 2

The Isolation and Characterization of a Human Non-Blocking Anti-CD137 mAb

To identify a CD137 binding domain having improved characteristics, particularly when incorporated into different CD137×TA Binding Molecules, a panel of monoclonal antibodies having fully human variable domains specific for human CD137 were generated using the TRIANNI MOUSE® platform by immunizing mice with a His-tagged soluble human CD137 fusion protein (huCD137) (containing an extracellular portion of human CD137 fused to a histidine-containing peptide). The supernatants from the resulting hybridomas were evaluated for CD137 binding, ability to mediate dose dependent T-cell signal transduction in a CD137 reporter assay, and for the ability to induce cytokine (e.g., IFN-γ, TNF-α) release from T cells. The VH and VL Domains of several hybridomas were cloned and expressed in CHO cells as human IgG1 (L234A/L235A) antibodies and evaluated for binding affinity, ligand blocking activity, binding to CD137 on the cell surface and again in both the CD137 reporter and cytokine release assays. An irrelevant negative control antibody and/or the previously described chimeric anti-CD137 antibody chCD137 MAB-3 (see, WO 2018/156740 and above) were included in these evaluations. The methods used for such evaluations are provided above. One antibody designated CD137 MAB-6 (1.1), was selected for further study. The amino acid sequences of the VH and VL Domains CD137 MAB-6 (1.1) are provide above and representative results from these evaluations are summarized in Tables 7A-D.

TABLE 7A

| Hybridoma Supernatants | | | | |
|---|---|---|---|---|
| | Reporter Assay (RLU) IgG conc | | ELISA (EC50 ng/mL) | |
| Antibody (conc.) | 0.02 μg/mL | 0.1 μg/mL | huCD137 | cyCD137 |
| CD137MAB-6(1.1) | 3280 | 11670 | 38 | 49 |
| chCD137MAB-3 | 5540 | 18650 | 34 | 44 |
| non-specific mAb | 1020 | 1240 | — | — |

TABLE 7B

| Hybridoma Supernatants | | | | | | | | |
|---|---|---|---|---|---|---|---|---|
| T cell assay-cytokine release | | | | | | | | |
| | IL-2 | | | | IL-10 | | | |
| | Donor 1 | | Donor 2 | | Donor 1 | | Donor 2 | |
| (conc.) | 0.1 | 1 | 0.1 | 1 | 0.1 | 1 | 0.1 | 1 |
| Antibody | μg/mL | μg/mL | μg/mL | μg/mL | μg/mL | μg/mL | μg/mL | μg/mL |
| CD137 MAB-6 (1.1) | 25 | 307 | 172 | 402 | 35 | 393 | 204 | 973 |
| chCD137 MAB-3 | 124 | 223 | 313 | 628 | 52 | 63 | 225 | 391 |
| non-specific mAb | 16 | 29 | 27 | 29 | 33 | 35 | 45 | 54 |

| | TNF-α | | | | IFN-γ | | | |
|---|---|---|---|---|---|---|---|---|
| | Donor 1 | | Donor 2 | | Donor 1 | | Donor 2 | |
| (conc.) | 0.1 | 1 | 0.1 | 1 | 0.1 | 1 | 0.1 | 1 |
| Antibody | μg/mL | μg/mL | μg/mL | μg/mL | μg/mL | μg/mL | μg/mL | μg/mL |
| CD137 MAB-6 (1.1) | 76 | 908 | 355 | 702 | 116 | 2901 | 546 | 2573 |
| chCD137 MAB-3 | 275 | 368 | 370 | 508 | 194 | 303 | 287 | 455 |
| non-specific mAb | 35 | 113 | 68 | 102 | 33 | 92 | 56 | 99 |

TABLE 7C

| CHO cell Supernatants | | | | | | |
|---|---|---|---|---|---|---|
| | | SPR | | | Surface Binding | |
| Antibody | Ligand Blocking | kon, 1/(Ms) | koff, 1/s | KD, nM | MFI max | EC50 ng/mL |
| CD137 MAB-6 (1.1) | no | 4.2E+5 | 6.7E−3 | 16 | 5745 | 21 |
| chCD137 MAB-3 | yes | 6.6E+5 | 2.5E−2 | 38 | 6046 | 10 |
| non-specific mAb | — | | — | — | 149 | — |

TABLE 7D

| CHO cell Supernatants | | | |
|---|---|---|---|
| | Reporter Assay | Primary T cell assay Donor 1 | |
| | (RLU) | INF γ | TNF-α |
| (conc.) | 0.08 | 0.1 | 0.1 |
| Antibody | μg/mL | μg/mL | μg/mL |
| CD137MAB-6(1.1) | 8530 | 174 | 101 |
| chCD137 MAB-3 | 9170 | 63 | 45 |
| non-specific mAb | 1250 | 0 | 6 |

Epitope binning was performed by cross-competition studies. The results of these and ligand binding competition studies indicate that CD137 MAB-6 binds an epitope distinct from a comparator antibody comprising the variable domains of utomilumab, a comparator antibody comprising the variable domains of urelumab, and all of the anti-CD137 antibodies described in WO 2018/156740 including chCD137 MAB-3. In sum, these studies demonstrate that CD137 MAB-6 binds a unique non-blocking epitope and exhibits better binding affinity than the previously described chCD137 MAB-3 as determined by ELISA, FACS and BIACORE™ assays. CD137 MAB-6 also exhibits higher activity in T-cell cytokine release assay.

Example 3

Characterization of CD137×TA Binding Molecules

CD137×TA Binding Molecules capable of binding to CD137 and to the representative TA, PD-L1, were generated incorporating the VH and VL Domains of CD137 MAB-6 (1.1) and hPD-1 MAB-2(1.1). In particular, a tetravalent bispecific diabody designated "DART-A," comprising two identical bispecific diabody binding domains and having the antibody-like Y structure shown in FIG. 1B, and a trivalent binding molecule designated "TRIDENT-A," comprising one mono-specific diabody-type binding domain, and a non-diabody-type binding domain having the structure shown in FIG. 3A, were generated. The domain attributes of these molecules, and certain bispecific control and comparator molecules having the same structures are discussed above (see e.g., Tables 5-6).

Figure 4:
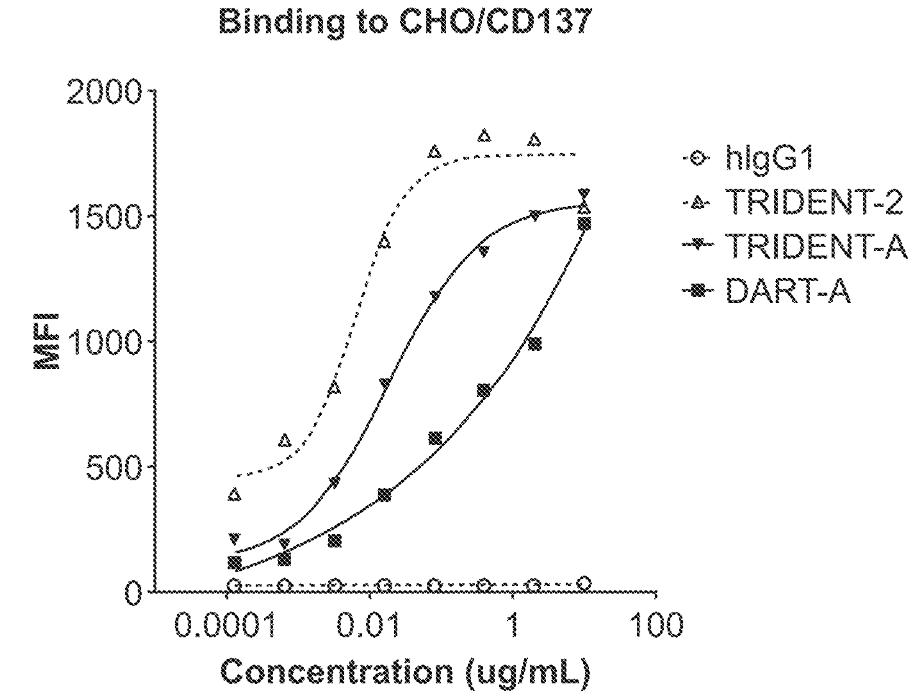
FIG. 4 shows the ability of CD137×TA Binding Molecules DART-A, TRIDENT-A, the comparator molecule TRIDENT-2, and the negative control hIgG1 to bind to CD137 expressed on the surface of engineered CHO cells.

DART-A, TRIDENT-A, a comparator molecule TRIDENT-2 (comprising the binding domain of hCD137 MAB-3(1B.3)), and a negative control (hIgG1—an irrelevant antibody as an isotype control) were evaluated for their ability to bind to cell surface CD137 by FACS analysis performed essentially as described-above, test articles were used at 10 μg/mL and five-fold serial dilutions. The results of a representative assay shown in FIG. 4 demonstrate that all the CD137×PD-L1 bispecific molecules were capable of efficiently binding to CD137 expressed on the cell surface. In this assay the comparator molecules appear to exhibit better binding.

Figure 5A:
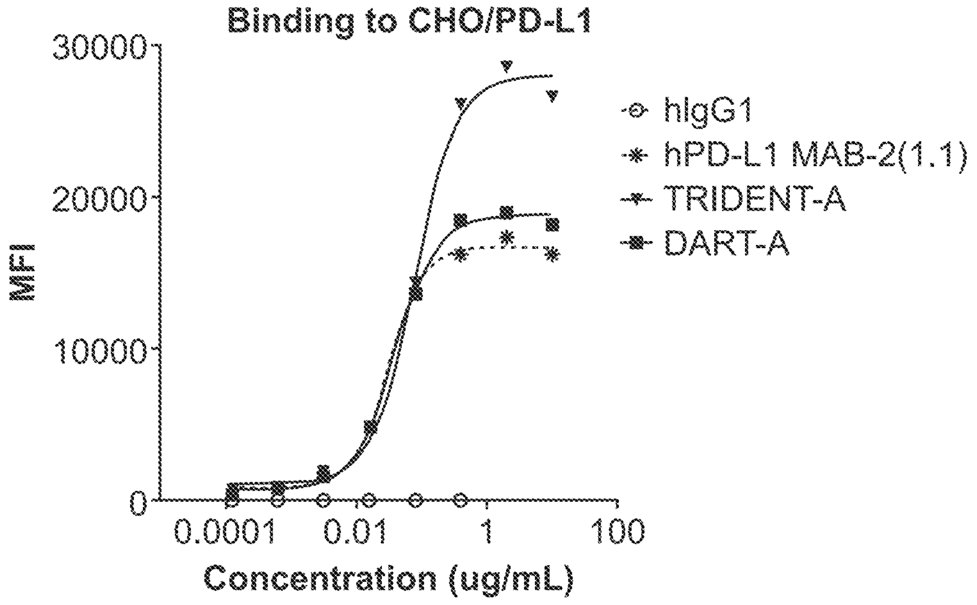
FIGS. 5A-5B show the ability of CD137×TA Binding Molecules DART-A, TRIDENT-A, hPD-L1 MAB-2(1.1), and the negative control hIgG1 to bind to PD-L1 expressed on the cell surface of engineered CHO cells (FIG. 5A) and to block PD-L1/PD-1 interactions in a PD-L1 reporter assay (FIG. 5B).
Figure 5B:
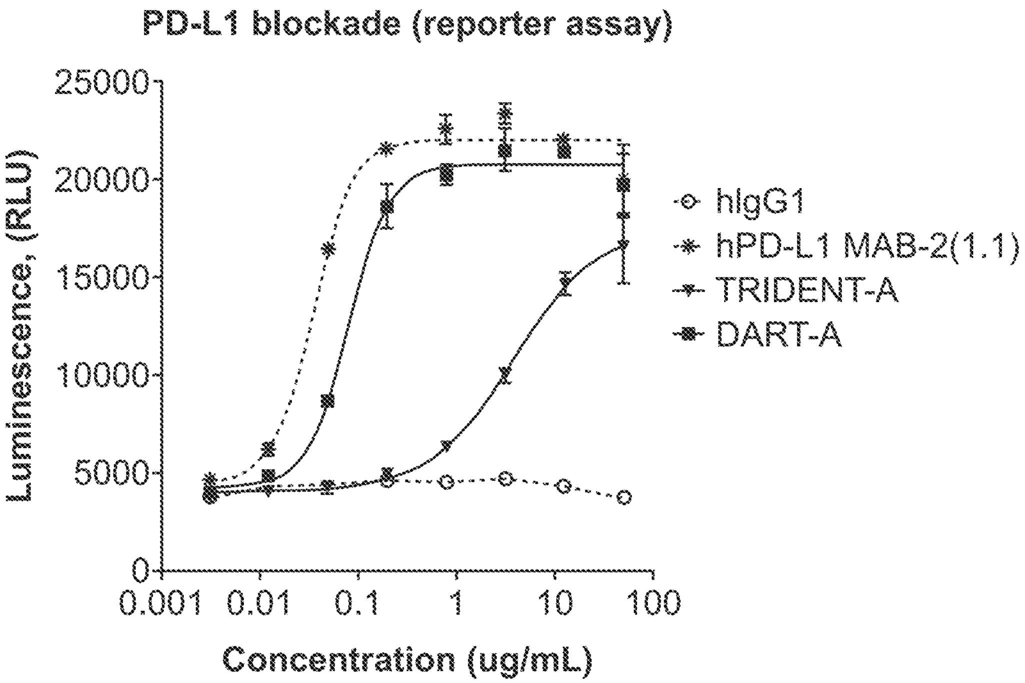

DART-A, TRIDENT-A, hPD-1 MAB-2(1.1), and the negative control, hIgG1, were evaluated for their ability to bind to the surface of CHO cells expressing PD-L1 (CHO/PD-L1) by FACS analysis, and for their ability to antagonize the PD-1/PD-L1 axis (i.e., block the PD-1/PD-L1 interaction and prevent down-regulation of T-cell responses) in the Jurkat-luc-NFAT/CHO/PD-L1 luciferase reporter assay, both assays were performed essentially as described above. Test articles were used at 10 μg/mL and five-fold serial dilutions for the FACS analysis and at 50 μg/mL and five-fold serial dilutions for the PD-L1 reporter assay. The results of a representative assay shown in FIGS. 5A-5B demonstrate that DART-A and TRIDENT-A were capable of efficiently binding to PD-L1 expressed on the cell surface (FIG. 5A), and of blocking PD-1/PD-L1 interactions (FIG. 5B). It will be noted that the binding curves of molecules having two PD-L1 binding sites (DART-A, and hPD-1 MAB-2(1.1)) reach saturation sooner indicating that some of the molecules are exhibiting bivalent binding (i.e., binding two PD-L1 molecules on the surface). Bivalent bonding is more likely in the presence of high concentrations of target ligand expressed on the CHO/PD-L1 cells. It was also observed that the molecules, possessing two PD-L1 binding sites, exhibited greater PD-L1 blocking activity relative to the trivalent molecules.

Figure 6:
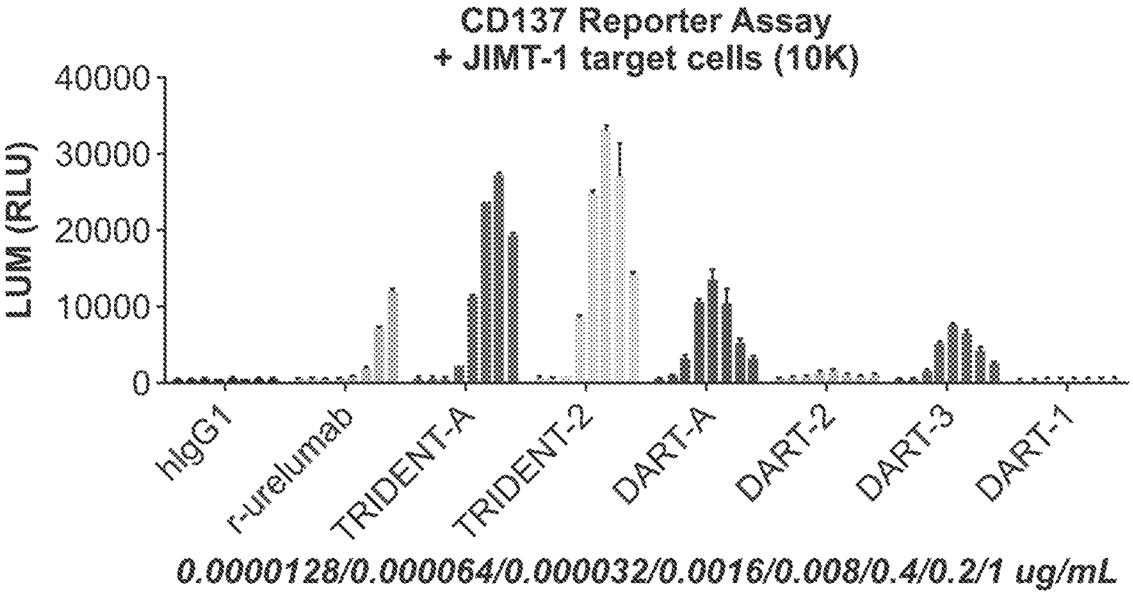
FIG. 6 shows the ability of CD137×TA Binding Molecules DART-A, TRIDENT-A, the comparator molecules: DART-2, and TRIDENT-2, DART-3, r-urelumab, and the negative controls: DART-1 and hIgG1 to mediate target-dependent signal transduction in a CD137 Reporter Assay.

The functional activity of DART-A, TRIDENT-A, the comparator molecules: DART-2, and TRIDENT-2 (each comprising the binding domain of hCD137 MAB-3(1B.3)), DART-3 (comprising the binding domain of utomilumab), a replica of the agonistic anti-CD137 mAb urelumab (r-urelumab), and the negative controls: DART-1 (an RSV×PD-L1 binding molecule) and hIgG1 was evaluated in a CD137 reporter assay performed essentially as described above in the presence and absence of PD-L1 expressing JIMT-1 cells (10,000 cells per well), test articles were used at 1 ug/mL and five-fold serial dilutions. The results of a representative assay shown in FIG. 6 demonstrate that both the tetravalent and trivalent CD137×PD-L1 bispecific molecules comprising the binding domain CD137 MAB-6 (1.1) (DART-A and TRIDENT-A, respectively) mediated target-dependent signal transduction, in contrast only the trivalent molecule comprising the binding domain of hCD137 MAB-3(1B.3) (TRIDENT-2) exhibited activity while the corresponding tetravalent molecule DART-2, did not exhibit any activity in the presence of target cells. Additionally, DART-A exhibited the highest activity of all the tetravalent molecules tested. None of the CD137×TA Bispecific Molecules exhibited activity in the absence of target cells. As expected, the agonist r-urelumab exhibited activity in the presence and absence of PD-L1 expressing target cells, and the negative controls did not exhibit activity at all.

Figure 7A:
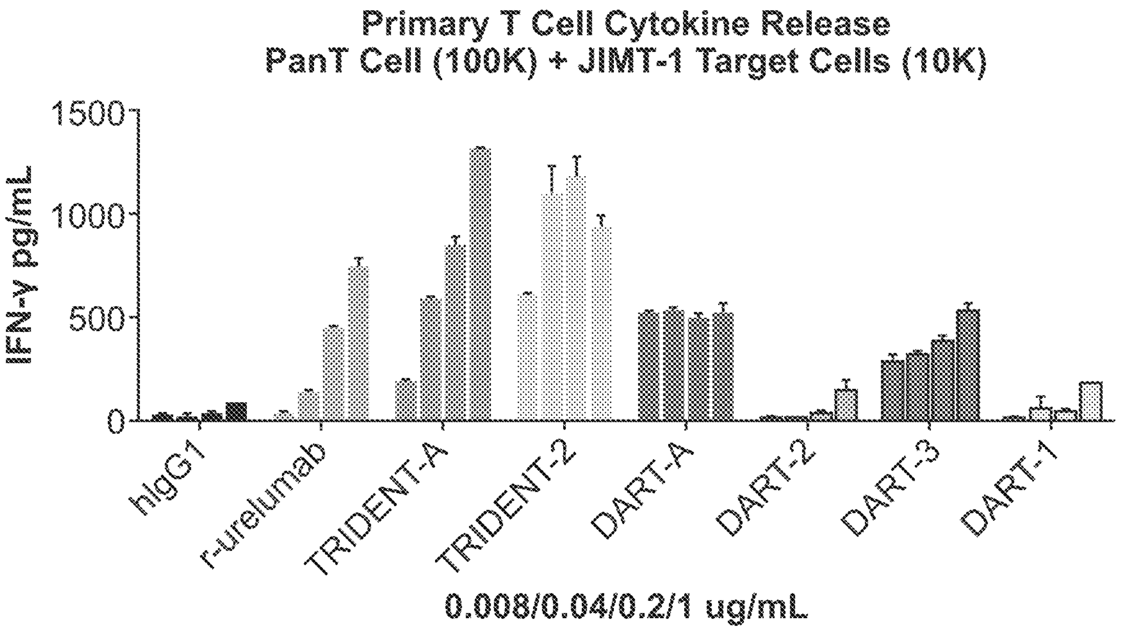
FIGS. 7A-7B show ability of CD137×TA Binding Molecules DART-A, TRIDENT-A, the comparator molecules: DART-2, and TRIDENT-2, DART-3, r-urelumab, and the negative controls: DART-1 and hIgG1 to mediate target-dependent release of cytokines INF-γ (FIG. 7A) and IL-2 (FIG. 7B) in a primary T cell cytokine release assay.
Figure 7B:
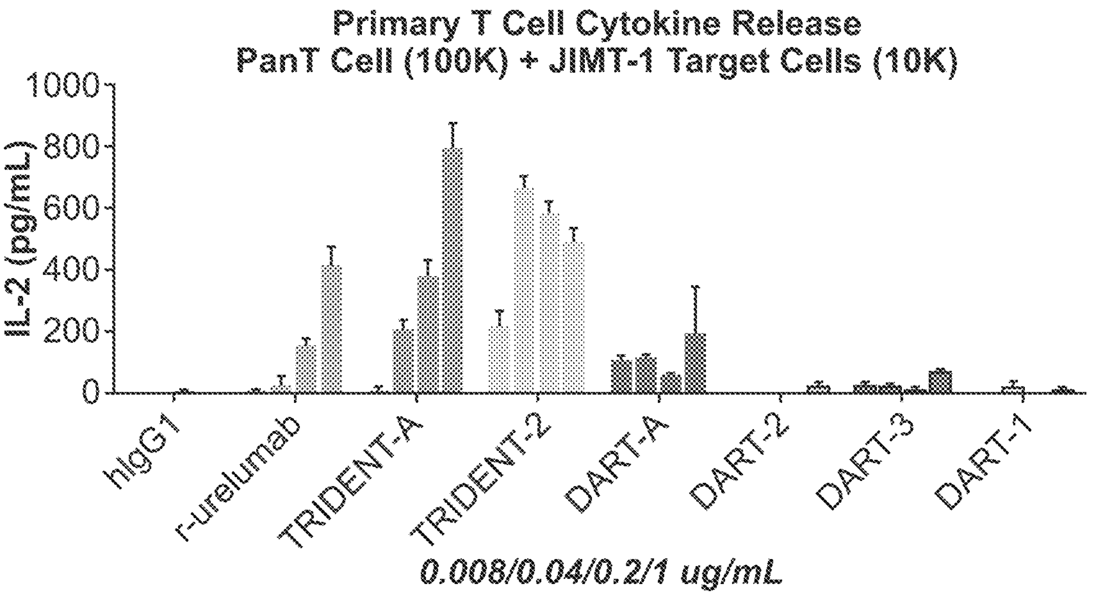

The functional activity of DART-A, TRIDENT-A, comparator molecules: DART-2, TRIDENT-2, DART-3, r-urelumab, and the negative controls: DART-1 and hIgG1 was also evaluated in the primary T cell cytokine release assay presence of PD-L1 expressing JIMT-1 cells (10,000 cells per well) performed essentially as described above, test articles were used at 1 μg/mL and five-fold serial dilutions. The results of a representative assay for the representative cytokines INF-γ and IL-2 are shown in FIGS. 7A and 7B, respectively. As was seen in the CD137 reporter assay, both the tetravalent and trivalent CD137×PD-L1 bispecific molecules comprising the binding domain CD137 MAB-6(1.1) (DART-A and TRIDENT-A, respectively) mediated cytokine release, in contrast only the trivalent molecule comprising the binding domain of hCD137 MAB-3(1B.3) (TRIDENT-2) exhibited activity while the tetravalent molecule DART-2, did not exhibit any activity. Again DART-A exhibited the highest activity of all the tetravalent molecules tested and the negative controls did not exhibit activity.

These studies demonstrate that the fully human binding domain CD137 MAB-6(1.1) is active in both tetravalent and trivalent CD137×TA bispecific molecules, and does not exhibit agonist activity in the absence of a PD-L1 expressing target cell. Although TRIDENT-2 exhibited higher binding to CHO/CD137 cells, the activity of TRIDENT-A and TRIDENT-2 were comparable while DART-2 exhibited no activity in either of the functional assays. Indeed, CD137 MAB-6(1.1) is more active in the tetravalent antibody-like structure shown in FIG. 1B than molecules comprising the binding domains of hCD137 MAB-3(1B.3) or utomilumab.

Example 4

Pharmacokinetics of CD137×TA Molecules

The pharmacokinetics of the trivalent CD137×TA bispecific molecules TRIDENT-A (comprising the binding domain of CD137 MAB-6(1.1)) and TRIDENT-2 (comprising the binding domain of hCD137 MAB-3(1B.3)) were evaluated in Cynomolgus monkeys. Briefly, two cynomolgus monkeys (females) were infused with a single dose of each test article at 1 mg/kg or 10 mg/kg (four groups) and the animals were monitored for 22 days, no necropsies were performed. Animals were monitored for food consumption, body weight, and full hematology, and clinical chemistry were performed during the study. Transient increases in liver enzymes (ALT, AST, and bilirubin) were observed. The test articles were well tolerated and no adverse effects were observed.

Figure 8A:
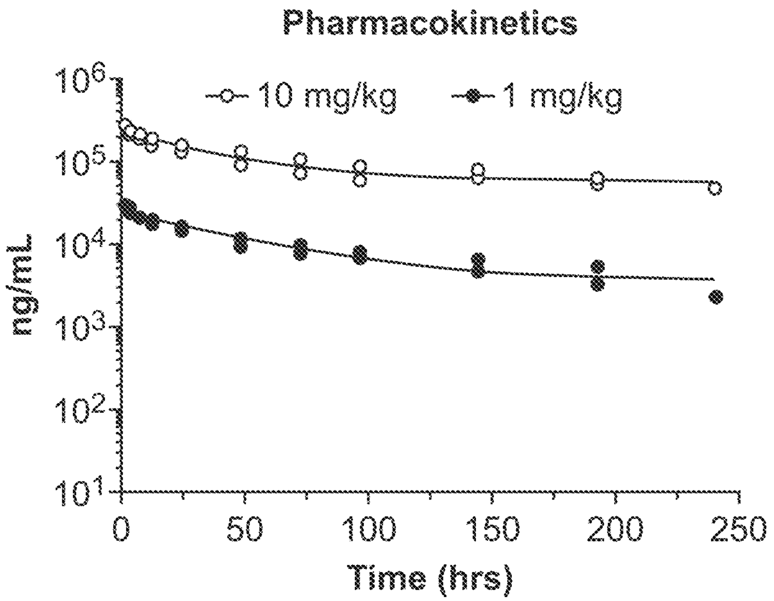
FIGS. 8A-8C show the serum levels and induction of immune cell proliferation by the CD137×TA Binding Molecule TRIDENT-A. Pharmacokinetics (serum clearance) (FIG. 8A), $CD8^{+}$ T cell proliferation (FIG. 8A), NK cell proliferation (FIG. 8A) through day 20-24 in cynomolgus monkeys treated with TRIDENT-A at 1 mg/kg (solid circles) or 10 mg/kg (open circles) are plotted.
Figure 8B:
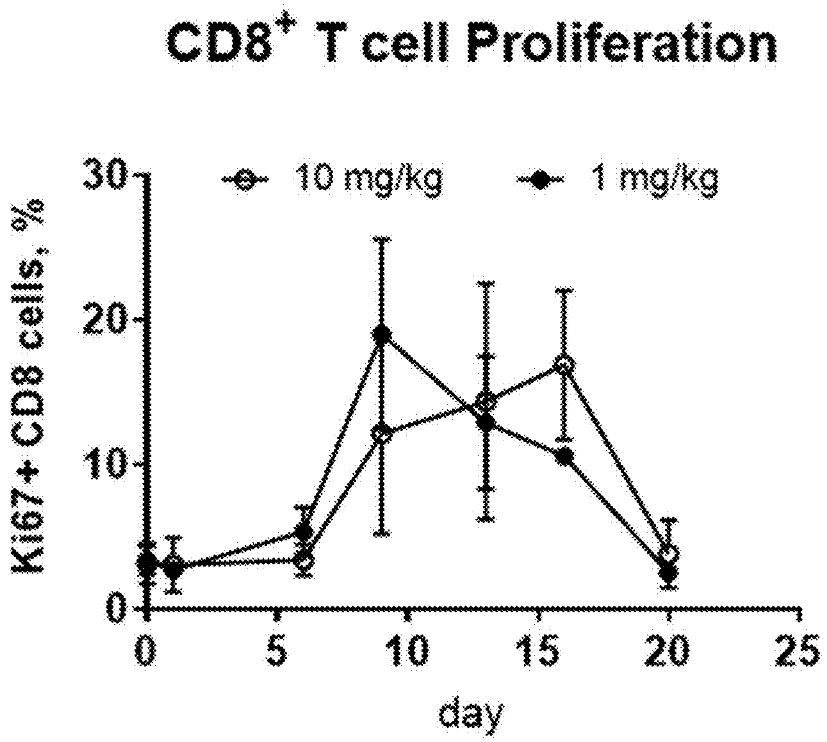
Figure 8C:
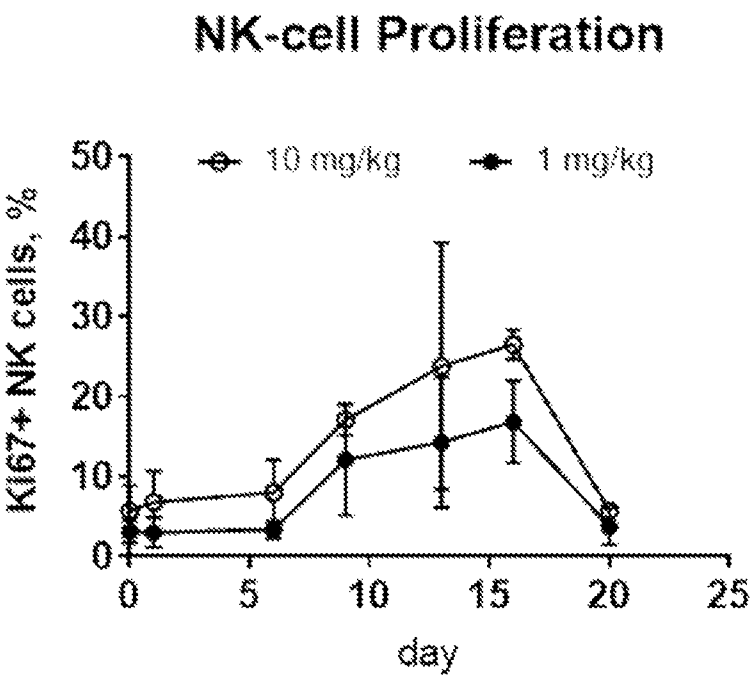

The serum concentration of the molecules was monitored over time, essentially as described above. The Cmax, AUC, t½beta and CL values are presented in Table 8 and show that the trivalent CD137×TA bispecific molecule comprising the binding domain of CD137 MAB-6(1.1) exhibits a serum half-life about two-fold longer than the one comprising hCD137 MAB-3(1B.3). The serum concentration of TRIDENT-A over the first 10 days (240 hours) is plotted in FIG. 8A. In addition, the proliferation of $CD8^+$ T cells (FIG. 8B), and NK cells (FIG. 8C) was examined essentially as described above. This study shows that the representative CD137×TA bispecific molecule TRIDENT-A, comprising CD137 binding domains of the novel anti-CD137 antibody CD137 MAB-6 exhibited slow clearance and administration correlated with a temporary induction in the proliferation of both $CD8^+$ T cells and NK cells indicating a stimulation of these immune cells. In addition, as noted above CD137 MAB-6 is more active in the tetravalent antibody-like structures. Thus, the CD137 MAB-6 binding domain provides several advantages as compared to previously described CD137 binding domains.

TABLE 8

| Pharmacokinetics | | | | | | |
|---|---|---|---|---|---|---|
| | Dose | Animal | Cmax | AUC | t½ Beta | CL |
| Molecule | (mg/kg) | ID | (ug/mL) | (hr*ug/mL) | (hr) | (mL/hr/kg) |
| TRIDENT-A | 1 | 1F001 | 28 | 1598 | 98 | 0.48 |
| | | 1F002 | 32 | 1968 | 148 | 0.32 |
| TRIDENT-A | 10 | 2F003 | 242 | 18752 | 217 | 0.30 |
| | | 2F004 | 293 | 21333 | 167 | 0.27 |
| TRIDENT-2 | 1 | 5F009 | 31 | 1227 | 29 | 0.81 |
| | | 5F010 | 26 | 945 | 42 | 0.97 |
| TRIDENT-2 | 10 | 6F011 | 282 | 10313 | 100 | 0.78 |
| | | 6F012 | 293 | 11486 | 99 | 0.69 |

Example 5

Deimmunization and Optimization of hPD-1 MAB-2 (1.1) Variable Domains

Intact hPD-1 MAB-2(1.1) antibody was analyzed using an MAPPs assay (performed by Abzena), to identify peptide clusters that could be presented by antigen presenting cells. This was followed by iTope™ in silico analysis of the amino acid sequence of the VH and VL Domains of hPD-1 MAB-2(1.1), in which peptide clusters were divided into overlapping 9-mer peptides (8 aa overlap between adjacent peptides) and binding affinity of the 9-mer peptides to HLA-DR proteins was predicted and the 9-mer peptides were cross-checked against a database of peptides which have been experimentally shown to stimulate T cell responses. A potential T cell epitope within Kabat residues 72-88 of the framework region 2 of hPD-1 MAB-2 VH1 (corresponding to residues 73-92 of SEQ ID NO:57) was identified. Further analysis identified three non-germline amino acids: T77, K83, and T84, numbered according to Kabat (corresponding to residues T78, K87, and T88 of SEQ ID NO:57) in this region and the following substitutions were introduced: T77S; K83R and T84A; or T77S, K83R and T84A, numbered according to Kabat. The binding of antibodies comprising these substitutions were evaluated for binding to a soluble PD-L1—fused to a His tag (shPD-L1) using an ELISA assay essentially as described above for CD137 binding except the plates were coated with shPD-L1 at 0.5 μg/mL and a goat anti-human IgG-HRP secondary antibody was used. The results are summarized in Table 9.

TABLE 9

| Summary of shPD-L1 ELISA | |
|---|---|
| Antibody | Binding |
| hPD-1 MAB-2 VH1 | ++++ |
| hPD-1 MAB-2 VH1 + T77S | ++ |
| hPD-1 MAB-2 VH1 + K83R and T84A | +++ |
| hPD-1 MAB-2 VH1 + T77S, K83R and T84A | ++++ |

All the deimmunized variants bound to shPD-L1, with the variant comprising the T77S, K83R and T84A substitutions exhibiting binding that was indistinguishable from the parental antibody. The VH comprising these mutations was designated hPD-L1 MAB-2 VH2.

Figure 9A:
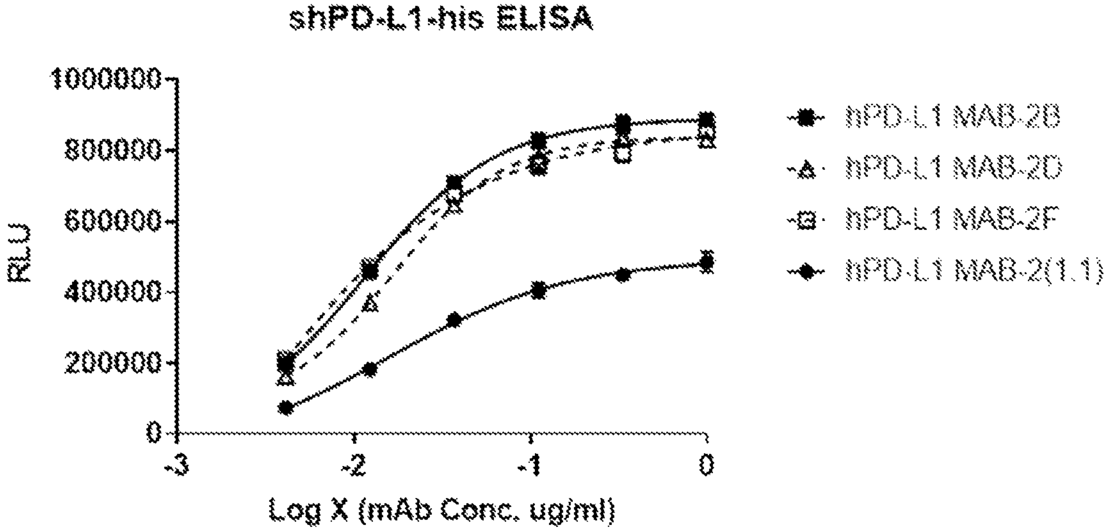
FIGS. 9A-9B show the binding activity of Fabs comprising deimmunized/optimized variants of hPD-L1 MAB-2 (1.1). The ELISA binding curves of Fab variants hPD-L1 MAB-2B, hPD-L1 MAB-2D, and hPD-L1 MAB-2F (FIG. 9A) and hPD-L1 MAB-2A, hPD-L1 MAB-2C, and hPD-L1 MAB-2E (FIG. 9B) are plotted.
Figure 9B:
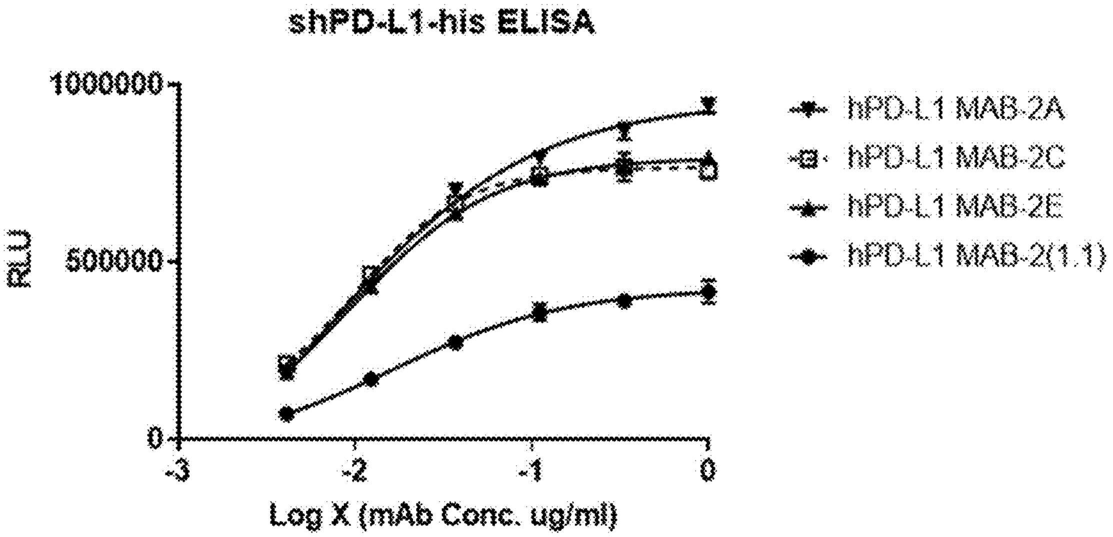

In addition, a mutational analysis was undertaken to identify amino acid substitutions in the CDRs of the VH and/or VL domains of hPD-L1 MAB-2(1.1) that enhanced binding to shPD-L1. A number of substitutions that resulted in improved binding were identified and are provided in Table 10 with the substitution presented using the Kabat numbering system and the corresponding amino acid residue in the sequences presented above indicated. The binding of Fab fragments comprising different combinations of these substitutions to shPD-L1-his was evaluated by ELISA essentially as described above except a goat anti-human kappa-HRP secondary antibody was used. Representative variants evaluated are summarized in Table 11, and the binding curves are presented in FIGS. 9A-9B. These studies show that Fabs comprising each of the variants (hPD-L1 MAB-2B, hPD-L1 MAB-2D, and hPD-L1 MAB-2F plotted in FIG. 9A; hPD-L1 MAB-2A, hPD-L1 MAB-2C, and hPD-L1 MAB-2E plotted in FIG. 9B) exhibited higher affinity than the Fab comprising the parental hPD-L1 MAB-2(1.1).

TABLE 10

| CDR Substitutions | | | |
|---|---|---|---|
| VH Domain | | VL Domain | |
| Kabat* | SEQ ID NO: 57^ | Kabat* | SEQ ID NO: 58^ |
| S31G | 31 | T31E | 31 |
| G53K | 54 | D28H or D28V or D28L | 28 |
| Q95A or Q95G | 99 | S52E | 52 |
| F100aG | 105 | | |

*substitution numbering according to Kabat

^corresponding amino acid residue number of the indicated sequence identification number

TABLE 11 hPD-L1 MAB-2 Variants Comprising CDR Substitutions

| Variant | Substitutions* |
|---|---|
| hPD-L1 MAB-2A | VH(S31G/G53K/Q95A) & VL(D28H) |
| hPD-L1 MAB-2B | VH(S31G/G53K/Q95G) & VL(D28V) |
| hPD-L1 MAB-2C | VH(S31G/G53K/F100aG) & VL(D28L) |
| hPD-L1 MAB-2D | VH(F100aG) & VL(D28L/S52E) |
| hPD-L1 MAB-2E | VH(G53K/Q95A) & VL(D28L) |
| hPD-L1 MAB-2F | VH(G53K/F100aG) & VL(T31E) |

*substitution numbering according to Kabat

A number of variant VH and/or VL Domains of hPD-L1 MAB-2 were used to generate CD137×TA bispecific molecules (all comprising two CD137 MAB-6(1.1) binding sites). The particular hPD-L1 MAB-2 VL and VH variants used are summarized in Table 12, the amino sequences of these variants and the bispecific molecules comprising them are provided above. As noted above molecules comprising PD-L1 MAB-2 VH/VL Domains are referred to by reference to the specific VH/VL Domains, for example, a molecule comprising the binding domains PD-L1 MAB-2 VH3 and hPD-L1 MAB-2 VL2 is specifically referred to as "PD-L1 MAB-2(3.2)."

TABLE 12 hPD-L1 MAB-2 Variant VH and VL Domains

| Variant | Substitutions* |
|---|---|
| hPD-L1 MAB-2 VH2 | T77S/K83R/T84A |
| hPD-L1 MAB-2 VH3 | T77S/K83R/T84A + G53K/F100aG |
| hPD-L1 MAB-2 VH4 | T77S/K83R/T84A + Q95A |
| hPD-L1 MAB-2 VH5 | T77S/K83R/T84A + G53K/Q95A |
| hPD-L1 MAB-2 VH6 | T77S/K83R/T84A + Q95A/F100aG |
| hPD-L1 MAB-2 VL2 | VL(T31E) |

*substitution numbering according to Kabat

Figure 10A:
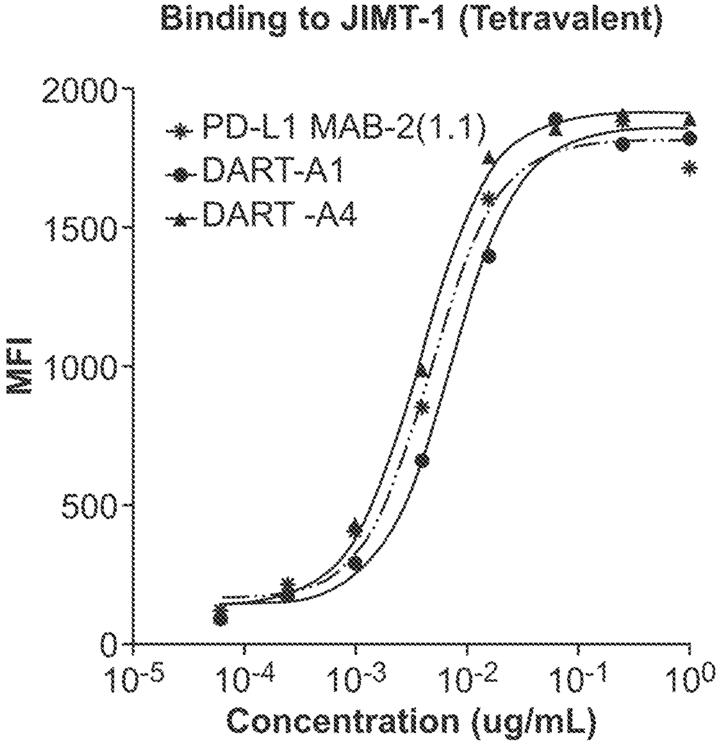
FIGS. 10A-10B show the ability of CD137×TA Binding Molecules comprising deimmunized or optimized PD-L1 binding domains to bind to PD-L1 expressed on the cell surface of engineered CHO cells. The binding curves of DART-A1, DART-A4, and the anti-PD-L1 antibody hPD-L1 MAB-2(1.1) (FIG. 10A), TRIDENT-A, TRIDENT-A4, and the negative control hIgG1 (FIG. 10B) are plotted.
Figure 10B:
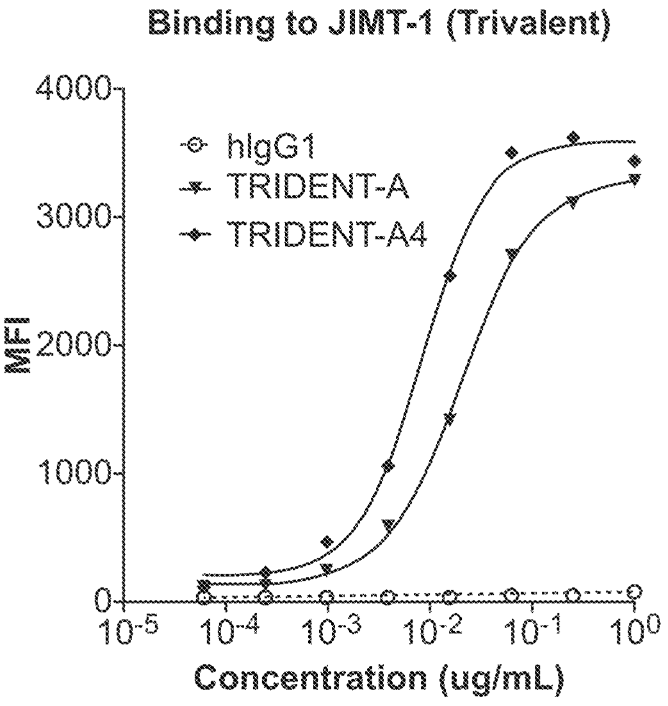
Figure 11A:
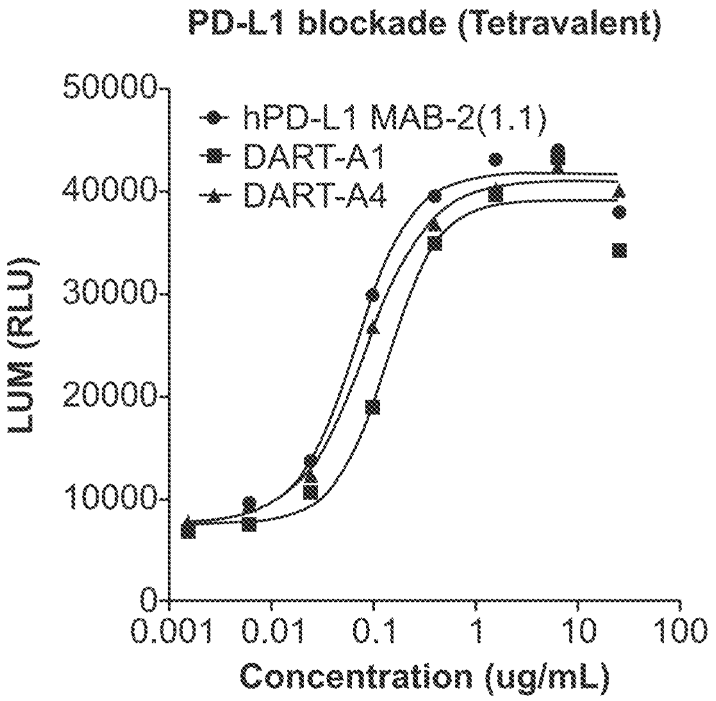
FIGS. 11A-11C show ability of CD137×TA Binding Molecules comprising deimmunized and/or optimized PD-L1 binding domains to block PD-L1/PD-1 interactions in a PD-L1 reporter assay. The activity curves of DART-A1, DART-A4, and the anti-PD-L1 antibody hPD-L1 MAB-2 (1.1) (FIG. 11A), TRIDENT-A, TRIDENT-A4, and the negative control hIgG1 (FIG. 11B), DART-A4, DART-A7, DART-A8, DART-A9, and the negative control hIgG1 (FIG. 11C) are plotted.
Figure 11B:
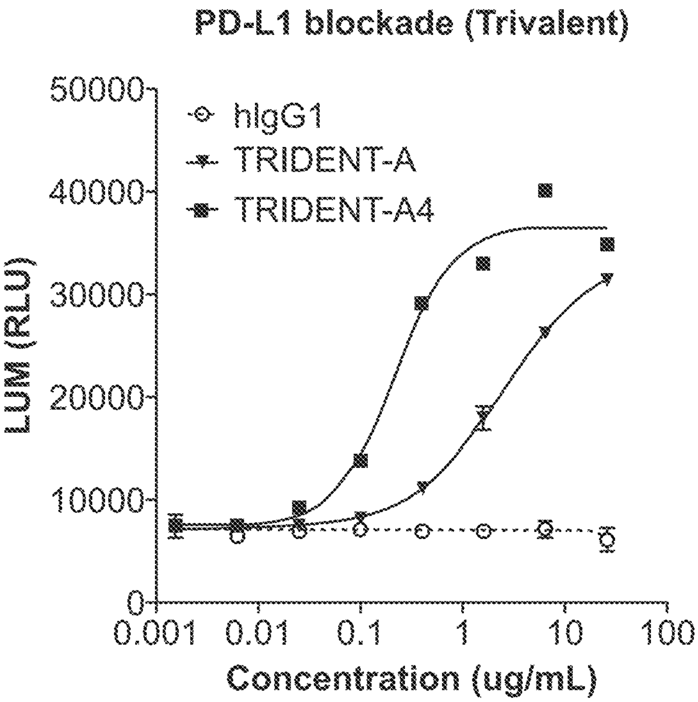
Figure 11C:
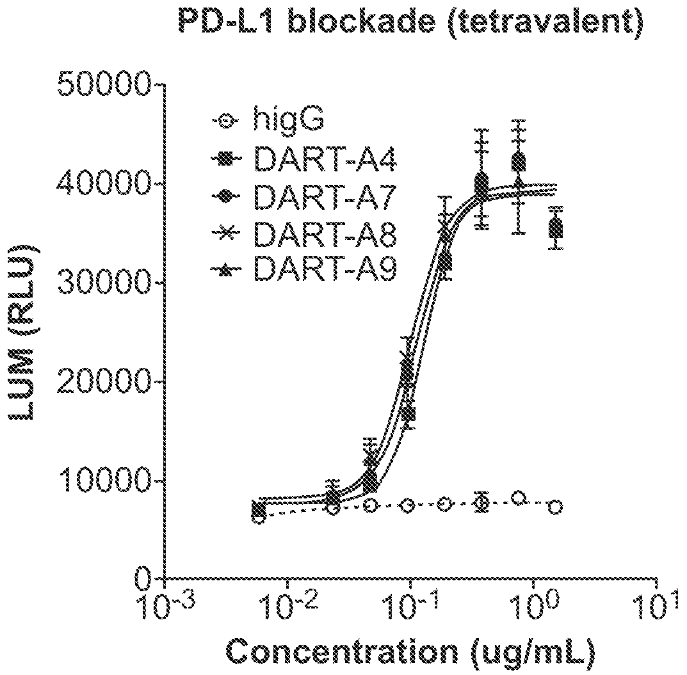

The following molecules comprising two PD-L1 binding sites: DART-A1 (comprising hPD-L1 MAB-2(2.1)); DART-A4 (comprising hPD-L1 MAB-2(3.2)); and hPD-L1 MAB-2(1.1), and the following molecules comprising one PD-L1 binding site: TRIDENT-A (detailed above); and TRIDENT-A4 (comprising hPD-L1 MAB-2(3.2)), were evaluated for PD-L1 binding on the surface of JIMT-1 cells by FACS analysis essentially as described above, test articles were used at 1 μg/mL and four-fold serial dilutions. The results of representative assays are shown in FIGS. 10A-10B. These molecules were also examined for their ability to block the PD-1/PD-L1 interaction in a PD-L1 reporter assay essentially as described above test articles at 25 μg/mL and four-fold serial dilutions. The results of representative assays are shown in FIGS. 11A-11B. These data show that the CD137×TA bispecific molecules comprising the binding domains of the deimmunized/optimized hPD-L1 MAB-2 (3.2) exhibited improved binding (FIGS. 10A-10B) and more efficient blocking of PD-1/PD-L1 interactions (FIGS. 11A-11B). A modest improvement was seen in the tetravalent molecules comprising two PD-L1 binding domains (DART-A4 in FIGS. 10A and 11A), a larger improvement in activity was seen in the trivalent molecules comprising only one PD-L1 binding domain (TRIDENT-A4 in FIGS. 10B and 11B). Additional molecules comprising two PD-L1 binding sites: DART-A4 (comprising hPD-L1 MAB-2(3.2)); DART-A7 (comprising hPD-L1 MAB-2(4.2)); DART-A8 (comprising hPD-L1 MAB-2(5.2)); and DART-A9 (comprising hPD-L1 MAB-2(6.2)); were evaluated for their ability to block the PD-1/PD-L1 interaction in a PD-L1 reporter assay essentially as described above with the test articles at 1.5 μg/mL and two-fold serial dilutions. The results of a representative assay is shown in FIG. 11C. This study shows that CD137×TA bispecific molecules comprising the alternative deimmunized/optimized hPD-L1 MAB-2(4.2), hPD-L1 MAB-2(5.2), and hPD-L1 MAB-2(6.2) exhibit a blocking activity similar or improved as compared to that of DART-A4 comprising hPD-L1 MAB-2(3.2).

Example 6

Deimmunization of CD137 MAB-6

To minimize the likelihood of immunogenicity substitutions were introduced into the framework regions of the VL Domain of CD137 MAB-6 to replace non-germline residues with those present in the human germline. In particular, combinations of the following substitutions were introduced T14S, F36Y and I39K, numbered according to Kabat (corresponding to residues 14, 37, and 40 of SEQ ID NO:50) the resulting CD137 MAB-6 VL Domains are summarized in Table 13 below and were used to generate CD137×TA bispecific molecules capable of binding to CD137 and to the representative TA, PD-L1, the amino sequences of these variants and the bispecific molecules comprising them are provided above.

TABLE 13

CD137 MAB-6 Variant VL Domains

| Variant | Substitutions* |
|---|---|
| CD137 MAB-6 VL2 | L14S/F36Y/I39K |
| CD137 MAB-6 VL3 | F14S/I39K |

*substitution numbering according to Kabat

Figure 12A:
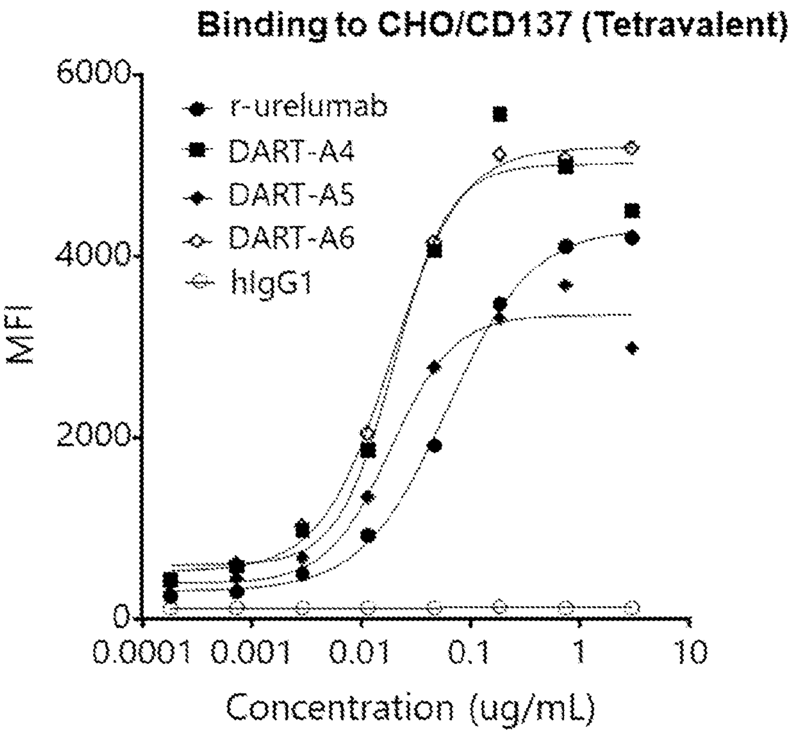
FIGS. 12A-12B show the ability of CD137×TA Binding Molecules comprising deimmunized CD137 binding domains and/or deimmunized/optimized PD-L1 binding domains to bind to CD137 expressed on the surface of engineered CHO cells. The binding curves for DART-A4, DART-A5, DART-A6 (FIG. 12A), TRIDENT-A4, TRIDENT-A5, TRIDENT-A6 (FIG. 12B) are plotted. Also plotted on both figures are the comparator r-urelumab and the negative control hIgG1.
Figure 12B:
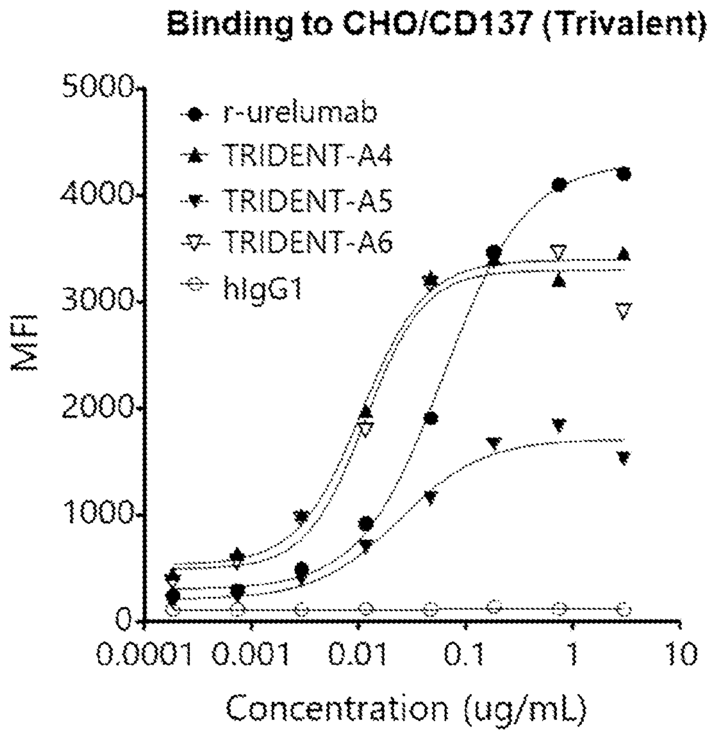

The following molecules comprising two hPD-L1 MAB-2(3.2) binding sites: DART-A4 (comprising CD137 MAB-6(1.1)); DART-A5 (comprising CD137 MAB-6(1.2)); DART-A6 (comprising CD137 MAB-6(1.3)); and the following molecules comprising one hPD-L1 MAB-2(3.2) binding site: TRIDENT-A4 (comprising CD137 MAB-6 (1.1)); TRIDENT-A5 (comprising CD137 MAB-6(1.2)); and TRIDENT-A6 (comprising CD137 MAB-6(1.3), a replica of urelumab (r-urelumab), and the negative control hIgG1, were evaluated for their ability to bind to cell surface CD137 by FACS analysis performed essentially as described-above, test articles were used at 3 μg/mL and four-fold serial dilutions. The results of a representative assay shown in FIGS. 12A-12B demonstrate that the tetravalent (FIG. 12A) and trivalent (FIG. 12B) CD137×PD-L1 bispecific molecules comprising the binding domains of CD137 MAB-6(1.3) exhibit binding profiles nearly identical to the same molecules comprising the binding domains of CD137 MAB-6(1.1), while those comprising CD137 MAB-6(1.2) exhibited reduced binding.

Figure 13A:
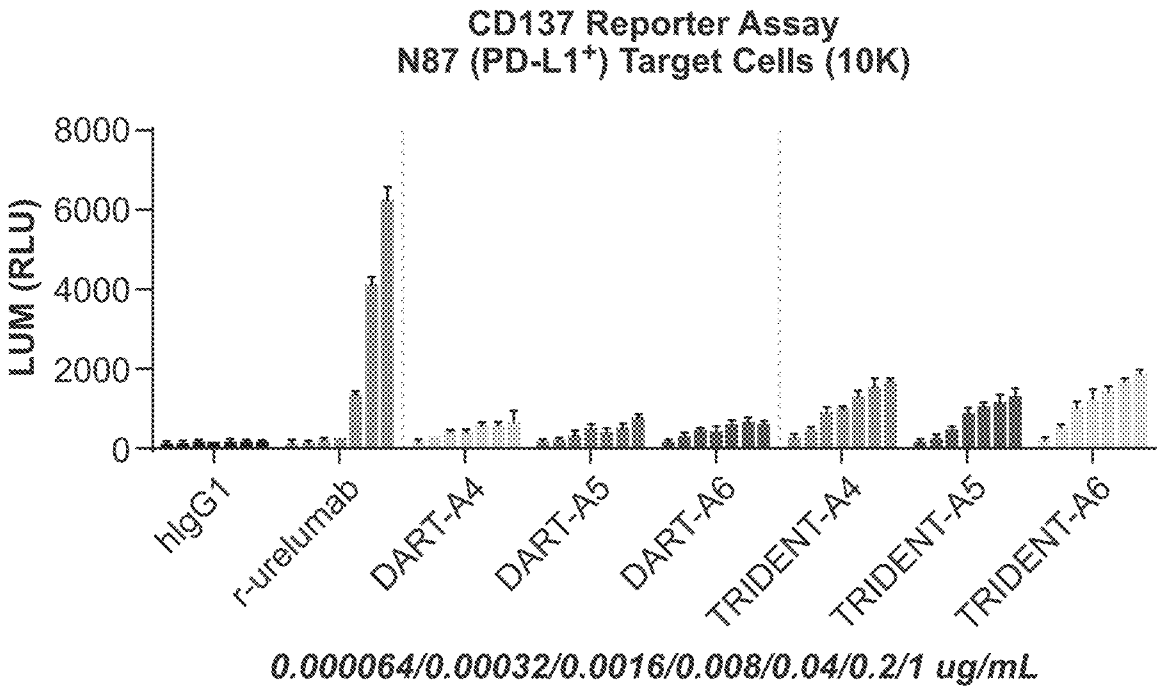
FIGS. 13A-13B show the ability of CD137×TA Binding Molecules comprising deimmunized CD137 binding domains, and/or deimmunized/optimized PD-L1 binding domains to mediate target-dependent signal transduction in a CD137 Reporter Assay performed with the low PD-L1 expressing N87 target cells (FIG. 13A), or the medium PD-L1 expressing JIMT-1 target cells (FIG. 13B). The activity of DART-A4, DART-A5, DART-A6, TRIDENT-A4, TRIDENT-A5, TRIDENT-A6, the comparator r-urelumab and the negative control hIgG1 are plotted.
Figure 13B:
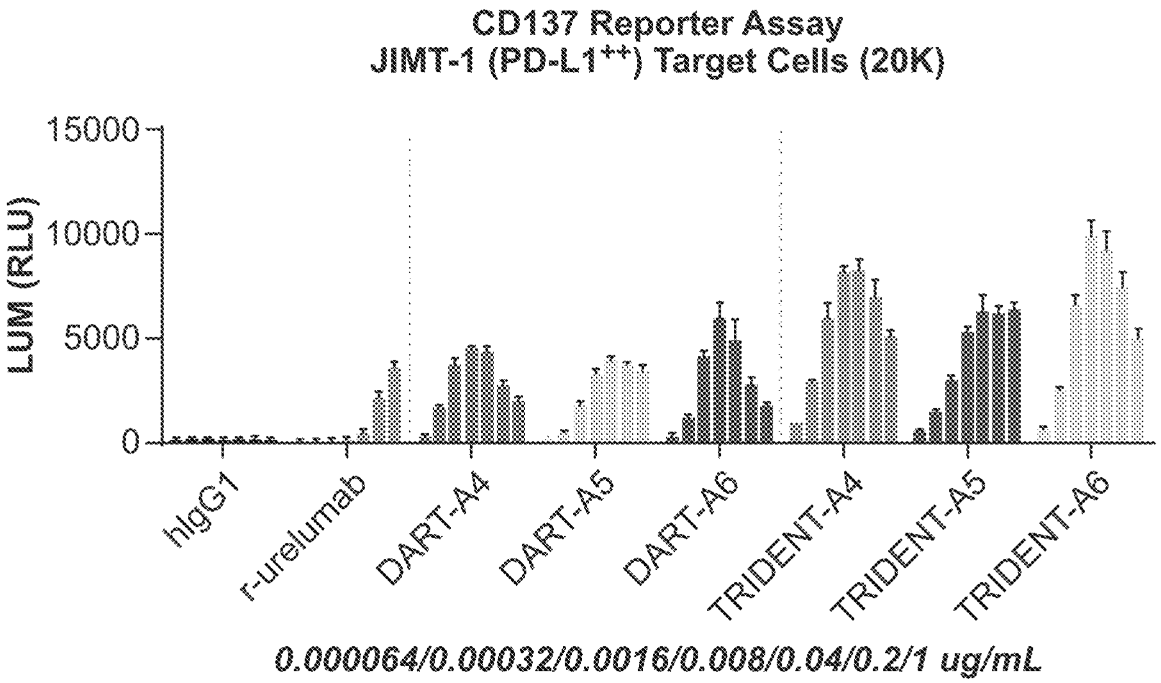

The functional activity of DART-A4, DART-A5, DART-A6, r-urelumab, TRIDENT-A4, TRIDENT-A5, and TRIDENT-A6, and the negative control hIgG1, was examined in a CD137 reporter assay performed essentially as described above in the presence and absence of PD-L1 expressing N87 Target cells (10,000 cells per well,) or JIMT-1 cells (20,000 cells per well), test articles were used at 1 ug/mL and five-fold serial dilutions. The results of a representative assay shown in FIGS. 13A-13B demonstrate that all the molecules exhibiting activity in a target dependent manner with higher activity in the presence of JIMT-1 cells (PD-L1$^{++}$, FIG. 13B) than in the presence of N87 cells (PD-L1$^{+}$, FIG. 13A). CD137×PD-L1 bispecific molecules comprising the binding domains of CD137 MAB-6(1.3) exhibit activity profiles nearly identical to the same molecules comprising the binding domains of CD137 MAB-6(1.1), while those comprising CD137 MAB-6(1.2) exhibited reduced activity. None of the CD137×PD-L1 bispecific molecules exhibited activity in the absence of target cells. As expected, the agonist r-urelumab exhibited activity in the presence and absence of PD-L1 expressing target cells, and the negative controls did not exhibit activity at all.

Figure 14A:
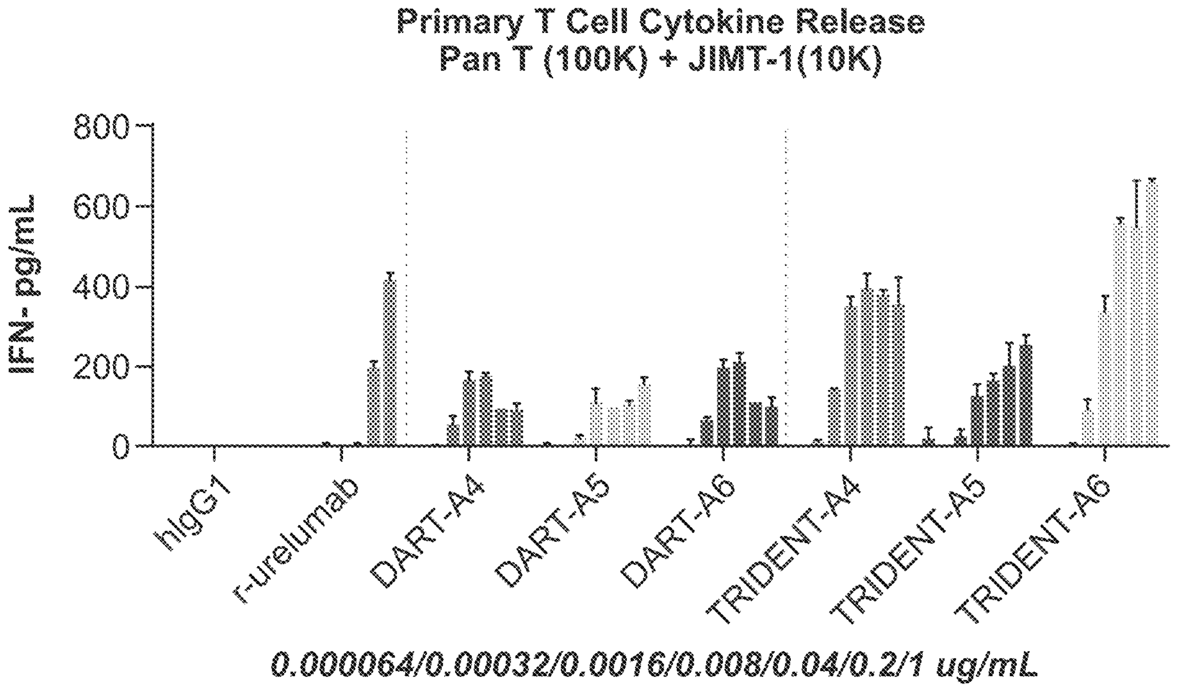
FIGS. 14A-14B show the ability of CD137×TA Binding Molecules comprising deimmunized CD137 binding domains, and deimmunized/optimized PD-L1 binding domains to mediate target-dependent release of cytokines INF-γ (FIG. 14A) and IL-2 (FIG. 14B) in a primary T cell cytokine release assay. The activity of DART-A4, DART-A5, DART-A6, TRIDENT-A4, TRIDENT-A5, TRIDENT-A6, the comparator r-urelumab and the negative control hIgG1 are plotted.
Figure 14B:
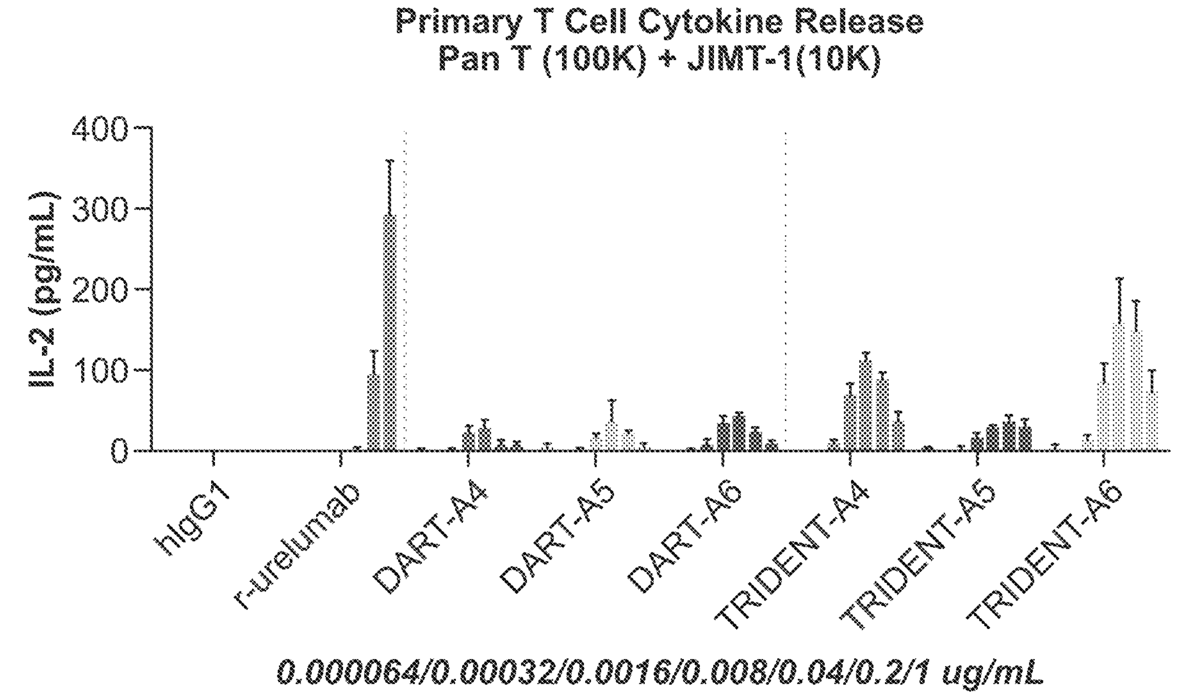

The functional activity of DART-A4, DART-A5, DART-A6, r-urelumab, TRIDENT-A4, TRIDENT-A5, and TRIDENT-A6, and the negative control hIgG1, was examined in the primary T cell cytokine release assay presence of PD-L1 expressing JIMT-1 cells (10,000 cells per well) performed essentially as described above, test articles were used at 1 μg/mL and five-fold serial dilutions. The results of a representative assay for the representative cytokines INF-γ and IL-2 are shown in FIGS. 14A and 14B, respectively. As was seen in the CD137 reporter assay, CD137×PD-L1 bispecific molecules comprising the binding domains of CD137 MAB-6(1.3) exhibit activity profiles nearly identical to, or slightly better than the same molecules comprising the binding domains of CD137 MAB-6(1.1), while those comprising CD137 MAB-6(1.2) exhibited reduced activity.

Example 7

Additional Characterization of CD137×TA Molecules

Additional in-vitro studies were undertaken to evaluate the activity of the following representative CD137×PD-L1 bispecific molecules comprising the PD-L1 and CD137 binding domains of PD-L1 MAB-2, the novel CD137 MAB-6, or the deimmunized/optimized variants thereof: DART-A; DART-A4; DART-A6; DART-A7; TRIDENT-A; TRIDENT-A4; TRIDENT-A6; and an additional tetravalent molecule: DART-A10 (comprising two hPD-L1 MAB-2 (4.2) binding sites and two CD137 MAB-6(1.3) binding sites). The CD137 and PD-L1 binding domains of these molecule are summarized in Table 5 above.

Figure 15A:
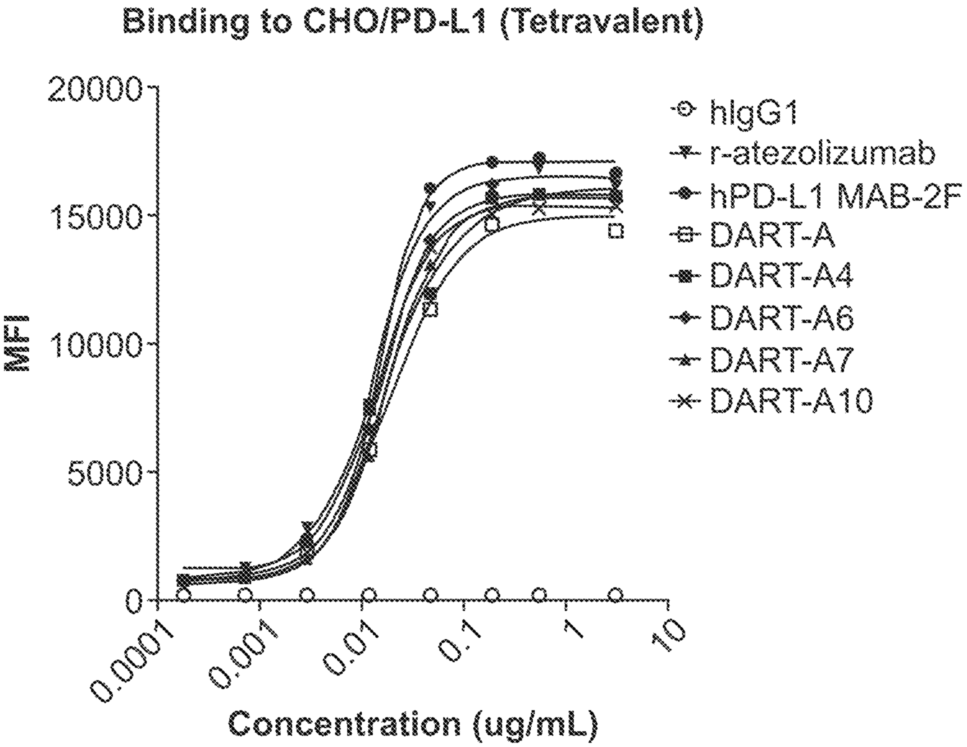
FIGS. 15A-15B show the ability of CD137×TA Binding Molecules comprising parental, or deimmunized/optimized PD-L1 and/or CD137 binding domains to bind to PD-L1 (FIG. 15A) and CD137 (FIG. 15B) expressed on the cell surface of engineered CHO cells. The binding curves of DART-A, DART-A4, DART-A6, DART-A7, DART-A10, the anti-PD-L1 antibodies hPD-L1 MAB-2(1.1), and r-atezolizumab, and the negative control hIgG1 (FIG. 15A), DART-A, DART-A4, DART-A6, DART-A7, DART-A10, r-urelumab, and the negative control hIgG1 (FIG. 15B) are plotted.
Figure 15B:
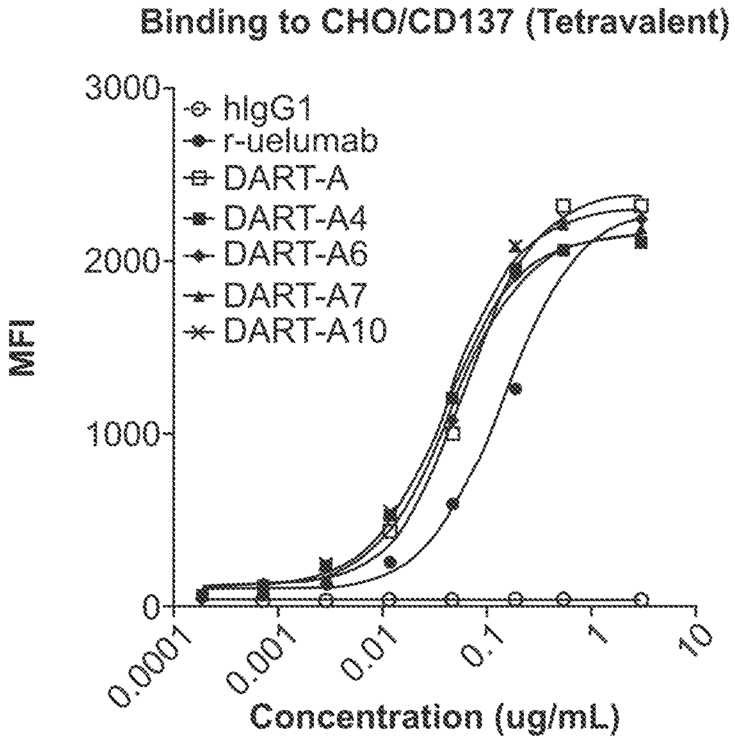

DART-A, DART-A4, DART-A6, DART-A7, DART-A10, the negative control hIgG1, and a replica of the anti-PD-L1 antibody atezolizumab (r-atezolizumab), hPD-L1 MAB-2F or r-urelumab, were evaluated for their ability to bind to the surface of CHO cells expressing PD-L1 (CHO/PD-L1) or expressing CD137 (CHO/CD137) by FACS analysis essentially as described above with the test articles used at a starting concentration of 3 μg/mL and 3 to 4-fold dilutions. The results of representative assays are shown in FIGS. 15A-15B. These binding studies demonstrate that the CD137×TA Binding Molecules comprising optimized PD-L1 binding domains (DART-A4, DART-A6, DART-A7, DART-A10) exhibit improved binding to PD-L1 as compared to DART-A (FIG. 15A). Similar PD-L1 binding profiles were observed for binding to JIMT-1 (PD-L1$^{+}$) cells. These studies also demonstrate that CD137×TA Binding Molecules comprising binding domains of CD137 MAB-6 (1.3) and CD137 MAB-6(1.1) exhibit similar binding that is improved as compared to r-uelumab (FIG. 15B).

Figure 16A:
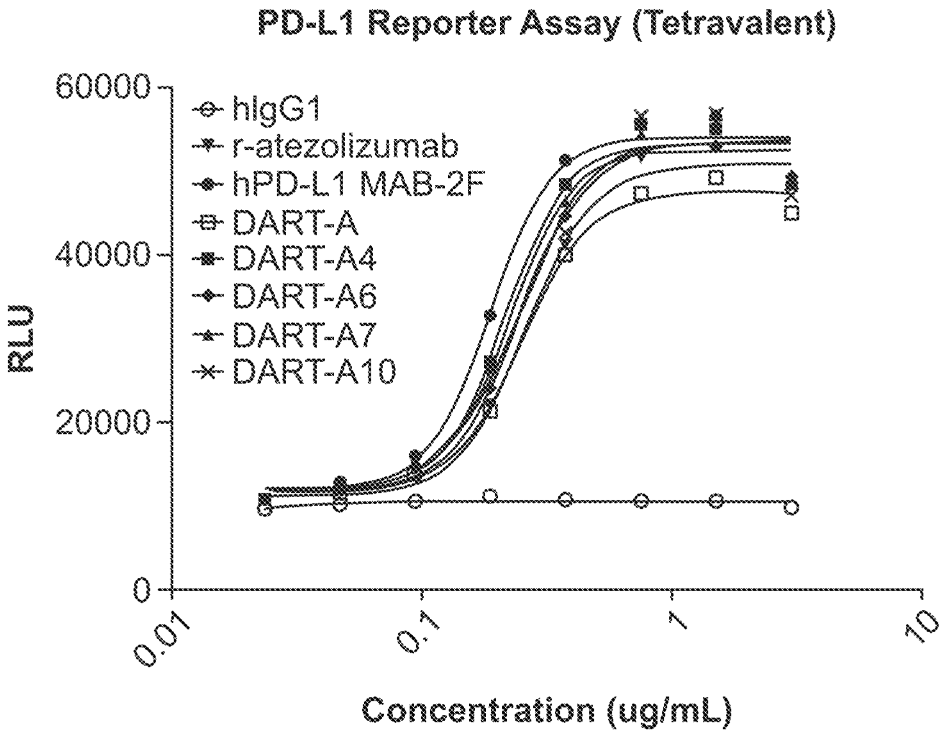
FIGS. 16A-16B show the ability of CD137×TA Binding Molecules comprising parental, or deimmunized/optimized PD-L1 and/or CD137 binding domains to block PD-L1/PD-1 interactions in a PD-L1 reporter assay. The results for the tetravalent molecules DART-A, DART-A4, DART-A6, DART-A7, DART-A10, are plotted in FIG. 16A, and for the trivalent molecule TRIDENT-A, TRIDENT-A4, and TRIDENT-A6, are plotted in FIG. 16B. Also plotted on both figures are the anti-PD-L1 antibodies hPD-L1 MAB-2F and r-atezolizumab, and the negative control hIgG1.
Figure 16B:
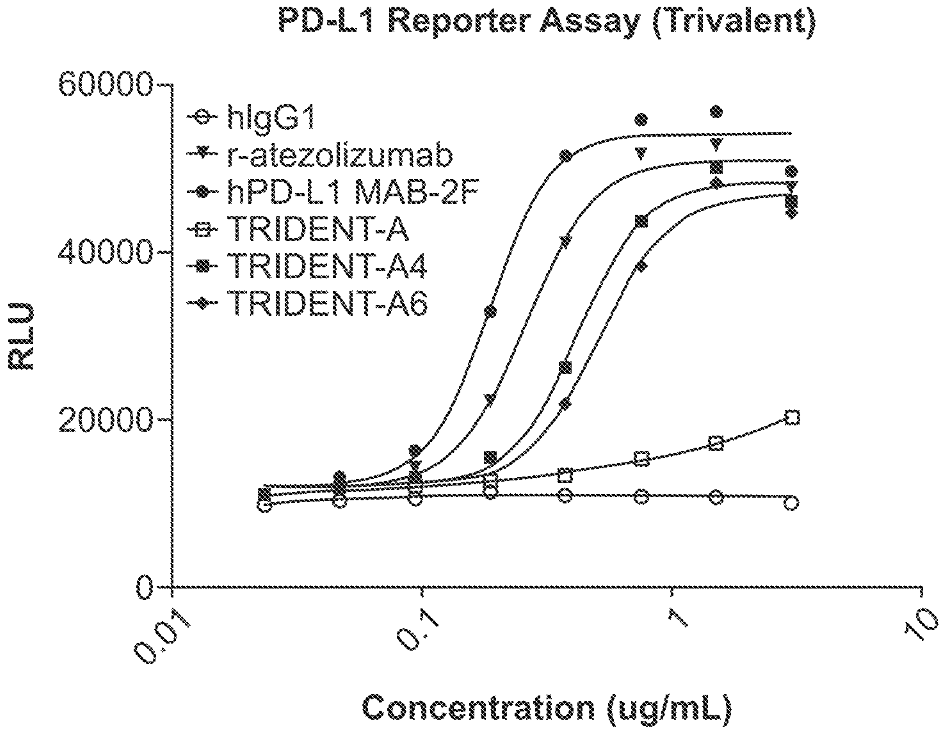

DART-A, DART-A4, DART-A6, DART-A7, DART-A10, TRIDENT-A, TRIDENT-A4, TRIDENT-A6, hPD-L1 MAB-2F, r-atezolizumab and the negative control hIgG1, were evaluated for their ability to block the PD-1/PD-L1 interaction in a PD-L1 reporter assay essentially as described above test articles at 3 μg/mL and two-fold serial dilutions. The results of representative assays are shown in FIGS. 16A-16B. These studies again show that tetravalent (FIG. 16A) and trivalent (FIG. 16B) CD137×TA bispecific molecules comprising the binding domains of the deimmunized/optimized hPD-L1 MAB-2(3.2) or hPD-L1 MAB-2 (4.2), exhibited more efficient blocking of PD-1/PD-L1 interactions as compared to molecules comprising the parental binding domain, hPD-L1 MAB-2(1.1), the enhanced activity was independent of the CD137 binding domain. As noted above, in this assay a larger improvement in activity was observed in the trivalent molecules comprising one PD-L1 binding domain, with activity approaching that observed with the anti-PD-L1 antibodies hPD-L1 MAB-2F and r-atezolizumab (each having two PD-L1 binding domains).

Figure 17A:
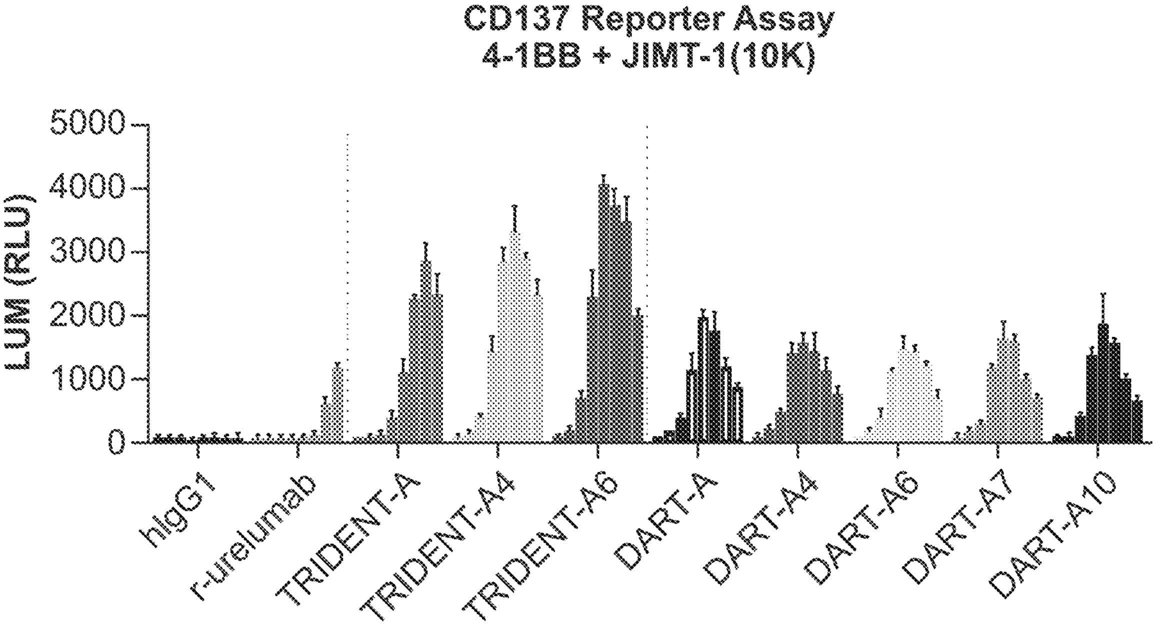
FIGS. 17A-17B show the ability of CD137×TA Binding Molecules comprising parental, or deimmunized/optimized PD-L1 and/or CD137 binding domains to mediate target-dependent signal transduction in a CD137 Reporter Assay performed in the presence the medium PD-L1 expressing JIMT-1 target cells (FIG. 17A), or in the absence of target cells (FIG. 17B). The activity of DART-A, DART-A4, DART-A6, DART-A7, DART-A10, TRIDENT-A, TRIDENT-A4, TRIDENT-A6, the comparator r-urelumab and the negative control hIgG1 are plotted.
Figure 17B:
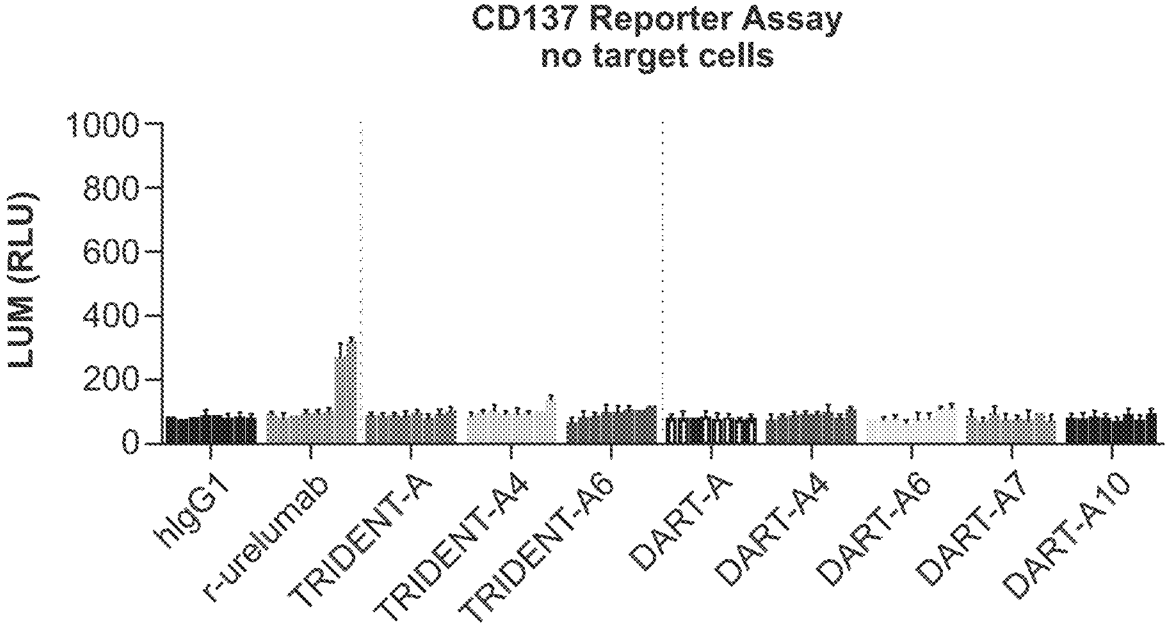

The functional activity of DART-A, DART-A4, DART-A5, DART-A6, TRIDENT-A4, TRIDENT-A5, and TRIDENT-A6, r-urelumab, and the negative control hIgG1, was examined in a CD137 reporter assay performed essentially as described above in the presence and absence of PD-L1 expressing JIMT-1 cells (10,000 cells per well), test articles were used at 1 ug/mL and five-fold serial dilutions (amounts are depicted at the bottom of FIG. 14A, for example). The results of a representative assay are shown in FIGS. 17A-17B and demonstrate that all the bivalent molecules exhibit activity in a target dependent manner with high levels of activity in the presence of JIMT-1 cells (FIG. 17A) and no activity in the absence of target cells (FIG. 17B). Molecules comprising the deimmunized/optimized PD-L1 and CD137 binding domains exhibited higher activity (e.g., TRIDENT-A6 and DART-A10) as compared to those comprising the parental domains. In this assay, the trivalent molecules exhibit higher activity and the increase in activity was greater for the trivalent molecules.

Figure 18A:
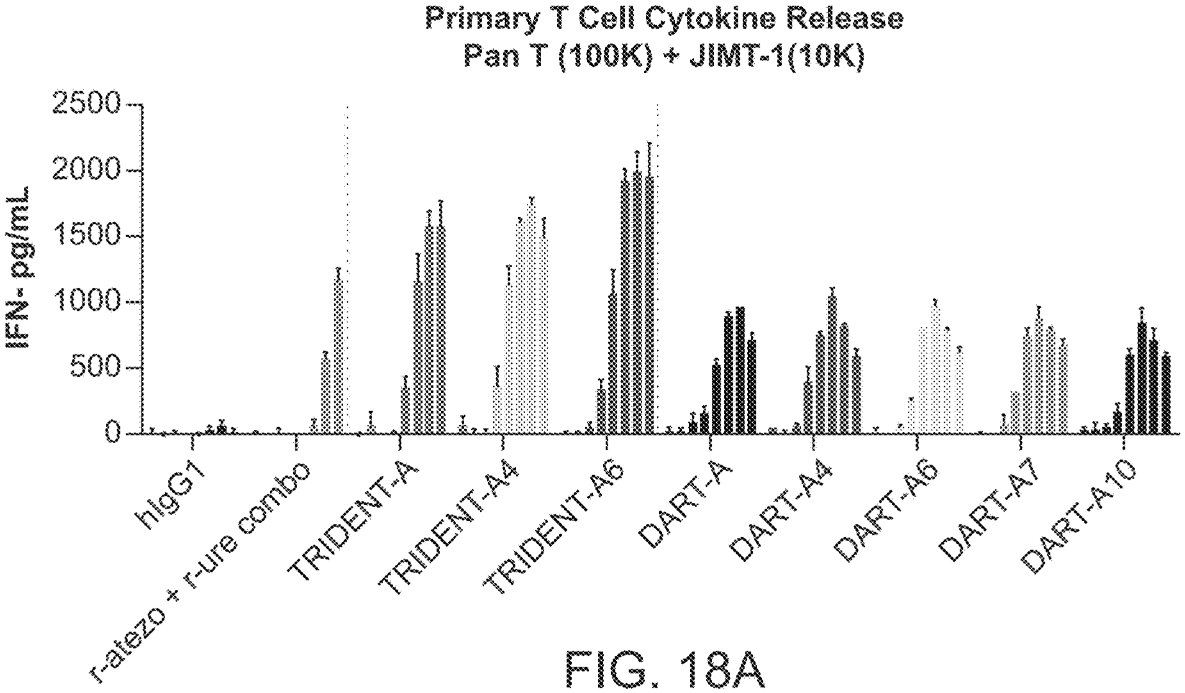
FIGS. 18A-18B show the ability of CD137×TA Binding Molecules comprising parental, or deimmunized/optimized PD-L1 and/or CD137 binding domains to mediate target-dependent release of cytokines INF-γ (FIG. 18A) and IL-2 (FIG. 18B). The activity of DART-A, DART-A4, DART-A6, DART-A7, DART-A10, TRIDENT-A, TRIDENT-A4, TRIDENT-A6, the combination of r-atezolizumab and r-urelumab (r-atezo+r-ure combo) and the negative control hIgG1 are plotted.
Figure 18B:
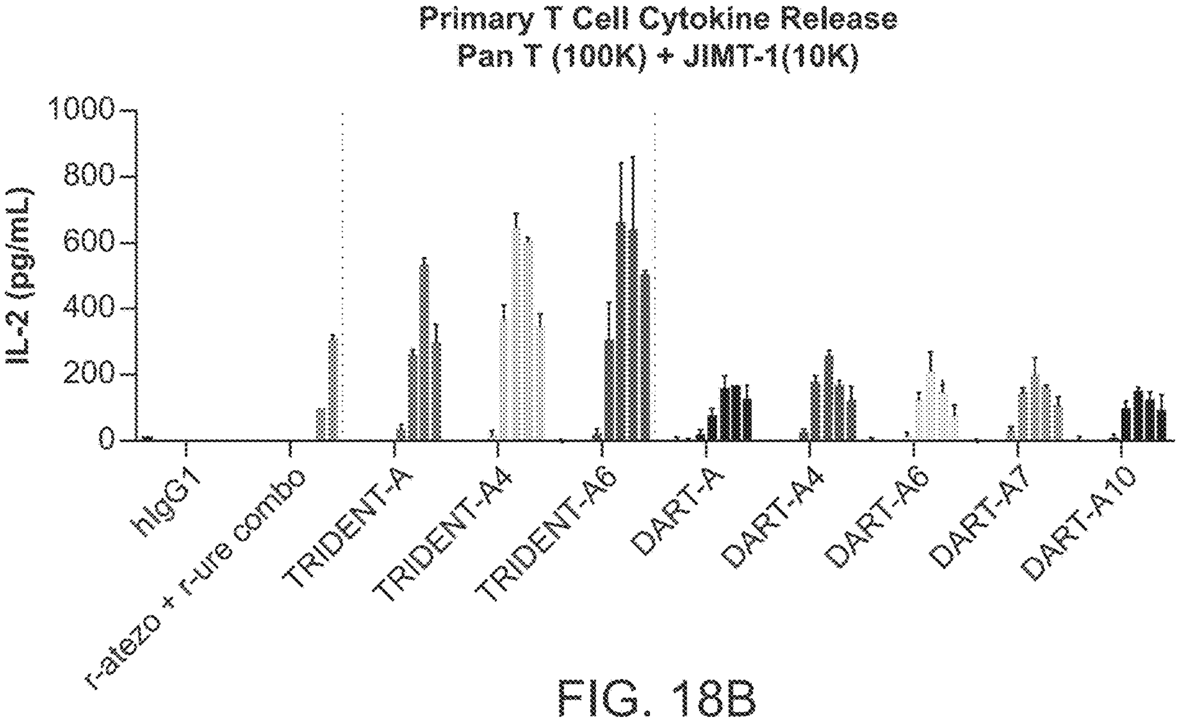

The functional activity of DART-A, DART-A4, DART-A5, DART-A6, r-urelumab, TRIDENT-A4, TRIDENT-A5, and TRIDENT-A6, a combination of r-urelumab and r-atezolizumab, and the negative control hIgG1, was also examined in the primary T cell cytokine release assay presence of PD-L1 expressing JIMT-1 cells (10,000 cells per well) performed essentially as described above, test articles were used at 1 μg/mL and five-fold serial dilutions (amounts are depicted at the bottom of FIG. 14A, for example). The results of a representative assay for the representative cytokines INF-γ and IL-2 are shown in FIGS. 18A and 18B, respectively. As was seen in the CD137 reporter assay, the trivalent CD137×PD-L1 bispecific molecules comprising the deimmunized/optimized PD-L1 and CD137 binding domains exhibited higher activity (e.g., TRIDENT-A6).

Example 8

Murine Xenograft Models

Figure 19A:
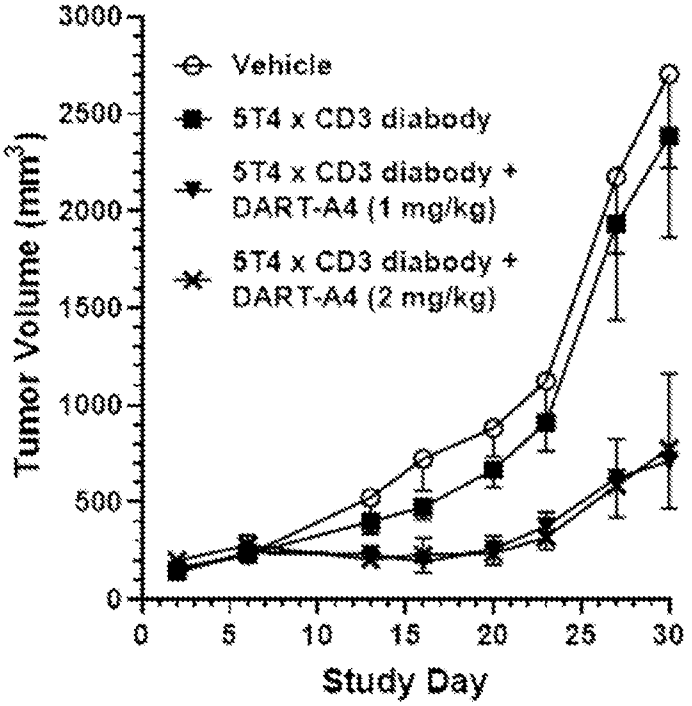
FIGS. 19A-19C show the ability of several representative PD-L1×CD137 bispecific molecules: DART-A (FIG. 19A), TRIDENT-A (FIG. 19B), or TRIDENT-A4 (FIG. 19C), in combination with a representative TA×CD3 bispecific molecules (5T4×CD3 diabody) to prevent or inhibit tumor growth or development of RKO colon carcinoma cells in vivo relative to a TA×CD3 bispecific molecule alone or a vehicle control in a murine PBMC-reconstituted xenograft model.
Figure 19B:
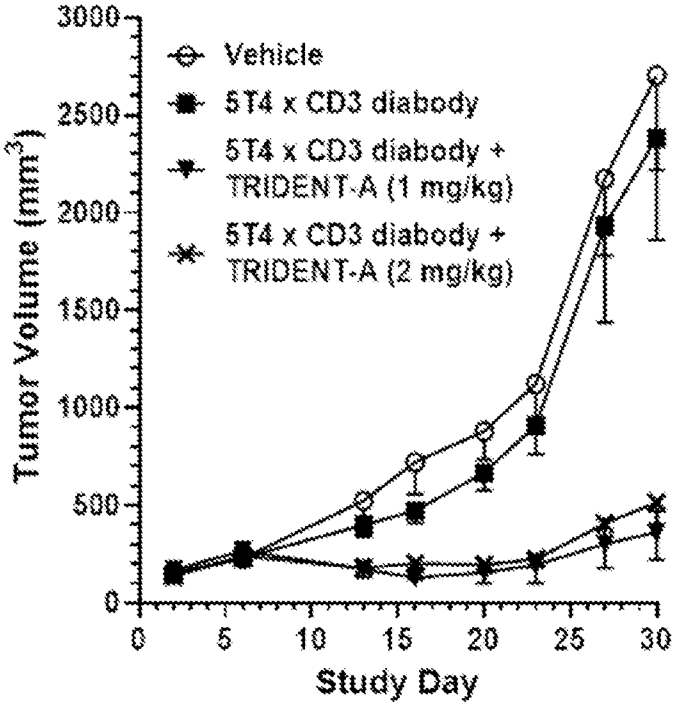
Figure 19C:
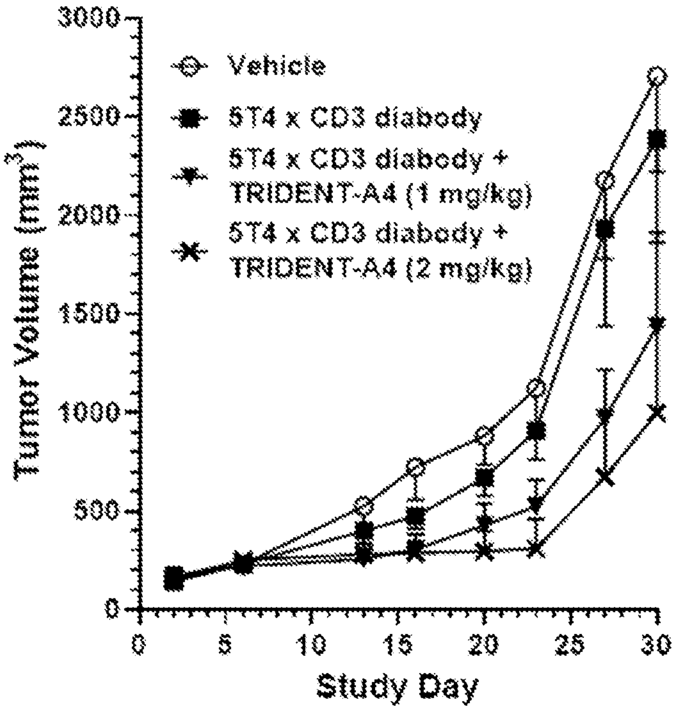

As provided herein, the CD137×TA Binding Molecules of the present invention may be used in combination with other tumor targeting agents. The ability of the representative PD-L1×CD137 bispecific molecules DART-A4, TRIDENT-A, and TRIDENT-A4 to enhance the anti-tumor active of a representative TA×CD3 bispecific molecule, 5T4×CD3 diabody (sequence provided below), was tested in vivo in a human PBMC-reconstituted murine xenograft model. Briefly, freshly isolated PBMCs ($8\times10^6$) were injected retro-orbitally on Study Day (SD) 0 into MHCI−/− mice. On SD7, RKO colon carcinoma cells ($5\times10^6$) were injected subcutaneously in a 1:1 mixture with Matrigel. On SD7 the mice were treated with OKT4. On SD14 treatment (IV) with the 5T4×CD3 diabody (twice weekly at 0.025 mg/kg), and treatment with the PD-L1×CD137 bispecific molecule (weekly at 1 or 2 mg/kg) was initiated. Tumor growth was measured twice weekly with calipers (N=7/group). As shown in FIGS. 19A-19C the TA×CD3 exhibited only minimal inhibition on tumor growth at the concentration tested. However, the combination of a PD-L1×CD137 bispecific molecule and the 5T4×CD3 diabody dramatically inhibited tumor growth. This study demonstrates that PD-L1×CD137 bispecific molecules comprising the binding domain of the novel CD137 MAB-6 antibody can inhibit tumor growth in-combination with a TA×CD3 bispecific molecule in vivo.

Figure 20A:
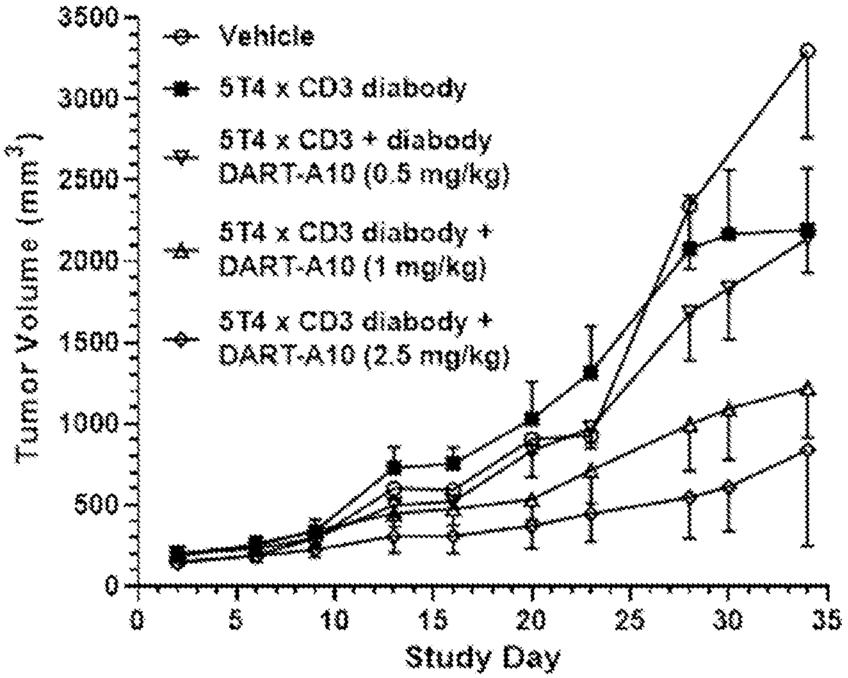
FIGS. 20A-20B show the ability of several representative PD-L1×CD137 bispecific molecules: DART-A6 (FIG. 20A), or TRIDENT-A6 (FIG. 20B), in combination with a representative TA×CD3 bispecific molecules (5T4×CD3 diabody), to prevent or inhibit tumor growth or development of RKO colon carcinoma cells in vivo relative to a TA×CD3 bispecific molecule alone or a vehicle control in a murine PBMC-reconstituted xenograft model.
Figure 20B:
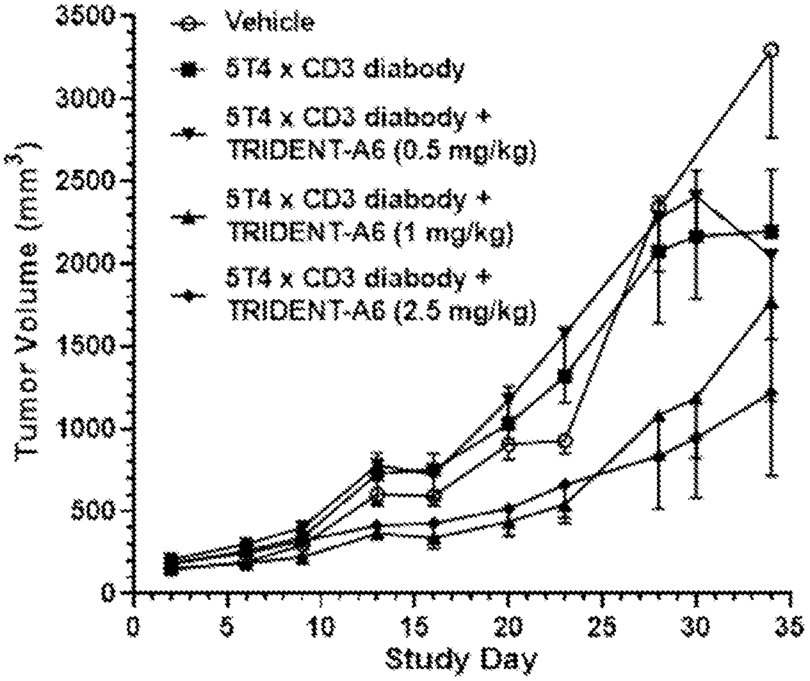

In another study, the ability of the representative PD-L1×CD137 bispecific molecules DART-A10, and TRIDENT-A6, each comprising two CD137 MAB-6(1.3) binding sites, to enhance the anti-tumor active of the 5T4×CD3 diabody, was examined. The study was performed essentially as described above except that the PD-L1×CD137 bispecific molecules were administered every 5 days (4 if over a weekend) at 0.5, 1, or 2.5 mg/kg. Tumor growth was measured twice weekly with calipers (N=8/group). As shown in FIGS. 20A-20B the DART-A10, and TRIDENT-A6 also inhibited tumor growth in combination with the 5T4×CD3 diabody. This study demonstrates that PD-L1×CD137 bispecific molecules comprising the binding domain of the deimmunized CD137 MAB-6 antibody can inhibit tumor growth in-combination with a TA×CD3 bispecific molecule in vivo.

Figure 21A:
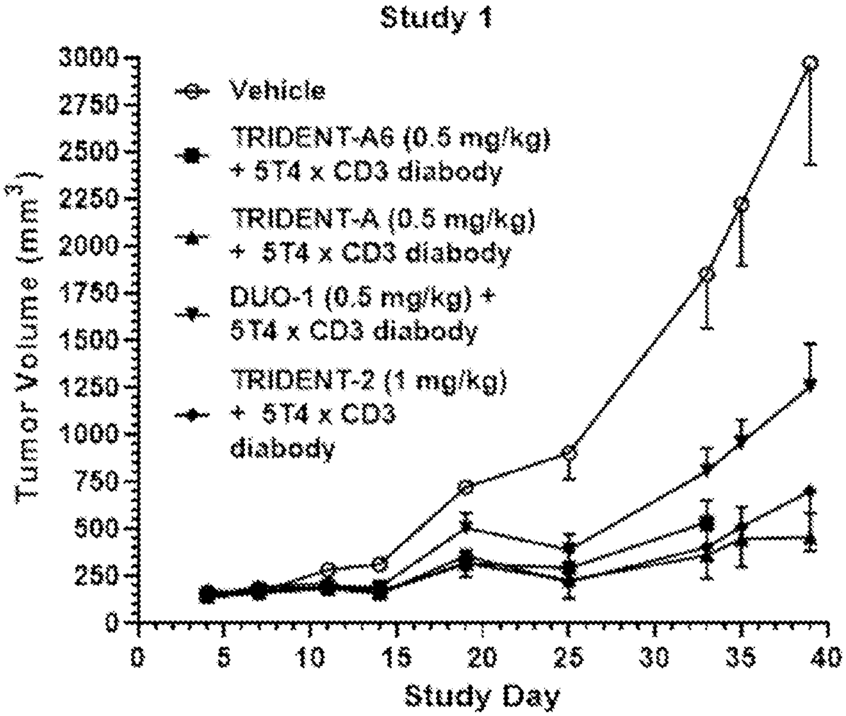
FIGS. 21A-21B show the ability of several representative PD-L1×CD137 bispecific molecules: TRIDENT-A, TRIDENT-A6 comprising the VH/VL of CD137 MAB-6 binding domain, or comparator molecules: TRIDENT-2, DUO-1 comprising the VH/VL of different CD137 binding domains, in combination with a representative TA×CD3 bispecific molecules (5T4×CD3 diabody), to prevent or inhibit tumor growth or development of RKO colon carcinoma cells in vivo relative to a vehicle control in a murine PBMC-reconstituted xenograft model. Representative data from a first study are plotted in FIG. 21A, and from a second study in FIG. 21B.
Figure 21B:
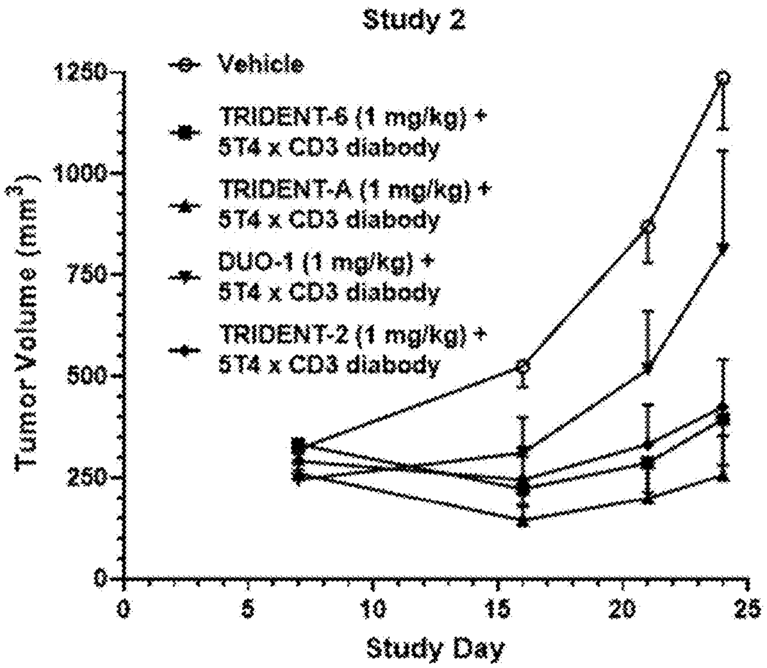

In additional combination treatment studies, the activity of the PD-L1×CD137 bispecific molecules TRIDENT-A6, TRIDENT-A (each comprising the VH/VL of a CD137 MAB-6 binding domain), was compared to that of TRIDENT-2, and a PD-L1×CD137 DUOBODY® bispecific molecule designated "PD-L1-547-FEAL×CD137-009-HC7LC2-FEAR" described in WO 2019/025545, abbreviated herein as DUO-1 (amino acid sequence provided below). The studies were conducted essentially as described above except that the PD-L1×CD137 bispecific molecules were administered every 5 days (4 if over a weekend) at concentrations ranging between 0.1 mg/kg and 5 mg/kg in the different experiments. Tumor growth was measured twice weekly with calipers (N=8/group). Representative data from two studies (note—TRIDENT-2 was only dosed at 1 mg/kg in study 1) are plotted in FIGS. 21A and 21B and show that TRIDENT-A and TRIDENT-A6 exhibit anti-tumor activity that is comparable or slightly better than that of TRIDENT-2, and are more active than DUO-1.

The representative TA×CD3 bispecific molecule, the 5T4×CD3 diabody used in the above murine xenograft studies, is a bivalent diabody having one binding site for the 5T4 tumor antigen and one binding site for CD3. The molecule has the general structure shown in FIG. 1D and comprises the following three polypeptide chains:

```
5T4 x CD3    DIQMTQSPSS LSASVGDRVT ITCRASQGIS NYLAWFQQKP GKAPKSLIYR
diabody      ANRLQSGVPS RFSGSGSGTD FTLTISSLQP EDVATYYCLQ YDDFPWTFGQ
Chain 1      GTKLEIKGGG SGGGGEVQLV ESGGGLVQPG GSLRLSCAAS GFTFSTYAMN
             WVRQAPGKGL EWVGRIRSKY NNYATYYADS VKGRFTISRD DSKNSLYLQM
             NSLKTEDTAV YYCVRHGNFG NSYVSWFAYW GQGTLVTVSS GGCGGGEVAA
             LEKEVAALEK EVAALEKEVA ALEKGGGDKT HTCPPCPAPE AAGGPSVFLF
             PPKPKDTLMI SRTPEVTCVV VDVSHEDPEV KFNWYVDGVE VHNAKTKPRE
             EQYNSTYRVV SVLTVLHQDW LNGKEYKCKV SNKALPAPIE KTISKAKGQP
             REPQVYTLPP SREEMTKNQV SLWCLVKGFY PSDIAVEWES NGQPENNYKT
             TPPVLDSDGS FFLYSKLTVD KSRWQQGNVF SCSVMHEALH NHYTQKSLSL
             SPGK (SEQ ID NO: 140)

5T4 x CD3    QAVVTQEPSL TVSPGGTVTL TCRSSTGAVT TSNYANWVQQ KPGQAPRGLI
diabody      GGTNKRAPWT PARFSGSLLG GKAALTITGA QAEDEADYYC ALWYSNLWVF
Chain 2      GGGTKLTVLG GGGSGGGGQV QLVQSGAEVK KPGASVKVSC KASGYTFTSF
             WMHWVRQAPG QGLEWMGRID PNRGGTEYNE KAKSRVTMTA DKSTSTAYME
             LSSLRSEDTA VYYCAGGNPY YPMDYWGQGT TVTVSSGGCG GGKVAALKEK
             VAALKEKVAA LKEKVAALKE (SEQ ID NO: 141)

5T4 x CD3    DKTHTCPPCP APEAAGGPSV FLFPPKPKDT LMISRTPEVT CVVVDVSHED
diabody      PEVKFNWYVD GVEVHNAKTK PREEQYNSTY RVVSVLTVLH QDWLNGKEYK
Chain 3      CKVSNKALPA PIEKTISKAK GQPREPQVYT LPPSREEMTK NQVSLSCAVK
             GFYPSDIAVE WESNGQPENN YKTTPPVLDS DGSFFLVSKL TVDKSRWQQG
             NVFSCSVMHE ALHNRYTQKS LSLSPGK (SEQ ID NO: 142)
```

The PD-L1-547-FEAL×CD137-009-HC7LC2-FEAR bispecific molecule used in the above murine xenograft studies is described in WO 2019/025545. The molecule comprises different PD-L1 and CD137 binding specificities from those provided herein and comprises the followings four polypeptide chains:

```
VH_CD137-    EVQLVESGGG LVQPGRSLRL SCTASGFSLN DYWMSWVRQA PGKGLEWVGY
009-H7       IDVGGSLYYA ASVKGRFTIS RDDSKSIAYL QMNSLKTEDT AVYYCARGGL
IgG1-        TYGFDLWGQG TLVTVSSAST KGPSVFPLAP SSKSTSGGTA ALGCLVKDYF
```

-continued

| | |
|---|---|
| FEAR-Fc | PEPVTVSWNS GALTSGVHTF PAVLQSSGLY SLSSVVTVPS SSLGTQTYIC NVNHKPSNTK VDKRVEPKSC DKTHTCPPCP APEFEGGPSV FLFPPKPKDT LMISRTPEVT CVVVAVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSRL TVDKSRWQQG NVFSCSVMHE ALHNHYTQKS LSLSPGK (SEQ ID NO: 157) |
| VL_CD137-009-L2 Kappa-C | DIVMTQSPSS LSASVGDRVT ITCQASEDIS SYLAWYQQKP GKAPKRLIYG ASDLASGVPS RFSASGSGTD YTFTISSLQP EDIATYYCHY YATISGLGVA FGGGTKVEIK RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 158) |
| VH-PD-L1-547 IgG1-FEAL-Fc | EVQLLEPGGG LVQPGGSLRL SCEASGSTFS TYAMSWVRQA PGKGLEWVSG FSGSGGFTFY ADSVRGRFTI SRDSSKNTLF LQMSSLRAED TAVYYCAIPA RGYNYGSFQH WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKRVE PKSCDKTHTC PPCPAPEFEG GPSVFLFPPK PKDTLMISRT PEVTCVVVAV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFLL YSKLTVDKSR WQQGNVFSCS VMHEALHNHY TQKSLSLSPGK (SEQ ID NO: 159) |
| VL-PD-L1-547 Lambda-C | SYVLTQPPSV SVAPGQTARI TCGGNNIGSK SVHWYQQKPG QAPVLVVYDD NDRPSGLPER FSGSNSGNTA TLTISRVEAG DEADYYCQVW DSSSDHVVFG GGTKLTVLGQ PKAAPSVTLF PPSSEELQAN KATLVCLISD FYPGAVTVAW KADSSPVKAG VETTTPSKQS NNKYAASSYL SLTPEQWKSH RSYSCQVTHE GSTVEKTVAP TECS (SEQ ID NO: 160) |

Example 9

Characterization of Additional CD137×TA Binding Molecules

CD137×TA Binding Molecules capable of binding to CD137 and to the representative TA, HER2, were generated incorporating the VH and VL Domains of CD137 MAB-6 (1.1) and the VH and VL Domains of hHER2 MAB-1(1.3). In this study a number of additional bispecific configurations were examined. In particular, a bivalent bispecific diabody designated "DART-B1," comprising bispecific diabody domains and having the asymmetric structure shown in FIG. 11D, and a trivalent binding molecule designated "TRIDENT-B2," comprising bispecific diabody-type binding domains (where Site A binds CD137, and site B binds the TA), and a non-diabody-type binding domain (Site C binding CD137), having the structure shown in FIG. 3A, were generated. In addition, molecules having the same general configurations as those previous characterized were generated. In particular, a tetravalent bispecific diabody designated "DART-B2," comprising identical bispecific diabody binding domains and having the antibody-like Y structure shown in FIG. 1B, and a trivalent binding molecule designated "TRIDENT-B1," comprising mono-specific diabody-type binding domains (where Sites A and B bind CD137), and a non-diabody-type binding domain (Site C binding the TA), were generated. The domain attributes of these molecules, and certain bispecific control and comparator molecules having the same structures are discussed above (see e.g., Tables 5-6).

Figure 22A:
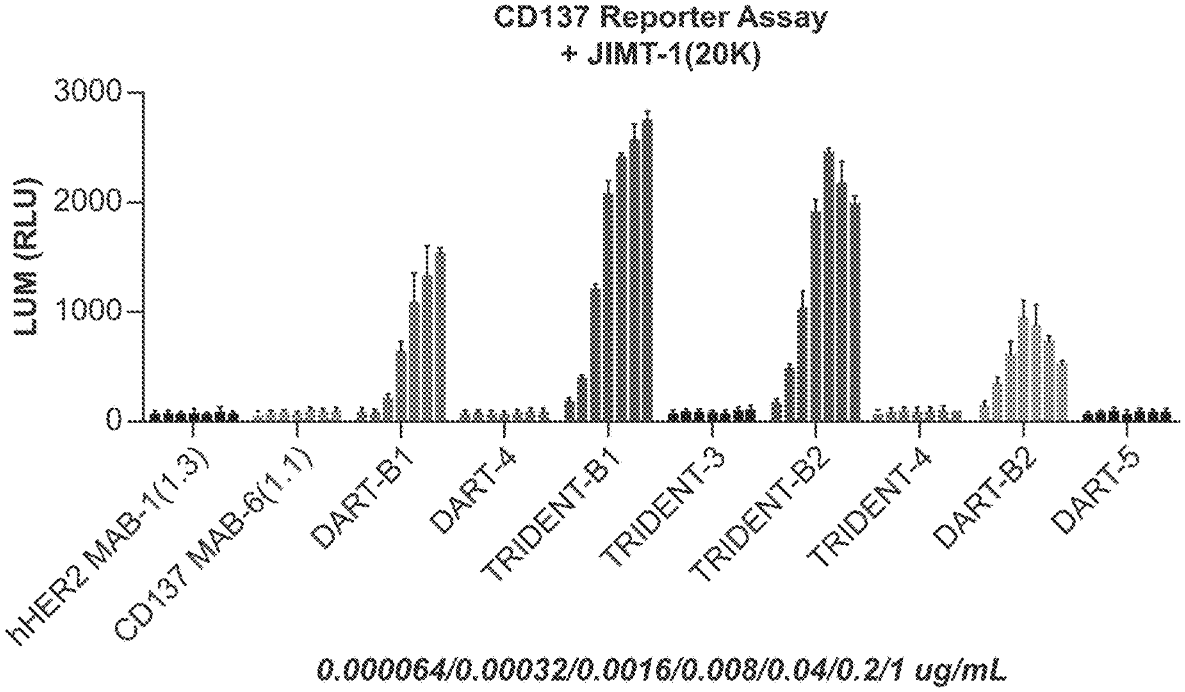
FIGS. 22A-22B show the ability of CD137×TA Binding Molecules comprising CD137 binding domains, and HER2 binding domains, to mediate target-dependent signal transduction in a CD137 Reporter Assay performed with medium HER2 expressing JIMT-1 cells (FIG. 22A), or high HER2 expressing N87 target cells (FIG. 22B). The activity of DART-1, DART-B2, TRIDENT-1, TRIDENT-B2, the parental hHER2 MAB-1(1.3) and CD137 MAB-6(1.1) antibodies, and the negative controls, DART-4, DART-5, TRIDENT-3, TRIDENT-4, are plotted.
Figure 22B:
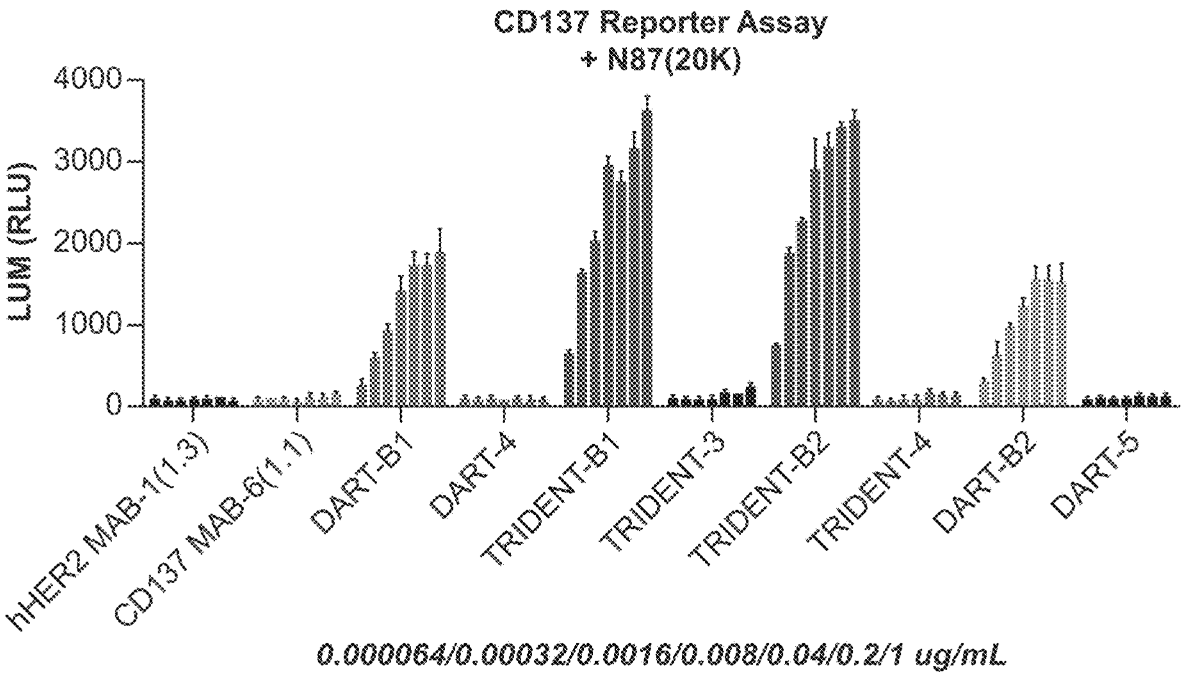

The functional activity of DART-1, DART-R2, TRIDENT-1, TRIDENT-R2, the parental CD137 MAB-6 (1.1) and HER2 MAB-1(1.3) antibodies, and the negative controls: DART-4, DART-5, TRIDENT-3, and TRIDENT-4 (CD137×RSV binding molecules having structures comparable to each test article), was evaluated in a CD137 reporter assay performed essentially as described above in the presence and absence of HER2 expressing cells (JIMT-1 ($HER2^{++}$) or N87 ($HER2^{+++}$) 20,000 cells per well). Test articles were used at 1 ug/mL and five-fold serial dilutions. The results of a representative assay using JIMT-1 and N87 cells are shown in FIGS. 22A and 22B, respectively, and demonstrate that all of CD137×HER2 bispecific molecules comprising the binding domain CD137 MAB-6 (1.1) mediated target-dependent signal transduction while the parental antibodies and the negative controls did not exhibit activity.

Figure 23A:
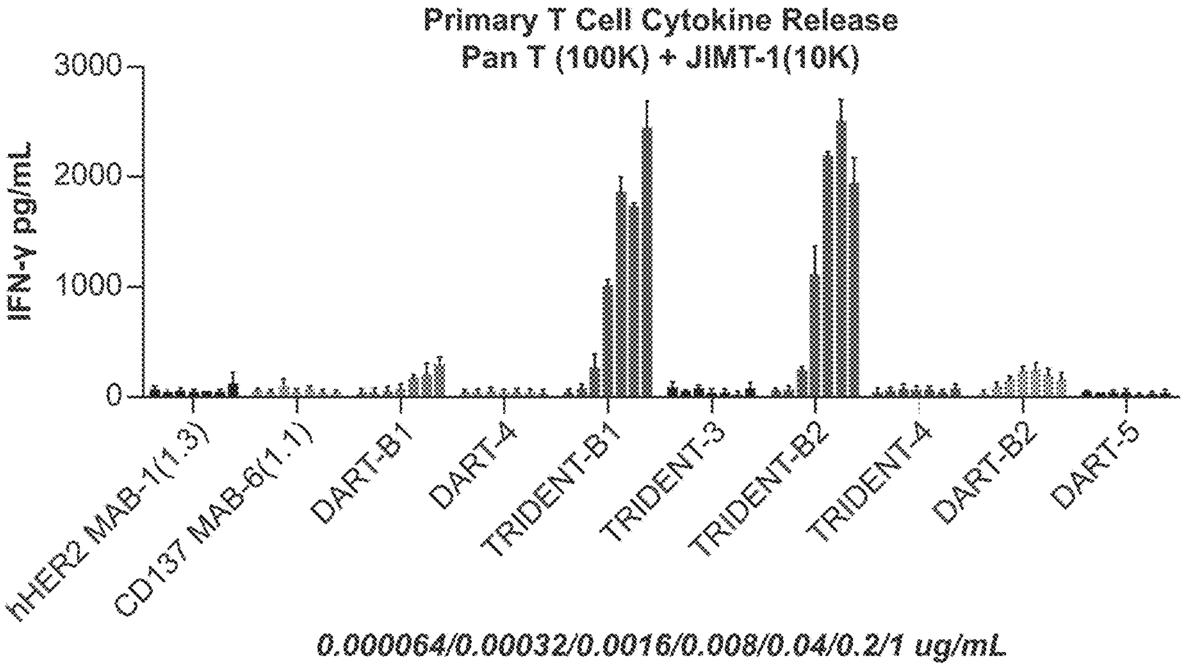
FIGS. 23A-23D show the ability of CD137×TA Binding Molecules comprising CD137 binding domains, and HER2 binding domains, to mediate target-dependent release of cytokines INF-γ (FIGS. 23A and 23B) and IL-2 (FIGS. 23C and 23D) in a primary T cell cytokine release assay performed with medium HER2 expressing JIMT-1 cells (FIGS. 22A and 23C), or high HER2 expressing N87 target cells (FIGS. 22B and 23D). The activity of DART-1, DART-B2, TRIDENT-1, TRIDENT-B2, the parental hHER2 MAB-1 (1.3) and CD137 MAB-6(1.1) antibodies, and the negative controls, DART-4, DART-5, TRIDENT-3, TRIDENT-4, are plotted.
Figure 23B:
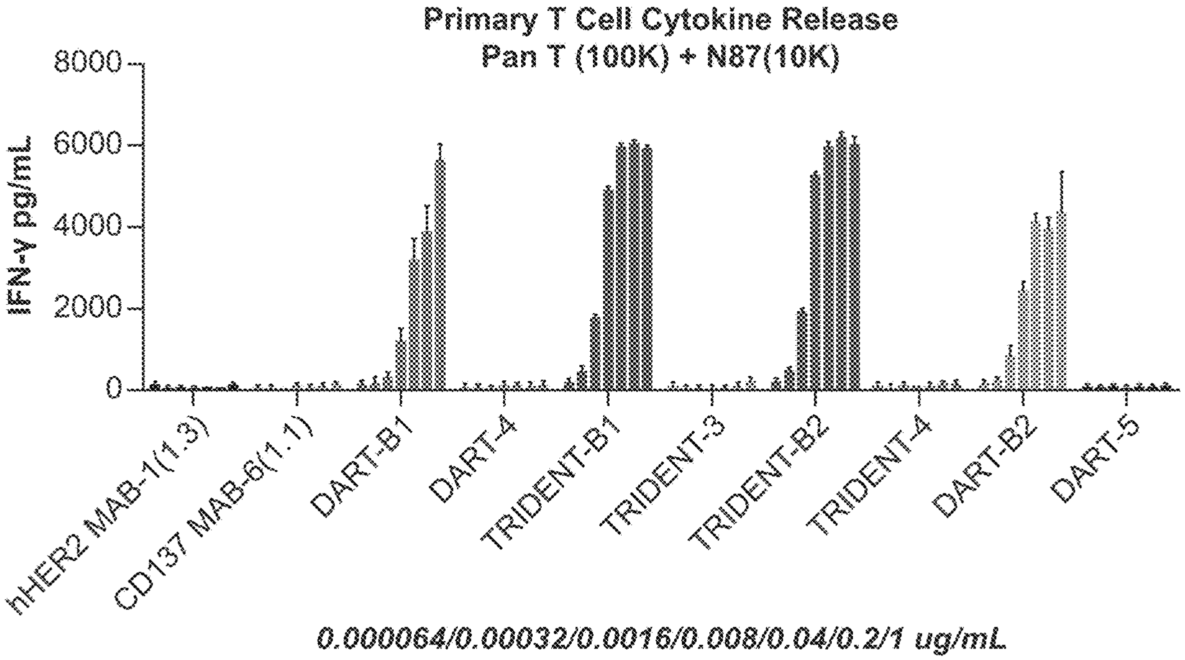
Figure 23C:
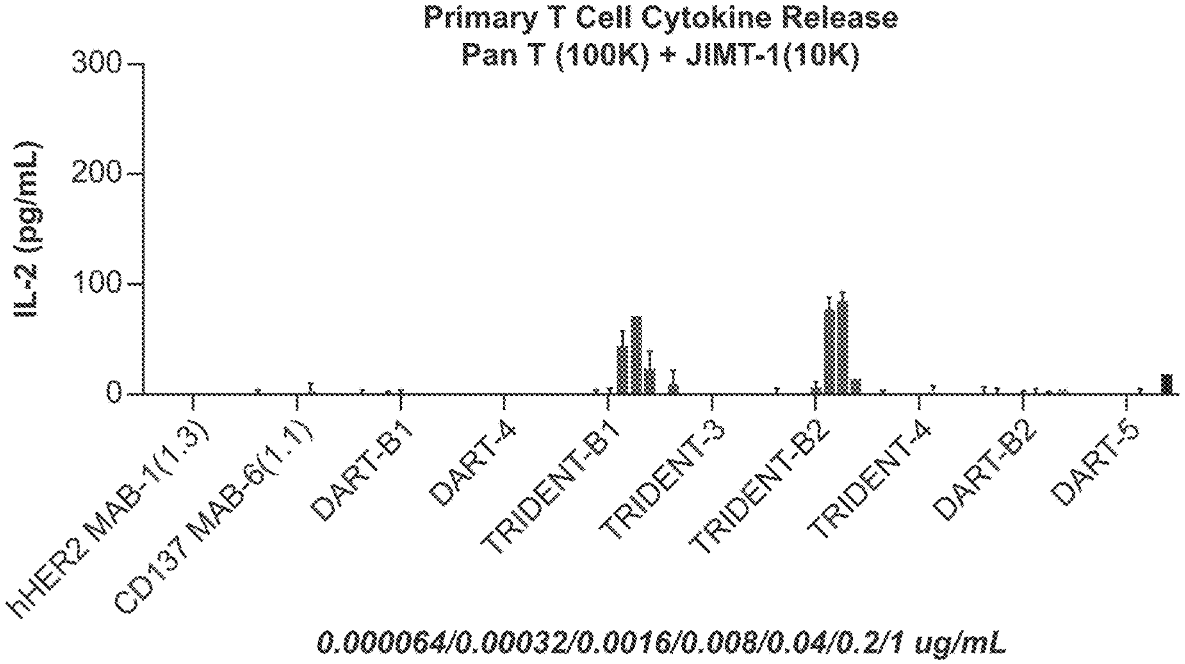
Figure 23D:
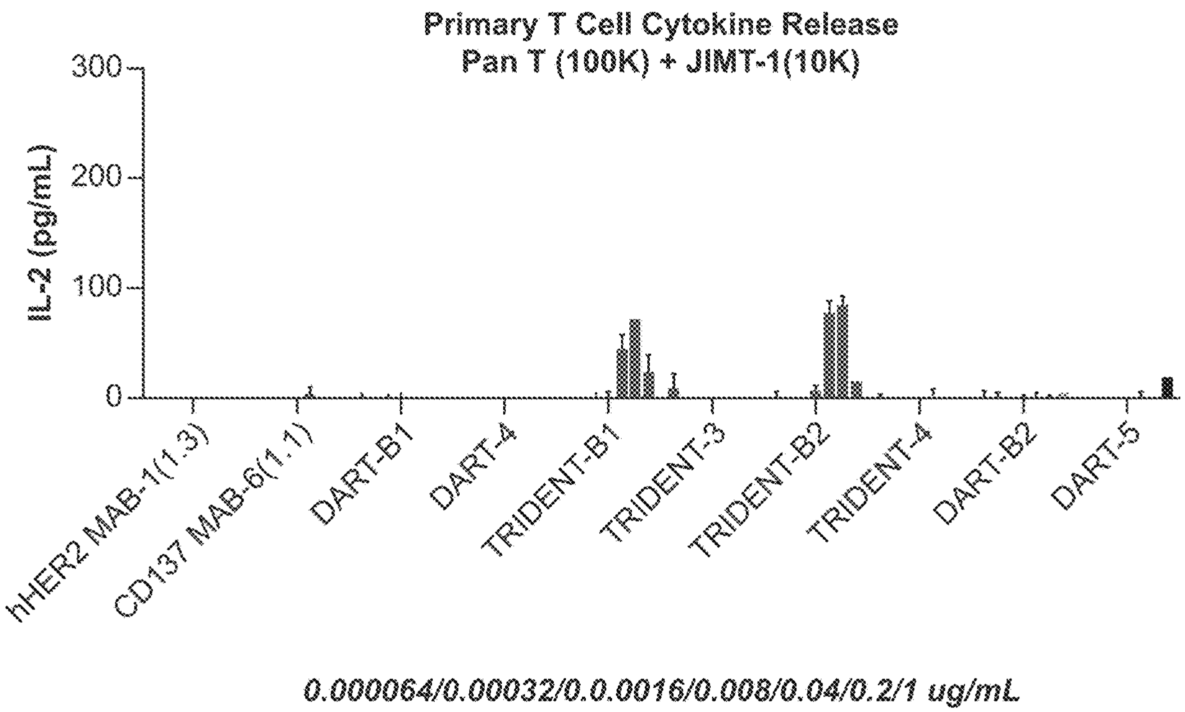

The functional activity of DART-1, DART-B2, TRIDENT-1, TRIDENT-B2, the parental CD137 MAB-6 (1.1) and HER2 MAB-1(1.3) antibodies, and the negative controls: DART-4, DART-5, TRIDENT-3, and TRIDENT-4, was also evaluated in the primary T cell cytokine release assay presence of HER2 expressing cells (JIMT-1 and N87 10,000 cells per well) performed essentially as described above. Test articles were used at 1 μg/mL and five-fold serial dilutions. The results of a representative assay using JIMT-1 cells are shown in FIGS. 23A (INF-γ) and 23C (IL-2), and using N87 cells are shown in FIGS. 23B (INF-γ) and 23D (IL-2). As was seen in the CD137 reporter assay, all of CD137×HER2 bispecific molecules comprising the binding domain CD137 MAB-6 (1.1) mediated target-dependent cytokine release, particularly with high HER2 expressing N87 cells, while the parental antibodies and the negative controls did not exhibit activity.

These studies demonstrate that bivalent, tetravalent, and trivalent CD137×TA bispecific molecules comprising the binding domain CD137 MAB-6 (1.1) (DART-R1, DART-B2, TRIDENT-B1/B2, respectively) mediated target-dependent signal transduction. In will be noted that the position of the CD137 binding domains is shifted in TRIDENT-B2 relative to TRIDENT-B1. This study demonstrates that CD137 MAB-6 is functional when paired with additional tumor antigens, in numerous configurations, and even when present as a single binding site.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A CD137 Binding Molecule comprising a first binding site that immunospecifically binds to an epitope of CD137, wherein said first binding site comprises a first Light Chain Variable Domain that comprises a $CDR_L1$, $CDR_L2$ and $CDR_L3$, and a first Heavy Chain Variable Domain that comprises a $CDR_H1$, $CDR_H2$ and $CDR_H3$; and wherein:
(A) said first Light Chain Variable Domain $CDR_L1$, $CDR_L2$, and $CDR_L3$ are the Light Chain CDRs of CD137 MAB-6 VL1 (SEQ ID NO:50), CD137 MAB-6 VL2 (SEQ ID NO:55); or CD137 MAB-6 VL3 (SEQ ID NO:56); and
(B) said first Heavy Chain Variable Domain $CDR_H1$, $CDR_H2$, and $CDR_H3$ are the Heavy Chain CDRs of CD137 MAB-6 VH1 (SEQ ID NO:46).

2. The CD137 Binding Molecule of claim 1, wherein:
(A) said first Heavy Chain Variable Domain comprises the amino acid sequence of: hCD137 MAB-6 VH1 (SEQ ID NO:46); and
(B) said first Light Chain Variable Domain comprises the amino acid sequence of: hCD137 MAB-6 VL3 (SEQ ID NO:56).

3. The CD137 Binding Molecule of claim 1, comprising a second binding site that immunospecifically binds to an epitope of PD-L1, wherein said second binding site comprises a second Light Chain Variable Domain that comprises a CDRL1, CDRL2 and CDRL3, and a second Heavy Chain Variable Domain that comprises a CDRH1, CDRH2 and CDRH3; and wherein:
(A) said second Light Chain Variable Domain $CDR_L1$, $CDR_L2$, and $CDR_L3$ are the Light Chain CDRs of hPD-L1 MAB-2 VLx (SEQ ID NO:63); and
(B) said second Heavy Chain Variable Domain $CDR_H1$, $CDR_H2$, and $CDR_H3$ are the Heavy Chain CDRs of hPD-L1 MAB-2 VHx (SEQ ID NO:59).

4. The CD137 Binding Molecule of claim 3, wherein:
(A) said second Heavy Chain Variable Domain comprises the amino acid sequence of:
(1) hPD-L1 MAB-2 VH1 (SEQ ID NO:57);
(2) hPD-L1 MAB-2 VH2 (SEQ ID NO:67);
(3) hPD-L1 MAB-2 VH3 (SEQ ID NO:68);
(4) hPD-L1 MAB-2 VH4 (SEQ ID NO:69);
(5) hPD-L1 MAB-2 VH5 (SEQ ID NO:70); or
(6) hPD-L1 MAB-2 VH6 (SEQ ID NO:71); and
(B) said second Light Chain Variable Domain comprises the amino acid sequence of:
(1) hPD-L1 MAB-2 VL1 (SEQ ID NO:58); or
(2) hPD-L1 MAB-2 VL2 (SEQ ID NO:72);
or optionally:
(C) said second Heavy Chain Variable Domain comprises the amino acid sequence of hPD-L1 MAB-2 VH4 (SEQ ID NO:69) and said second Light Chain Variable Domain comprises the amino acid sequence of hPD-L1 MAB-2 VL2 (SEQ ID NO:72);
or optionally:
(D) said first Heavy Chain Variable Domain comprises the amino acid sequence of hCD137 MAB-6 VH1 (SEQ ID NO:46), said first Light Chain Variable Domain comprises the amino acid sequence of hCD137 MAB-6 VL3 (SEQ ID NO:56), said second Heavy Chain Variable Domain comprises the amino acid sequence of hPD-L1 MAB-2 VH4 (SEQ ID NO:69) and said second Light Chain Variable Domain comprises the amino acid sequence of hPD-L1 MAB-2 VL2 (SEQ ID NO: 72).

5. The CD137 Binding Molecule of claim 1, comprising a second binding site that immunospecifically binds to an epitope of HER2, wherein said second binding site comprises a second Light Chain Variable Domain that comprises a $CDR_L1$, $CDR_L2$ and $CDR_L3$, and a second Heavy Chain Variable Domain that comprises a $CDR_H1$, $CDR_H2$ and $CDR_H3$; and wherein:
(A) (1) said second Light Chain Variable Domain $CDR_L1$, $CDR_L2$, and $CDR_L3$ are the Light Chain CDRs of hHER2-MAB-1 VLx (SEQ ID NO: 79); and
(2) said second Heavy Chain Variable Domain $CDR_H1$, $CDR_H2$, and $CDR_H3$ are the Heavy Chain CDRs of hHER2-MAB-1 VHx (SEQ ID NO: 78);
or optionally:
(B) (1) said second Heavy Chain Variable Domain comprises the amino acid sequence of hHER2-MAB-1 VH1 (SEQ ID NO:80); hHER2-MAB-1 VH2 (SEQ ID NO:81); or hHER2-MAB-1 VH3 (SEQ ID NO: 82); and
(2) said second Light Chain Variable Domain comprises the amino acid sequence of: hHER2-MAB-1 VL1 (SEQ ID NO:83); hHER2-MAB-1 VL2 (SEQ ID NO:84); or hHER2-MAB-1 VL3 (SEQ ID NO: 85);
or optionally:
(C) said second Heavy Chain Variable Domain comprises the amino acid sequence of hHER2-MAB-1 VH1 (SEQ ID NO:80) and said second Light Chain Variable Domain comprises the amino acid sequence of hHER2-MAB-1 VL3 (SEQ ID NO:85).

6. The CD137 Binding Molecule of claim 1, which is an antibody or a bispecific tetravalent Fc-bearing diabody, or a bispecific trivalent molecule.

7. The CD137 Binding Molecule of claim 1, wherein:
said molecule is bispecific and tetravalent, and comprises a first polypeptide chain, a second polypeptide chain, a third polypeptide chain, and a fourth polypeptide chain, and said polypeptide chains form a covalently bonded complex;
and optionally, the first polypeptide chain comprises the amino acid sequence of SEQ ID NO:120; the second polypeptide chain comprises the amino acid sequence of SEQ ID NO:139; the third polypeptide chain comprises the amino acid sequence of SEQ ID NO: 120 and the fourth polypeptide chain comprises the amino acid sequence of SEQ ID NO:139.

8. The CD137 Binding Molecule of claim 1, wherein:

said molecule is bispecific and trivalent, and comprises a first polypeptide chain, a second polypeptide chain, a third polypeptide chain, and a fourth polypeptide chain, and said polypeptide chains form a covalently bonded complex; and optionally, the first polypeptide chain comprises the amino acid sequence of SEQ ID NO:135; the second polypeptide chain comprises the amino acid sequence of SEQ ID NO: 136; the third polypeptide chain comprises the amino acid sequence of SEQ ID NO:131 and the fourth polypeptide chain comprises the amino acid sequence of SEQ ID NO:132; and optionally, the first polypeptide chain comprises the amino acid sequence of SEQ ID NO:127; the second polypeptide chain comprises the amino acid sequence of SEQ ID NO:128; the third polypeptide chain comprises the amino acid sequence of SEQ ID NO: 129 and the fourth polypeptide chain comprises the amino acid sequence of SEQ ID NO:130.

9. A PD-L1 Binding Molecule, comprising a Light Chain Variable Domain that comprises a CDRL1, CDRL2 and CDRL3, and a Heavy Chain Variable Domain that comprises a CDRH1, CDRH2 and CDRH3; wherein:

(A) said Light Chain Variable Domain $CDR_L1$, $CDR_L2$, and $CDR_L3$ are the Light Chain CDRs of hPD-L1 MAB-2 VLx (SEQ ID NO:63); and (B) said Heavy Chain Variable Domain $CDR_H1$, $CDR_H2$, and $CDR_H3$ are the Heavy Chain CDRs of hPD-L1 MAB-2 VHx (SEQ ID NO:59); and optionally, said Heavy Chain Variable Domain comprises the amino acid sequence of hPD-L1 MAB-2 VH4 (SEQ ID NO:69) and said Light Chain Variable Domain comprises the amino acid sequence of hPD-L1 MAB-2 VL2 (SEQ ID NO:72).

10. A pharmaceutical composition comprising the CD137 Binding Molecule of claim 1 and a physiologically acceptable carrier.

11. A pharmaceutical composition comprising the PD-L1 Binding Molecule of claim 9, and a physiologically acceptable carrier.

12. A method for treating a cancer, comprising administering to a subject in need thereof a therapeutically effective amount of the CD137 Binding Molecule of claim 1 to treat the cancer.

13. The method of claim 12, wherein the cancer is selected from the group consisting: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer.

14. A method for treating a cancer, comprising administering to a subject in need thereof a therapeutically effective amount of the PD-L1 Binding Molecule of claim 9 to treat the cancer.

15. The method of claim 14, wherein the cancer is selected from the group consisting: bladder cancer, bone cancer, a brain and spinal cord cancer, breast cancer, cervical cancer, colorectal cancer, gallbladder or bile duct cancer, gastric cancer, glioblastoma, head and neck cancer, hepatocellular carcinoma, kidney cancer, leukemia, liver cancer, lung cancer, melanoma, neuroblastoma, non-small cell lung cancer (NSCLC), ovarian cancer, pancreatic cancer, pharyngeal cancer, prostate cancer, renal cell carcinoma, rhabdomyosarcoma, skin cancer, squamous cell cancer of the head and neck (SCCHN), stomach cancer, testicular cancer, thymic carcinoma, and uterine cancer.

16. A nucleic acid encoding the CD137 Binding Molecule of claim 1.

17. A nucleic acid encoding the PD-L1 Binding Molecule of claim 9.

* * * * *

SEQUENCE LISTING

```
<160> NUMBER OF SEQ ID NOS: 160

<210> SEQ ID NO 1
<211> LENGTH: 107
<212> TYPE: PRT
<213> ORGANISM: Homo sapiens

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 2
<211> LENGTH: 104
<212> TYPE: PRT
<213> ORGANISM: Homo sapiens

<400> SEQUENCE: 2

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100


<210> SEQ ID NO 3
<211> LENGTH: 98
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
```

1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val

<210> SEQ ID NO 4
<211> LENGTH: 98
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val

<210> SEQ ID NO 5
<211> LENGTH: 98
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Thr Cys Asn Val Asn His Lys Pro Ser Asn Thr Lys Val Asp Lys
85 90 95

Arg Val

<210> SEQ ID NO 6
<211> LENGTH: 98
<212> TYPE: PRT

<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 7
<211> LENGTH: 15
<212> TYPE: PRT
<213> ORGANISM: Homo sapiens

<400> SEQUENCE: 7

Glu Pro Lys Ser Cys Asp Lys Thr His Thr Cys Pro Pro Cys Pro
1               5                   10                  15

<210> SEQ ID NO 8
<211> LENGTH: 12
<212> TYPE: PRT
<213> ORGANISM: Homo sapiens

<400> SEQUENCE: 8

Glu Arg Lys Cys Cys Val Glu Cys Pro Pro Cys Pro
1               5                   10

<210> SEQ ID NO 9
<211> LENGTH: 62
<212> TYPE: PRT
<213> ORGANISM: Homo sapiens

<400> SEQUENCE: 9

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
            20                  25                  30

Glu Pro Lys Ser Cys Asp Thr Pro Pro Pro Cys Pro Arg Cys Pro Glu
        35                  40                  45

Pro Lys Ser Cys Asp Thr Pro Pro Pro Cys Pro Arg Cys Pro
    50                  55                  60

<210> SEQ ID NO 10
<211> LENGTH: 12
<212> TYPE: PRT
<213> ORGANISM: Homo sapiens

<400> SEQUENCE: 10

Glu Ser Lys Tyr Gly Pro Pro Cys Pro Ser Cys Pro
1               5                   10

<210> SEQ ID NO 11

```
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 11

Glu Ser Lys Tyr Gly Pro Pro Cys Pro Pro Cys Pro
1               5                   10


<210> SEQ ID NO 12
<211> LENGTH: 217
<212> TYPE: PRT
<213> ORGANISM: Homo sapiens
<220> FEATURE:
<221> NAME/KEY: MOD_RES
<222> LOCATION: (217)..(217)
<223> OTHER INFORMATION: Lysine (K) or is absent

<400> SEQUENCE: 12

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215


<210> SEQ ID NO 13
<211> LENGTH: 216
<212> TYPE: PRT
<213> ORGANISM: Homo sapiens
<220> FEATURE:
<221> NAME/KEY: MOD_RES
<222> LOCATION: (216)..(216)
<223> OTHER INFORMATION: Lysine (K) or is absent

<400> SEQUENCE: 13

Ala Pro Pro Val Ala Gly Pro Ser Val Phe Leu Phe Pro Pro Lys Pro
```

```
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
    130                 135                 140

Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Xaa
    210                 215


<210> SEQ ID NO 14
<211> LENGTH: 217
<212> TYPE: PRT
<213> ORGANISM: Homo sapiens
<220> FEATURE:
<221> NAME/KEY: MOD_RES
<222> LOCATION: (217)..(217)
<223> OTHER INFORMATION: Lysine (K) or is absent

<400> SEQUENCE: 14

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140
```

```
Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Xaa
    210                 215


<210> SEQ ID NO 15
<211> LENGTH: 217
<212> TYPE: PRT
<213> ORGANISM: Homo sapiens
<220> FEATURE:
<221> NAME/KEY: MOD_RES
<222> LOCATION: (217)..(217)
<223> OTHER INFORMATION: Lysine (K) or is absent

<400> SEQUENCE: 15

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215


<210> SEQ ID NO 16
<211> LENGTH: 8
<212> TYPE: PRT
<213> ORGANISM: Homo sapiens

<400> SEQUENCE: 16

Gly Gly Gly Ser Gly Gly Gly Gly
```

1 5

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic construct

<400> SEQUENCE: 17

Gly Gly Gly Gly Ser Gly Gly Gly Gly Ser Gly Gly Gly Gly Ser
1 5 10 15

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic construct

<400> SEQUENCE: 18

Gly Gly Cys Gly Gly Gly
1 5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic construct

<400> SEQUENCE: 19

Ala Ser Thr Lys Gly
1 5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic construct

<400> SEQUENCE: 20

Asp Lys Thr His Thr Cys Pro Pro Cys Pro
1 5 10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic construct

<400> SEQUENCE: 21

Gly Gly Gly Asp Lys Thr His Thr Cys Pro Pro Cys Pro
1 5 10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic construct

<400> SEQUENCE: 22

Ala Pro Ser Ser Ser
1 5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
construct

<400> SEQUENCE: 23

Ala Pro Ser Ser Ser Pro Met Glu
1 5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
construct

<400> SEQUENCE: 24

Gly Gly Gly Ser Gly Gly Gly Ser Gly Gly Gly
1 5 10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
construct

<400> SEQUENCE: 25

Gly Gly Gly Gly Ser Gly Gly Gly Ser Gly Gly Gly
1 5 10

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
construct

<400> SEQUENCE: 26

Leu Gly Gly Gly Ser Gly
1 5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
construct

<400> SEQUENCE: 27

Gly Gly Gly Ser
1

<210> SEQ ID NO 28

<211> LENGTH: 6
<212> TYPE: PRT
<213> ORGANISM: Artificial Sequence
<220> FEATURE:
<223> OTHER INFORMATION: Description of Artificial Sequence: Synthetic construct

<400> SEQUENCE: 28

Leu Glu Pro Lys Ser Ser
1 5

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic construct

<400> SEQUENCE: 29

Val Glu Pro Lys Ser Ala Asp Lys Thr His Thr Cys Pro Pro Cys Pro
1 5 10 15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic construct

<400> SEQUENCE: 30

Leu Glu Pro Lys Ser Ala Asp Lys Thr His Thr Cys Pro Pro Cys Pro
1 5 10 15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic construct

<400> SEQUENCE: 31

Leu Glu Pro Lys Ser Ser Asp Lys Thr His Thr Cys Pro Pro Cys Pro
1 5 10 15

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic construct

<400> SEQUENCE: 32

Gly Val Glu Pro Lys Ser Cys
1 5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic construct

<400> SEQUENCE: 33

Val Glu Pro Lys Ser Cys
1 5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic construct

<400> SEQUENCE: 34

Ala Glu Pro Lys Ser Cys
1 5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic construct

<400> SEQUENCE: 35

Gly Phe Asn Arg Gly Glu Cys
1 5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic construct

<400> SEQUENCE: 36

Phe Asn Arg Gly Glu Cys
1 5

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic construct

<400> SEQUENCE: 37

Glu Val Ala Ala Leu Glu Lys Glu Val Ala Ala Leu Glu Lys Glu Val
1 5 10 15

Ala Ala Leu Glu Lys Glu Val Ala Ala Leu Glu Lys
20 25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic construct

<400> SEQUENCE: 38

Lys Val Ala Ala Leu Lys Glu Lys Val Ala Ala Leu Lys Glu Lys Val
1 5 10 15

Ala Ala Leu Lys Glu Lys Val Ala Ala Leu Lys Glu
20 25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic construct

<400> SEQUENCE: 39

```
Glu Val Ala Ala Cys Glu Lys Glu Val Ala Ala Leu Glu Lys Glu Val
1               5                   10                  15

Ala Ala Leu Glu Lys Glu Val Ala Ala Leu Glu Lys
            20                  25
```

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic construct

<400> SEQUENCE: 40

```
Lys Val Ala Ala Cys Lys Glu Lys Val Ala Ala Leu Lys Glu Lys Val
1               5                   10                  15

Ala Ala Leu Lys Glu Lys Val Ala Ala Leu Lys Glu
            20                  25
```

<210> SEQ ID NO 41
<211> LENGTH: 217
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (217)..(217)
<223> OTHER INFORMATION: Lysine (K) or is absent

<400> SEQUENCE: 41

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160
```

```
Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215


<210> SEQ ID NO 42
<211> LENGTH: 217
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (217)..(217)
<223> OTHER INFORMATION: Lysine (K) or is absent

<400> SEQUENCE: 42

Ala Pro Glu Leu Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215


<210> SEQ ID NO 43
<211> LENGTH: 217
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
```

<222> LOCATION: (217)..(217)
<223> OTHER INFORMATION: Lysine (K) or is absent

<400> SEQUENCE: 43

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 44
<211> LENGTH: 217
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (217)..(217)
<223> OTHER INFORMATION: Lysine (K) or is absent

<400> SEQUENCE: 44

```
Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215


<210> SEQ ID NO 45
<211> LENGTH: 217
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (217)..(217)
<223> OTHER INFORMATION: Lysine (K) or is absent

<400> SEQUENCE: 45

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Xaa
    210                 215


<210> SEQ ID NO 46
<211> LENGTH: 123
<212> TYPE: PRT
<213> ORGANISM: Homo sapiens

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Trp Tyr Asp Glu Asp Tyr Asn Tyr Tyr Gly Met Asp Val
            100                 105                 110

Trp Gly Gln Gly Thr Thr Val Thr Val Ser Ser
        115                 120


<210> SEQ ID NO 47
<211> LENGTH: 5
<212> TYPE: PRT
<213> ORGANISM: Homo sapiens

<400> SEQUENCE: 47

Ser Tyr Tyr Trp Ser
1               5


<210> SEQ ID NO 48
<211> LENGTH: 16
<212> TYPE: PRT
<213> ORGANISM: Homo sapiens

<400> SEQUENCE: 48

Arg Ile Tyr Thr Ser Gly Ser Thr Asn Tyr Asn Pro Ser Leu Lys Ser
1               5                   10                  15


<210> SEQ ID NO 49
<211> LENGTH: 15
<212> TYPE: PRT
<213> ORGANISM: Homo sapiens

<400> SEQUENCE: 49

Asp Gly Trp Tyr Asp Glu Asp Tyr Asn Tyr Tyr Gly Met Asp Val
1               5                   10                  15


<210> SEQ ID NO 50
<211> LENGTH: 108
<212> TYPE: PRT
<213> ORGANISM: Homo sapiens

<400> SEQUENCE: 50

Glu Ile Val Met Thr Gln Ser Pro Ala Thr Leu Ser Leu Thr Pro Gly
1               5                   10                  15
```

```
Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys
            100                 105


<210> SEQ ID NO 51
<211> LENGTH: 12
<212> TYPE: PRT
<213> ORGANISM: Homo sapiens

<400> SEQUENCE: 51

Arg Ala Ser Gln Ser Val Ser Ser Asn Tyr Leu Ser
1               5                   10


<210> SEQ ID NO 52
<211> LENGTH: 7
<212> TYPE: PRT
<213> ORGANISM: Homo sapiens

<400> SEQUENCE: 52

Gly Ala Ser Thr Arg Ala Thr
1               5


<210> SEQ ID NO 53
<211> LENGTH: 9
<212> TYPE: PRT
<213> ORGANISM: Homo sapiens

<400> SEQUENCE: 53

Gln Gln Asp Tyr Asp Leu Pro Trp Thr
1               5


<210> SEQ ID NO 54
<211> LENGTH: 108
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (14)..(14)
<223> OTHER INFORMATION: Serine (S) or Threonine (T)
<220> FEATURE:
<221> NAME/KEY: MOD_RES
<222> LOCATION: (37)..(37)
<223> OTHER INFORMATION: Phenylalanine (F) or Tyrosine (Y)
<220> FEATURE:
<221> NAME/KEY: MOD_RES
<222> LOCATION: (40)..(40)
<223> OTHER INFORMATION: Isoleucine (I) or Lysine (K)

<400> SEQUENCE: 54

Glu Ile Val Met Thr Gln Ser Pro Ala Thr Leu Ser Leu Xaa Pro Gly
1               5                   10                  15

Glu Arg Ala Thr Leu Ser Cys Arg Ala Ser Gln Ser Val Ser Ser Asn
            20                  25                  30
```

Tyr Leu Ser Trp Xaa Gln Gln Xaa Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys
            100                 105

<210> SEQ ID NO 55
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 55

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys
            100                 105

<210> SEQ ID NO 56
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 56

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys
            100                 105

<210> SEQ ID NO 57
<211> LENGTH: 118
<212> TYPE: PRT
<213> ORGANISM: Artificial Sequence
<220> FEATURE:
<223> OTHER INFORMATION: Description of Artificial Sequence: Synthetic construct

<400> SEQUENCE: 57

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ile Gly Gly Gly Thr Thr Tyr Tyr Pro Asp Thr Val
50 55 60

Lys Gly Arg Phe Thr Ile Ser Arg Asp Asn Ala Lys Asn Thr Leu Tyr
65 70 75 80

Leu Gln Met Asn Ser Leu Lys Thr Glu Asp Thr Ala Val Tyr Tyr Cys
85 90 95

Ala Arg Gln Gly Leu Pro Tyr Tyr Phe Asp Tyr Trp Gly Gln Gly Thr
100 105 110

Leu Val Thr Val Ser Ser
115

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic construct

<400> SEQUENCE: 58

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Asn Thr Pro Leu
85 90 95

Thr Phe Gly Gln Gly Thr Lys Val Glu Ile Lys
100 105

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (54)..(54)

<223> OTHER INFORMATION: Glycine (G) or Lysine (K)
<220> FEATURE:
<221> NAME/KEY: MOD_RES
<222> LOCATION: (78)..(78)
<223> OTHER INFORMATION: Threonine (T) or Serine (S)
<220> FEATURE:
<221> NAME/KEY: MOD_RES
<222> LOCATION: (87)..(87)
<223> OTHER INFORMATION: Lysine (K) or Arginine (R)
<220> FEATURE:
<221> NAME/KEY: MOD_RES
<222> LOCATION: (88)..(88)
<223> OTHER INFORMATION: Alanine (A) or Threonine (T)
<220> FEATURE:
<221> NAME/KEY: MOD_RES
<222> LOCATION: (99)..(99)
<223> OTHER INFORMATION: Alanine (A) or Glutamine (Q)
<220> FEATURE:
<221> NAME/KEY: MOD_RES
<222> LOCATION: (105)..(105)
<223> OTHER INFORMATION: Phenylalanine (F) or Glycine (G)

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Tyr Ile Ser Ile Xaa Gly Gly Thr Thr Tyr Tyr Pro Asp Thr Val
    50                  55                  60

Lys Gly Arg Phe Thr Ile Ser Arg Asp Asn Ala Lys Asn Xaa Leu Tyr
65                  70                  75                  80

Leu Gln Met Asn Ser Leu Xaa Xaa Glu Asp Thr Ala Val Tyr Tyr Cys
                85                  90                  95

Ala Arg Xaa Gly Leu Pro Tyr Tyr Xaa Asp Tyr Trp Gly Gln Gly Thr
            100                 105                 110

Leu Val Thr Val Ser Ser
        115
```

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic construct

<400> SEQUENCE: 60

```
Ser Tyr Thr Met Ser
1               5
```

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (5)..(5)
<223> OTHER INFORMATION: Glysine (G) or Lysine (K)

<400> SEQUENCE: 61

```
Tyr Ile Ser Ile Xaa Gly Gly Thr Thr Tyr Tyr Pro Asp Thr Val Lys
1               5                   10                  15
```

Gly

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (1)..(1)
<223> OTHER INFORMATION: Alanine (A) or Glutamine (Q)
<220> FEATURE:
<221> NAME/KEY: MOD_RES
<222> LOCATION: (7)..(7)
<223> OTHER INFORMATION: Phenylalanine (F) or Glycine (G)

<400> SEQUENCE: 62

```
Xaa Gly Leu Pro Tyr Tyr Xaa Asp Tyr
1               5
```

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (31)..(31)
<223> OTHER INFORMATION: Glutamate (E) or Threonine (T)

<400> SEQUENCE: 63

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Xaa Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Asn Thr Pro Leu
                85                  90                  95

Thr Phe Gly Gln Gly Thr Lys Val Glu Ile Lys
            100                 105
```

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (8)..(8)
<223> OTHER INFORMATION: Glutamate (E) or Threonine (T)

<400> SEQUENCE: 64

```
Lys Ala Ser Gln Asp Val Asn Xaa Ala Val Ala
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic construct

<400> SEQUENCE: 65

Trp Ala Ser Thr Arg His Thr
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic construct

<400> SEQUENCE: 66

Gln Gln His Tyr Asn Thr Pro Leu Thr
1 5

<210> SEQ ID NO 67
<211> LENGTH: 118
<212> TYPE: PRT
<213> ORGANISM: Artificial Sequence
<220> FEATURE:
<223> OTHER INFORMATION: Description of Artificial Sequence: Synthetic construct

<400> SEQUENCE: 67

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ile Gly Gly Gly Thr Thr Tyr Tyr Pro Asp Thr Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Leu Pro Tyr Tyr Phe Asp Tyr Trp Gly Gln Gly Thr
100 105 110

Leu Val Thr Val Ser Ser
115

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic construct

<400> SEQUENCE: 68

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ile Lys Gly Gly Thr Thr Tyr Tyr Pro Asp Thr Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Leu Pro Tyr Tyr Gly Asp Tyr Trp Gly Gln Gly Thr
100 105 110

Leu Val Thr Val Ser Ser
115

<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic construct

<400> SEQUENCE: 69

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ile Gly Gly Gly Thr Thr Tyr Tyr Pro Asp Thr Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Ala Gly Leu Pro Tyr Tyr Phe Asp Tyr Trp Gly Gln Gly Thr
100 105 110

Leu Val Thr Val Ser Ser
115

<210> SEQ ID NO 70
<211> LENGTH: 118
<212> TYPE: PRT
<213> ORGANISM: Artificial Sequence
<220> FEATURE:
<223> OTHER INFORMATION: Description of Artificial Sequence: Synthetic construct

<400> SEQUENCE: 70

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ile Lys Gly Gly Thr Thr Tyr Tyr Pro Asp Thr Val
50 55 60

Lys Gly Arg Phe Thr Ile Ser Arg Asp Asn Ala Lys Asn Ser Leu Tyr
65 70 75 80

```
Leu Gln Met Asn Ser Leu Arg Ala Glu Asp Thr Ala Val Tyr Tyr Cys
                85                  90                  95

Ala Arg Ala Gly Leu Pro Tyr Tyr Phe Asp Tyr Trp Gly Gln Gly Thr
            100                 105                 110

Leu Val Thr Val Ser Ser
        115


<210> SEQ ID NO 71
<211> LENGTH: 118
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Tyr Ile Ser Ile Gly Gly Gly Thr Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Pro Tyr Tyr Gly Asp Tyr Trp Gly Gln Gly Thr
            100                 105                 110

Leu Val Thr Val Ser Ser
        115


<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Glu Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Asn Thr Pro Leu
                85                  90                  95

Thr Phe Gly Gln Gly Thr Lys Val Glu Ile Lys
            100                 105


<210> SEQ ID NO 73
```

<211> LENGTH: 17
<212> TYPE: PRT
<213> ORGANISM: Artificial Sequence
<220> FEATURE:
<223> OTHER INFORMATION: Description of Artificial Sequence: Synthetic construct

<400> SEQUENCE: 73

Tyr Ile Ser Ile Lys Gly Gly Thr Thr Tyr Tyr Pro Asp Thr Val Lys
1 5 10 15

Gly

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic construct

<400> SEQUENCE: 74

Gln Gly Leu Pro Tyr Tyr Gly Asp Tyr
1 5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic construct

<400> SEQUENCE: 75

Ala Gly Leu Pro Tyr Tyr Phe Asp Tyr
1 5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic construct

<400> SEQUENCE: 76

Ala Gly Leu Pro Tyr Tyr Gly Asp Tyr
1 5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic construct

<400> SEQUENCE: 77

Lys Ala Ser Gln Asp Val Asn Glu Ala Val Ala
1 5 10

<210> SEQ ID NO 78
<211> LENGTH: 119
<212> TYPE: PRT
<213> ORGANISM: Artificial Sequence
<220> FEATURE:
<223> OTHER INFORMATION: Description of Artificial Sequence: Synthetic construct
<220> FEATURE:

```
<221> NAME/KEY: MOD_RES
<222> LOCATION: (100)..(100)
<223> OTHER INFORMATION: Apartate (D) or Glutamate (E)
<220> FEATURE:
<221> NAME/KEY: MOD_RES
<222> LOCATION: (101)..(101)
<223> OTHER INFORMATION: Gycine (G) or Isoleucine (I)

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Xaa Xaa Tyr Gly Asn Arg Val Ser Tyr Trp Gly Gln Gly
            100                 105                 110

Thr Leu Val Thr Val Ser Ser
        115


<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (30)..(30)
<223> OTHER INFORMATION: Asparagine (N) or Serine (S)
<220> FEATURE:
<221> NAME/KEY: MOD_RES
<222> LOCATION: (31)..(31)
<223> OTHER INFORMATION: Serine (S) or Threonine (T) or Aparagine (N)
<220> FEATURE:
<221> NAME/KEY: MOD_RES
<222> LOCATION: (55)..(55)
<223> OTHER INFORMATION: Valine (V) or Glutamine (Q)
<220> FEATURE:
<221> NAME/KEY: MOD_RES
<222> LOCATION: (56)..(56)
<223> OTHER INFORMATION: Aspartate (D) or Glutamate (E) or Serine (S)

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Xaa Xaa Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Xaa Xaa Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95
```

Thr Phe Gly Gln Gly Thr Lys Leu Glu Ile Lys
100 105

<210> SEQ ID NO 80
<211> LENGTH: 119
<212> TYPE: PRT
<213> ORGANISM: Artificial Sequence
<220> FEATURE:
<223> OTHER INFORMATION: Description of Artificial Sequence: Synthetic construct

<400> SEQUENCE: 80

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Arg Gln Ala Pro Gly Gln Gly Leu Glu Trp Met
35 40 45

Gly Trp Ile Asn Thr Asn Ile Gly Glu Pro Thr Tyr Thr Glu Glu Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Asp Gly Tyr Gly Asn Arg Val Ser Tyr Trp Gly Gln Gly
100 105 110

Thr Leu Val Thr Val Ser Ser
115

<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic construct

<400> SEQUENCE: 81

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Arg Gln Ala Pro Gly Gln Gly Leu Glu Trp Met
35 40 45

Gly Trp Ile Asn Thr Asn Ile Gly Glu Pro Thr Tyr Thr Glu Glu Phe
50 55 60

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Asp Glu Gly Tyr Gly Asn Arg Val Ser Tyr Trp Gly Gln Gly
100 105 110

Thr Leu Val Thr Val Ser Ser
115

<210> SEQ ID NO 82
<211> LENGTH: 119
<212> TYPE: PRT
<213> ORGANISM: Artificial Sequence
<220> FEATURE:

<223> OTHER INFORMATION: Description of Artificial Sequence: Synthetic
construct

<400> SEQUENCE: 82

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Ile Gly Glu Pro Thr Tyr Thr Glu Glu Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Ile Tyr Gly Asn Arg Val Ser Tyr Trp Gly Gln Gly
            100                 105                 110

Thr Leu Val Thr Val Ser Ser
        115
```

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
construct

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105
```

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
construct

<400> SEQUENCE: 84

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Thr Tyr
            20                  25                  30

Leu Ser Trp Phe Gln Gln Lys Pro Gly Lys Ala Pro Lys Thr Leu Ile
```

```
        35                  40                  45

Tyr Arg Ala Asn Arg Leu Val Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105


<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Ser Asn Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Glu Phe Pro Trp
                85                  90                  95

Thr Phe Gly Gln Gly Thr Lys Leu Glu Ile Lys
            100                 105


<210> SEQ ID NO 86
<211> LENGTH: 118
<212> TYPE: PRT
<213> ORGANISM: Mus musculus

<400> SEQUENCE: 86

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Lys His Gly Asn Tyr Tyr Thr Met Asp Tyr Trp Gly Gln Gly Thr
            100                 105                 110

Ser Val Thr Val Ser Ser
        115
```

<210> SEQ ID NO 87
<211> LENGTH: 106
<212> TYPE: PRT
<213> ORGANISM: Mus musculus

<400> SEQUENCE: 87

Asp Ile Gln Met Thr Gln Thr Thr Ser Ser Leu Ser Ala Ser Leu Gly
1               5                   10                  15

Asp Arg Ile Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Tyr Thr Leu Tyr Thr
                85                  90                  95

Phe Gly Gly Gly Thr Lys Leu Glu Ile Lys
            100                 105

<210> SEQ ID NO 88
<211> LENGTH: 118
<212> TYPE: PRT
<213> ORGANISM: Mus musculus

<400> SEQUENCE: 88

Gln Ile Gln Leu Val Gln Ser Gly Pro Glu Leu Lys Lys Pro Gly Glu
1               5                   10                  15

Thr Val Lys Ile Ser Cys Lys Ala Ser Gly Phe Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Ile Gly Glu Pro Thr Tyr Ala Asp Asp Phe
    50                  55                  60

Lys Gly Arg Phe Val Phe Ser Leu Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Glu Leu Gly Pro Tyr Tyr Phe Asp Tyr Trp Gly Gln Gly Thr
            100                 105                 110

Thr Leu Thr Val Ser Ser
        115

<210> SEQ ID NO 89
<211> LENGTH: 111
<212> TYPE: PRT
<213> ORGANISM: Mus musculus

<400> SEQUENCE: 89

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Ser Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Thr Phe Gly Ser Gly Thr Lys Leu Glu Ile Lys
            100                 105                 110


<210> SEQ ID NO 90
<211> LENGTH: 118
<212> TYPE: PRT
<213> ORGANISM: Mus musculus

<400> SEQUENCE: 90

Glu Val Gln Leu Val Glu Ser Gly Gly Gly Ser Val Lys Pro Gly Gly
1               5                   10                  15

Ser Leu Lys Leu Ser Cys Ala Ala Ser Gly Phe Thr Phe Thr Asp His
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Phe Thr Ser Tyr Pro Asp Ser Val
    50                  55                  60

Lys Gly Arg Phe Thr Ile Ser Arg Asp Ile Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Thr Arg Asp Glu Ser Asp Arg Pro Phe Pro Tyr Trp Gly Gln Gly Thr
            100                 105                 110

Leu Val Thr Val Ser Ser
        115


<210> SEQ ID NO 91
<211> LENGTH: 107
<212> TYPE: PRT
<213> ORGANISM: Mus musculus

<400> SEQUENCE: 91

Asp Ile Val Leu Thr Gln Ser His Arg Ser Met Ser Thr Ser Val Gly
1               5                   10                  15

Asp Arg Val Asn Ile Thr Cys Lys Ala Ser Gln Asp Val Thr Thr Ala
            20                  25                  30

Val Ala Trp Tyr Gln Gln Lys Pro Gly Gln Ser Pro Lys Leu Leu Ile
        35                  40                  45

Phe Trp Ala Ser Thr Arg His Ala Gly Val Pro Asp Arg Phe Thr Gly
    50                  55                  60

Ser Gly Ser Gly Thr Asp Phe Thr Leu Thr Ile Ser Ser Val Gln Ala
65                  70                  75                  80

Gly Asp Leu Ala Leu Tyr Tyr Cys Gln Gln His Tyr Ser Thr Pro Tyr
                85                  90                  95

Thr Phe Gly Gly Gly Thr Lys Leu Glu Ile Lys
            100                 105


<210> SEQ ID NO 92
<211> LENGTH: 118
<212> TYPE: PRT
<213> ORGANISM: Artificial Sequence
<220> FEATURE:
<223> OTHER INFORMATION: Description of Artificial Sequence: Synthetic
      construct
```

<400> SEQUENCE: 92

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Phe
20 25 30

Trp Met His Trp Val Arg Gln Ala Pro Gly Gln Gly Leu Glu Trp Met
35 40 45

Gly Arg Ile Asp Pro Asn Arg Gly Gly Thr Glu Tyr Asn Glu Lys Ala
50 55 60

Lys Ser Arg Val Thr Met Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Gly Gly Asn Pro Tyr Tyr Pro Met Asp Tyr Trp Gly Gln Gly Thr
100 105 110

Thr Val Thr Val Ser Ser
115

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic construct

<400> SEQUENCE: 93

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Phe Gln Gln Lys Pro Gly Lys Ala Pro Lys Ser Leu Ile
35 40 45

Tyr Arg Ala Asn Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Leu Gln Tyr Asp Asp Phe Pro Trp
85 90 95

Thr Phe Gly Gln Gly Thr Lys Leu Glu Ile Lys
100 105

<210> SEQ ID NO 94
<211> LENGTH: 127
<212> TYPE: PRT
<213> ORGANISM: Mus musculus

<400> SEQUENCE: 94

Gln Val Gln Leu Gln Gln Pro Gly Ala Glu Leu Val Lys Pro Gly Ala
1 5 10 15

Ser Val Lys Met Ser Cys Lys Ala Ser Gly Tyr Thr Phe Thr Ser Tyr
20 25 30

Trp Ile Thr Trp Val Lys Gln Arg Pro Gly Gln Gly Leu Glu Trp Ile
35 40 45

Gly Asp Ile Tyr Pro Gly Ser Gly Arg Ala Asn Tyr Asn Glu Lys Phe
50 55 60

Lys Ser Lys Ala Thr Leu Thr Val Asp Thr Ser Ser Ser Thr Ala Tyr
65 70 75 80

Met Gln Leu Ser Ser Leu Thr Ser Glu Asp Ser Ala Val Tyr Asn Cys
85 90 95

Ala Arg Tyr Gly Pro Leu Phe Thr Thr Val Val Asp Pro Asn Ser Tyr
100 105 110

Ala Met Asp Tyr Trp Gly Gln Gly Thr Ser Val Thr Val Ser Ser
115 120 125

<210> SEQ ID NO 95
<211> LENGTH: 112
<212> TYPE: PRT
<213> ORGANISM: Mus musculus

<400> SEQUENCE: 95

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val Tyr Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Phe Thr Phe Gly Ser Gly Thr Lys Leu Glu Ile Lys
100 105 110

<210> SEQ ID NO 96
<211> LENGTH: 120
<212> TYPE: PRT
<213> ORGANISM: Artificial Sequence
<220> FEATURE:
<223> OTHER INFORMATION: Description of Artificial Sequence: Synthetic
construct

<400> SEQUENCE: 96

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Gln Trp Val Arg Gln Ala Pro Gly Gln Gly Leu Glu Trp Met
35 40 45

Gly Thr Ile Tyr Pro Gly Asp Gly Asp Thr Arg Tyr Thr Gln Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Arg Gly Ile Pro Arg Leu Trp Tyr Phe Asp Val Trp Gly Gln
100 105 110

Gly Thr Thr Val Thr Val Ser Ser
115 120

<210> SEQ ID NO 97
<211> LENGTH: 120

<212> TYPE: PRT
<213> ORGANISM: Artificial Sequence
<220> FEATURE:
<223> OTHER INFORMATION: Description of Artificial Sequence: Synthetic
construct

<400> SEQUENCE: 97

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Trp Met Gln Trp Val Arg Gln Ala Pro Gly Gln Gly Leu Glu Trp Met
35 40 45

Gly Thr Ile Tyr Pro Gly Gly Gly Asp Thr Arg Tyr Thr Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Arg Gly Ile Pro Arg Leu Trp Tyr Phe Asp Val Trp Gly Gln
100 105 110

Gly Thr Thr Val Thr Val Ser Ser
115 120

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
construct

<400> SEQUENCE: 98

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Ile Ala Thr Tyr Tyr Cys Gln Gln Gly Asn Thr Leu Pro Pro
85 90 95

Thr Phe Gly Gly Gly Thr Lys Leu Glu Ile Lys
100 105

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
construct

<400> SEQUENCE: 99

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr

```
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Pro
                85                  90                  95

Thr Phe Gly Gly Gly Thr Lys Leu Glu Ile Lys
            100                 105


<210> SEQ ID NO 100
<211> LENGTH: 117
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 100

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Asp Gly Gly Ala Met Asp Tyr Trp Gly Gln Gly Thr Thr
            100                 105                 110

Val Thr Val Ser Ser
        115


<210> SEQ ID NO 101
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Tyr Ser Tyr
            20                  25                  30

Leu Ala Trp Tyr Gln Gln Lys Pro Gly Lys Ala Pro Lys Leu Leu Val
        35                  40                  45

Tyr Asn Thr Lys Thr Leu Pro Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Thr Pro Pro
```

```
                85                  90                  95

Trp Thr Phe Gly Gln Gly Thr Arg Leu Glu Ile Lys
            100                 105


<210> SEQ ID NO 102
<211> LENGTH: 119
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Ser
            20                  25                  30

Trp Met Asn Trp Val Arg Gln Ala Pro Gly Gln Gly Leu Glu Trp Ile
        35                  40                  45

Gly Arg Ile Tyr Pro Gly Asp Gly Glu Thr Asn Tyr Asn Gly Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Asn Asn Val Tyr Phe Asp Val Trp Gly Gln Gly
            100                 105                 110

Thr Thr Val Thr Val Ser Ser
        115


<210> SEQ ID NO 103
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 103

Asp Ile Gln Leu Thr Gln Ser Pro Ser Phe Leu Ser Ala Ser Val Gly
1               5                   10                  15

Asp Arg Val Thr Ile Thr Cys Ser Ala Arg Ser Ser Ile Ser Phe Met
            20                  25                  30

Tyr Trp Tyr Gln Gln Lys Pro Gly Lys Ala Pro Lys Leu Leu Ile Tyr
        35                  40                  45

Asp Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Glu Ala Glu
65                  70                  75                  80

Asp Ala Ala Thr Tyr Tyr Cys Gln Gln Trp Ser Ser Tyr Pro Leu Thr
                85                  90                  95

Phe Gly Gln Gly Thr Lys Leu Glu Ile Lys
            100                 105


<210> SEQ ID NO 104
<211> LENGTH: 121
<212> TYPE: PRT
<213> ORGANISM: Artificial Sequence
<220> FEATURE:
<223> OTHER INFORMATION: Description of Artificial Sequence: Synthetic
```

construct

<400> SEQUENCE: 104

Gln Val Gln Leu Gln Gln Ser Gly Pro Glu Val Val Arg Pro Gly Val
1 5 10 15

Ser Val Lys Ile Ser Cys Lys Gly Ser Gly Tyr Thr Phe Thr Asp Tyr
20 25 30

Ala Met His Trp Val Lys Gln Ser His Ala Lys Ser Leu Glu Trp Ile
35 40 45

Gly Leu Ile Ser Thr Tyr Ser Gly Asp Thr Lys Tyr Asn Gln Asn Phe
50 55 60

Lys Gly Lys Ala Thr Met Thr Val Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Gly Asp Tyr Ser Gly Ser Arg Tyr Trp Phe Ala Tyr Trp Gly
100 105 110

Gln Gly Thr Leu Val Thr Val Ser Ser
115 120

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
construct

<400> SEQUENCE: 105

Asp Ile Gln Met Thr Gln Ser Pro Ser Ser Leu Ser Ala Ser Val Gly
1 5 10 15

Asp Arg Val Thr Ile Thr Cys Gly Ala Ser Glu Asn Ile Tyr Gly Ala
20 25 30

Leu Asn Trp Tyr Gln Arg Lys Pro Gly Lys Ser Pro Lys Leu Leu Ile
35 40 45

Trp Gly Ala Ser Asn Leu Ala Asp Gly Met Pro Ser Arg Phe Ser Gly
50 55 60

Ser Gly Ser Gly Arg Gln Tyr Thr Leu Thr Ile Ser Ser Leu Gln Pro
65 70 75 80

Glu Asp Val Ala Thr Tyr Tyr Cys Gln Asn Val Leu Ser Ser Pro Tyr
85 90 95

Thr Phe Gly Gly Gly Thr Lys Leu Glu Ile Lys
100 105

<210> SEQ ID NO 106
<211> LENGTH: 121
<212> TYPE: PRT
<213> ORGANISM: Artificial Sequence
<220> FEATURE:
<223> OTHER INFORMATION: Description of Artificial Sequence: Synthetic
construct

<400> SEQUENCE: 106

Gln Val Gln Leu Val Glu Ser Gly Gly Gly Val Val Gln Pro Gly Arg
1 5 10 15

Ser Leu Arg Leu Ser Cys Ser Ser Ser Gly Phe Ala Leu Thr Asp Tyr
20 25 30

Tyr Met Ser Trp Val Arg Gln Ala Pro Gly Lys Gly Leu Glu Trp Leu
35 40 45

Gly Phe Ile Ala Asn Lys Ala Asn Gly His Thr Thr Asp Tyr Ser Pro
    50                  55                  60

Ser Val Lys Gly Arg Phe Thr Ile Ser Arg Asp Asn Ser Lys Asn Thr
65                  70                  75                  80

Leu Phe Leu Gln Met Asp Ser Leu Arg Pro Glu Asp Thr Gly Val Tyr
                85                  90                  95

Phe Cys Ala Arg Asp Met Gly Ile Arg Trp Asn Phe Asp Val Trp Gly
            100                 105                 110

Gln Gly Thr Pro Val Thr Val Ser Ser
        115                 120

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 107

Asp Ile Gln Leu Thr Gln Ser Pro Ser Ser Leu Ser Ala Ser Val Gly
1               5                   10                  15

Asp Arg Val Thr Met Thr Cys Ser Ala Ser Ser Arg Val Ser Tyr Ile
            20                  25                  30

His Trp Tyr Gln Gln Lys Pro Gly Lys Ala Pro Lys Arg Trp Ile Tyr
        35                  40                  45

Gly Thr Ser Thr Leu Ala Ser Gly Val Pro Ala Arg Phe Ser Gly Ser
    50                  55                  60

Gly Ser Gly Thr Asp Phe Thr Phe Thr Ile Ser Ser Leu Gln Pro Glu
65                  70                  75                  80

Asp Ile Ala Thr Tyr Tyr Cys Gln Gln Trp Ser Tyr Asn Pro Pro Thr
                85                  90                  95

Phe Gly Gln Gly Thr Lys Val Glu Ile Lys Arg
            100                 105

<210> SEQ ID NO 108
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 108

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asp Lys Arg Tyr Asn Pro Ala
    50                  55                  60

Leu Lys Ser Arg Leu Thr Ile Ser Lys Asp Thr Ser Lys Asn Gln Val
65                  70                  75                  80

Phe Leu Thr Met Thr Asn Met Asp Pro Val Asp Thr Ala Thr Tyr Tyr
                85                  90                  95

Cys Ala Arg Met Glu Leu Trp Ser Tyr Tyr Phe Asp Tyr Trp Gly Gln
            100                 105                 110

Gly Thr Thr Val Thr Val Ser Ser
115 120

<210> SEQ ID NO 109
<211> LENGTH: 106
<212> TYPE: PRT
<213> ORGANISM: Artificial Sequence
<220> FEATURE:
<223> OTHER INFORMATION: Description of Artificial Sequence: Synthetic construct

<400> SEQUENCE: 109

Glu Asn Val Leu Thr Gln Ser Pro Ala Thr Leu Ser Val Thr Pro Gly
1 5 10 15

Glu Lys Ala Thr Ile Thr Cys Arg Ala Ser Gln Ser Val Ser Tyr Met
20 25 30

His Trp Tyr Gln Gln Lys Pro Gly Gln Ala Pro Arg Leu Leu Ile Tyr
35 40 45

Asp Ala Ser Asn Arg Ala Ser Gly Val Pro Ser Arg Phe Ser Gly Ser
50 55 60

Gly Ser Gly Thr Asp His Thr Leu Thr Ile Ser Ser Leu Glu Ala Glu
65 70 75 80

Asp Ala Ala Thr Tyr Tyr Cys Phe Gln Gly Ser Val Tyr Pro Phe Thr
85 90 95

Phe Gly Gln Gly Thr Lys Leu Glu Ile Lys
100 105

<210> SEQ ID NO 110
<211> LENGTH: 120
<212> TYPE: PRT
<213> ORGANISM: Artificial Sequence
<220> FEATURE:
<223> OTHER INFORMATION: Description of Artificial Sequence: Synthetic construct

<400> SEQUENCE: 110

Glu Val Gln Leu Val Gln Ser Gly Ala Glu Leu Lys Lys Pro Gly Ala
1 5 10 15

Ser Val Lys Val Ser Cys Lys Ala Ser Gly Tyr Thr Phe Thr Asp Tyr
20 25 30

Tyr Met Lys Trp Val Arg Gln Ala Pro Gly Gln Gly Leu Glu Trp Ile
35 40 45

Gly Asp Ile Ile Pro Ser Asn Gly Ala Thr Phe Tyr Asn Gln Lys Phe
50 55 60

Lys Gly Arg Val Thr Ile Thr Val Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser His Leu Leu Arg Ala Ser Trp Phe Ala Tyr Trp Gly Gln
100 105 110

Gly Thr Leu Val Thr Val Ser Ser
115 120

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic construct

<400> SEQUENCE: 111

Asp Phe Val Met Thr Gln Ser Pro Asp Ser Leu Ala Val Ser Leu Gly
1 5 10 15

Glu Arg Val Thr Met Ser Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Asp Tyr Ser Tyr Pro Tyr Thr Phe Gly Gln Gly Thr Lys Leu Glu Ile
100 105 110

Lys

<210> SEQ ID NO 112
<211> LENGTH: 122
<212> TYPE: PRT
<213> ORGANISM: Artificial Sequence
<220> FEATURE:
<223> OTHER INFORMATION: Description of Artificial Sequence: Synthetic construct

<400> SEQUENCE: 112

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Asn
20 25 30

Gly Met Ser Trp Val Arg Gln Ala Pro Gly Lys Gly Leu Glu Trp Val
35 40 45

Ala Thr Val Ser Ser Gly Gly Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Thr Thr Ala Leu Ala Thr Arg Phe Phe Asp Val Trp
100 105 110

Gly Gln Gly Thr Leu Val Thr Val Ser Ser
115 120

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic construct

<400> SEQUENCE: 113

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Gly Thr Ala
20 25 30

Val Ala Trp Tyr Gln Gln Lys Pro Gly Lys Ala Pro Lys Leu Leu Ile

```
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105


<210> SEQ ID NO 114
<211> LENGTH: 121
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (37)..(37)
<223> OTHER INFORMATION: Valine (V) or Isoleucine (I)

<400> SEQUENCE: 114

Gln Glu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Xaa Arg Gln Ala Pro Gly Lys Gly Leu Glu Trp Val
        35                  40                  45

Ala Thr Ile Tyr Pro Ser Ser Gly Lys Thr Tyr Tyr Ala Asp Ser Ala
    50                  55                  60

Lys Gly Arg Leu Thr Ile Ser Ser Asp Asn Ala Lys Asp Ser Leu Tyr
65                  70                  75                  80

Leu Gln Met Asn Ser Leu Arg Ala Glu Asp Thr Ala Val Tyr Tyr Cys
                85                  90                  95

Thr Arg Asp Ser Tyr Ala Asp Asp Ala Ala Leu Phe Asp Ile Trp Gly
            100                 105                 110

Gln Gly Thr Thr Val Thr Val Ser Ser
        115                 120


<210> SEQ ID NO 115
<211> LENGTH: 112
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 115

Gln Leu Val Leu Thr Gln Ser Pro Ser Ala Ser Ala Ser Leu Gly Ser
1               5                   10                  15

Ser Val Lys Leu Thr Cys Thr Leu Ser Ser Gly His Lys Thr Asp Thr
            20                  25                  30

Ile Asp Trp Tyr Gln Gln Gln Pro Gly Lys Ala Pro Arg Tyr Leu Met
        35                  40                  45

Lys Leu Glu Gly Ser Gly Ser Tyr Asn Lys Gly Ser Gly Val Pro Asp
    50                  55                  60

Arg Phe Ser Gly Ser Ser Ser Gly Ala Asp Trp Tyr Leu Thr Ile Ser
65                  70                  75                  80
```

Ser Leu Gln Ser Glu Asp Glu Ala Asp Tyr Tyr Cys Gly Thr Asp Tyr
85 90 95

Pro Gly Asn Tyr Leu Phe Gly Gly Gly Thr Gln Leu Thr Val Leu Gly
100 105 110

<210> SEQ ID NO 116
<211> LENGTH: 504
<212> TYPE: PRT
<213> ORGANISM: Artificial Sequence
<220> FEATURE:
<223> OTHER INFORMATION: Description of Artificial Sequence: Synthetic construct

<400> SEQUENCE: 116

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Asn Thr Pro Leu
85 90 95

Thr Phe Gly Gln Gly Thr Lys Val Glu Ile Lys Gly Gly Gly Ser Gly
100 105 110

Gly Gly Gly Gln Val Gln Leu Gln Glu Ser Gly Pro Gly Leu Val Lys
115 120 125

Pro Ser Glu Thr Leu Ser Leu Thr Cys Thr Val Ser Gly Gly Ser Ile
130 135 140

Ser Ser Tyr Tyr Trp Ser Trp Ile Arg Gln Pro Pro Gly Lys Gly Leu
145 150 155 160

Glu Trp Ile Gly Arg Ile Tyr Thr Ser Gly Ser Thr Asn Tyr Asn Pro
165 170 175

Ser Leu Lys Ser Arg Val Thr Met Ser Val Asp Thr Ser Lys Asn Gln
180 185 190

Phe Ser Leu Lys Leu Ser Ser Val Thr Ala Ala Asp Thr Ala Val Tyr
195 200 205

Tyr Cys Ala Arg Asp Gly Trp Tyr Asp Glu Asp Tyr Asn Tyr Tyr Gly
210 215 220

Met Asp Val Trp Gly Gln Gly Thr Thr Val Thr Val Ser Ser Gly Gly
225 230 235 240

Cys Gly Gly Gly Glu Val Ala Ala Cys Glu Lys Glu Val Ala Ala Leu
245 250 255

Glu Lys Glu Val Ala Ala Leu Glu Lys Glu Val Ala Ala Leu Glu Lys
260 265 270

Leu Glu Pro Lys Ser Ala Asp Lys Thr His Thr Cys Pro Pro Cys Pro
275 280 285

Ala Pro Glu Ala Ala Gly Gly Pro Ser Val Phe Leu Phe Pro Pro Lys
290 295 300

Pro Lys Asp Thr Leu Tyr Ile Thr Arg Glu Pro Glu Val Thr Cys Val
305 310 315 320

Val Val Asp Val Ser His Glu Asp Pro Glu Val Lys Phe Asn Trp Tyr
325 330 335

Val Asp Gly Val Glu Val His Asn Ala Lys Thr Lys Pro Arg Glu Glu
340 345 350

Gln Tyr Asn Ser Thr Tyr Arg Val Val Ser Val Leu Thr Val Leu His
355 360 365

Gln Asp Trp Leu Asn Gly Lys Glu Tyr Lys Cys Lys Val Ser Asn Lys
370 375 380

Ala Leu Pro Ala Pro Ile Glu Lys Thr Ile Ser Lys Ala Lys Gly Gln
385 390 395 400

Pro Arg Glu Pro Gln Val Tyr Thr Leu Pro Pro Ser Arg Glu Glu Met
405 410 415

Thr Lys Asn Gln Val Ser Leu Thr Cys Leu Val Lys Gly Phe Tyr Pro
420 425 430

Ser Asp Ile Ala Val Glu Trp Glu Ser Asn Gly Gln Pro Glu Asn Asn
435 440 445

Tyr Lys Thr Thr Pro Pro Val Leu Asp Ser Asp Gly Ser Phe Phe Leu
450 455 460

Tyr Ser Lys Leu Thr Val Asp Lys Ser Arg Trp Gln Gln Gly Asn Val
465 470 475 480

Phe Ser Cys Ser Val Met His Glu Ala Leu His Asn His Tyr Thr Gln
485 490 495

Lys Ser Leu Ser Leu Ser Pro Gly
500

<210> SEQ ID NO 117
<211> LENGTH: 268
<212> TYPE: PRT
<213> ORGANISM: Artificial Sequence
<220> FEATURE:
<223> OTHER INFORMATION: Description of Artificial Sequence: Synthetic construct

<400> SEQUENCE: 117

Glu Ile Val Met Thr Gln Ser Pro Ala Thr Leu Ser Leu Thr Pro Gly
1 5 10 15

Glu Arg Ala Thr Leu Ser Cys Arg Ala Ser Gln Ser Val Ser Ser Asn
20 25 30

Tyr Leu Ser Trp Phe Gln Gln Ile Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Glu Val Gln Leu Val Glu Ser Gly Gly Gly Leu Val
115 120 125

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Gly Gly Gly Thr Thr Tyr Tyr
165 170 175

Pro Asp Thr Val Lys Gly Arg Phe Thr Ile Ser Arg Asp Asn Ala Lys

```
            180                 185                 190

Asn Thr Leu Tyr Leu Gln Met Asn Ser Leu Lys Thr Glu Asp Thr Ala
        195                 200                 205

Val Tyr Tyr Cys Ala Arg Gln Gly Leu Pro Tyr Tyr Phe Asp Tyr Trp
    210                 215                 220

Gly Gln Gly Thr Leu Val Thr Val Ser Ser Gly Gly Cys Gly Gly Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265


<210> SEQ ID NO 118
<211> LENGTH: 505
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Asn Thr Pro Leu
                85                  90                  95

Thr Phe Gly Gln Gly Thr Lys Val Glu Ile Lys Gly Gly Gly Ser Gly
            100                 105                 110

Gly Gly Gly Gln Val Gln Leu Gln Glu Ser Gly Pro Gly Leu Val Lys
        115                 120                 125

Pro Ser Glu Thr Leu Ser Leu Thr Cys Thr Val Ser Gly Gly Ser Ile
    130                 135                 140

Ser Ser Tyr Tyr Trp Ser Trp Ile Arg Gln Pro Pro Gly Lys Gly Leu
145                 150                 155                 160

Glu Trp Ile Gly Arg Ile Tyr Thr Ser Gly Ser Thr Asn Tyr Asn Pro
                165                 170                 175

Ser Leu Lys Ser Arg Val Thr Met Ser Val Asp Thr Ser Lys Asn Gln
            180                 185                 190

Phe Ser Leu Lys Leu Ser Ser Val Thr Ala Ala Asp Thr Ala Val Tyr
        195                 200                 205

Tyr Cys Ala Arg Asp Gly Trp Tyr Asp Glu Asp Tyr Asn Tyr Tyr Gly
    210                 215                 220

Met Asp Val Trp Gly Gln Gly Thr Thr Val Thr Val Ser Ser Gly Gly
225                 230                 235                 240

Cys Gly Gly Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270
```

```
Leu Glu Pro Lys Ser Ala Asp Lys Thr His Thr Cys Pro Pro Cys Pro
        275                 280                 285

Ala Pro Glu Ala Ala Gly Gly Pro Ser Val Phe Leu Phe Pro Pro Lys
    290                 295                 300

Pro Lys Asp Thr Leu Tyr Ile Thr Arg Glu Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505


<210> SEQ ID NO 119
<211> LENGTH: 268
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 119

Glu Ile Val Met Thr Gln Ser Pro Ala Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Glu Val Gln Leu Val Glu Ser Gly Gly Gly Leu Val
        115                 120                 125
```

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Gly Gly Gly Thr Thr Tyr Tyr
165 170 175

Pro Asp Thr Val Lys Gly Arg Phe Thr Ile Ser Arg Asp Asn Ala Lys
180 185 190

Asn Ser Leu Tyr Leu Gln Met Asn Ser Leu Arg Ala Glu Asp Thr Ala
195 200 205

Val Tyr Tyr Cys Ala Arg Gln Gly Leu Pro Tyr Tyr Phe Asp Tyr Trp
210 215 220

Gly Gln Gly Thr Leu Val Thr Val Ser Ser Gly Gly Cys Gly Gly Gly
225 230 235 240

Lys Val Ala Ala Cys Lys Glu Lys Val Ala Ala Leu Lys Glu Lys Val
245 250 255

Ala Ala Leu Lys Glu Lys Val Ala Ala Leu Lys Glu
260 265

<210> SEQ ID NO 120
<211> LENGTH: 505
<212> TYPE: PRT
<213> ORGANISM: Artificial Sequence
<220> FEATURE:
<223> OTHER INFORMATION: Description of Artificial Sequence: Synthetic construct

<400> SEQUENCE: 120

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Asn Glu Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Asn Thr Pro Leu
85 90 95

Thr Phe Gly Gln Gly Thr Lys Val Glu Ile Lys Gly Gly Gly Ser Gly
100 105 110

Gly Gly Gly Gln Val Gln Leu Gln Glu Ser Gly Pro Gly Leu Val Lys
115 120 125

Pro Ser Glu Thr Leu Ser Leu Thr Cys Thr Val Ser Gly Gly Ser Ile
130 135 140

Ser Ser Tyr Tyr Trp Ser Trp Ile Arg Gln Pro Pro Gly Lys Gly Leu
145 150 155 160

Glu Trp Ile Gly Arg Ile Tyr Thr Ser Gly Ser Thr Asn Tyr Asn Pro
165 170 175

Ser Leu Lys Ser Arg Val Thr Met Ser Val Asp Thr Ser Lys Asn Gln
180 185 190

Phe Ser Leu Lys Leu Ser Ser Val Thr Ala Ala Asp Thr Ala Val Tyr
195 200 205

Tyr Cys Ala Arg Asp Gly Trp Tyr Asp Glu Asp Tyr Asn Tyr Tyr Gly

```
    210                 215                 220

Met Asp Val Trp Gly Gln Gly Thr Thr Val Thr Val Ser Ser Gly Gly
225                 230                 235                 240

Cys Gly Gly Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

Leu Glu Pro Lys Ser Ala Asp Lys Thr His Thr Cys Pro Pro Cys Pro
        275                 280                 285

Ala Pro Glu Ala Ala Gly Gly Pro Ser Val Phe Leu Phe Pro Pro Lys
    290                 295                 300

Pro Lys Asp Thr Leu Tyr Ile Thr Arg Glu Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505


<210> SEQ ID NO 121
<211> LENGTH: 268
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 121

Glu Ile Val Met Thr Gln Ser Pro Ala Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60
```

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Glu Val Gln Leu Val Glu Ser Gly Gly Gly Leu Val
115 120 125

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Lys Gly Gly Thr Thr Tyr Tyr
165 170 175

Pro Asp Thr Val Lys Gly Arg Phe Thr Ile Ser Arg Asp Asn Ala Lys
180 185 190

Asn Ser Leu Tyr Leu Gln Met Asn Ser Leu Arg Ala Glu Asp Thr Ala
195 200 205

Val Tyr Tyr Cys Ala Arg Gln Gly Leu Pro Tyr Tyr Gly Asp Tyr Trp
210 215 220

Gly Gln Gly Thr Leu Val Thr Val Ser Ser Gly Gly Cys Gly Gly Gly
225 230 235 240

Lys Val Ala Ala Cys Lys Glu Lys Val Ala Ala Leu Lys Glu Lys Val
245 250 255

Ala Ala Leu Lys Glu Lys Val Ala Ala Leu Lys Glu
260 265

<210> SEQ ID NO 122
<211> LENGTH: 268
<212> TYPE: PRT
<213> ORGANISM: Artificial Sequence
<220> FEATURE:
<223> OTHER INFORMATION: Description of Artificial Sequence: Synthetic construct

<400> SEQUENCE: 122

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Asn
20 25 30

Tyr Leu Ser Trp Tyr Gln Gln Lys Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Glu Val Gln Leu Val Glu Ser Gly Gly Gly Leu Val
115 120 125

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Lys Gly Gly Thr Thr Tyr Tyr
165 170 175

Pro Asp Thr Val Lys Gly Arg Phe Thr Ile Ser Arg Asp Asn Ala Lys
180 185 190

Asn Ser Leu Tyr Leu Gln Met Asn Ser Leu Arg Ala Glu Asp Thr Ala
195 200 205

Val Tyr Tyr Cys Ala Arg Gln Gly Leu Pro Tyr Tyr Gly Asp Tyr Trp
210 215 220

Gly Gln Gly Thr Leu Val Thr Val Ser Ser Gly Gly Cys Gly Gly Gly
225 230 235 240

Lys Val Ala Ala Cys Lys Glu Lys Val Ala Ala Leu Lys Glu Lys Val
245 250 255

Ala Ala Leu Lys Glu Lys Val Ala Ala Leu Lys Glu
260 265

<210> SEQ ID NO 123
<211> LENGTH: 268
<212> TYPE: PRT
<213> ORGANISM: Artificial Sequence
<220> FEATURE:
<223> OTHER INFORMATION: Description of Artificial Sequence: Synthetic construct

<400> SEQUENCE: 123

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Asn
20 25 30

Tyr Leu Ser Trp Phe Gln Gln Lys Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Glu Val Gln Leu Val Glu Ser Gly Gly Gly Leu Val
115 120 125

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Lys Gly Gly Thr Thr Tyr Tyr
165 170 175

Pro Asp Thr Val Lys Gly Arg Phe Thr Ile Ser Arg Asp Asn Ala Lys
180 185 190

Asn Ser Leu Tyr Leu Gln Met Asn Ser Leu Arg Ala Glu Asp Thr Ala
195 200 205

Val Tyr Tyr Cys Ala Arg Gln Gly Leu Pro Tyr Tyr Gly Asp Tyr Trp
210 215 220

Gly Gln Gly Thr Leu Val Thr Val Ser Ser Gly Gly Cys Gly Gly Gly
225 230 235 240

Lys Val Ala Ala Cys Lys Glu Lys Val Ala Ala Leu Lys Glu Lys Val 245 250 255

Ala Ala Leu Lys Glu Lys Val Ala Ala Leu Lys Glu
260 265

<210> SEQ ID NO 124
<211> LENGTH: 268
<212> TYPE: PRT
<213> ORGANISM: Artificial Sequence
<220> FEATURE:
<223> OTHER INFORMATION: Description of Artificial Sequence: Synthetic construct

<400> SEQUENCE: 124

Glu Ile Val Met Thr Gln Ser Pro Ala Thr Leu Ser Leu Thr Pro Gly
1 5 10 15

Glu Arg Ala Thr Leu Ser Cys Arg Ala Ser Gln Ser Val Ser Ser Asn
20 25 30

Tyr Leu Ser Trp Phe Gln Gln Ile Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Glu Val Gln Leu Val Glu Ser Gly Gly Gly Leu Val
115 120 125

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Gly Gly Gly Thr Thr Tyr Tyr
165 170 175

Pro Asp Thr Val Lys Gly Arg Phe Thr Ile Ser Arg Asp Asn Ala Lys
180 185 190

Asn Ser Leu Tyr Leu Gln Met Asn Ser Leu Arg Ala Glu Asp Thr Ala
195 200 205

Val Tyr Tyr Cys Ala Arg Ala Gly Leu Pro Tyr Tyr Phe Asp Tyr Trp
210 215 220

Gly Gln Gly Thr Leu Val Thr Val Ser Ser Gly Gly Cys Gly Gly Gly
225 230 235 240

Lys Val Ala Ala Cys Lys Glu Lys Val Ala Ala Leu Lys Glu Lys Val
245 250 255

Ala Ala Leu Lys Glu Lys Val Ala Ala Leu Lys Glu
260 265

<210> SEQ ID NO 125
<211> LENGTH: 268
<212> TYPE: PRT
<213> ORGANISM: Artificial Sequence
<220> FEATURE:
<223> OTHER INFORMATION: Description of Artificial Sequence: Synthetic construct

<400> SEQUENCE: 125

Glu Ile Val Met Thr Gln Ser Pro Ala Thr Leu Ser Leu Thr Pro Gly

```
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Ser Ser Tyr Thr Met Ser Trp Val Arg Gln Ala Pro Gly Lys Gly
145                 150                 155                 160

Leu Glu Trp Val Ala Tyr Ile Ser Ile Lys Gly Gly Thr Thr Tyr Tyr
                165                 170                 175

Pro Asp Thr Val Lys Gly Arg Phe Thr Ile Ser Arg Asp Asn Ala Lys
            180                 185                 190

Asn Ser Leu Tyr Leu Gln Met Asn Ser Leu Arg Ala Glu Asp Thr Ala
        195                 200                 205

Val Tyr Tyr Cys Ala Arg Ala Gly Leu Pro Tyr Tyr Phe Asp Tyr Trp
    210                 215                 220

Gly Gln Gly Thr Leu Val Thr Val Ser Ser Gly Gly Cys Gly Gly Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265


<210> SEQ ID NO 126
<211> LENGTH: 268
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 126

Glu Ile Val Met Thr Gln Ser Pro Ala Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95
```

Trp Thr Phe Gly Gln Gly Thr Lys Val Glu Ile Lys Gly Gly Gly Ser
100 105 110

Gly Gly Gly Gly Glu Val Gln Leu Val Glu Ser Gly Gly Gly Leu Val
115 120 125

Gln Pro Gly Gly Ser Leu Arg Leu Ser Cys Ala Ala Ser Gly Phe Thr
130 135 140

Phe Ser Ser Tyr Thr Met Ser Trp Val Arg Gln Ala Pro Gly Lys Gly
145 150 155 160

Leu Glu Trp Val Ala Tyr Ile Ser Ile Gly Gly Gly Thr Thr Tyr Tyr
165 170 175

Pro Asp Thr Val Lys Gly Arg Phe Thr Ile Ser Arg Asp Asn Ala Lys
180 185 190

Asn Ser Leu Tyr Leu Gln Met Asn Ser Leu Arg Ala Glu Asp Thr Ala
195 200 205

Val Tyr Tyr Cys Ala Arg Ala Gly Leu Pro Tyr Tyr Gly Asp Tyr Trp
210 215 220

Gly Gln Gly Thr Leu Val Thr Val Ser Ser Gly Gly Cys Gly Gly Gly
225 230 235 240

Lys Val Ala Ala Cys Lys Glu Lys Val Ala Ala Leu Lys Glu Lys Val
245 250 255

Ala Ala Leu Lys Glu Lys Val Ala Ala Leu Lys Glu
260 265

<210> SEQ ID NO 127
<211> LENGTH: 503
<212> TYPE: PRT
<213> ORGANISM: Artificial Sequence
<220> FEATURE:
<223> OTHER INFORMATION: Description of Artificial Sequence: Synthetic construct

<400> SEQUENCE: 127

Glu Ile Val Met Thr Gln Ser Pro Ala Thr Leu Ser Leu Thr Pro Gly
1 5 10 15

Glu Arg Ala Thr Leu Ser Cys Arg Ala Ser Gln Ser Val Ser Ser Asn
20 25 30

Tyr Leu Ser Trp Phe Gln Gln Ile Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Gln Val Gln Leu Gln Glu Ser Gly Pro Gly Leu Val
115 120 125

Lys Pro Ser Glu Thr Leu Ser Leu Thr Cys Thr Val Ser Gly Gly Ser
130 135 140

Ile Ser Ser Tyr Tyr Trp Ser Trp Ile Arg Gln Pro Pro Gly Lys Gly
145 150 155 160

Leu Glu Trp Ile Gly Arg Ile Tyr Thr Ser Gly Ser Thr Asn Tyr Asn
165 170 175

Pro Ser Leu Lys Ser Arg Val Thr Met Ser Val Asp Thr Ser Lys Asn
180 185 190

```
Gln Phe Ser Leu Lys Leu Ser Ser Val Thr Ala Ala Asp Thr Ala Val
        195                 200                 205

Tyr Tyr Cys Ala Arg Asp Gly Trp Tyr Asp Glu Asp Tyr Asn Tyr Tyr
    210                 215                 220

Gly Met Asp Val Trp Gly Gln Gly Thr Thr Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Tyr Ile Thr Arg Glu Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500


<210> SEQ ID NO 128
<211> LENGTH: 273
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 128

Glu Ile Val Met Thr Gln Ser Pro Ala Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
```

```
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Gln Glu Ser Gly Pro Gly Leu Val
        115                 120                 125

Lys Pro Ser Glu Thr Leu Ser Leu Thr Cys Thr Val Ser Gly Gly Ser
    130                 135                 140

Ile Ser Ser Tyr Tyr Trp Ser Trp Ile Arg Gln Pro Pro Gly Lys Gly
145                 150                 155                 160

Leu Glu Trp Ile Gly Arg Ile Tyr Thr Ser Gly Ser Thr Asn Tyr Asn
                165                 170                 175

Pro Ser Leu Lys Ser Arg Val Thr Met Ser Val Asp Thr Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Asp Gly Trp Tyr Asp Glu Asp Tyr Asn Tyr Tyr
    210                 215                 220

Gly Met Asp Val Trp Gly Gln Gly Thr Thr Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu


<210> SEQ ID NO 129
<211> LENGTH: 448
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Tyr Ile Ser Ile Gly Gly Gly Thr Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Gln Gly Leu Pro Tyr Tyr Phe Asp Tyr Trp Gly Gln Gly Thr
            100                 105                 110

Leu Val Thr Val Ser Ser Ala Ser Thr Lys Gly Pro Ser Val Phe Pro
```

```
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Tyr Ile Thr Arg
                245                 250                 255

Glu Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Tyr Thr Gln Lys Ser Leu Ser Leu Ser Pro Gly Lys
        435                 440                 445


<210> SEQ ID NO 130
<211> LENGTH: 214
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30
```

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Asn Thr Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 131
<211> LENGTH: 448
<212> TYPE: PRT
<213> ORGANISM: Artificial Sequence
<220> FEATURE:
<223> OTHER INFORMATION: Description of Artificial Sequence: Synthetic construct

<400> SEQUENCE: 131

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Thr Met Ser Trp Val Arg Gln Ala Pro Gly Lys Gly Leu Glu Trp Val
35 40 45

Ala Tyr Ile Ser Ile Lys Gly Gly Thr Thr Tyr Tyr Pro Asp Thr Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gln Gly Leu Pro Tyr Tyr Gly Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Arg Val Glu Pro Lys Ser Cys Asp Lys Thr
210 215 220

His Thr Cys Pro Pro Cys Pro Ala Pro Glu Ala Ala Gly Gly Pro Ser
225 230 235 240

Val Phe Leu Phe Pro Pro Lys Pro Lys Asp Thr Leu Tyr Ile Thr Arg
245 250 255

Glu Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Ser Cys
355 360 365

Ala Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Val Ser Lys Leu Thr Val Asp Lys Ser
405 410 415

Arg Trp Gln Gln Gly Asn Val Phe Ser Cys Ser Val Met His Glu Ala
420 425 430

Leu His Asn Arg Tyr Thr Gln Lys Ser Leu Ser Leu Ser Pro Gly Lys
435 440 445

<210> SEQ ID NO 132
<211> LENGTH: 214
<212> TYPE: PRT
<213> ORGANISM: Artificial Sequence
<220> FEATURE:
<223> OTHER INFORMATION: Description of Artificial Sequence: Synthetic construct

<400> SEQUENCE: 132

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Asn Glu Ala
20 25 30

Val Ala Trp Tyr Gln Gln Lys Pro Gly Lys Ala Pro Lys Leu Leu Ile
35 40 45

Tyr Trp Ala Ser Thr Arg His Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln His Tyr Asn Thr Pro Leu

```
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 133
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 133

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Gln Glu Ser Gly Pro Gly Leu Val
        115                 120                 125

Lys Pro Ser Glu Thr Leu Ser Leu Thr Cys Thr Val Ser Gly Gly Ser
    130                 135                 140

Ile Ser Ser Tyr Tyr Trp Ser Trp Ile Arg Gln Pro Pro Gly Lys Gly
145                 150                 155                 160

Leu Glu Trp Ile Gly Arg Ile Tyr Thr Ser Gly Ser Thr Asn Tyr Asn
                165                 170                 175

Pro Ser Leu Lys Ser Arg Val Thr Met Ser Val Asp Thr Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Asp Gly Trp Tyr Asp Glu Asp Tyr Asn Tyr Tyr
    210                 215                 220
```

Gly Met Asp Val Trp Gly Gln Gly Thr Thr Val Thr Val Ser Ser Gly
225 230 235 240

Gly Cys Gly Gly Gly Glu Val Ala Ala Leu Glu Lys Glu Val Ala Ala
245 250 255

Leu Glu Lys Glu Val Ala Ala Leu Glu Lys Glu Val Ala Ala Leu Glu
260 265 270

Lys Gly Gly Gly Asp Lys Thr His Thr Cys Pro Pro Cys Pro Ala Pro
275 280 285

Glu Ala Ala Gly Gly Pro Ser Val Phe Leu Phe Pro Pro Lys Pro Lys
290 295 300

Asp Thr Leu Tyr Ile Thr Arg Glu Pro Glu Val Thr Cys Val Val Val
305 310 315 320

Asp Val Ser His Glu Asp Pro Glu Val Lys Phe Asn Trp Tyr Val Asp
325 330 335

Gly Val Glu Val His Asn Ala Lys Thr Lys Pro Arg Glu Glu Gln Tyr
340 345 350

Asn Ser Thr Tyr Arg Val Val Ser Val Leu Thr Val Leu His Gln Asp
355 360 365

Trp Leu Asn Gly Lys Glu Tyr Lys Cys Lys Val Ser Asn Lys Ala Leu
370 375 380

Pro Ala Pro Ile Glu Lys Thr Ile Ser Lys Ala Lys Gly Gln Pro Arg
385 390 395 400

Glu Pro Gln Val Tyr Thr Leu Pro Pro Ser Arg Glu Glu Met Thr Lys
405 410 415

Asn Gln Val Ser Leu Trp Cys Leu Val Lys Gly Phe Tyr Pro Ser Asp
420 425 430

Ile Ala Val Glu Trp Glu Ser Asn Gly Gln Pro Glu Asn Asn Tyr Lys
435 440 445

Thr Thr Pro Pro Val Leu Asp Ser Asp Gly Ser Phe Phe Leu Tyr Ser
450 455 460

Lys Leu Thr Val Asp Lys Ser Arg Trp Gln Gln Gly Asn Val Phe Ser
465 470 475 480

Cys Ser Val Met His Glu Ala Leu His Asn His Tyr Thr Gln Lys Ser
485 490 495

Leu Ser Leu Ser Pro Gly Lys
500

<210> SEQ ID NO 134
<211> LENGTH: 273
<212> TYPE: PRT
<213> ORGANISM: Artificial Sequence
<220> FEATURE:
<223> OTHER INFORMATION: Description of Artificial Sequence: Synthetic construct

<400> SEQUENCE: 134

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Asn
20 25 30

Tyr Leu Ser Trp Tyr Gln Gln Lys Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

```
Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Gln Glu Ser Gly Pro Gly Leu Val
        115                 120                 125

Lys Pro Ser Glu Thr Leu Ser Leu Thr Cys Thr Val Ser Gly Gly Ser
    130                 135                 140

Ile Ser Ser Tyr Tyr Trp Ser Trp Ile Arg Gln Pro Pro Gly Lys Gly
145                 150                 155                 160

Leu Glu Trp Ile Gly Arg Ile Tyr Thr Ser Gly Ser Thr Asn Tyr Asn
                165                 170                 175

Pro Ser Leu Lys Ser Arg Val Thr Met Ser Val Asp Thr Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Asp Gly Trp Tyr Asp Glu Asp Tyr Asn Tyr Tyr
    210                 215                 220

Gly Met Asp Val Trp Gly Gln Gly Thr Thr Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu


<210> SEQ ID NO 135
<211> LENGTH: 503
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 135

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Gln Glu Ser Gly Pro Gly Leu Val
        115                 120                 125

Lys Pro Ser Glu Thr Leu Ser Leu Thr Cys Thr Val Ser Gly Gly Ser
    130                 135                 140

Ile Ser Ser Tyr Tyr Trp Ser Trp Ile Arg Gln Pro Pro Gly Lys Gly
145                 150                 155                 160
```

```
Leu Glu Trp Ile Gly Arg Ile Tyr Thr Ser Gly Ser Thr Asn Tyr Asn
                165                 170                 175

Pro Ser Leu Lys Ser Arg Val Thr Met Ser Val Asp Thr Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Asp Gly Trp Tyr Asp Glu Asp Tyr Asn Tyr Tyr
    210                 215                 220

Gly Met Asp Val Trp Gly Gln Gly Thr Thr Val Thr Val Ser Ser Gly
225                 230                 235                 240

Gly Cys Gly Gly Gly Glu Val Ala Ala Leu Glu Lys Glu Val Ala Ala
                245                 250                 255

Leu Glu Lys Glu Val Ala Ala Leu Glu Lys Glu Val Ala Ala Leu Glu
            260                 265                 270

Lys Gly Gly Gly Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
    290                 295                 300

Asp Thr Leu Tyr Ile Thr Arg Glu Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500
```

<210> SEQ ID NO 136
<211> LENGTH: 273
<212> TYPE: PRT
<213> ORGANISM: Artificial Sequence
<220> FEATURE:
<223> OTHER INFORMATION: Description of Artificial Sequence: Synthetic construct

<400> SEQUENCE: 136

```
Glu Ile Val Met Thr Gln Ser Pro Ala Thr Leu Ser Leu Ser Pro Gly
```

```
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Gln Glu Ser Gly Pro Gly Leu Val
        115                 120                 125

Lys Pro Ser Glu Thr Leu Ser Leu Thr Cys Thr Val Ser Gly Gly Ser
    130                 135                 140

Ile Ser Ser Tyr Tyr Trp Ser Trp Ile Arg Gln Pro Pro Gly Lys Gly
145                 150                 155                 160

Leu Glu Trp Ile Gly Arg Ile Tyr Thr Ser Gly Ser Thr Asn Tyr Asn
                165                 170                 175

Pro Ser Leu Lys Ser Arg Val Thr Met Ser Val Asp Thr Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Asp Gly Trp Tyr Asp Glu Asp Tyr Asn Tyr Tyr
    210                 215                 220

Gly Met Asp Val Trp Gly Gln Gly Thr Thr Val Thr Val Ser Ser Gly
225                 230                 235                 240

Gly Cys Gly Gly Gly Lys Val Ala Ala Leu Lys Glu Lys Val Ala Ala
                245                 250                 255

Leu Lys Glu Lys Val Ala Ala Leu Lys Glu Lys Val Ala Ala Leu Lys
            260                 265                 270

Glu


<210> SEQ ID NO 137
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 137

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
```

```
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120


<210> SEQ ID NO 138
<211> LENGTH: 106
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 138

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105


<210> SEQ ID NO 139
<211> LENGTH: 268
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 139

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Ser Ser Tyr Thr Met Ser Trp Val Arg Gln Ala Pro Gly Lys Gly
```

```
145                 150                 155                 160

Leu Glu Trp Val Ala Tyr Ile Ser Ile Gly Gly Gly Thr Thr Tyr Tyr
                165                 170                 175

Pro Asp Thr Val Lys Gly Arg Phe Thr Ile Ser Arg Asp Asn Ala Lys
            180                 185                 190

Asn Ser Leu Tyr Leu Gln Met Asn Ser Leu Arg Ala Glu Asp Thr Ala
        195                 200                 205

Val Tyr Tyr Cys Ala Arg Ala Gly Leu Pro Tyr Tyr Phe Asp Tyr Trp
    210                 215                 220

Gly Gln Gly Thr Leu Val Thr Val Ser Ser Gly Gly Cys Gly Gly Gly
225                 230                 235                 240

Lys Val Ala Ala Cys Lys Glu Lys Val Ala Ala Leu Lys Glu Lys Val
                245                 250                 255

Ala Ala Leu Lys Glu Lys Val Ala Ala Leu Lys Glu
            260                 265


<210> SEQ ID NO 140
<211> LENGTH: 504
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Gly Gly Gly Ser Gly
            100                 105                 110

Gly Gly Gly Glu Val Gln Leu Val Glu Ser Gly Gly Gly Leu Val Gln
        115                 120                 125

Pro Gly Gly Ser Leu Arg Leu Ser Cys Ala Ala Ser Gly Phe Thr Phe
    130                 135                 140

Ser Thr Tyr Ala Met Asn Trp Val Arg Gln Ala Pro Gly Lys Gly Leu
145                 150                 155                 160

Glu Trp Val Gly Arg Ile Arg Ser Lys Tyr Asn Asn Tyr Ala Thr Tyr
                165                 170                 175

Tyr Ala Asp Ser Val Lys Gly Arg Phe Thr Ile Ser Arg Asp Asp Ser
            180                 185                 190

Lys Asn Ser Leu Tyr Leu Gln Met Asn Ser Leu Lys Thr Glu Asp Thr
        195                 200                 205

Ala Val Tyr Tyr Cys Val Arg His Gly Asn Phe Gly Asn Ser Tyr Val
    210                 215                 220

Ser Trp Phe Ala Tyr Trp Gly Gln Gly Thr Leu Val Thr Val Ser Ser
225                 230                 235                 240
```

Gly Gly Cys Gly Gly Gly Glu Val Ala Ala Leu Glu Lys Glu Val Ala
245 250 255

Ala Leu Glu Lys Glu Val Ala Ala Leu Glu Lys Glu Val Ala Ala Leu
260 265 270

Glu Lys Gly Gly Gly Asp Lys Thr His Thr Cys Pro Pro Cys Pro Ala
275 280 285

Pro Glu Ala Ala Gly Gly Pro Ser Val Phe Leu Phe Pro Pro Lys Pro
290 295 300

Lys Asp Thr Leu Met Ile Ser Arg Thr Pro Glu Val Thr Cys Val Val
305 310 315 320

Val Asp Val Ser His Glu Asp Pro Glu Val Lys Phe Asn Trp Tyr Val
325 330 335

Asp Gly Val Glu Val His Asn Ala Lys Thr Lys Pro Arg Glu Glu Gln
340 345 350

Tyr Asn Ser Thr Tyr Arg Val Val Ser Val Leu Thr Val Leu His Gln
355 360 365

Asp Trp Leu Asn Gly Lys Glu Tyr Lys Cys Lys Val Ser Asn Lys Ala
370 375 380

Leu Pro Ala Pro Ile Glu Lys Thr Ile Ser Lys Ala Lys Gly Gln Pro
385 390 395 400

Arg Glu Pro Gln Val Tyr Thr Leu Pro Pro Ser Arg Glu Glu Met Thr
405 410 415

Lys Asn Gln Val Ser Leu Trp Cys Leu Val Lys Gly Phe Tyr Pro Ser
420 425 430

Asp Ile Ala Val Glu Trp Glu Ser Asn Gly Gln Pro Glu Asn Asn Tyr
435 440 445

Lys Thr Thr Pro Pro Val Leu Asp Ser Asp Gly Ser Phe Phe Leu Tyr
450 455 460

Ser Lys Leu Thr Val Asp Lys Ser Arg Trp Gln Gln Gly Asn Val Phe
465 470 475 480

Ser Cys Ser Val Met His Glu Ala Leu His Asn His Tyr Thr Gln Lys
485 490 495

Ser Leu Ser Leu Ser Pro Gly Lys
500

<210> SEQ ID NO 141
<211> LENGTH: 270
<212> TYPE: PRT
<213> ORGANISM: Artificial Sequence
<220> FEATURE:
<223> OTHER INFORMATION: Description of Artificial Sequence: Synthetic construct

<400> SEQUENCE: 141

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Trp Thr Pro Ala Arg Phe
50 55 60

Ser Gly Ser Leu Leu Gly Gly Lys Ala Ala Leu Thr Ile Thr Gly Ala
65 70 75 80

Gln Ala Glu Asp Glu Ala Asp Tyr Tyr Cys Ala Leu Trp Tyr Ser Asn
85 90 95

```
Leu Trp Val Phe Gly Gly Gly Thr Lys Leu Thr Val Leu Gly Gly Gly
            100                 105                 110

Gly Ser Gly Gly Gly Gly Gln Val Gln Leu Val Gln Ser Gly Ala Glu
        115                 120                 125

Val Lys Lys Pro Gly Ala Ser Val Lys Val Ser Cys Lys Ala Ser Gly
    130                 135                 140

Tyr Thr Phe Thr Ser Phe Trp Met His Trp Val Arg Gln Ala Pro Gly
145                 150                 155                 160

Gln Gly Leu Glu Trp Met Gly Arg Ile Asp Pro Asn Arg Gly Gly Thr
                165                 170                 175

Glu Tyr Asn Glu Lys Ala Lys Ser Arg Val Thr Met Thr Ala Asp Lys
            180                 185                 190

Ser Thr Ser Thr Ala Tyr Met Glu Leu Ser Ser Leu Arg Ser Glu Asp
        195                 200                 205

Thr Ala Val Tyr Tyr Cys Ala Gly Gly Asn Pro Tyr Tyr Pro Met Asp
    210                 215                 220

Tyr Trp Gly Gln Gly Thr Thr Val Thr Val Ser Ser Gly Gly Cys Gly
225                 230                 235                 240

Gly Gly Lys Val Ala Ala Leu Lys Glu Lys Val Ala Ala Leu Lys Glu
                245                 250                 255

Lys Val Ala Ala Leu Lys Glu Lys Val Ala Ala Leu Lys Glu
            260                 265                 270
```

<210> SEQ ID NO 142
<211> LENGTH: 227
<212> TYPE: PRT
<213> ORGANISM: Artificial Sequence
<220> FEATURE:
<223> OTHER INFORMATION: Description of Artificial Sequence: Synthetic construct

<400> SEQUENCE: 142

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
```

```
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225


<210> SEQ ID NO 143
<211> LENGTH: 499
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 143

Glu Ile Val Met Thr Gln Ser Pro Ala Thr Leu Ser Leu Thr Pro Gly
1               5                   10                  15

Glu Arg Ala Thr Leu Ser Cys Arg Ala Ser Gln Ser Val Ser Ser Asn
            20                  25                  30

Tyr Leu Ser Trp Phe Gln Gln Ile Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asp Leu Pro
                85                  90                  95

Trp Thr Phe Gly Gln Gly Thr Lys Val Glu Ile Lys Gly Gly Gly Ser
            100                 105                 110

Gly Gly Gly Gly Gln Val Gln Leu Val Gln Ser Gly Ala Glu Val Lys
        115                 120                 125

Lys Pro Gly Ala Ser Val Lys Val Ser Cys Lys Ala Ser Gly Tyr Thr
    130                 135                 140

Phe Thr Asn Tyr Gly Met Asn Trp Val Arg Gln Ala Pro Gly Gln Gly
145                 150                 155                 160

Leu Glu Trp Met Gly Trp Ile Asn Thr Asn Ile Gly Glu Pro Thr Tyr
                165                 170                 175

Thr Glu Glu Phe Lys Gly Arg Val Thr Met Thr Arg Asp Thr Ser Ile
            180                 185                 190

Ser Thr Ala Tyr Met Glu Leu Ser Arg Leu Arg Ser Asp Asp Thr Ala
        195                 200                 205

Val Tyr Tyr Cys Ala Arg Asp Asp Gly Tyr Gly Asn Arg Val Ser Tyr
    210                 215                 220

Trp Gly Gln Gly Thr Leu Val Thr Val Ser Ser Gly Gly Cys Gly Gly
225                 230                 235                 240

Gly Glu Val Ala Ala Leu Glu Lys Glu Val Ala Ala Leu Glu Lys Glu
                245                 250                 255

Val Ala Ala Leu Glu Lys Glu Val Ala Ala Leu Glu Lys Gly Gly Gly
            260                 265                 270

Asp Lys Thr His Thr Cys Pro Pro Cys Pro Ala Pro Glu Ala Ala Gly
        275                 280                 285

Gly Pro Ser Val Phe Leu Phe Pro Pro Lys Pro Lys Asp Thr Leu Tyr
    290                 295                 300
```

Ile Thr Arg Glu Pro Glu Val Thr Cys Val Val Val Asp Val Ser His
305 310 315 320

Glu Asp Pro Glu Val Lys Phe Asn Trp Tyr Val Asp Gly Val Glu Val
325 330 335

His Asn Ala Lys Thr Lys Pro Arg Glu Glu Gln Tyr Asn Ser Thr Tyr
340 345 350

Arg Val Val Ser Val Leu Thr Val Leu His Gln Asp Trp Leu Asn Gly
355 360 365

Lys Glu Tyr Lys Cys Lys Val Ser Asn Lys Ala Leu Pro Ala Pro Ile
370 375 380

Glu Lys Thr Ile Ser Lys Ala Lys Gly Gln Pro Arg Glu Pro Gln Val
385 390 395 400

Tyr Thr Leu Pro Pro Ser Arg Glu Glu Met Thr Lys Asn Gln Val Ser
405 410 415

Leu Trp Cys Leu Val Lys Gly Phe Tyr Pro Ser Asp Ile Ala Val Glu
420 425 430

Trp Glu Ser Asn Gly Gln Pro Glu Asn Asn Tyr Lys Thr Thr Pro Pro
435 440 445

Val Leu Asp Ser Asp Gly Ser Phe Phe Leu Tyr Ser Lys Leu Thr Val
450 455 460

Asp Lys Ser Arg Trp Gln Gln Gly Asn Val Phe Ser Cys Ser Val Met
465 470 475 480

His Glu Ala Leu His Asn His Tyr Thr Gln Lys Ser Leu Ser Leu Ser
485 490 495

Pro Gly Lys

<210> SEQ ID NO 144
<211> LENGTH: 272
<212> TYPE: PRT
<213> ORGANISM: Artificial Sequence
<220> FEATURE:
<223> OTHER INFORMATION: Description of Artificial Sequence: Synthetic construct

<400> SEQUENCE: 144

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Ser Asn Tyr
20 25 30

Leu Ser Trp Phe Gln Gln Lys Pro Gly Lys Ala Pro Lys Thr Leu Ile
35 40 45

Tyr Arg Ala Asn Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln His Asp Glu Phe Pro Trp
85 90 95

Thr Phe Gly Gln Gly Thr Lys Leu Glu Ile Lys Gly Gly Gly Ser Gly
100 105 110

Gly Gly Gly Gln Val Gln Leu Gln Glu Ser Gly Pro Gly Leu Val Lys
115 120 125

Pro Ser Glu Thr Leu Ser Leu Thr Cys Thr Val Ser Gly Gly Ser Ile
130 135 140

Ser Ser Tyr Tyr Trp Ser Trp Ile Arg Gln Pro Pro Gly Lys Gly Leu
145 150 155 160

```
Glu Trp Ile Gly Arg Ile Tyr Thr Ser Gly Ser Thr Asn Tyr Asn Pro
                165                 170                 175

Ser Leu Lys Ser Arg Val Thr Met Ser Val Asp Thr Ser Lys Asn Gln
            180                 185                 190

Phe Ser Leu Lys Leu Ser Ser Val Thr Ala Ala Asp Thr Ala Val Tyr
        195                 200                 205

Tyr Cys Ala Arg Asp Gly Trp Tyr Asp Glu Asp Tyr Asn Tyr Tyr Gly
    210                 215                 220

Met Asp Val Trp Gly Gln Gly Thr Thr Val Thr Val Ser Ser Gly Gly
225                 230                 235                 240

Cys Gly Gly Gly Lys Val Ala Ala Leu Lys Glu Lys Val Ala Ala Leu
                245                 250                 255

Lys Glu Lys Val Ala Ala Leu Lys Glu Lys Val Ala Ala Leu Lys Glu
            260                 265                 270


<210> SEQ ID NO 145
<211> LENGTH: 227
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 145

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly Lys
225


<210> SEQ ID NO 146
```

<211> LENGTH: 217
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (217)..(217)
<223> OTHER INFORMATION: Lysine (K) or is absent

<400> SEQUENCE: 146

```
Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Xaa
    210                 215
```

<210> SEQ ID NO 147
<211> LENGTH: 217
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (217)..(217)
<223> OTHER INFORMATION: Lysine (K) or is absent

<400> SEQUENCE: 147

```
Ala Pro Glu Phe Leu Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser Gln Glu Asp Pro Glu Val Gln Phe Asn Trp Tyr
        35                  40                  45
```

```
Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Trp Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Xaa
    210                 215


<210> SEQ ID NO 148
<211> LENGTH: 217
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (217)..(217)
<223> OTHER INFORMATION: Lysine (K) or is absent

<400> SEQUENCE: 148

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
```

```
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215


<210> SEQ ID NO 149
<211> LENGTH: 217
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (217)..(217)
<223> OTHER INFORMATION: Lysine (K) or is absent

<400> SEQUENCE: 149

Ala Pro Glu Ala Ala Gly Gly Pro Ser Val Phe Leu Phe Pro Pro Lys
1               5                   10                  15

Pro Lys Asp Thr Leu Tyr Ile Thr Arg Glu Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Ser Cys Ala Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Val Ser Lys Leu Thr Val Asp Lys Ser Arg Trp Gln Gln Gly Asn Val
            180                 185                 190

Phe Ser Cys Ser Val Met His Glu Ala Leu His Asn Arg Tyr Thr Gln
        195                 200                 205

Lys Ser Leu Ser Leu Ser Pro Gly Xaa
    210                 215


<210> SEQ ID NO 150
<211> LENGTH: 217
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (217)..(217)
```

<223> OTHER INFORMATION: Lysine (K) or is absent

<400> SEQUENCE: 150

Ala Pro Glu Phe Leu Gly Gly Pro Ser Val Phe Leu Phe Pro Pro Lys
1 5 10 15

Pro Lys Asp Thr Leu Tyr Ile Thr Arg Glu Pro Glu Val Thr Cys Val
20 25 30

Val Val Asp Val Ser Gln Glu Asp Pro Glu Val Gln Phe Asn Trp Tyr
35 40 45

Val Asp Gly Val Glu Val His Asn Ala Lys Thr Lys Pro Arg Glu Glu
50 55 60

Gln Phe Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Gly Leu Pro Ser Ser Ile Glu Lys Thr Ile Ser Lys Ala Lys Gly Gln
100 105 110

Pro Arg Glu Pro Gln Val Tyr Thr Leu Pro Pro Ser Gln Glu Glu Met
115 120 125

Thr Lys Asn Gln Val Ser Leu Ser Cys Ala Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Val Ser Arg Leu Thr Val Asp Lys Ser Arg Trp Gln Glu Gly Asn Val
180 185 190

Phe Ser Cys Ser Val Met His Glu Ala Leu His Asn Arg Tyr Thr Gln
195 200 205

Lys Ser Leu Ser Leu Ser Leu Gly Xaa
210 215

<210> SEQ ID NO 151
<211> LENGTH: 505
<212> TYPE: PRT
<213> ORGANISM: Artificial Sequence
<220> FEATURE:
<223> OTHER INFORMATION: Description of Artificial Sequence: Synthetic construct

<400> SEQUENCE: 151

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Ser Asn Tyr
20 25 30

Leu Ser Trp Phe Gln Gln Lys Pro Gly Lys Ala Pro Lys Thr Leu Ile
35 40 45

Tyr Arg Ala Asn Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln His Asp Glu Phe Pro Trp
85 90 95

Thr Phe Gly Gln Gly Thr Lys Leu Glu Ile Lys Gly Gly Gly Ser Gly
100 105 110

Gly Gly Gly Gln Val Gln Leu Gln Glu Ser Gly Pro Gly Leu Val Lys

```
        115                 120                 125

Pro Ser Glu Thr Leu Ser Leu Thr Cys Thr Val Ser Gly Gly Ser Ile
    130                 135                 140

Ser Ser Tyr Tyr Trp Ser Trp Ile Arg Gln Pro Pro Gly Lys Gly Leu
145                 150                 155                 160

Glu Trp Ile Gly Arg Ile Tyr Thr Ser Gly Ser Thr Asn Tyr Asn Pro
                165                 170                 175

Ser Leu Lys Ser Arg Val Thr Met Ser Val Asp Thr Ser Lys Asn Gln
            180                 185                 190

Phe Ser Leu Lys Leu Ser Ser Val Thr Ala Ala Asp Thr Ala Val Tyr
        195                 200                 205

Tyr Cys Ala Arg Asp Gly Trp Tyr Asp Glu Asp Tyr Asn Tyr Tyr Gly
    210                 215                 220

Met Asp Val Trp Gly Gln Gly Thr Thr Val Thr Val Ser Ser Gly Gly
225                 230                 235                 240

Cys Gly Gly Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
            260                 265                 270

Leu Glu Pro Lys Ser Ala Asp Lys Thr His Thr Cys Pro Pro Cys Pro
        275                 280                 285

Ala Pro Glu Ala Ala Gly Gly Pro Ser Val Phe Leu Phe Pro Pro Lys
    290                 295                 300

Pro Lys Asp Thr Leu Tyr Ile Thr Arg Glu Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
    370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
            500                 505


<210> SEQ ID NO 152
<211> LENGTH: 269
<212> TYPE: PRT
<213> ORGANISM: Artificial Sequence
```

<220> FEATURE:
<223> OTHER INFORMATION: Description of Artificial Sequence: Synthetic
construct

<400> SEQUENCE: 152

Glu Ile Val Met Thr Gln Ser Pro Ala Thr Leu Ser Leu Thr Pro Gly
1 5 10 15

Glu Arg Ala Thr Leu Ser Cys Arg Ala Ser Gln Ser Val Ser Ser Asn
20 25 30

Tyr Leu Ser Trp Phe Gln Gln Ile Pro Gly Gln Ala Pro Arg Leu Leu
35 40 45

Ile Tyr Gly Ala Ser Thr Arg Ala Thr Gly Ile Pro Ala Arg Phe Ser
50 55 60

Gly Ser Gly Ser Gly Thr Asp Phe Thr Leu Thr Ile Ser Ser Leu Gln
65 70 75 80

Pro Glu Asp Phe Ala Val Tyr Tyr Cys Gln Gln Asp Tyr Asp Leu Pro
85 90 95

Trp Thr Phe Gly Gln Gly Thr Lys Val Glu Ile Lys Gly Gly Gly Ser
100 105 110

Gly Gly Gly Gly Gln Val Gln Leu Val Gln Ser Gly Ala Glu Val Lys
115 120 125

Lys Pro Gly Ala Ser Val Lys Val Ser Cys Lys Ala Ser Gly Tyr Thr
130 135 140

Phe Thr Asn Tyr Gly Met Asn Trp Val Arg Gln Ala Pro Gly Gln Gly
145 150 155 160

Leu Glu Trp Met Gly Trp Ile Asn Thr Asn Ile Gly Glu Pro Thr Tyr
165 170 175

Thr Glu Glu Phe Lys Gly Arg Val Thr Met Thr Arg Asp Thr Ser Ile
180 185 190

Ser Thr Ala Tyr Met Glu Leu Ser Arg Leu Arg Ser Asp Asp Thr Ala
195 200 205

Val Tyr Tyr Cys Ala Arg Asp Asp Gly Tyr Gly Asn Arg Val Ser Tyr
210 215 220

Trp Gly Gln Gly Thr Leu Val Thr Val Ser Ser Gly Gly Cys Gly Gly
225 230 235 240

Gly Lys Val Ala Ala Cys Lys Glu Lys Val Ala Ala Leu Lys Glu Lys
245 250 255

Val Ala Ala Leu Lys Glu Lys Val Ala Ala Leu Lys Glu
260 265

<210> SEQ ID NO 153
<211> LENGTH: 449
<212> TYPE: PRT
<213> ORGANISM: Artificial Sequence
<220> FEATURE:
<223> OTHER INFORMATION: Description of Artificial Sequence: Synthetic
construct

<400> SEQUENCE: 153

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Gly Met Asn Trp Val Arg Gln Ala Pro Gly Gln Gly Leu Glu Trp Met
35 40 45

Gly Trp Ile Asn Thr Asn Ile Gly Glu Pro Thr Tyr Thr Glu Glu Phe
50 55 60

```
Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Gly Tyr Gly Asn Arg Val Ser Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Lys Ser Leu Ser Leu Ser Pro Gly
        435                 440                 445

Lys
```

<210> SEQ ID NO 154
<211> LENGTH: 214
<212> TYPE: PRT

<213> ORGANISM: Artificial Sequence
<220> FEATURE:
<223> OTHER INFORMATION: Description of Artificial Sequence: Synthetic construct

<400> SEQUENCE: 154

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Ser Asn Tyr
20 25 30

Leu Ser Trp Phe Gln Gln Lys Pro Gly Lys Ala Pro Lys Thr Leu Ile
35 40 45

Tyr Arg Ala Asn Arg Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln His Asp Glu Phe Pro Trp
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 155
<211> LENGTH: 453
<212> TYPE: PRT
<213> ORGANISM: Artificial Sequence
<220> FEATURE:
<223> OTHER INFORMATION: Description of Artificial Sequence: Synthetic construct

<400> SEQUENCE: 155

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

Gly Arg Ile Tyr Thr Ser Gly Ser Thr Asn Tyr Asn Pro Ser Leu Lys
50 55 60

Ser Arg Val Thr Met Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Asp Gly Trp Tyr Asp Glu Asp Tyr Asn Tyr Tyr Gly Met Asp Val

```
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Tyr Ile Thr Arg Glu Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn Arg Tyr Thr Gln Lys Ser Leu Ser
        435                 440                 445

Leu Ser Pro Gly Lys
    450
```

```
<210> SEQ ID NO 156
<211> LENGTH: 134
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 156
```

```
Glu Asp Phe Ala Val Tyr Tyr Cys Gln Gln Asp Tyr Asp Leu Pro Trp
1               5                   10                  15

Thr Phe Gly Gln Gly Thr Lys Val Glu Ile Lys Arg Thr Val Ala Ala
            20                  25                  30

Pro Ser Val Phe Ile Phe Pro Pro Ser Asp Glu Gln Leu Lys Ser Gly
        35                  40                  45

Thr Ala Ser Val Val Cys Leu Leu Asn Asn Phe Tyr Pro Arg Glu Ala
    50                  55                  60

Lys Val Gln Trp Lys Val Asp Asn Ala Leu Gln Ser Gly Asn Ser Gln
65                  70                  75                  80

Glu Ser Val Thr Glu Gln Asp Ser Lys Asp Ser Thr Tyr Ser Leu Ser
                85                  90                  95

Ser Thr Leu Thr Leu Ser Lys Ala Asp Tyr Glu Lys His Lys Val Tyr
            100                 105                 110

Ala Cys Glu Val Thr His Gln Gly Leu Ser Ser Pro Val Thr Lys Ser
        115                 120                 125

Phe Asn Arg Gly Glu Cys
    130


<210> SEQ ID NO 157
<211> LENGTH: 447
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 157

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Ser Leu Asn Asp Tyr
            20                  25                  30

Trp Met Ser Trp Val Arg Gln Ala Pro Gly Lys Gly Leu Glu Trp Val
        35                  40                  45

Gly Tyr Ile Asp Val Gly Gly Ser Leu Tyr Tyr Ala Ala Ser Val Lys
    50                  55                  60

Gly Arg Phe Thr Ile Ser Arg Asp Asp Ser Lys Ser Ile Ala Tyr Leu
65                  70                  75                  80

Gln Met Asn Ser Leu Lys Thr Glu Asp Thr Ala Val Tyr Tyr Cys Ala
                85                  90                  95

Arg Gly Gly Leu Thr Tyr Gly Phe Asp Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220
```

```
Thr Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Ala Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 158
<211> LENGTH: 217
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 158

Asp Ile Val Met Thr Gln Ser Pro Ser Ser Leu Ser Ala Ser Val Gly
1               5                   10                  15

Asp Arg Val Thr Ile Thr Cys Gln Ala Ser Glu Asp Ile Ser Ser Tyr
            20                  25                  30

Leu Ala Trp Tyr Gln Gln Lys Pro Gly Lys Ala Pro Lys Arg Leu Ile
        35                  40                  45

Tyr Gly Ala Ser Asp Leu Ala Ser Gly Val Pro Ser Arg Phe Ser Ala
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys His Tyr Tyr Ala Thr Ile Ser Gly
                85                  90                  95

Leu Gly Val Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
```

```
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 159
<211> LENGTH: 451
<212> TYPE: PRT
<213> ORGANISM: Artificial Sequence
<220> FEATURE:
<223> OTHER INFORMATION: Description of Artificial Sequence: Synthetic construct

<400> SEQUENCE: 159

```
Glu Val Gln Leu Leu Glu Pro Gly Gly Gly Leu Val Gln Pro Gly Gly
1               5                   10                  15

Ser Leu Arg Leu Ser Cys Glu Ala Ser Gly Ser Thr Phe Ser Thr Tyr
            20                  25                  30

Ala Met Ser Trp Val Arg Gln Ala Pro Gly Lys Gly Leu Glu Trp Val
        35                  40                  45

Ser Gly Phe Ser Gly Ser Gly Gly Phe Thr Phe Tyr Ala Asp Ser Val
    50                  55                  60

Arg Gly Arg Phe Thr Ile Ser Arg Asp Ser Ser Lys Asn Thr Leu Phe
65                  70                  75                  80

Leu Gln Met Ser Ser Leu Arg Ala Glu Asp Thr Ala Val Tyr Tyr Cys
                85                  90                  95

Ala Ile Pro Ala Arg Gly Tyr Asn Tyr Gly Ser Phe Gln His Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ala Val Ser His
            260                 265                 270
```

```
Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 160
<211> LENGTH: 214
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 160

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Asn Asp Arg Pro Ser Gly Leu Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175
```

-continued

```
Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```